US008884039B2

(12) United States Patent
DeLuca et al.

(10) Patent No.: US 8,884,039 B2
(45) Date of Patent: Nov. 11, 2014

(54) CRYSTALLIZATION OF (20R) AND (20S) ANALOGS OF 2-METHYLENE-19-NOR-24-DIMETHYL-1α,25-DIHYDROXYVITAMIN $D_3$

(71) Applicant: Wisconsin Alumni Research Foundation, Madison, WI (US)

(72) Inventors: Hector F. DeLuca, Deerfield, WI (US); Agnieszka Flores, Madison, WI (US); James B. Thoden, Madison, WI (US); Hazel M. Holden, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/828,120

(22) Filed: Mar. 14, 2013

(65) Prior Publication Data

US 2013/0324749 A1 Dec. 5, 2013

Related U.S. Application Data

(60) Provisional application No. 61/652,965, filed on May 30, 2012.

(51) Int. Cl.
*C07C 401/00* (2006.01)

(52) U.S. Cl.
CPC .................................. *C07C 401/00* (2013.01); *C07B 2200/13* (2013.01)
USPC ........................................................ 552/653

(58) Field of Classification Search
USPC ........................................................ 552/653
See application file for complete search history.

(56) References Cited

U.S. PATENT DOCUMENTS

| | | | | |
|---|---|---|---|---|
| 5,086,191 | A | 2/1992 | DeLuca et al. | |
| 5,536,713 | A | 7/1996 | DeLuca et al. | |
| 5,843,928 | A | 12/1998 | DeLuca et al. | |
| 8,604,009 | B2 * | 12/2013 | DeLuca et al. | 514/167 |
| 8,664,206 | B2 * | 3/2014 | DeLuca et al. | 514/167 |
| 2011/0237556 | A1 | 9/2011 | DeLuca et al. | |

OTHER PUBLICATIONS

Andrews et al., "A Direct, Regio- and Stereoselective 1Alpha-Hydroxylation of (5E)-Calciferol Derivatives", Journal of Organic Chemistry, 1986, 51: 1635-1637.

Baggiolini et al., "Stereocontrolled Total Synthesis of 1[alpha],25-Dihydroxycholecaliferol and 1[alpha],25-Dihydroxy-ergocalciferol", Journal of Organic Chemistry, 1986, 51: 3098-3108.

Calverley et al., "A Biologically Active Vitamin D Metabolite Analogue", Tetrahedron, 1987, 43(20): 4609-4619.

Choudhry et al., "Synthesis of a Biologically Active Vitamin-D2 Metabolite", Journal of Organic Chemistry, 1993, 58:1496-1500.

(Continued)

*Primary Examiner* — Sabiha N Qazi

(74) *Attorney, Agent, or Firm* — Andrus Intellectual Property Law, LLP

(57) ABSTRACT

Disclosed are methods of purifying (20R) and (20S) analogs of 2-methylene-19-nor-22-dimethyl-1α,25-dihydroxyvitamin $D_3$ to obtain the (20R) and (20S) analogs in crystalline form. The method includes the steps of preparing a solvent of either diethyl ether or a mixture of 2-propanol and hexane, dissolving a product containing the (20R) and (20S) analog to be purified in the solvent, cooling the solvent and dissolved product below ambient temperature for a sufficient amount of time to form a precipitate of crystals, and recovering the crystals.

17 Claims, 2 Drawing Sheets

C26 O25 C25 C27 C24 C21 C23 C20 C22 C12 C18 C28 C30 C11 C13 C17 C9 C14 C16 C8 C15 C6 C7 C4 C5 C3 C10 O3 C1 C2 O1 C29

(56) References Cited

OTHER PUBLICATIONS

Lythgoe et al., "Calciferol and its Relatives. Part 22. A Direct Total Synthesis of Vitamin D2 and Vitamin D3", J. Chem. Soc. Perkin I, 1978, 590-595.
Lythgoe, "Synthetic Approaches to Vitamin D and its Relatives", Chem. Soc. Rev., 1983, 9: 449-475.
Paaren et al., "Direct C-1 Hydroxylation of Vitamin D Compounds: Convenient Preparation of 1alpha-Hydroxyvitamin D3,1alpha-Dihydroxyvitamin D3 and 1alpha,Hydroxyvitamin D2", Proc. Natl. Acad. Sci. USA, 1978, 75(5): 2080-2081.
Paaren et al., "Direct C-1 Hydroxylation of Vitamin D3 and Related Compounds", J. Org. Chem., 1980, 45: 3253-3258.
Perlman et al., "Novel Synthesis of 19-Nor-Vitamin D Compounds", Tetrahedron Letters, 1991, 32: 7663-7666.
Nerinckx et al., "An Improved Synthesis of 1Alpha-Hydroxy Vitamin D3", Tetrahedron, 1991, 47(45): 9419-9430.
Sardina et al., "Studies on the Synthesis of Side-Chain Hydroxylated Metabolites of Vitamin D. 2. Stereocontrolled Synthesis of 25-Hydroxyvitamin D2", Journal of Organic Chemistry, 1986, 51: 1264-1269.
Sicinski et al., "New 1alpha,25-Dihydroxy-19-norvitamin D3 Compounds of High Biological Activity: Synthesis and Biological Evaluation of 2-Hydroxymethyl, 2-Methyl, and 2-Methylene Analogs", J. Med. Chem., 1998, 41: 4662-4674.
Sheldrick, "Phase Annealing in SHELX-90: Direct Methods for Larger Structures", Acta Cryst., 1990, A46: 467-473.
Toh et al., "Studies on a Convergent Route to Side-Chain Analogues of Vitamin D:25-Hydroxy-23-oxavitamin D3", Journal of Organic Chemistry, 1983, 48: 1414-1417.
Vanmaele et al., "A Stereocontrolled Partial Synthesis of 1Alpha-Hydroxy Vitamin D3", Tetrahedron Letters, 1982, 23 (9): 995-998.
Vanmaele et al., "1Alpha-Hydroxy Previtamin D3 and its Selective Formation From 1-Keto Previtamin D3", Tetrahedron, 1984, 40(7): 1179-1182.
Vanmaele et al., "An Efficient Synthesis of 1Alpha-25-Dihydroxy Vitamin D3", Tetrahedron, 1985, 41(1): 141-144.
Flores et al., "A 20S Combined with a 22R Configuration Markedly Increases both in Vivo and in Vitro Biological Activity of 1[alpha],25-Dihydroxy-22-methyl-2-methylene-19-norvitamin D3", Journal of Medical Chemistry, 2012, 55: 4352-4366.
International Search Report and Written Opinion, PCT International Application No. PCT/US2013/038883, mailed Aug. 13, 2013.

* cited by examiner

CRYSTALLIZATION OF (20R) AND (20S) ANALOGS OF 2-METHYLENE-19-NOR-24-DIMETHYL-1α,25-DIHYDROXYVITAMIN $D_3$

CROSS-REFERENCE TO RELATED PATENT APPLICATIONS

The present application claims the benefit under 35 U.S.C. §119(e) to U.S. Provisional Patent Application No. 61/652,965, filed on May 30, 2012, the content of which is incorporated herein by reference in its entirety.

STATEMENT REGARDING FEDERALLY SPONSORED RESEARCH OR DEVELOPMENT

This invention was made with government support under DK047814 awarded by the National Institutes of Health. The government has certain rights in the invention.

BACKGROUND

The field of the present invention relates to purification of organic compounds, and more particularly to the purification of (20S) and (20R) analogs of 2-Methylene-19-nor-22-dimethyl-1α,25-dihydroxyvitamin $D_3$ (referred to herein as "MET-1" and "MET-2" respectively) by preparing them in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of the 5,6-trans geometric isomer of vitamin D is performed, followed by $SeO_2$/NMO oxidation and photochemical irradiation, (see Andrews et al., *J. Org. Chem.* 51, 1635 (1986); Calverley et al., *Tetrahedron* 43, 4609 (1987); Choudry et al., *J. Org. Chem.* 58, 1496 (1993)), the final 1α-hydroxyvitamin D product can be contaminated with 1β-hydroxy—as well as 5,6-trans isomers. If the method consists of C-1 allylic oxidation of the 4-phenyl-1,2,4-triazoline-3,5-dione adduct of the pre-vitamin D compound, followed by cycloreversion of the modified adduct under basic conditions, (see Nevinckx et al., *Tetrahedron* 47, 9419 (1991); Vanmaele et al., *Tetrahedron* 41, 141 (1985) and 40, 1179 (1994); Vanmaele et al., *Tetrahedron Lett.* 23. 995 (1982)), one can expect that the desired 1α-hydroxyvitamin can be contaminated with the pre-vitamin 5(10), 6,8-triene and 1β-hydroxy isomer. One of the most useful C-1 hydroxylation methods, of very broad scope and numerous applications, is the experimentally simple procedure elaborated by Paaren et al., *J. Org. Chem.* 45, 3253 (1980) and *Proc. Natl. Acad. Sci. U.S.A.* 75, 2080 (1978). This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1α-hydroxy compounds. Taking into account this synthetic path, it is reasonable to assume that the final product can be contaminated with 1α-hydroxy epimer, 5,6-trans isomer and the previtamin D form. 1α-hydroxyvitamin $D_4$ is another undesirable contaminant found in 1α-hydroxyvitamin D compounds synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 0.1-0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of some water-elimination reactions. The driving force for these reactions is the allylic (1α-) and homoallylic (3β-) position of the hydroxy groups. The presence of such above-mentioned oxidation and elimination products can be easily detected by thin-layer chromatography.

Usually, all 1α-hydroxylatation procedures require at least one chromatographic purification. However, even chromatographically purified 1α-hydroxyvitamin D compounds, although showing consistent spectroscopic data that suggests homogeneity, do not meet the purity criteria required for therapeutic agents that can be orally, parenterally or transdermally administered. Therefore, it is evident that a suitable method of purification of the 1α-hydroxylated vitamin D compounds MET-1 and MET-2 is required.

SUMMARY

Disclosed are methods of purifying MET-1 and MET-2 by means of crystallization to obtain MET-1 and MET-2 in crystalline form. The solvent plays an important role in the crystallization process, and is typically an individual liquid substance or a suitable mixture of different liquids. For crystallizing MET-1 and MET-2, the most appropriate solvent and/or solvent system is characterized by the following factors:

(1) low toxicity;

(2) low boiling point;

(3) significant dependence of solubility properties with regard to temperature (condition necessary for providing satisfactory crystallization yield); and (4) relatively low cost.

Interestingly, hexane, so frequently used for crystallization purposes, was found less suitable as the sole solvent for crystallization of MET-1 and MET-2. However, it was found that diethyl ether ($Et_2O$) was most useful for the crystallization of MET-1, and a mixture of 2-propanol and hexane, was most useful for the crystallization of MET-2. In particular, it was determined that a mixture of about 10% to about 20% 2-propanol with about 90% to about 80% hexane by volume, (preferably 15% 2-propanol with about 85% hexane by volume) performed well. The diethyl ether solvent and the 2-propanol/hexane solvent mixture both were easy to remove by evaporation or other well-known methods. In all cases the crystallization process occurred easily and efficiently. The precipitated crystals were sufficiently large to assure their recovery by filtration or other means, and thus were suitable for x-ray analysis.

Accordingly, disclosed is a compound having the formula:

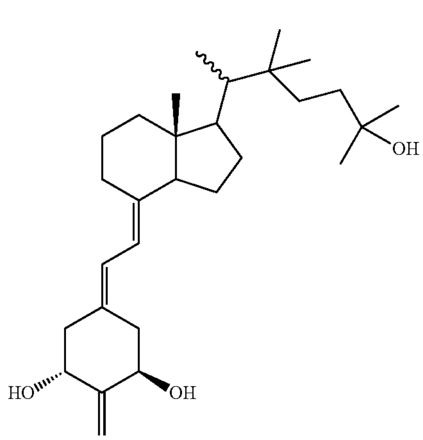 [SMILES: C=C1[C@H](O)CC(=C/C=C2\CCC[C@@]3(C)C2CCC3C(C)C(C)(C)CCC(C)(C)O)C[C@H]1O]

in crystalline form, where the wavy line at carbon 20 indicates the methyl group attached to carbon 20 may be in its R or S orientation. More specifically, disclosed are (20S)-2-methylene-19-nor-22-dimethyl-1α,25-dihydroxyvitamin $D_3$ in crystalline form (otherwise referred to as "MET-1"), and (20R)-2-methylene-19-nor-22-dimethyl-1α,25-dihydroxyvitamin $D_3$ in crystalline form, (otherwise referred to as "MET-2").

DETAILED DESCRIPTION

Figure 1:
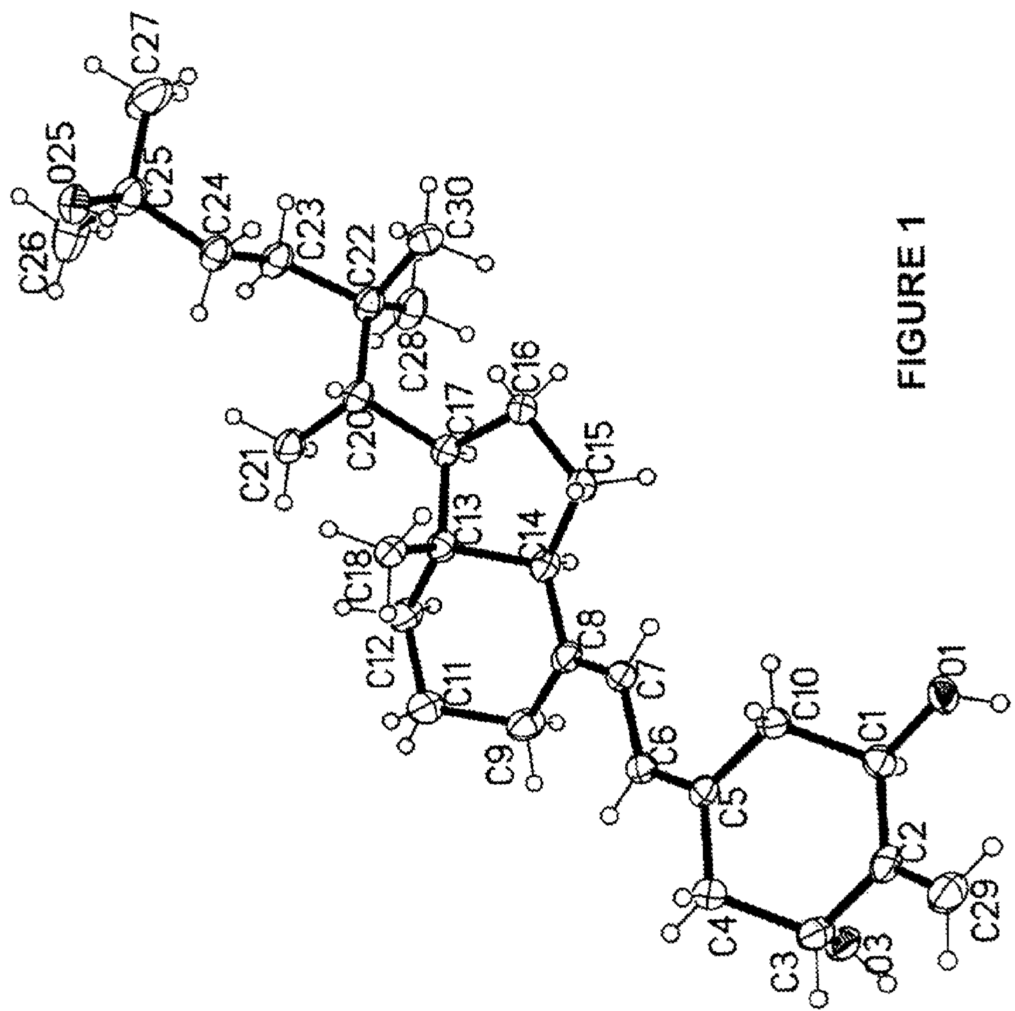
FIG. 1 is an illustration of the three dimensional molecular structure for MET-1 as defined by the atomic positional parameters discovered and set forth herein.

Disclosed herein is (20S)-2-methylene-19-nor-22-dimethyl-1α,25-dihydroxyvitamin D3 (MET-1) in crystalline form, which is a pharmacologically important compound characterized by the formula I shown below:

I

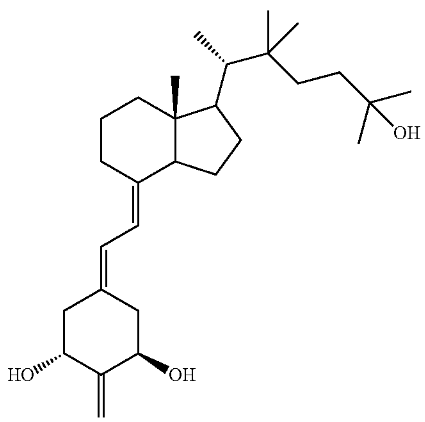

Also disclosed herein is (20R)-2-methylene-19-nor-22-dimethyl-1α,25-dihydroxyvitamin D3 (MET-2) in crystalline form, which also is a pharmacologically important compound characterized by the formula II shown below:

II

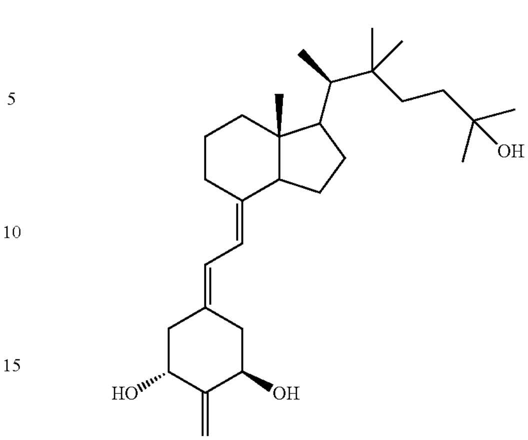

Also disclosed herein are methods of purifying MET-1 and MET-2. The purification technique typically involves obtaining the MET-1 and MET-2 products in crystalline form by utilizing a crystallization procedure wherein the material to be purified is dissolved using as the solvent either diethyl ether ($Et_2O$) as the sole solvent to obtain MET-1, or a mixture comprised of 2-propanol and hexane to obtain MET-2. In particular, it was determined that a mixture of about 10% to about 20% 2-propanol (v/v) with about 90% to about 80% hexane (v/v) performed well. Preferably the mixture comprises about 15% 2-propanol (v/v) and about 85% hexane (v/v). Thereafter, the solvent can be removed by evaporation, with or without vacuum, or other means as is well-known in the art. Alternatively, the resultant crystals may be filtered from the mother liquor. The technique can be used to purify a wide range of final products containing MET-1 and MET-2 obtained from any known synthesis thereof, and in varying concentrations, which may range from microgram amounts to kilogram amounts. As is well known to those skilled in this art, the amount of solvent utilized should be modulated according to the amount of MET-1 and MET-2 to be purified.

EXAMPLES

The following examples are illustrative and should not be interpreted as limiting the claimed subject matter.

The usefulness and advantages of the present crystallization procedure is shown in the following specific Examples. After crystallization, the precipitated material was observed under a microscope to confirm its crystalline form. Yields of crystals were relatively high and the obtained crystals showed a relatively sharp melting point of 99° C. (MET-1) and 154° C. (MET-2).

The described crystallization process of the synthetic MET-1 and MET-2 products represents a valuable purification method, which can remove most side products derived from the synthetic path. Such impurity may result from contamination of starting raw materials. The crystallization process occurred easily and efficiently. The precipitated crystals were sufficiently large to assure their recovery by filtration, or other means, and thus were suitable for x-ray analysis.

Example 1

Crystallization of (20S)-2-methylene-19-nor-22-dimethyl-1α,25 dihydroxyvitamin $D_3$ (MET-1)

Crystallization from Diethyl Ether.

(20 S2-methylene-19-nor-22-dimethyl-1α,25-dihydroxyvitamin $D_3$ (MET-1) (14.3 mg), was dissolved in boiling diethyl ether (3 mL) and left at room temperature for about 1 hour, then it was kept in a refrigerator for about 48 hours. The precipitated crystals were filtered off, washed with a small volume of a cold (0° C.) diethyl ether, and dried to give crystalline material.

Experimental.

A colorless prism-shaped crystal of dimensions 0.25×0.34×0.55 mm was selected for structural analysis. Intensity data were collected using a Bruker AXS Platinum 135 CCD detector controlled with the PROTEUM software suite (Bruker AXS Inc., Madison, Wis.). The x-ray source was CuK radiation (1.54178 Å) from a Rigaku RU200 x-ray generator equipped with Montel optics, operated at 50 kV and 90 mA. The x-ray data were processed with SAINT version 7.06A (Broker AXS Inc.) and internally scaled with SADABS version 2005/1 (Broker AXS Inc.). The sample was mounted on a glass fiber using vacuum grease and cooled to 100 K. The intensity data were measured as a series of phi and omega oscillation frames each of 1° for 10-25 sec/frame. The detector was operated in 1024×1024 mode and was positioned 4.5 cm from the sample. Cell parameters were determined from a non-linear least squares fit of 3265 peaks in the range of 4.0<theta<55°. The data were merged to form a set of 4624 independent data with R(int)=0.0287.

The monoclinic space group P2(1) was determined by systematic absences and statistical tests and verified by subsequent refinement. The structure was solved by direct methods and refined by full-matrix least-squares methods on $F^2$, (a) G. M. Sheldrick (1994), SHELXTL Version 5 Reference Manual, Broker AXS Inc.; (b) *International Tables for Crystallography, Vol. C*, Kluwer: Boston (1995). Hydrogen atom positions were determined from difference peaks and ultimately refined by a riding model with idealized geometry. Non-hydrogen atoms were refined with anisotropic displacement parameters. In addition to the molecule of MET-1, one molecule of diethyl ether was present in the asymmetric unit of the crystalline lattice. A total of 334 parameters were refined against 1 restraint and 4624 data to give wR2=0.0995 and S=1.040 for weights of $w=1/[s^2(F^2)\ (0.0675P)^2]$, where $P=[F_o^2+2F_c^2]/3$. The final R(F) was 0.0332 for the 4624 observed data. The largest shift/s.u. was 0.001 in the final refinement cycle and the final difference map had maxima and minima of 0.238 and −0.201 e/Å$^3$, respectively. The absolute structure was determined by refinement of the Flack parameter, H. D. Flack, *Acta Cryst. A*, vol. 39, 876-881 (1983).

The three dimensional structure of MET-1 as defined by the following physical data and atomic positional parameters described and calculated herein (Tables 1-8) is illustrated in FIG. 1.

Example 2

Crystallization of (20R)-2-methylene-19-nor-22-dimethyl-1α,25-dihydroxyvitamin $D_3$ (MET-2)

Crystallization from 2-propanol/hexane.

(20R)-2-methylene-19-nor-22-dimethyl-1α,25-dihydroxyvitamin $D_3$ (22.7 mg), was suspended in hexane (4 mL) and then 2-propanol was added dropwise to the suspension. The mixture was heated in a water bath to dissolve the vitamin, then was left at room temperature for about 1 hour, and finally was kept in a refrigerator for about 48 hours. The precipitated crystals were filtered off, washed with a small volume of a cold (0° C.) 2-propanol/hexane (3:1) mixture, and dried to give crystalline material. It should be noted that an excess of 2-propanol should be avoided to get the point of saturation, i.e. only about 1 mole or less of 2-propanol should be added.

Experimental.

A colorless prism-shaped crystal of dimensions 0.36×0.17×0.03 mm was selected for structural analysis. Intensity data were collected using a Bruker AXS Platinum 135 CCD detector controlled with the PROTEUM software suite (Bruker AXS Inc., Madison, Wis.). The x-ray source was CuK radiation (1.54178 Å) from a Rigaku RU200 x-ray generator equipped with Montel optics, operated at 50 kV and 90 mA. The x-ray data were processed with SAINT version 7.06A (Bruker AXS Inc.) and internally scaled with SADABS version 2005/1 (Bruker AXS Inc.). The sample was mounted in a quartz capillary tube and data collected at 298 K. The intensity data were measured as a series of phi and omega oscillation frames each of 1° for 20-40 sec/frame. The detector was operated in 1024×1024 mode and was positioned 4.5 cm from the sample. Cell parameters were determined from a non-linear least squares fit of 9999 peaks in the range of 2.51<theta<58.69°. The data were merged to form a set of 3985 independent data with R(int)=0.0473.

The monoclinic space group C2 was determined by systematic absences and statistical tests and verified by subsequent refinement. The structure was solved by direct methods and refined by full-matrix least-squares methods on $F^2$, (a) G. M. Sheldrick (1994), SHELXTL Version 5 Reference Manual, Bruker AXS Inc.; (b) *International Tables for Crystallography, Vol. C*, Kluwer: Boston (1995). Hydrogen atom positions were determined from difference peaks and ultimately refined by a riding model with idealized geometry. Non-hydrogen atoms were refined with anisotropic displacement parameters. In addition to the molecule of MET-2, one molecule of isopropanol was present in the asymmetric unit of the crystalline lattice. A total of 325 parameters were refined against 1 restraint and 3985 data to give wR2=0.1600 and S=1.073 for weights of $w=1/[s^2(F^2)+(0.1033P)^2]$, where $P=[F_o^2+2F_c^2]/3$. The final R(F) was 0.0844 for the 3985 observed data. The largest shift/s.u. was 0.001 in the final refinement cycle and the final difference map had maxima and minima of 0.140 and −0.190 e/Å$^3$, respectively. The absolute structure was determined by refinement of the Flack parameter, H. D. Flack, *Acta Cryst. A*, vol. 39, 876-881 (1983).

Figure 2:
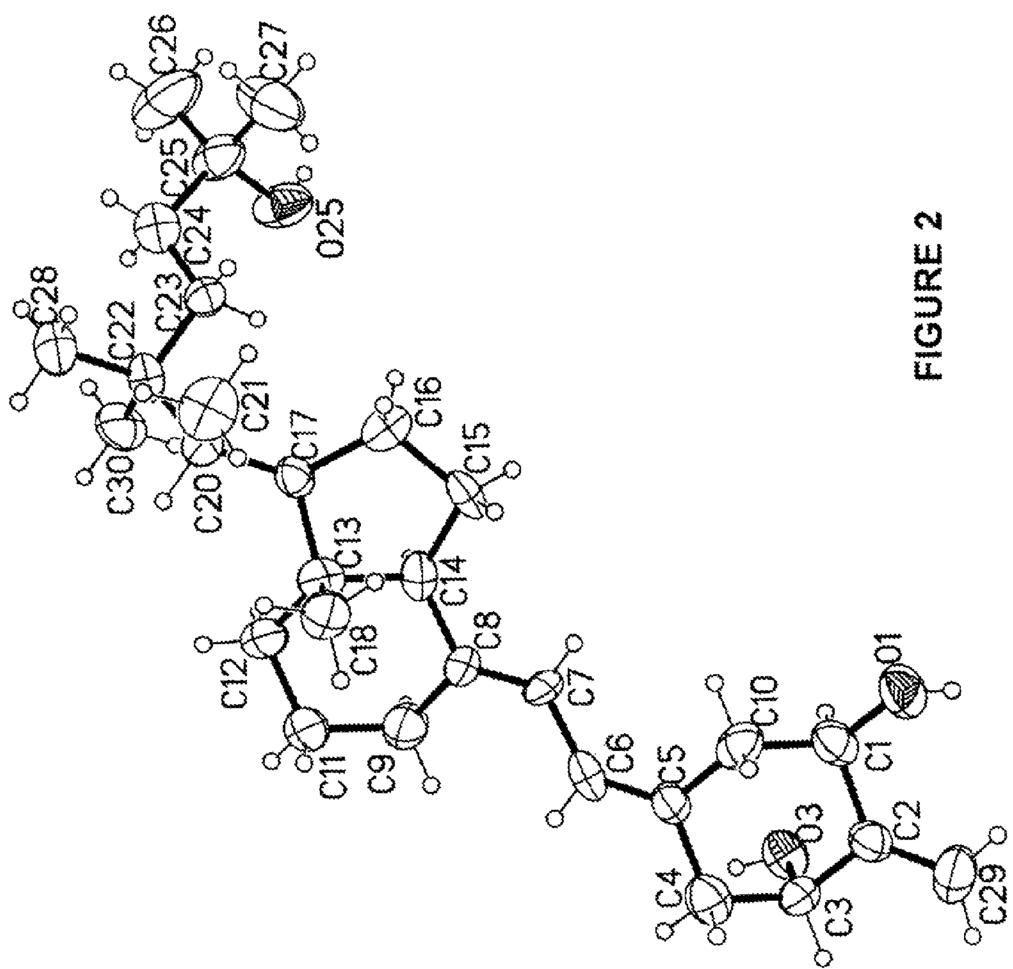
FIG. 2 is an illustration of the three dimensional molecular structure for MET-2 as defined by the atomic positional parameters discovered and set forth herein.

The three dimensional structure of MET-2 as defined by the following physical data and atomic positional parameters described and calculated herein (Tables 9-16) is illustrated in FIG. 2.

TABLE 1

Crystal data and structure refinement for MET-1.

| | | |
|---|---|---|
| Empirical formula | C33H58O4 | |
| Formula weight | 518.79 | |
| Temperature | 100(1) K | |
| Wavelength | 1.54178 Å | |
| Crystal system, space group | Monoclinic, P2(1) | |
| Unit cell dimensions | a = 7.5780(15)Å | α = 90° |
| | b = 14.792(3) Å | β = 102.22(3)° |
| | c = 14.481(3) Å | γ = 90° |
| Volume | 1586.5(6) Å$^3$ | |
| Z | 2 | |
| Calculated density | 1.086 Mg/m$^3$ | |
| Absorption coefficient | 0.532 mm$^{-1}$ | |
| F(000) | 576 | |
| Crystal size | 0.25 × 0.34 × 0.55 mm | |
| Theta range for data collection | 3.12 to 63.06° | |
| Limiting indices | −8 <= h <= 8, −17 <= k <= 16, 0 <= l <= 16 | |

TABLE 1-continued

| Crystal data and structure refinement for MET-1. | |
|---|---|
| Reflections collected/unique | 7564/4624 [R(int) = 0.0287] |
| Data/restraints/parameters | 4624/1/334 |
| Goodness-of-fit on $F^2$ | 1.040 |
| Final R indices [I > 2□(I)] | R1 = 0.0330, wR2 = 0.0955 |
| R indices (all data) | R1 = 0.0332, wR2 = 0.0959 |
| Absolute structure parameter | −0.01(15) |
| Largest diff. peak and hole | 0.238 and −0.201 e/Å$^3$ |

TABLE 2

Atomic coordinates (Å$^2$ × $10^4$) and equivalent isotropic displacement parameters (Å$^2$ × $10^3$) for MET-1 U(eq) is defined as one third of the trace of the orthogonalized Uij tensor.

| | x | y | z | U(eq) |
|---|---|---|---|---|
| O(3) | −1435(2) | 3847(1) | 11389(1) | 26(1) |
| O(100) | −1576(2) | 5643(1) | 10959(1) | 32(1) |
| O(25) | −4404(2) | −6333(1) | 12194(1) | 27(1) |
| O(1) | 3382(2) | 2361(1) | 11284(1) | 28(1) |
| C(5) | −1471(2) | 1831(1) | 11117(1) | 22(1) |
| C(13) | −3621(2) | −1411(1) | 13186(1) | 22(1) |
| C(6) | −2465(2) | 1391(1) | 11638(1) | 23(1) |
| C(20) | −3217(2) | −3144(1) | 13759(1) | 23(1) |
| C(14) | −2234(2) | −617(1) | 13380(1) | 23(1) |
| C(2) | 716(2) | 3237(1) | 10539(1) | 24(1) |
| C(22) | −2071(2) | −3839(1) | 14466(1) | 27(1) |
| C(7) | −1882(2) | 618(1) | 12255(1) | 23(1) |
| C(4) | −2313(2) | 2542(1) | 10414(1) | 24(1) |
| C(8) | −2850(2) | 217(1) | 12818(1) | 24(1) |
| C(23) | −2980(2) | −4791(1) | 14332(1) | 28(1) |
| C(3) | −1246(2) | 3423(1) | 10520(1) | 25(1) |
| C(21) | −5206(2) | −3181(1) | 13826(1) | 30(1) |
| C(24) | −3359(2) | −5161(1) | 13320(1) | 27(1) |
| C(1) | 1560(2) | 2561(1) | 11290(1) | 23(1) |
| C(10) | 502(2) | 1670(1) | 11152(1) | 22(1) |
| C(15) | −456(2) | −1058(1) | 13319(1) | 26(1) |
| C(12) | −5392(2) | −1054(1) | 13413(1) | 28(1) |
| C(9) | −4631(2) | 555(1) | 12982(1) | 29(1) |
| C(17) | −2546(2) | −2145(1) | 13863(1) | 22(1) |
| C(101) | −280(3) | 6264(1) | 11455(1) | 40(1) |
| C(29) | 1591(3) | 3619(1) | 9940(1) | 31(1) |
| C(30) | −125(2) | −3978(1) | 14326(1) | 31(1) |
| C(16) | −580(2) | −2012(1) | 13723(1) | 25(1) |
| C(18) | −3930(2) | −1723(1) | 12152(1) | 24(1) |
| C(11) | −6056(2) | −197(1) | 12851(1) | 29(1) |
| C(25) | −3972(3) | −6149(1) | 13189(1) | 31(1) |
| C(201) | −3380(3) | 6000(1) | 10736(1) | 38(1) |
| C(27) | −2516(4) | −6804(2) | 13656(2) | 65(1) |
| C(28) | −1941(3) | −3553(1) | 15498(1) | 35(1) |
| C(202) | −4591(3) | 5306(2) | 10178(2) | 48(1) |
| C(26) | −5726(3) | −6301(2) | 13518(1) | 50(1) |
| C(102) | 1535(3) | 5832(2) | 11596(2) | 54(1) |

TABLE 3

Bond lengths [Å] for MET-1.

| | | | |
|---|---|---|---|
| O(3)—C(3) | 1.440(2) | O(100)—C(101) | 1.423(2) |
| O(100)—C(201) | 1.437(2) | O(25)—C(25) | 1.435(2) |
| O(1)—C(1) | 1.4140(19) | C(5)—C(6) | 1.342(2) |
| C(5)—C(10) | 1.504(2) | C(5)—C(4) | 1.508(2) |
| C(13)—C(18) | 1.537(2) | C(13)—C(12) | 1.542(2) |
| C(13)—C(14) | 1.561(2) | C(13)—C(17) | 1.570(2) |
| C(6)—C(7) | 1.461(2) | C(20)—C(21) | 1.532(2) |
| C(20)—C(17) | 1.559(2) | C(20)—C(22) | 1.575(2) |
| C(14)—C(8) | 1.497(2) | C(14)—C(15) | 1.516(2) |
| C(2)—C(29) | 1.325(2) | C(2)—C(3) | 1.506(2) |
| C(2)—C(1) | 1.516(2) | C(22)—C(28) | 1.536(2) |
| C(22)—C(30) | 1.544(2) | C(22)—C(23) | 1.562(2) |
| C(7)—C(8) | 1.345(2) | C(4)—C(3) | 1.524(2) |
| C(8)—C(9) | 1.505(2) | C(23)—C(24) | 1.533(2) |
| C(24)—C(25) | 1.532(2) | C(1)—C(10) | 1.533(2) |

TABLE 3-continued

Bond lengths [Å] for MET-1.

| | | | |
|---|---|---|---|
| C(15)—C(16) | 1.539(2) | C(12)—C(11) | 1.532(2) |
| C(9)—C(11) | 1.534(2) | C(17)—C(16) | 1.558(2) |
| C(101)—C(102) | 1.491(3) | C(25)—C(27) | 1.516(3) |
| C(25)—C(26) | 1.521(3) | C(201)—C(202) | 1.495(3) |

TABLE 4

| Bond angles [°] for MET-1. | |
|---|---|
| C(101)—O(100)—C(201) | 113.47(15) |
| C(6)—C(5)—C(10) | 125.17(14) |
| C(6)—C(5)—C(4) | 120.68(15) |
| C(10)—C(5)—C(4) | 114.14(13) |
| C(18)—C(13)—C(12) | 110.52(13) |
| C(18)—C(13)—C(14) | 111.04(12) |
| C(12)—C(13)—C(14) | 106.64(13) |
| C(18)—C(13)—C(17) | 110.70(13) |
| C(12)—C(13)—C(17) | 117.67(13) |
| C(14)—C(13)—C(17) | 99.63(12) |
| C(5)—C(6)—C(7) | 126.18(15) |
| C(21)—C(20)—C(17) | 109.44(13) |
| C(21)—C(20)—C(22) | 110.45(13) |
| C(17)—C(20)—C(22) | 115.60(13) |
| C(8)—C(14)—C(15) | 120.05(14) |
| C(8)—C(14)—C(13) | 113.68(13) |
| C(15)—C(14)—C(13) | 103.82(13) |
| C(29)—C(2)—C(3) | 122.61(16) |
| C(29)—C(2)—C(1) | 123.89(16) |
| C(3)—C(2)—C(1) | 113.49(13) |
| C(28)—C(22)—C(30) | 107.31(14) |
| C(28)—C(22)—C(23) | 107.77(13) |
| C(30)—C(22)—C(23) | 105.76(14) |
| C(28)—C(22)—C(20) | 111.43(14) |
| C(30)—C(22)—C(20) | 114.34(13) |
| C(23)—C(22)—C(20) | 109.89(13) |
| C(8)—C(7)—C(6) | 125.67(15) |
| C(5)—C(4)—C(3) | 112.89(14) |
| C(7)—C(8)—C(14) | 123.11(15) |
| C(7)—C(8)—C(9) | 124.84(15) |
| C(14)—C(8)—C(9) | 112.04(14) |
| C(24)—C(23)—C(22) | 115.43(13) |
| O(3)—C(3)—C(2) | 110.16(13) |
| O(3)—C(3)—C(4) | 108.15(12) |
| C(2)—C(3)—C(4) | 110.21(13) |
| C(25)—C(24)—C(23) | 116.71(14) |
| O(1)—C(1)—C(2) | 113.40(13) |
| O(1)—C(1)—C(10) | 107.71(12) |
| C(2)—C(1)—C(10) | 110.12(13) |
| C(5)—C(10)—C(1) | 110.88(13) |
| C(14)—C(15)—C(16) | 104.17(13) |
| C(11)—C(12)—C(13) | 111.93(13) |
| C(8)—C(9)—C(11) | 111.72(14) |
| C(20)—C(17)—C(16) | 114.06(13) |
| C(20)—C(17)—C(13) | 118.64(13) |
| C(16)—C(17)—C(13) | 102.46(12) |
| O(100)—C(101)—C(102) | 108.10(16) |
| C(15)—C(16)—C(17) | 107.60(13) |
| C(12)—C(11)—C(9) | 113.01(14) |
| O(25)—C(25)—C(27) | 108.39(16) |
| O(25)—C(25)—C(26) | 104.95(14) |
| C(27)—C(25)—C(26) | 111.5(2) |
| O(25)—C(25)—C(24) | 107.75(13) |
| C(27)—C(25)—C(24) | 112.43(16) |
| C(26)—C(25)—C(24) | 111.40(16) |
| O(100)—C(201)—C(202) | 108.38(16) |

TABLE 5

Anisotropic displacement parameters ($Å^2 \times 10^3$) for MET-1. The anisotropic displacement factor exponent takes the form: $-2\pi^2[h^2a*^2U_{11} + \ldots + 2hka*b*U_{12}$.

| | $U_{11}$ | $U_{22}$ | $U_{33}$ | $U_{23}$ | $U_{13}$ | $U_{12}$ |
|---|---|---|---|---|---|---|
| O(3) | 26(1) | 17(1) | 37(1) | 0(1) | 10(1) | 1(1) |
| O(100) | 40(1) | 19(1) | 37(1) | 2(1) | 9(1) | 3(1) |
| O(25) | 28(1) | 28(1) | 26(1) | −2(1) | 6(1) | −7(1) |
| O(1) | 17(1) | 23(1) | 44(1) | −6(1) | 8(1) | −2(1) |
| C(5) | 21(1) | 16(1) | 27(1) | −4(1) | 4(1) | −2(1) |
| C(13) | 23(1) | 21(1) | 24(1) | 0(1) | 8(1) | −2(1) |
| C(6) | 19(1) | 18(1) | 32(1) | −2(1) | 6(1) | 0(1) |
| C(20) | 28(1) | 20(1) | 23(1) | 1(1) | 8(1) | −5(1) |
| C(14) | 25(1) | 20(1) | 25(1) | −2(1) | 6(1) | −3(1) |
| C(2) | 27(1) | 17(1) | 29(1) | −5(1) | 7(1) | −4(1) |
| C(22) | 33(1) | 22(1) | 24(1) | 3(1) | 4(1) | −6(1) |
| C(7) | 19(1) | 18(1) | 30(1) | −2(1) | 6(1) | −1(1) |
| C(4) | 21(1) | 21(1) | 30(1) | 1(1) | 3(1) | 1(1) |
| C(8) | 25(1) | 18(1) | 29(1) | −3(1) | 6(1) | −1(1) |
| C(23) | 38(1) | 21(1) | 25(1) | 3(1) | 6(1) | −5(1) |
| C(3) | 29(1) | 20(1) | 28(1) | 4(1) | 7(1) | 2(1) |
| C(21) | 29(1) | 23(1) | 39(1) | 2(1) | 11(1) | −6(1) |
| C(24) | 34(1) | 22(1) | 24(1) | 2(1) | 6(1) | −4(1) |
| C(1) | 20(1) | 22(1) | 29(1) | −2(1) | 8(1) | 0(1) |
| C(10) | 21(1) | 20(1) | 27(1) | 2(1) | 7(1) | 2(1) |
| C(15) | 20(1) | 23(1) | 33(1) | 3(1) | 4(1) | −3(1) |
| C(12) | 29(1) | 24(1) | 34(1) | 1(1) | 14(1) | −2(1) |
| C(9) | 30(1) | 24(1) | 38(1) | 2(1) | 16(1) | 4(1) |
| C(17) | 25(1) | 20(1) | 20(1) | 0(1) | 6(1) | −4(1) |
| C(101) | 65(1) | 25(1) | 29(1) | −1(1) | 10(1) | −9(1) |
| C(29) | 33(1) | 24(1) | 39(1) | 3(1) | 13(1) | −2(1) |
| C(30) | 33(1) | 23(1) | 36(1) | 9(1) | 1(1) | −1(1) |
| C(16) | 22(1) | 21(1) | 29(1) | 2(1) | 1(1) | −2(1) |
| C(18) | 25(1) | 20(1) | 26(1) | 0(1) | 4(1) | −1(1) |
| C(11) | 25(1) | 28(1) | 39(1) | 3(1) | 16(1) | 3(1) |
| C(25) | 42(1) | 23(1) | 25(1) | 2(1) | 1(1) | −6(1) |
| C(201) | 48(1) | 28(1) | 44(1) | 11(1) | 22(1) | 15(1) |
| C(27) | 93(2) | 25(1) | 55(1) | 0(1) | −32(1) | 8(1) |
| C(28) | 49(1) | 29(1) | 26(1) | 2(1) | 4(1) | −12(1) |
| C(202) | 35(1) | 46(1) | 58(1) | 14(1) | 2(1) | 13(1) |
| C(26) | 75(2) | 50(1) | 31(1) | −7(1) | 23(1) | −34(1) |
| C(102) | 54(1) | 41(1) | 57(1) | 2(1) | −10(1) | −14(1) |

TABLE 6

Hydrogen coordinates ($Å^2 \times 10^4$) and isotropic displacement parameters ($Å^2 \times 10^3$) for MET-1.

| | | | | |
|---|---|---|---|---|
| H(3A) | −1246 | 4391 | 11360 | 40 |
| H(25A) | −3854 | −5981 | 11920 | 41 |
| H(1A) | 4033 | 2763 | 11559 | 41 |
| H(6A) | −3636 | 1598 | 11604 | 27 |
| H(20F) | −3157 | −3339 | 13120 | 28 |
| H(14A) | −2129 | −451 | 14045 | 28 |
| H(7A) | −743 | 383 | 12258 | 27 |
| H(4A) | −3529 | 2665 | 10495 | 29 |
| H(4B) | −2398 | 2310 | 9780 | 29 |
| H(23A) | −2206 | −5217 | 14739 | 34 |
| H(23B) | −4112 | −4761 | 14542 | 34 |
| H(3B) | −1735 | 3823 | 9988 | 30 |
| H(21A) | −5886 | −2755 | 13392 | 45 |
| H(21B) | −5311 | −3033 | 14458 | 45 |
| H(21C) | −5668 | −3779 | 13671 | 45 |
| H(24A) | −4282 | −4787 | 12936 | 40 |
| H(24B) | −2270 | −5094 | 13075 | 40 |
| H(1B) | 1502 | 2809 | 11910 | 28 |
| H(10F) | 646 | 1386 | 10569 | 27 |
| H(10G) | 983 | 1262 | 11669 | 27 |
| H(15A) | 554 | −727 | 13690 | 31 |
| H(15B) | −316 | −1087 | 12669 | 31 |
| H(12A) | −6313 | −1518 | 13267 | 33 |
| H(12B) | −5200 | −923 | 14084 | 33 |
| H(9A) | −5058 | 1043 | 12544 | 35 |
| H(9B) | −4464 | 795 | 13618 | 35 |
| H(17A) | −2559 | −1957 | 14511 | 26 |
| H(10A) | −557 | 6412 | 12061 | 48 |

TABLE 6-continued

Hydrogen coordinates ($Å^2 \times 10^4$) and isotropic displacement parameters ($Å^2 \times 10^3$) for MET-1.

| | | | | |
|---|---|---|---|---|
| H(10B) | −298 | 6817 | 11094 | 48 |
| H(29A) | 994 | 4020 | 9485 | 37 |
| H(29B) | 2803 | 3486 | 9975 | 37 |
| H(30A) | 485 | −4408 | 14780 | 47 |
| H(30B) | 509 | −3412 | 14411 | 47 |
| H(30C) | −160 | −4201 | 13700 | 47 |
| H(16A) | 271 | −2075 | 14322 | 30 |
| H(16B) | −299 | −2463 | 13290 | 30 |
| H(18A) | −4591 | −1267 | 11750 | 35 |
| H(18B) | −4607 | −2276 | 12077 | 35 |
| H(18C) | −2787 | −1820 | 11983 | 35 |
| H(11A) | −7122 | 26 | 13048 | 35 |
| H(11B) | −6400 | −349 | 12186 | 35 |
| H(20A) | −3409 | 6551 | 10371 | 46 |
| H(20B) | −3782 | 6139 | 11313 | 46 |
| H(27A) | −1429 | −6689 | 13435 | 97 |
| H(27B) | −2910 | −7412 | 13498 | 97 |
| H(27C) | −2288 | −6726 | 14328 | 97 |
| H(28A) | −1234 | −3988 | 15910 | 53 |
| H(28B) | −3130 | −3522 | 15627 | 53 |
| H(28C) | −1377 | −2970 | 15600 | 53 |
| H(20C) | −5804 | 5534 | 10022 | 71 |
| H(20D) | −4560 | 4764 | 10546 | 71 |
| H(20E) | −4187 | 5175 | 9607 | 71 |
| H(26A) | −6077 | −6924 | 13425 | 75 |
| H(26B) | −6654 | −5923 | 13161 | 75 |
| H(26C) | −5554 | −6154 | 14177 | 75 |
| H(10C) | 2433 | 6241 | 11927 | 81 |
| H(10D) | 1798 | 5688 | 10993 | 81 |
| H(10E) | 1544 | 5288 | 11958 | |

TABLE 7

Torsion angles [deg] for MET-1.

| | |
|---|---|
| C(10)—C(5)—C(6)—C(7) | −6.9(3) |
| C(4)—C(5)—C(6)—C(7) | 172.04(14) |
| C(18)—C(13)—C(14)—C(8) | 62.64(17) |
| C(12)—C(13)—C(14)—C(8) | −57.81(17) |
| C(17)—C(13)—C(14)—C(8) | 179.34(12) |
| C(18)—C(13)—C(14)—C(15) | −69.49(16) |
| C(12)—C(13)—C(14)—C(15) | 170.05(13) |
| C(17)—C(13)—C(14)—C(15) | 47.21(14) |
| C(21)—C(20)—C(22)—C(28) | −68.60(17) |
| C(17)—C(20)—C(22)—C(28) | 56.32(18) |
| C(21)—C(20)—C(22)—C(30) | 169.50(14) |
| C(17)—C(20)—C(22)—C(30) | −65.58(18) |
| C(21)—C(20)—C(22)—C(23) | 50.77(17) |
| C(17)—C(20)—C(22)—C(23) | 175.69(13) |
| C(5)—C(6)—C(7)—C(8) | 175.69(16) |
| C(6)—C(5)—C(4)—C(3) | 129.93(16) |
| C(10)—C(5)—C(4)—C(3) | −50.98(18) |
| C(6)—C(7)—C(8)—C(14) | 175.28(14) |
| C(6)—C(7)—C(8)—C(9) | −6.4(3) |
| C(15)—C(14)—C(8)—C(7) | −0.9(2) |
| C(13)—C(14)—C(8)—C(7) | −124.65(17) |
| C(15)—C(14)—C(8)—C(9) | −179.41(15) |
| C(13)—C(14)—C(8)—C(9) | 56.87(17) |
| C(28)—C(22)—C(23)—C(24) | 175.53(15) |
| C(30)—C(22)—C(23)—C(24) | −69.94(18) |
| C(20)—C(22)—C(23)—C(24) | 53.94(19) |
| C(29)—C(2)—C(3)—O(3) | −116.79(17) |
| C(1)—C(2)—C(3)—O(3) | 64.38(16) |
| C(29)—C(2)—C(3)—C(4) | 123.95(17) |
| C(1)—C(2)—C(3)—C(4) | −54.88(17) |
| C(5)—C(4)—C(3)—O(3) | −69.91(16) |
| C(5)—C(4)—C(3)—C(2) | 50.56(17) |
| C(22)—C(23)—C(24)—C(25) | 170.72(15) |
| C(29)—C(2)—C(1)—O(1) | −1.0(2) |
| C(3)—C(2)—C(1)—O(1) | 177.82(12) |
| C(29)—C(2)—C(1)—C(10) | −121.76(17) |
| C(3)—C(2)—C(1)—C(10) | 57.05(16) |
| C(6)—C(5)—C(10)—C(1) | −128.78(16) |
| C(4)—C(5)—C(10)—C(1) | 52.18(17) |

TABLE 7-continued

| Torsion angles [deg] for MET-1. | |
|---|---|
| O(1)—C(1)—C(10)—C(5) | −178.02(11) |
| C(2)—C(1)—C(10)—C(5) | −53.90(16) |
| C(8)—C(14)—C(15)—C(16) | −163.10(13) |
| C(13)—C(14)—C(15)—C(16) | −34.78(16) |
| C(18)—C(13)—C(12)—C(11) | −65.07(17) |
| C(14)—C(13)—C(12)—C(11) | 55.72(17) |
| C(17)—C(13)—C(12)—C(11) | 166.45(14) |
| C(7)—C(8)—C(9)—C(11) | 130.33(18) |
| C(14)—C(8)—C(9)—C(11) | −51.22(17) |
| C(21)—C(20)—C(17)—C(16) | −175.23(13) |
| C(22)—C(20)—C(17)—C(16) | 59.33(17) |
| C(21)—C(20)—C(17)—C(13) | −54.36(17) |
| C(22)—C(20)—C(17)—C(13) | −179.80(12) |
| C(18)—C(13)—C(17)—C(20) | −50.06(18) |

TABLE 7-continued

| Torsion angles [deg] for MET-1. | |
|---|---|
| C(12)—C(13)—C(17)—C(20) | 78.34(18) |
| C(14)—C(13)—C(17)—C(20) | −167.02(12) |
| C(18)—C(13)—C(17)—C(16) | 76.56(15) |
| C(12)—C(13)—C(17)—C(16) | −155.04(14) |
| C(14)—C(13)—C(17)—C(16) | −40.40(14) |
| C(201)—O(100)—C(101)—C(102) | −177.01(16) |
| C(14)—C(15)—C(16)—C(17) | 8.55(16) |
| C(20)—C(17)—C(16)—C(15) | 150.05(13) |
| C(13)—C(17)—C(16)—C(15) | 20.53(16) |
| C(13)—C(12)—C(11)—C(9) | −54.82(19) |
| C(8)—C(9)—C(11)—C(12) | 50.78(18) |
| C(23)—C(24)—C(25)—O(25) | 175.01(14) |
| C(23)—C(24)—C(25)—C(27) | −65.6(2) |
| C(23)—C(24)—C(25)—C(26) | 60.4(2) |
| C(101)—O(100)—C(201)—C(202) | 177.20(15) |

TABLE 8

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | −16 | 0 | 150 | 149 | 2 | 1 | 2 | 0 | 479 | 489 | 5 | 2 | 15 | 0 | 41 | 44 | 1 | 3 | −9 | 1 | 37 | 37 | 1 | 4 | 1 | 1 | 139 | 136 | 2 |
| 1 | −16 | 0 | 52 | 52 | 1 | 2 | 2 | 0 | 217 | 210 | 2 | 3 | 15 | 0 | 34 | 36 | 1 | 4 | −9 | 1 | 188 | 187 | 3 | 5 | 1 | 1 | 75 | 72 | 1 |
| 2 | −16 | 0 | 77 | 74 | 1 | 3 | 2 | 0 | 118 | 120 | 1 | 4 | 15 | 0 | 95 | 95 | 1 | 5 | −9 | 1 | 192 | 181 | 3 | 6 | 1 | 1 | 131 | 124 | 2 |
| 3 | −16 | 0 | 134 | 137 | 2 | 4 | 2 | 0 | 253 | 245 | 3 | 2 | 16 | 0 | 76 | 74 | 1 | 6 | −9 | 1 | 3 | 6 | 3 | 7 | 1 | 1 | 154 | 157 | 2 |
| 1 | −15 | 0 | 106 | 109 | 1 | 5 | 2 | 0 | 56 | 51 | 1 | 0 | −17 | 1 | 74 | 72 | 1 | −6 | −8 | 1 | 25 | 23 | 1 | 8 | 1 | 1 | 21 | 20 | 1 |
| 2 | −15 | 0 | 44 | 45 | 1 | 6 | 2 | 0 | 195 | 199 | 3 | −3 | −16 | 1 | 41 | 39 | 1 | −5 | −8 | 1 | 142 | 141 | 2 | −8 | 2 | 1 | 47 | 49 | 1 |
| 3 | −15 | 0 | 34 | 36 | 1 | 7 | 2 | 0 | 79 | 74 | 1 | −2 | −16 | 1 | 75 | 77 | 1 | −4 | −8 | 1 | 24 | 21 | 1 | −7 | 2 | 1 | 143 | 145 | 2 |
| 4 | −15 | 0 | 91 | 94 | 1 | 8 | 2 | 0 | 50 | 49 | 1 | −1 | −16 | 1 | 5 | 5 | 4 | −3 | −8 | 1 | 44 | 43 | 1 | −6 | 2 | 1 | 40 | 38 | 1 |
| 0 | −14 | 0 | 137 | 148 | 1 | 1 | 3 | 0 | 141 | 142 | 1 | 0 | −16 | 1 | 51 | 50 | 1 | −2 | −8 | 1 | 66 | 64 | 1 | −5 | 2 | 1 | 46 | 49 | 1 |
| 1 | −14 | 0 | 18 | 16 | 1 | 2 | 3 | 0 | 272 | 281 | 3 | 1 | −16 | 1 | 167 | 170 | 1 | −1 | −8 | 1 | 103 | 98 | 1 | −4 | 2 | 1 | 59 | 51 | 1 |
| 2 | −14 | 0 | 98 | 96 | 1 | 3 | 3 | 0 | 252 | 247 | 3 | 2 | −16 | 1 | 4 | 6 | 4 | 0 | −8 | 1 | 149 | 161 | 3 | −3 | 2 | 1 | 448 | 429 | 5 |
| 3 | −14 | 0 | 110 | 106 | 1 | 4 | 3 | 0 | 55 | 60 | 1 | −4 | −15 | 1 | 112 | 113 | 2 | 1 | −8 | 1 | 187 | 189 | 2 | −2 | 2 | 1 | 146 | 146 | 1 |
| 4 | −14 | 0 | 22 | 21 | 1 | 5 | 3 | 0 | 70 | 68 | 1 | −3 | −15 | 1 | 114 | 109 | 1 | 2 | −8 | 1 | 160 | 151 | 1 | −1 | 2 | 1 | 328 | 333 | 3 |
| 1 | −13 | 0 | 104 | 107 | 1 | 6 | 3 | 0 | 151 | 145 | 2 | −2 | −15 | 1 | 105 | 99 | 1 | 3 | −8 | 1 | 88 | 80 | 1 | 0 | 2 | 1 | 275 | 279 | 4 |
| 2 | −13 | 0 | 74 | 72 | 1 | 7 | 3 | 0 | 72 | 70 | 1 | −1 | −15 | 1 | 63 | 66 | 1 | 4 | −8 | 1 | 203 | 198 | 3 | 1 | 2 | 1 | 372 | 371 | 4 |
| 3 | −13 | 0 | 102 | 95 | 1 | 8 | 3 | 0 | 30 | 33 | 1 | 0 | −15 | 1 | 57 | 53 | 1 | 5 | −8 | 1 | 115 | 116 | 2 | 2 | 2 | 1 | 189 | 195 | 2 |
| 4 | −13 | 0 | 123 | 117 | 2 | 0 | 4 | 0 | 924 | 916 | 22 | 1 | −15 | 1 | 39 | 39 | 1 | 6 | −8 | 1 | 27 | 27 | 1 | 3 | 2 | 1 | 167 | 170 | 2 |
| 5 | −13 | 0 | 41 | 42 | 1 | 1 | 4 | 0 | 319 | 318 | 4 | 2 | −15 | 1 | 72 | 73 | 1 | −4 | −7 | 1 | 268 | 270 | 5 | 4 | 2 | 1 | 66 | 71 | 1 |
| 0 | −12 | 0 | 43 | 42 | 1 | 2 | 4 | 0 | 399 | 410 | 4 | 3 | −15 | 1 | 48 | 46 | 1 | −3 | −7 | 1 | 110 | 109 | 1 | 5 | 2 | 1 | 63 | 65 | 1 |
| 1 | −12 | 0 | 76 | 72 | 1 | 3 | 4 | 0 | 250 | 245 | 3 | −5 | −14 | 1 | 57 | 62 | 1 | −2 | −7 | 1 | 153 | 142 | 1 | 6 | 2 | 1 | 123 | 120 | 2 |
| 2 | −12 | 0 | 67 | 63 | 1 | 4 | 4 | 0 | 87 | 81 | 1 | −4 | −14 | 1 | 66 | 72 | 1 | −1 | −7 | 1 | 391 | 378 | 5 | 7 | 2 | 1 | 130 | 133 | 2 |
| 3 | −12 | 0 | 44 | 40 | 1 | 5 | 4 | 0 | 153 | 154 | 1 | −3 | −14 | 1 | 7 | 10 | 3 | 0 | −7 | 1 | 185 | 171 | 2 | 8 | 2 | 1 | 56 | 50 | 1 |
| 4 | −12 | 0 | 75 | 86 | 1 | 6 | 4 | 0 | 31 | 38 | 1 | −2 | −14 | 1 | 49 | 45 | 1 | 1 | −7 | 1 | 354 | 336 | 4 | −8 | 3 | 1 | 22 | 20 | 1 |
| 5 | −12 | 0 | 79 | 74 | 1 | 7 | 4 | 0 | 69 | 74 | 1 | −1 | −14 | 1 | 63 | 65 | 1 | 2 | −7 | 1 | 236 | 227 | 2 | −7 | 3 | 1 | 101 | 95 | 1 |
| 6 | −12 | 0 | 66 | 61 | 1 | 8 | 4 | 0 | 12 | 18 | 1 | 0 | −14 | 1 | 34 | 35 | 1 | 3 | −7 | 1 | 211 | 209 | 3 | −6 | 3 | 1 | 74 | 74 | 1 |
| 1 | −11 | 0 | 88 | 88 | 1 | 1 | 5 | 0 | 48 | 55 | 1 | 1 | −14 | 1 | 83 | 88 | 1 | −3 | −6 | 1 | 480 | 451 | 5 | −5 | 3 | 1 | 117 | 119 | 1 |
| 2 | −11 | 0 | 105 | 103 | 1 | 2 | 5 | 0 | 241 | 222 | 3 | 2 | −14 | 1 | 31 | 30 | 1 | −2 | −6 | 1 | 598 | 575 | 6 | −4 | 3 | 1 | 251 | 235 | 3 |
| 3 | −11 | 0 | 158 | 162 | 1 | 3 | 5 | 0 | 163 | 165 | 2 | 3 | −14 | 1 | 10 | 8 | 2 | −1 | −6 | 1 | 152 | 146 | 1 | −3 | 3 | 1 | 143 | 128 | 1 |
| 4 | −11 | 0 | 50 | 52 | 1 | 4 | 5 | 0 | 158 | 167 | 1 | 4 | −14 | 1 | 26 | 28 | 1 | 0 | −6 | 1 | 303 | 302 | 4 | −2 | 3 | 1 | 191 | 189 | 2 |
| 5 | −11 | 0 | 133 | 130 | 2 | 5 | 5 | 0 | 89 | 87 | 1 | −5 | −13 | 1 | 125 | 128 | 2 | 1 | −6 | 1 | 562 | 533 | 6 | −1 | 3 | 1 | 406 | 413 | 6 |
| 6 | −11 | 0 | 18 | 22 | 1 | 6 | 5 | 0 | 192 | 193 | 3 | −4 | −13 | 1 | 41 | 41 | 1 | 2 | −6 | 1 | 254 | 234 | 2 | 0 | 3 | 1 | 293 | 280 | 5 |
| 0 | −10 | 0 | 186 | 194 | 1 | 7 | 5 | 0 | 43 | 42 | 1 | −3 | −13 | 1 | 76 | 76 | 1 | −3 | −5 | 1 | 126 | 122 | 3 | 1 | 3 | 1 | 364 | 373 | 4 |
| 1 | −10 | 0 | 65 | 57 | 1 | 8 | 5 | 0 | 35 | 37 | 1 | −2 | −13 | 1 | 57 | 52 | 1 | −2 | −5 | 1 | 54 | 55 | 1 | 2 | 3 | 1 | 242 | 241 | 2 |
| 2 | −10 | 0 | 167 | 171 | 1 | 0 | 6 | 0 | 382 | 366 | 8 | −1 | −13 | 1 | 137 | 144 | 1 | −1 | −5 | 1 | 358 | 351 | 3 | 3 | 3 | 1 | 275 | 287 | 5 |
| 3 | −10 | 0 | 238 | 244 | 1 | 1 | 6 | 0 | 453 | 436 | 8 | 0 | −13 | 1 | 91 | 97 | 1 | 0 | −5 | 1 | 275 | 275 | 2 | 4 | 3 | 1 | 137 | 135 | 1 |
| 4 | −10 | 0 | 158 | 152 | 2 | 3 | 6 | 0 | 312 | 309 | 4 | 1 | −13 | 1 | 193 | 196 | 1 | 1 | −5 | 1 | 58 | 66 | 1 | 5 | 3 | 1 | 36 | 39 | 1 |
| 5 | −10 | 0 | 96 | 90 | 1 | 4 | 6 | 0 | 232 | 222 | 1 | 2 | −13 | 1 | 199 | 205 | 1 | 2 | −5 | 1 | 37 | 36 | 1 | 6 | 3 | 1 | 134 | 135 | 2 |
| 6 | −10 | 0 | 92 | 92 | 1 | 5 | 6 | 0 | 158 | 155 | 1 | 3 | −13 | 1 | 82 | 85 | 1 | −3 | −4 | 1 | 406 | 386 | 10 | 7 | 3 | 1 | 84 | 81 | 1 |
| 1 | −9 | 0 | 185 | 185 | 1 | 6 | 6 | 0 | 170 | 175 | 2 | 4 | −13 | 1 | 29 | 27 | 1 | −2 | −4 | 1 | 198 | 185 | 2 | 8 | 3 | 1 | 45 | 44 | 1 |
| 2 | −9 | 0 | 171 | 177 | 1 | 7 | 6 | 0 | 138 | 133 | 2 | 5 | −13 | 1 | 23 | 21 | 1 | −1 | −4 | 1 | 367 | 368 | 3 | −8 | 4 | 1 | 37 | 38 | 1 |
| 3 | −9 | 0 | 86 | 87 | 1 | 8 | 6 | 0 | 57 | 61 | 1 | −6 | −12 | 1 | 40 | 39 | 1 | 0 | −4 | 1 | 229 | 233 | 1 | −7 | 4 | 1 | 113 | 118 | 2 |
| 4 | −9 | 0 | 185 | 178 | 3 | 1 | 7 | 0 | 256 | 225 | 4 | −5 | −12 | 1 | 80 | 74 | 1 | 1 | −4 | 1 | 508 | 500 | 5 | −6 | 4 | 1 | 116 | 116 | 2 |
| 5 | −9 | 0 | 128 | 130 | 2 | 2 | 7 | 0 | 113 | 122 | 3 | −4 | −12 | 1 | 88 | 92 | 1 | 2 | −4 | 1 | 242 | 228 | 2 | −5 | 4 | 1 | 108 | 109 | 1 |
| 6 | −9 | 0 | 53 | 55 | 1 | 3 | 7 | 0 | 87 | 95 | 1 | −3 | −12 | 1 | 64 | 66 | 1 | −3 | −3 | 1 | 146 | 127 | 3 | −4 | 4 | 1 | 69 | 60 | 1 |
| 0 | −8 | 0 | 262 | 252 | 6 | 4 | 7 | 0 | 119 | 119 | 1 | −2 | −12 | 1 | 170 | 176 | 1 | −2 | −3 | 1 | 189 | 189 | 2 | −3 | 4 | 1 | 402 | 384 | 6 |
| 1 | −8 | 0 | 168 | 164 | 2 | 5 | 7 | 0 | 180 | 184 | 1 | −1 | −12 | 1 | 151 | 147 | 1 | −1 | −3 | 1 | 403 | 412 | 4 | −2 | 4 | 1 | 191 | 185 | 2 |
| 2 | −8 | 0 | 44 | 41 | 1 | 6 | 7 | 0 | 25 | 23 | 1 | 0 | −12 | 1 | 147 | 146 | 1 | 0 | −3 | 1 | 289 | 281 | 2 | −1 | 4 | 1 | 365 | 367 | 4 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 3 | −8 | 0 | 155 | 149 | 1 | 7 | 7 | 0 | 73 | 73 | 1 | 1 | −12 | 1 | 39 | 40 | 1 | 1 | −3 | 1 | 377 | 373 | 3 | 0 | 4 | 1 | 227 | 233 | 4 |
| 4 | −8 | 0 | 232 | 231 | 4 | 0 | 8 | 0 | 267 | 253 | 6 | 2 | −12 | 1 | 125 | 128 | 1 | 2 | −3 | 1 | 240 | 242 | 2 | 1 | 4 | 1 | 504 | 501 | 8 |
| 5 | −8 | 0 | 120 | 115 | 2 | 1 | 8 | 0 | 170 | 164 | 4 | 3 | −12 | 1 | 93 | 94 | 1 | −2 | −2 | 1 | 142 | 145 | 1 | 2 | 4 | 1 | 236 | 228 | 2 |
| 6 | −8 | 0 | 88 | 85 | 1 | 2 | 8 | 0 | 41 | 41 | 1 | 4 | −12 | 1 | 30 | 34 | 1 | −1 | −2 | 1 | 330 | 333 | 3 | 3 | 4 | 1 | 315 | 294 | 4 |
| 1 | −7 | 0 | 254 | 225 | 3 | 3 | 8 | 0 | 154 | 150 | 1 | 5 | −12 | 1 | 40 | 35 | 1 | 0 | −2 | 1 | 274 | 279 | 2 | 4 | 4 | 1 | 235 | 230 | 2 |
| 2 | −7 | 0 | 120 | 123 | 1 | 4 | 8 | 0 | 231 | 231 | 2 | −6 | −11 | 1 | 81 | 84 | 1 | 1 | −2 | 1 | 375 | 372 | 3 | 5 | 4 | 1 | 243 | 242 | 1 |
| 3 | −7 | 0 | 89 | 96 | 1 | 5 | 8 | 0 | 118 | 115 | 1 | −5 | −11 | 1 | 66 | 65 | 1 | 2 | −2 | 1 | 186 | 196 | 4 | 6 | 4 | 1 | 79 | 80 | 1 |
| 0 | −6 | 0 | 346 | 368 | 9 | 6 | 8 | 0 | 87 | 85 | 1 | −4 | −11 | 1 | 36 | 33 | 1 | −8 | −1 | 1 | 23 | 27 | 1 | 7 | 4 | 1 | 48 | 50 | 1 |
| 1 | −6 | 0 | 458 | 436 | 4 | 7 | 8 | 0 | 56 | 57 | 1 | −3 | −11 | 1 | 10 | 12 | 1 | −7 | −1 | 1 | 107 | 107 | 1 | 8 | 4 | 1 | 53 | 57 | 1 |
| 2 | −6 | 0 | 246 | 233 | 2 | 1 | 9 | 0 | 180 | 185 | 3 | −2 | −11 | 1 | 113 | 112 | 1 | −2 | −1 | 1 | 44 | 48 | 1 | −8 | 5 | 1 | 75 | 75 | 1 |
| 3 | −6 | 0 | 318 | 309 | 7 | 2 | 9 | 0 | 171 | 176 | 2 | −1 | −11 | 1 | 122 | 122 | 1 | −1 | −1 | 1 | 228 | 240 | 2 | −7 | 5 | 1 | 131 | 135 | 2 |
| 1 | −5 | 0 | 47 | 53 | 1 | 3 | 9 | 0 | 87 | 88 | 1 | 0 | −11 | 1 | 120 | 110 | 1 | 0 | −1 | 1 | 99 | 95 | 1 | −6 | 5 | 1 | 218 | 238 | 2 |
| 2 | −5 | 0 | 247 | 222 | 2 | 4 | 9 | 0 | 186 | 178 | 2 | 1 | −11 | 1 | 138 | 138 | 1 | 1 | −1 | 1 | 339 | 344 | 3 | −5 | 5 | 1 | 131 | 120 | 1 |
| 3 | −5 | 0 | 168 | 164 | 4 | 5 | 9 | 0 | 129 | 130 | 1 | 2 | −11 | 1 | 268 | 266 | 2 | 2 | −1 | 1 | 364 | 386 | 9 | −4 | 5 | 1 | 106 | 117 | 1 |
| 0 | −4 | 0 | 922 | 916 | 10 | 6 | 9 | 0 | 50 | 55 | 1 | 3 | −11 | 1 | 126 | 119 | 1 | 7 | −1 | 1 | 151 | 157 | 2 | −3 | 5 | 1 | 129 | 121 | 2 |
| 1 | −4 | 0 | 324 | 317 | 3 | 1 | 10 | 0 | 66 | 57 | 1 | 4 | −11 | 1 | 163 | 163 | 2 | −8 | 0 | 1 | 6 | 0 | 3 | −2 | 5 | 1 | 53 | 56 | 1 |
| 2 | −4 | 0 | 405 | 410 | 4 | 2 | 10 | 0 | 168 | 171 | 2 | 5 | −11 | 1 | 35 | 36 | 1 | −7 | 0 | 1 | 63 | 70 | 1 | −1 | 5 | 1 | 357 | 351 | 4 |
| 1 | −3 | 0 | 141 | 141 | 1 | 3 | 10 | 0 | 237 | 243 | 2 | 6 | −11 | 1 | 31 | 32 | 1 | −6 | 0 | 1 | 57 | 60 | 1 | 0 | 5 | 1 | 274 | 276 | 4 |
| 2 | −3 | 0 | 269 | 280 | 2 | 4 | 10 | 0 | 154 | 152 | 1 | −6 | −10 | 1 | 83 | 81 | 1 | −3 | 0 | 1 | 226 | 236 | 3 | 1 | 5 | 1 | 57 | 67 | 1 |
| 0 | −2 | 0 | 115 | 113 | 2 | 5 | 10 | 0 | 96 | 90 | 1 | −5 | −10 | 1 | 166 | 167 | 3 | −2 | 0 | 1 | 5 | 9 | 5 | 2 | 5 | 1 | 38 | 37 | 1 |
| 1 | −2 | 0 | 485 | 488 | 5 | 6 | 10 | 0 | 91 | 93 | 1 | −4 | −10 | 1 | 217 | 215 | 3 | −1 | 0 | 1 | 526 | 532 | 5 | 3 | 5 | 1 | 288 | 270 | 4 |
| 2 | −2 | 0 | 217 | 210 | 5 | 1 | 11 | 0 | 90 | 90 | 1 | −3 | −10 | 1 | 214 | 216 | 1 | 0 | 0 | 1 | 128 | 131 | 1 | 4 | 5 | 1 | 266 | 273 | 2 |
| 1 | −1 | 0 | 460 | 471 | 11 | 2 | 11 | 0 | 105 | 103 | 2 | −2 | −10 | 1 | 169 | 175 | 1 | 1 | 0 | 1 | 1440 | 1454 | 16 | 5 | 5 | 1 | 303 | 307 | 2 |
| 2 | −1 | 0 | 239 | 259 | 6 | 3 | 11 | 0 | 157 | 162 | 2 | −1 | −10 | 1 | 136 | 145 | 1 | 2 | 0 | 1 | 78 | 75 | 1 | 6 | 5 | 1 | 46 | 52 | 1 |
| 7 | −1 | 0 | 120 | 126 | 2 | 4 | 11 | 0 | 50 | 52 | 1 | 0 | −10 | 1 | 287 | 290 | 1 | 3 | 0 | 1 | 393 | 391 | 6 | 7 | 5 | 1 | 92 | 93 | 1 |
| 1 | 0 | 0 | 86 | 93 | 1 | 5 | 11 | 0 | 133 | 130 | 1 | 1 | −10 | 1 | 188 | 180 | 1 | 6 | 0 | 1 | 101 | 102 | 1 | 8 | 5 | 1 | 23 | 28 | 1 |
| 2 | 0 | 0 | 181 | 158 | 2 | 6 | 11 | 0 | 19 | 22 | 1 | 2 | −10 | 1 | 145 | 142 | 1 | 7 | 0 | 1 | 61 | 65 | 1 | −8 | 6 | 1 | 61 | 65 | 1 |
| 3 | 0 | 0 | 173 | 170 | 4 | 3 | 12 | 0 | 44 | 40 | 1 | 3 | −10 | 1 | 91 | 93 | 1 | 8 | 0 | 1 | 57 | 56 | 1 | −7 | 6 | 1 | 27 | 30 | 1 |
| 6 | 0 | 0 | 105 | 106 | 1 | 4 | 12 | 0 | 79 | 86 | 1 | 4 | −10 | 1 | 119 | 109 | 2 | −8 | 1 | 1 | 24 | 27 | 1 | −6 | 6 | 1 | 112 | 110 | 1 |
| 7 | 0 | 0 | 25 | 20 | 1 | 5 | 12 | 0 | 79 | 75 | 1 | 5 | −10 | 1 | 67 | 70 | 1 | −7 | 1 | 1 | 110 | 107 | 1 | −5 | 6 | 1 | 243 | 241 | 3 |
| 8 | 0 | 0 | 30 | 34 | 1 | 6 | 12 | 0 | 65 | 62 | 1 | 6 | −10 | 1 | 42 | 43 | 1 | −6 | 1 | 1 | 63 | 58 | 1 | −4 | 6 | 1 | 77 | 84 | 1 |
| 1 | 1 | 0 | 467 | 471 | 5 | 1 | 13 | 0 | 107 | 107 | 2 | −6 | −9 | 1 | 32 | 35 | 1 | −5 | 1 | 1 | 25 | 23 | 1 | −3 | 6 | 1 | 484 | 451 | 11 |
| 2 | 1 | 0 | 253 | 258 | 2 | 2 | 13 | 0 | 77 | 73 | 1 | −5 | −9 | 1 | 111 | 105 | 2 | −4 | 1 | 1 | 311 | 301 | 5 | −2 | 6 | 1 | 552 | 575 | 15 |
| 3 | 1 | 0 | 275 | 267 | 5 | 3 | 13 | 0 | 102 | 95 | 1 | −4 | −9 | 1 | 22 | 25 | 1 | −3 | 1 | 1 | 570 | 528 | 6 | −1 | 6 | 1 | 151 | 146 | 2 |
| 4 | 1 | 0 | 406 | 383 | 7 | 4 | 13 | 0 | 125 | 117 | 1 | −3 | −9 | 1 | 123 | 121 | 1 | −2 | 1 | 1 | 46 | 49 | 1 | 0 | 6 | 1 | 309 | 301 | 5 |
| 5 | 1 | 0 | 126 | 127 | 2 | 5 | 13 | 0 | 41 | 42 | 1 | −2 | −9 | 1 | 98 | 101 | 1 | −1 | 1 | 1 | 230 | 240 | 2 | 1 | 6 | 1 | 560 | 533 | 9 |
| 6 | 1 | 0 | 218 | 223 | 3 | 1 | 14 | 0 | 21 | 17 | 2 | −1 | −9 | 1 | 28 | 17 | 1 | 0 | 1 | 1 | 95 | 94 | 1 | 2 | 6 | 1 | 243 | 234 | 6 |
| 7 | 1 | 0 | 121 | 126 | 2 | 2 | 14 | 0 | 100 | 96 | 2 | 0 | −9 | 1 | 349 | 341 | 2 | 1 | 1 | 1 | 325 | 343 | 6 | 3 | 6 | 1 | 44 | 56 | 1 |
| 8 | 1 | 0 | 26 | 24 | 1 | 3 | 14 | 0 | 113 | 106 | 1 | 1 | −9 | 1 | 96 | 94 | 1 | 2 | 1 | 1 | 372 | 386 | 4 | 4 | 6 | 1 | 178 | 179 | 1 |
| 0 | 2 | 0 | 115 | 112 | 3 | 4 | 14 | 0 | 25 | 21 | 1 | 2 | −9 | 1 | 59 | 51 | 1 | 3 | 1 | 1 | 248 | 249 | 3 | 5 | 6 | 1 | 100 | 100 | 1 |
| 6 | 6 | 1 | 178 | 184 | 3 | −3 | 14 | 1 | 11 | 9 | 2 | −7 | −9 | 2 | 46 | 48 | 1 | 3 | 0 | 2 | 62 | 71 | 1 | −7 | 6 | 2 | 29 | 26 | 1 |
| 7 | 6 | 1 | 61 | 60 | 1 | −2 | 14 | 1 | 49 | 45 | 1 | −6 | −9 | 2 | 62 | 62 | 1 | 6 | 0 | 2 | 88 | 96 | 1 | −6 | 6 | 2 | 107 | 103 | 1 |
| −7 | 7 | 1 | 13 | 13 | 1 | 1 | 14 | 1 | 86 | 88 | 2 | −5 | −9 | 2 | 30 | 26 | 1 | 7 | 0 | 2 | 77 | 80 | 1 | −5 | 6 | 2 | 99 | 101 | 1 |
| −6 | 7 | 1 | 80 | 84 | 1 | 2 | 14 | 1 | 33 | 30 | 1 | −4 | −9 | 2 | 210 | 206 | 3 | 8 | 0 | 2 | 25 | 23 | 1 | −4 | 6 | 2 | 232 | 229 | 1 |
| −5 | 7 | 1 | 233 | 226 | 2 | 3 | 14 | 1 | 10 | 9 | 2 | −3 | −9 | 2 | 100 | 97 | 1 | −8 | 1 | 2 | 15 | 15 | 1 | −3 | 6 | 2 | 247 | 241 | 6 |
| −4 | 7 | 1 | 275 | 271 | 2 | 4 | 14 | 1 | 29 | 29 | 1 | −2 | −9 | 2 | 136 | 142 | 1 | −7 | 1 | 2 | 152 | 155 | 2 | −2 | 6 | 2 | 380 | 388 | 10 |
| −3 | 7 | 1 | 109 | 109 | 1 | −4 | 15 | 1 | 116 | 113 | 2 | −1 | −9 | 2 | 156 | 157 | 1 | −6 | 1 | 2 | 106 | 102 | 1 | −1 | 6 | 2 | 213 | 187 | 3 |
| −2 | 7 | 1 | 148 | 142 | 4 | −3 | 15 | 1 | 117 | 109 | 1 | 0 | −9 | 2 | 97 | 107 | 1 | −5 | 1 | 2 | 133 | 137 | 2 | 0 | 6 | 2 | 193 | 179 | 4 |
| −1 | 7 | 1 | 393 | 379 | 6 | −2 | 15 | 1 | 104 | 99 | 1 | 1 | −9 | 2 | 165 | 164 | 1 | −4 | 1 | 2 | 163 | 167 | 2 | 1 | 6 | 2 | 273 | 253 | 5 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | 7 | 1 | 189 | 170 | 3 | 2 | 15 | 1 | 73 | 74 | 1 | 2 | −9 | 2 | 273 | 274 | 2 | −3 | 1 | 2 | 497 | 473 | 5 | 3 | 6 | 2 | 130 | 136 | 1 |
| 1 | 7 | 1 | 350 | 336 | 9 | 3 | 15 | 1 | 49 | 46 | 1 | 3 | −9 | 2 | 61 | 61 | 1 | −2 | 1 | 2 | 212 | 218 | 2 | 4 | 6 | 2 | 263 | 274 | 2 |
| 2 | 7 | 1 | 234 | 227 | 6 | −3 | 16 | 1 | 42 | 39 | 1 | 4 | −9 | 2 | 174 | 169 | 3 | −1 | 1 | 2 | 664 | 676 | 7 | 5 | 6 | 2 | 107 | 98 | 1 |
| 3 | 7 | 1 | 212 | 208 | 2 | −2 | 16 | 1 | 75 | 77 | 1 | 5 | −9 | 2 | 111 | 109 | 2 | 0 | 1 | 2 | 1028 | 1060 | 13 | 6 | 6 | 2 | 71 | 75 | 1 |
| 4 | 7 | 1 | 109 | 108 | 1 | 2 | 16 | 1 | 9 | 6 | 2 | 6 | −9 | 2 | 57 | 54 | 1 | 1 | 1 | 2 | 470 | 471 | 5 | 7 | 6 | 2 | 27 | 33 | 1 |
| 5 | 7 | 1 | 119 | 122 | 1 | −3 | −16 | 2 | 5 | 2 | 5 | −6 | −8 | 2 | 55 | 56 | 1 | 2 | 1 | 2 | 101 | 101 | 1 | −7 | 7 | 2 | 80 | 80 | 1 |
| 6 | 7 | 1 | 87 | 89 | 1 | −2 | −16 | 2 | 101 | 95 | 1 | −5 | −8 | 2 | 211 | 206 | 3 | 3 | 1 | 2 | 115 | 109 | 1 | −6 | 7 | 2 | 102 | 97 | 1 |
| 7 | 7 | 1 | 23 | 22 | 1 | −1 | −16 | 2 | 96 | 93 | 1 | −4 | −8 | 2 | 61 | 65 | 1 | 4 | 1 | 2 | 96 | 103 | 1 | −5 | 7 | 2 | 136 | 141 | 1 |
| −7 | 8 | 1 | 30 | 28 | 1 | 0 | −16 | 2 | 59 | 57 | 1 | −3 | −8 | 2 | 122 | 111 | 1 | 5 | 1 | 2 | 64 | 65 | 1 | −4 | 7 | 2 | 131 | 128 | 1 |
| −6 | 8 | 1 | 25 | 23 | 1 | 1 | −16 | 2 | 39 | 37 | 1 | −2 | −8 | 2 | 181 | 189 | 1 | 6 | 1 | 2 | 23 | 24 | 1 | −3 | 7 | 2 | 133 | 133 | 1 |
| −5 | 8 | 1 | 140 | 141 | 1 | 2 | −16 | 2 | 29 | 31 | 1 | −1 | −8 | 2 | 227 | 225 | 3 | 7 | 1 | 2 | 46 | 44 | 1 | −2 | 7 | 2 | 132 | 127 | 4 |
| −4 | 8 | 1 | 25 | 20 | 1 | −4 | −15 | 2 | 22 | 26 | 1 | 0 | −8 | 2 | 47 | 44 | 2 | 8 | 1 | 2 | 16 | 19 | 1 | −1 | 7 | 2 | 160 | 135 | 3 |
| −3 | 8 | 1 | 43 | 43 | 1 | −3 | −15 | 2 | 153 | 147 | 1 | 1 | −8 | 2 | 177 | 185 | 1 | −8 | 2 | 2 | 26 | 24 | 1 | 0 | 7 | 2 | 266 | 257 | 6 |
| −2 | 8 | 1 | 67 | 64 | 1 | −2 | −15 | 2 | 75 | 71 | 1 | 2 | −8 | 2 | 154 | 153 | 1 | −7 | 2 | 2 | 28 | 29 | 1 | 1 | 7 | 2 | 56 | 54 | 2 |
| −1 | 8 | 1 | 103 | 99 | 3 | −1 | −15 | 2 | 109 | 111 | 1 | 3 | −8 | 2 | 140 | 133 | 2 | −6 | 2 | 2 | 168 | 167 | 2 | 3 | 7 | 2 | 216 | 211 | 1 |
| 0 | 8 | 1 | 152 | 161 | 3 | 0 | −15 | 2 | 119 | 118 | 1 | 4 | −8 | 2 | 127 | 131 | 2 | −5 | 2 | 2 | 132 | 134 | 1 | 4 | 7 | 2 | 184 | 197 | 1 |
| 1 | 8 | 1 | 182 | 190 | 5 | 1 | −15 | 2 | 55 | 53 | 1 | 5 | −8 | 2 | 249 | 255 | 4 | −4 | 2 | 2 | 230 | 224 | 2 | 5 | 7 | 2 | 37 | 32 | 1 |
| 2 | 8 | 1 | 165 | 151 | 2 | 2 | −15 | 2 | 27 | 28 | 1 | 6 | −8 | 2 | 56 | 53 | 1 | −3 | 2 | 2 | 365 | 363 | 4 | 6 | 7 | 2 | 93 | 91 | 1 |
| 3 | 8 | 1 | 86 | 79 | 1 | 3 | −15 | 2 | 94 | 97 | 1 | −6 | −7 | 2 | 100 | 97 | 1 | −2 | 2 | 2 | 142 | 150 | 1 | 7 | 7 | 2 | 64 | 63 | 1 |
| 4 | 8 | 1 | 200 | 197 | 1 | −5 | −14 | 2 | 64 | 62 | 1 | −5 | −7 | 2 | 135 | 141 | 2 | −1 | 2 | 2 | 642 | 650 | 8 | −7 | 8 | 2 | 54 | 49 | 1 |
| 5 | 8 | 1 | 116 | 116 | 1 | −4 | −14 | 2 | 115 | 114 | 1 | −4 | −7 | 2 | 131 | 127 | 2 | 0 | 2 | 2 | 581 | 595 | 10 | −6 | 8 | 2 | 55 | 56 | 1 |
| 6 | 8 | 1 | 29 | 28 | 1 | −3 | −14 | 2 | 50 | 50 | 1 | −3 | −7 | 2 | 133 | 133 | 1 | 1 | 2 | 2 | 169 | 179 | 1 | −5 | 8 | 2 | 209 | 206 | 2 |
| 7 | 8 | 1 | 42 | 44 | 1 | −2 | −14 | 2 | 70 | 71 | 1 | −2 | −7 | 2 | 133 | 127 | 1 | 2 | 2 | 2 | 349 | 336 | 4 | −4 | 8 | 2 | 63 | 65 | 1 |
| −6 | 9 | 1 | 32 | 35 | 1 | −1 | −14 | 2 | 48 | 52 | 1 | −1 | −7 | 2 | 160 | 135 | 2 | 3 | 2 | 2 | 120 | 113 | 1 | −3 | 8 | 2 | 122 | 111 | 1 |
| −5 | 9 | 1 | 111 | 105 | 1 | 0 | −14 | 2 | 52 | 50 | 1 | 0 | −7 | 2 | 252 | 255 | 3 | 4 | 2 | 2 | 102 | 107 | 1 | −2 | 8 | 2 | 181 | 189 | 2 |
| −4 | 9 | 1 | 23 | 24 | 1 | 1 | −14 | 2 | 111 | 116 | 1 | 1 | −7 | 2 | 58 | 54 | 1 | 5 | 2 | 2 | 195 | 196 | 3 | −1 | 8 | 2 | 225 | 224 | 6 |
| −3 | 9 | 1 | 121 | 121 | 1 | 2 | −14 | 2 | 45 | 47 | 1 | 2 | −7 | 2 | 149 | 153 | 1 | 6 | 2 | 2 | 141 | 139 | 2 | 0 | 8 | 2 | 49 | 44 | 3 |
| −2 | 9 | 1 | 96 | 101 | 1 | 3 | −14 | 2 | 23 | 23 | 1 | 3 | −7 | 2 | 214 | 211 | 4 | 7 | 2 | 2 | 79 | 80 | 1 | 2 | 8 | 2 | 146 | 154 | 2 |
| −1 | 9 | 1 | 28 | 17 | 1 | 4 | −14 | 2 | 46 | 44 | 1 | 4 | −7 | 2 | 182 | 198 | 3 | 8 | 2 | 2 | 27 | 24 | 1 | 3 | 8 | 2 | 142 | 133 | 1 |
| 0 | 9 | 1 | 357 | 341 | 6 | −5 | −13 | 2 | 25 | 21 | 1 | −3 | −6 | 2 | 247 | 241 | 3 | −8 | 3 | 2 | 43 | 42 | 1 | 4 | 8 | 2 | 128 | 131 | 1 |
| 1 | 9 | 1 | 99 | 95 | 1 | −4 | −13 | 2 | 169 | 174 | 3 | −2 | −6 | 2 | 399 | 389 | 4 | −7 | 3 | 2 | 130 | 126 | 2 | 5 | 8 | 2 | 253 | 255 | 3 |
| 2 | 9 | 1 | 56 | 51 | 1 | −3 | −13 | 2 | 87 | 89 | 1 | −1 | −6 | 2 | 207 | 187 | 2 | −6 | 3 | 2 | 181 | 168 | 3 | 6 | 8 | 2 | 56 | 53 | 1 |
| 3 | 9 | 1 | 38 | 37 | 1 | −2 | −13 | 2 | 234 | 237 | 1 | 0 | −6 | 2 | 187 | 178 | 2 | −5 | 3 | 2 | 166 | 161 | 1 | 7 | 8 | 2 | 67 | 68 | 1 |
| 4 | 9 | 1 | 187 | 187 | 2 | −1 | −13 | 2 | 94 | 92 | 1 | 1 | −6 | 2 | 277 | 253 | 3 | −4 | 3 | 2 | 425 | 403 | 5 | −6 | 9 | 2 | 61 | 63 | 1 |
| 5 | 9 | 1 | 187 | 181 | 1 | 0 | −13 | 2 | 97 | 100 | 1 | 2 | −6 | 2 | 303 | 285 | 3 | −3 | 3 | 2 | 152 | 139 | 1 | −5 | 9 | 2 | 34 | 27 | 1 |
| 6 | 9 | 1 | 8 | 6 | 1 | 1 | −13 | 2 | 83 | 89 | 1 | −3 | −5 | 2 | 127 | 125 | 1 | −2 | 3 | 2 | 176 | 184 | 1 | −4 | 9 | 2 | 210 | 206 | 2 |
| −6 | 10 | 1 | 86 | 81 | 1 | 2 | −13 | 2 | 129 | 131 | 1 | −2 | −5 | 2 | 73 | 68 | 1 | −1 | 3 | 2 | 512 | 520 | 6 | −3 | 9 | 2 | 100 | 97 | 1 |
| −5 | 10 | 1 | 165 | 166 | 2 | 3 | −13 | 2 | 111 | 110 | 1 | −1 | −5 | 2 | 83 | 81 | 1 | 0 | 3 | 2 | 456 | 458 | 7 | −2 | 9 | 2 | 137 | 143 | 2 |
| −4 | 10 | 1 | 212 | 214 | 2 | 4 | −13 | 2 | 116 | 112 | 2 | 0 | −5 | 2 | 512 | 508 | 5 | 1 | 3 | 2 | 676 | 684 | 7 | −1 | 9 | 2 | 153 | 157 | 2 |
| −3 | 10 | 1 | 212 | 216 | 2 | 5 | −13 | 2 | 76 | 75 | 1 | 1 | −5 | 2 | 219 | 202 | 2 | 2 | 3 | 2 | 160 | 155 | 2 | 0 | 9 | 2 | 101 | 108 | 2 |
| −2 | 10 | 1 | 172 | 175 | 2 | −6 | −12 | 2 | 81 | 76 | 1 | 2 | −5 | 2 | 298 | 295 | 3 | 3 | 3 | 2 | 132 | 114 | 1 | 2 | 9 | 2 | 274 | 274 | 4 |
| −1 | 10 | 1 | 134 | 145 | 2 | −5 | −12 | 2 | 50 | 50 | 1 | −3 | −4 | 2 | 143 | 136 | 2 | 4 | 3 | 2 | 117 | 125 | 1 | 3 | 9 | 2 | 61 | 61 | 1 |
| 1 | 10 | 1 | 186 | 180 | 3 | −4 | −12 | 2 | 93 | 90 | 1 | −2 | −4 | 2 | 186 | 180 | 2 | 5 | 3 | 2 | 83 | 90 | 1 | 4 | 9 | 2 | 170 | 169 | 1 |
| 3 | 10 | 1 | 91 | 93 | 1 | −3 | −12 | 2 | 128 | 127 | 1 | −1 | −4 | 2 | 314 | 312 | 2 | 6 | 3 | 2 | 175 | 174 | 3 | 5 | 9 | 2 | 106 | 109 | 1 |
| 4 | 10 | 1 | 111 | 109 | 1 | −2 | −12 | 2 | 112 | 118 | 1 | 0 | −4 | 2 | 99 | 102 | 1 | 7 | 3 | 2 | 77 | 78 | 1 | 6 | 9 | 2 | 56 | 53 | 1 |
| 5 | 10 | 1 | 68 | 69 | 1 | −1 | −12 | 2 | 83 | 79 | 1 | 1 | −4 | 2 | 795 | 786 | 8 | 8 | 3 | 2 | 22 | 21 | 1 | −6 | 10 | 2 | 97 | 97 | 1 |
| 6 | 10 | 1 | 42 | 43 | 1 | 0 | −12 | 2 | 161 | 166 | 1 | 2 | −4 | 2 | 299 | 283 | 3 | −8 | 4 | 2 | 39 | 36 | 1 | −5 | 10 | 2 | 120 | 117 | 2 |
| −6 | 11 | 1 | 81 | 84 | 1 | 1 | −12 | 2 | 116 | 112 | 1 | −3 | −3 | 2 | 146 | 137 | 2 | −7 | 4 | 2 | 51 | 62 | 1 | −4 | 10 | 2 | 153 | 163 | 2 |
| −5 | 11 | 1 | 67 | 65 | 1 | 2 | −12 | 2 | 23 | 28 | 1 | −2 | −3 | 2 | 176 | 184 | 1 | −6 | 4 | 2 | 279 | 284 | 4 | −3 | 10 | 2 | 31 | 35 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −4 | 11 | 1 | 33 | 32 | 1 | 3 | −12 | 2 | 92 | 101 | 1 | −1 | −3 | 2 | 514 | 520 | 5 | −5 | 4 | 2 | 113 | 114 | 1 | −2 | 10 | 2 | 182 | 185 | 2 |
| −3 | 11 | 1 | 12 | 11 | 2 | 4 | −12 | 2 | 70 | 68 | 1 | 0 | −3 | 2 | 453 | 459 | 4 | −4 | 4 | 2 | 99 | 98 | 1 | −1 | 10 | 2 | 20 | 14 | 2 |
| −2 | 11 | 1 | 116 | 111 | 2 | 5 | −12 | 2 | 53 | 52 | 1 | 1 | −3 | 2 | 693 | 684 | 7 | −3 | 4 | 2 | 142 | 136 | 2 | 0 | 10 | 2 | 146 | 148 | 4 |
| −1 | 11 | 1 | 118 | 121 | 2 | −6 | −11 | 2 | 77 | 74 | 1 | 2 | −3 | 2 | 159 | 156 | 1 | −2 | 4 | 2 | 191 | 181 | 2 | 1 | 10 | 2 | 203 | 208 | 3 |
| 2 | 11 | 1 | 263 | 266 | 5 | −5 | −11 | 2 | 52 | 52 | 1 | −3 | −2 | 2 | 348 | 364 | 4 | −1 | 4 | 2 | 315 | 313 | 4 | 2 | 10 | 2 | 53 | 51 | 1 |
| 3 | 11 | 1 | 128 | 118 | 1 | −4 | −11 | 2 | 20 | 28 | 1 | −2 | −2 | 2 | 144 | 150 | 1 | 0 | 4 | 2 | 99 | 103 | 2 | 3 | 10 | 2 | 93 | 91 | 1 |
| 4 | 11 | 1 | 159 | 163 | 1 | −3 | −11 | 2 | 143 | 140 | 1 | −1 | −2 | 2 | 644 | 650 | 6 | 1 | 4 | 2 | 774 | 787 | 19 | 4 | 10 | 2 | 63 | 65 | 1 |
| 5 | 11 | 1 | 35 | 35 | 1 | −2 | −11 | 2 | 159 | 158 | 1 | 0 | −2 | 2 | 579 | 595 | 5 | 3 | 4 | 2 | 65 | 68 | 1 | 5 | 10 | 2 | 93 | 94 | 1 |
| 6 | 11 | 1 | 33 | 33 | 1 | −1 | −11 | 2 | 107 | 107 | 1 | 1 | −2 | 2 | 170 | 180 | 1 | 4 | 4 | 2 | 96 | 97 | 1 | 6 | 10 | 2 | 73 | 75 | 1 |
| −6 | 12 | 1 | 38 | 38 | 1 | 0 | −11 | 2 | 161 | 161 | 1 | 2 | −2 | 2 | 344 | 337 | 3 | 5 | 4 | 2 | 175 | 172 | 1 | −6 | 11 | 2 | 75 | 73 | 1 |
| −5 | 12 | 1 | 78 | 74 | 1 | 1 | −11 | 2 | 176 | 181 | 1 | −8 | −1 | 2 | 14 | 15 | 1 | 6 | 4 | 2 | 74 | 80 | 1 | −5 | 11 | 2 | 52 | 52 | 1 |
| −4 | 12 | 1 | 92 | 92 | 1 | 2 | −11 | 2 | 91 | 94 | 1 | −7 | −1 | 2 | 149 | 155 | 2 | 7 | 4 | 2 | 54 | 58 | 1 | −4 | 11 | 2 | 26 | 29 | 1 |
| −3 | 12 | 1 | 64 | 65 | 1 | 3 | −11 | 2 | 101 | 106 | 1 | −3 | −1 | 2 | 483 | 472 | 5 | 8 | 4 | 2 | 14 | 17 | 1 | −3 | 11 | 2 | 140 | 140 | 2 |
| −2 | 12 | 1 | 169 | 176 | 3 | 4 | −11 | 2 | 54 | 58 | 1 | −2 | −1 | 2 | 215 | 218 | 2 | −8 | 5 | 2 | 63 | 61 | 1 | −2 | 11 | 2 | 161 | 159 | 2 |
| −1 | 12 | 1 | 151 | 147 | 3 | 5 | −11 | 2 | 10 | 12 | 2 | −1 | −1 | 2 | 666 | 677 | 7 | −7 | 5 | 2 | 52 | 56 | 1 | −1 | 11 | 2 | 105 | 106 | 2 |
| 1 | 12 | 1 | 37 | 40 | 1 | 6 | −11 | 2 | 40 | 46 | 1 | 0 | −1 | 2 | 1043 | 1061 | 10 | −6 | 5 | 2 | 316 | 313 | 3 | 1 | 11 | 2 | 178 | 181 | 2 |
| 2 | 12 | 1 | 123 | 127 | 2 | −6 | −10 | 2 | 97 | 96 | 1 | 1 | −1 | 2 | 471 | 472 | 4 | −5 | 5 | 2 | 248 | 251 | 1 | 2 | 11 | 2 | 90 | 94 | 1 |
| 3 | 12 | 1 | 92 | 95 | 1 | −5 | −10 | 2 | 118 | 117 | 2 | 2 | −1 | 2 | 99 | 101 | 1 | −4 | 5 | 2 | 70 | 71 | 1 | 3 | 11 | 2 | 104 | 106 | 1 |
| 4 | 12 | 1 | 34 | 35 | 1 | −4 | −10 | 2 | 157 | 162 | 2 | 7 | −1 | 2 | 45 | 44 | 1 | −3 | 5 | 2 | 125 | 127 | 2 | 4 | 11 | 2 | 57 | 58 | 1 |
| 5 | 12 | 1 | 39 | 36 | 1 | −3 | −10 | 2 | 36 | 36 | 1 | −8 | 0 | 2 | 24 | 24 | 1 | −2 | 5 | 2 | 73 | 68 | 2 | 5 | 11 | 2 | 10 | 13 | 2 |
| −5 | 13 | 1 | 129 | 128 | 1 | −2 | −10 | 2 | 181 | 185 | 1 | −7 | 0 | 2 | 49 | 50 | 1 | −1 | 5 | 2 | 83 | 80 | 1 | −6 | 12 | 2 | 81 | 76 | 1 |
| −4 | 13 | 1 | 41 | 41 | 1 | −1 | −10 | 2 | 22 | 15 | 1 | −6 | 0 | 2 | 240 | 262 | 4 | 0 | 5 | 2 | 518 | 509 | 12 | −5 | 12 | 2 | 49 | 49 | 1 |
| −3 | 13 | 1 | 75 | 76 | 1 | 0 | −10 | 2 | 154 | 148 | 1 | −4 | 0 | 2 | 543 | 562 | 10 | 1 | 5 | 2 | 214 | 202 | 2 | −4 | 12 | 2 | 93 | 91 | 1 |
| 1 | 13 | 1 | 191 | 196 | 3 | 1 | −10 | 2 | 208 | 209 | 1 | −3 | 0 | 2 | 456 | 444 | 5 | 3 | 5 | 2 | 247 | 244 | 3 | −3 | 12 | 2 | 128 | 127 | 1 |
| 2 | 13 | 1 | 201 | 205 | 3 | 2 | −10 | 2 | 56 | 51 | 1 | −2 | 0 | 2 | 332 | 332 | 3 | 4 | 5 | 2 | 172 | 181 | 1 | −2 | 12 | 2 | 115 | 117 | 2 |
| 3 | 13 | 1 | 82 | 85 | 1 | 3 | −10 | 2 | 91 | 91 | 1 | −1 | 0 | 2 | 967 | 976 | 10 | 5 | 5 | 2 | 76 | 68 | 1 | −1 | 12 | 2 | 85 | 79 | 2 |
| 4 | 13 | 1 | 26 | 27 | 1 | 4 | −10 | 2 | 63 | 64 | 1 | 0 | 0 | 2 | 198 | 202 | 2 | 6 | 5 | 2 | 84 | 101 | 1 | 1 | 12 | 2 | 116 | 113 | 2 |
| 5 | 13 | 1 | 20 | 20 | 1 | 5 | −10 | 2 | 93 | 93 | 1 | 1 | 0 | 2 | 282 | 287 | 3 | 7 | 5 | 2 | 0 | 4 | 1 | 2 | 12 | 2 | 21 | 27 | 1 |
| −4 | 14 | 1 | 71 | 72 | 1 | 6 | −10 | 2 | 73 | 75 | 1 | 2 | 0 | 2 | 33 | 49 | 1 | −8 | 6 | 2 | 84 | 85 | 1 | 3 | 12 | 2 | 93 | 100 | 1 |
| 4 | 12 | 2 | 70 | 67 | 1 | −5 | −10 | 3 | 147 | 150 | 2 | −2 | −2 | 3 | 513 | 511 | 5 | −3 | 4 | 3 | 169 | 164 | 2 | −2 | 10 | 3 | 79 | 78 | 1 |
| 5 | 12 | 2 | 53 | 52 | 1 | −4 | −10 | 3 | 50 | 55 | 1 | −1 | −2 | 3 | 621 | 628 | 6 | −2 | 4 | 3 | 62 | 70 | 1 | −1 | 10 | 3 | 272 | 279 | 4 |
| −5 | 13 | 2 | 25 | 22 | 1 | −3 | −10 | 3 | 183 | 194 | 1 | 0 | −2 | 3 | 994 | 1008 | 9 | −1 | 4 | 3 | 130 | 134 | 1 | 0 | 10 | 3 | 122 | 135 | 2 |
| −4 | 13 | 2 | 175 | 174 | 2 | −2 | −10 | 3 | 80 | 79 | 1 | 1 | −2 | 3 | 465 | 462 | 4 | 0 | 4 | 3 | 176 | 179 | 3 | 1 | 10 | 3 | 138 | 132 | 2 |
| −3 | 13 | 2 | 86 | 89 | 1 | −1 | −10 | 3 | 271 | 279 | 1 | 2 | −2 | 3 | 160 | 168 | 1 | 1 | 4 | 3 | 196 | 194 | 2 | 2 | 10 | 3 | 32 | 29 | 1 |
| −2 | 13 | 2 | 236 | 236 | 4 | 0 | −10 | 3 | 126 | 135 | 1 | 7 | −2 | 3 | 92 | 97 | 1 | 2 | 4 | 3 | 328 | 305 | 5 | 3 | 10 | 3 | 222 | 221 | 2 |
| −1 | 13 | 2 | 94 | 92 | 2 | 1 | −10 | 3 | 138 | 132 | 1 | −8 | −1 | 3 | 10 | 17 | 1 | 3 | 4 | 3 | 55 | 53 | 1 | 4 | 10 | 3 | 69 | 65 | 1 |
| 1 | 13 | 2 | 80 | 89 | 2 | 2 | −10 | 3 | 29 | 29 | 1 | −7 | −1 | 3 | 16 | 9 | 1 | 4 | 4 | 3 | 100 | 109 | 1 | 5 | 10 | 3 | 52 | 53 | 1 |
| 2 | 13 | 2 | 127 | 131 | 1 | 3 | −10 | 3 | 222 | 221 | 4 | −6 | −1 | 3 | 67 | 65 | 1 | 5 | 4 | 3 | 185 | 186 | 1 | −6 | 11 | 3 | 69 | 68 | 1 |
| 3 | 13 | 2 | 114 | 111 | 1 | 4 | −10 | 3 | 68 | 64 | 1 | −4 | −1 | 3 | 327 | 314 | 6 | 6 | 4 | 3 | 59 | 58 | 1 | −5 | 11 | 3 | 111 | 114 | 2 |
| 4 | 13 | 2 | 118 | 111 | 1 | 5 | −10 | 3 | 54 | 52 | 1 | −3 | −1 | 3 | 60 | 62 | 1 | 7 | 4 | 3 | 37 | 33 | 1 | −4 | 11 | 3 | 99 | 106 | 1 |
| 5 | 13 | 2 | 76 | 75 | 1 | 6 | −10 | 3 | 27 | 24 | 1 | −2 | −1 | 3 | 475 | 474 | 5 | −8 | 5 | 3 | 22 | 24 | 1 | −3 | 11 | 3 | 251 | 251 | 3 |
| −5 | 14 | 2 | 65 | 62 | 1 | −7 | −9 | 3 | 44 | 45 | 1 | −1 | −1 | 3 | 219 | 224 | 2 | −7 | 5 | 3 | 35 | 28 | 1 | −2 | 11 | 3 | 140 | 128 | 2 |
| −4 | 14 | 2 | 117 | 114 | 1 | −6 | −9 | 3 | 132 | 130 | 2 | 0 | −1 | 3 | 807 | 818 | 8 | −6 | 5 | 3 | 109 | 104 | 1 | −1 | 11 | 3 | 93 | 94 | 2 |
| −3 | 14 | 2 | 51 | 50 | 1 | −5 | −9 | 3 | 106 | 104 | 2 | 1 | −1 | 3 | 206 | 200 | 2 | −5 | 5 | 3 | 207 | 205 | 1 | 1 | 11 | 3 | 239 | 244 | 3 |
| 1 | 14 | 2 | 112 | 116 | 2 | −4 | −9 | 3 | 95 | 97 | 1 | 2 | −1 | 3 | 103 | 104 | 1 | −4 | 5 | 3 | 75 | 77 | 1 | 2 | 11 | 3 | 155 | 162 | 2 |
| 2 | 14 | 2 | 44 | 47 | 1 | −3 | −9 | 3 | 111 | 103 | 1 | 3 | −1 | 3 | 33 | 40 | 1 | −3 | 5 | 3 | 200 | 197 | 3 | 3 | 11 | 3 | 81 | 82 | 1 |
| 3 | 14 | 2 | 24 | 23 | 1 | −2 | −9 | 3 | 103 | 104 | 1 | 6 | −1 | 3 | 118 | 120 | 2 | −2 | 5 | 3 | 117 | 111 | 3 | 4 | 11 | 3 | 106 | 104 | 1 |
| 4 | 14 | 2 | 45 | 44 | 1 | −1 | −9 | 3 | 153 | 158 | 1 | 7 | −1 | 3 | 72 | 74 | 1 | −1 | 5 | 3 | 162 | 158 | 3 | 5 | 11 | 3 | 92 | 88 | 1 |
| −4 | 15 | 2 | 26 | 26 | 1 | 0 | −9 | 3 | 185 | 193 | 1 | −8 | 0 | 3 | 67 | 61 | 1 | 0 | 5 | 3 | 339 | 325 | 5 | −6 | 12 | 3 | 52 | 48 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −3 | 15 | 2 | 157 | 147 | 2 | 1 | −9 | 3 | 177 | 187 | 1 | −7 | 0 | 3 | 17 | 17 | 1 | 1 | 5 | 3 | 703 | 701 | 12 | −5 | 12 | 3 | 30 | 27 | 1 |
| −2 | 15 | 2 | 74 | 71 | 1 | 2 | −9 | 3 | 125 | 114 | 1 | −6 | 0 | 3 | 87 | 91 | 1 | 2 | 5 | 3 | 251 | 257 | 4 | −4 | 12 | 3 | 119 | 130 | 1 |
| 1 | 15 | 2 | 56 | 53 | 1 | 3 | −9 | 3 | 75 | 68 | 1 | −5 | 0 | 3 | 68 | 76 | 1 | 3 | 5 | 3 | 81 | 86 | 1 | −3 | 12 | 3 | 15 | 7 | 2 |
| 2 | 15 | 2 | 26 | 27 | 1 | 4 | −9 | 3 | 182 | 179 | 3 | −4 | 0 | 3 | 82 | 68 | 1 | 4 | 5 | 3 | 59 | 59 | 1 | −2 | 12 | 3 | 162 | 163 | 3 |
| 3 | 15 | 2 | 95 | 97 | 1 | 5 | −9 | 3 | 123 | 115 | 2 | −3 | 0 | 3 | 510 | 487 | 6 | 5 | 5 | 3 | 104 | 106 | 1 | −1 | 12 | 3 | 128 | 129 | 2 |
| −3 | 16 | 2 | 3 | 2 | 3 | 6 | −9 | 3 | 29 | 28 | 1 | −2 | 0 | 3 | 41 | 45 | 1 | 5 | 5 | 3 | 102 | 112 | 1 | 1 | 12 | 3 | 93 | 96 | 2 |
| −2 | 16 | 2 | 100 | 95 | 1 | −7 | −8 | 3 | 49 | 46 | 1 | −1 | 0 | 3 | 962 | 987 | 10 | 7 | 5 | 3 | 40 | 41 | 1 | 2 | 12 | 3 | 172 | 173 | 2 |
| 2 | 16 | 2 | 27 | 30 | 1 | −6 | −8 | 3 | 79 | 82 | 1 | 0 | 0 | 3 | 544 | 559 | 7 | −8 | 6 | 3 | 34 | 34 | 1 | 3 | 12 | 3 | 71 | 77 | 1 |
| −2 | −16 | 3 | 106 | 98 | 2 | −5 | −8 | 3 | 34 | 32 | 1 | 1 | 0 | 3 | 293 | 301 | 3 | −7 | 6 | 3 | 28 | 27 | 1 | 4 | 12 | 3 | 39 | 40 | 1 |
| −1 | −16 | 3 | 68 | 65 | 1 | −4 | −8 | 3 | 151 | 152 | 2 | 2 | 0 | 3 | 386 | 375 | 4 | −6 | 6 | 3 | 250 | 250 | 3 | 5 | 12 | 3 | 49 | 49 | 1 |
| 0 | −16 | 3 | 57 | 54 | 1 | −3 | −8 | 3 | 68 | 72 | 1 | 3 | 0 | 3 | 84 | 85 | 1 | −5 | 6 | 3 | 217 | 224 | 1 | −5 | 13 | 3 | 101 | 99 | 1 |
| 1 | −16 | 3 | 38 | 35 | 1 | −2 | −8 | 3 | 172 | 177 | 1 | 5 | 0 | 3 | 179 | 177 | 3 | −4 | 6 | 3 | 182 | 188 | 1 | −4 | 13 | 3 | 119 | 117 | 2 |
| 2 | −16 | 3 | 43 | 45 | 1 | −1 | −8 | 3 | 79 | 80 | 1 | 6 | 0 | 3 | 133 | 128 | 2 | −3 | 6 | 3 | 37 | 32 | 3 | −3 | 13 | 3 | 159 | 157 | 2 |
| −4 | −15 | 3 | 124 | 123 | 2 | 0 | −8 | 3 | 109 | 99 | 1 | 7 | 0 | 3 | 148 | 158 | 2 | −2 | 6 | 3 | 116 | 110 | 3 | −2 | 13 | 3 | 146 | 153 | 3 |
| −3 | −15 | 3 | 102 | 101 | 1 | 1 | −8 | 3 | 181 | 172 | 1 | −8 | 1 | 3 | 13 | 18 | 1 | −1 | 6 | 3 | 7 | 8 | 6 | 1 | 13 | 3 | 125 | 127 | 2 |
| −2 | −15 | 3 | 97 | 95 | 1 | 2 | −8 | 3 | 77 | 77 | 1 | −7 | 1 | 3 | 14 | 9 | 1 | 0 | 6 | 3 | 311 | 307 | 5 | 2 | 13 | 3 | 134 | 135 | 1 |
| −1 | −15 | 3 | 75 | 72 | 1 | 3 | −8 | 3 | 18 | 16 | 1 | −6 | 1 | 3 | 71 | 66 | 1 | 1 | 6 | 3 | 279 | 255 | 7 | 3 | 13 | 3 | 98 | 96 | 1 |
| 0 | −15 | 3 | 72 | 73 | 1 | 4 | −8 | 3 | 130 | 141 | 2 | −5 | 1 | 3 | 73 | 76 | 1 | 2 | 6 | 3 | 381 | 377 | 9 | 4 | 13 | 3 | 64 | 61 | 1 |
| 1 | −15 | 3 | 68 | 67 | 1 | 5 | −8 | 3 | 138 | 140 | 2 | −4 | 1 | 3 | 333 | 314 | 3 | 3 | 6 | 3 | 51 | 47 | 1 | −4 | 14 | 3 | 159 | 149 | 2 |
| 2 | −15 | 3 | 47 | 47 | 1 | 6 | −8 | 3 | 84 | 82 | 1 | −3 | 1 | 3 | 60 | 61 | 1 | 4 | 6 | 3 | 178 | 181 | 1 | −3 | 14 | 3 | 51 | 47 | 1 |
| 3 | −15 | 3 | 52 | 53 | 1 | −7 | −7 | 3 | 85 | 88 | 1 | −2 | 1 | 3 | 478 | 474 | 5 | 5 | 6 | 3 | 224 | 219 | 2 | −2 | 14 | 3 | 62 | 59 | 1 |
| −5 | −14 | 3 | 57 | 57 | 1 | −6 | −7 | 3 | 110 | 109 | 2 | −1 | 1 | 3 | 222 | 224 | 2 | 6 | 6 | 3 | 84 | 83 | 1 | 1 | 14 | 3 | 9 | 12 | 6 |
| −4 | −14 | 3 | 154 | 149 | 2 | −5 | −7 | 3 | 99 | 99 | 2 | 0 | 1 | 3 | 798 | 818 | 10 | 7 | 6 | 3 | 41 | 39 | 1 | 2 | 14 | 3 | 18 | 18 | 1 |
| −3 | −14 | 3 | 49 | 47 | 1 | −4 | −7 | 3 | 76 | 80 | 1 | 1 | 1 | 3 | 201 | 198 | 2 | −7 | 7 | 3 | 87 | 88 | 1 | 3 | 14 | 3 | 54 | 54 | 1 |
| −2 | −14 | 3 | 61 | 59 | 1 | −3 | −7 | 3 | 138 | 141 | 1 | 2 | 1 | 3 | 101 | 104 | 1 | −6 | 7 | 3 | 115 | 110 | 1 | 4 | 14 | 3 | 70 | 65 | 1 |
| −1 | −14 | 3 | 131 | 131 | 1 | −2 | −7 | 3 | 235 | 237 | 3 | 3 | 1 | 3 | 33 | 41 | 1 | −5 | 7 | 3 | 101 | 100 | 1 | −4 | 15 | 3 | 124 | 123 | 2 |
| 0 | −14 | 3 | 42 | 36 | 1 | −1 | −7 | 3 | 57 | 67 | 1 | 4 | 1 | 3 | 143 | 141 | 1 | −4 | 7 | 3 | 76 | 80 | 1 | −3 | 15 | 3 | 103 | 101 | 1 |
| 1 | −14 | 3 | 9 | 12 | 1 | 0 | −7 | 3 | 47 | 42 | 1 | 5 | 1 | 3 | 68 | 65 | 1 | −3 | 7 | 3 | 136 | 141 | 1 | −2 | 15 | 3 | 96 | 96 | 2 |
| 2 | −14 | 3 | 14 | 18 | 1 | 1 | −7 | 3 | 109 | 98 | 1 | 6 | 1 | 3 | 120 | 120 | 2 | −2 | 7 | 3 | 236 | 236 | 6 | 1 | 15 | 3 | 67 | 67 | 1 |
| 3 | −14 | 3 | 52 | 53 | 1 | 2 | −7 | 3 | 122 | 112 | 1 | 7 | 1 | 3 | 71 | 73 | 1 | −1 | 7 | 3 | 57 | 67 | 1 | 2 | 15 | 3 | 45 | 48 | 1 |
| 4 | −14 | 3 | 68 | 65 | 1 | 3 | −7 | 3 | 203 | 212 | 3 | −8 | 2 | 3 | 17 | 26 | 1 | 0 | 7 | 3 | 48 | 43 | 2 | 3 | 15 | 3 | 53 | 53 | 1 |
| −5 | −13 | 3 | 97 | 99 | 2 | 4 | −7 | 3 | 102 | 104 | 1 | −7 | 2 | 3 | 68 | 64 | 1 | 1 | 7 | 3 | 106 | 98 | 3 | −2 | 16 | 3 | 102 | 97 | 1 |
| −4 | −13 | 3 | 116 | 117 | 1 | 5 | −7 | 3 | 176 | 176 | 3 | −6 | 2 | 3 | 31 | 27 | 1 | 2 | 7 | 3 | 122 | 112 | 2 | 2 | 16 | 3 | 47 | 46 | 1 |
| −3 | −13 | 3 | 156 | 157 | 1 | 6 | −7 | 3 | 81 | 84 | 1 | −5 | 2 | 3 | 166 | 176 | 1 | 3 | 7 | 3 | 198 | 211 | 1 | −2 | −16 | 4 | 48 | 45 | 1 |
| −2 | −13 | 3 | 145 | 153 | 1 | −7 | −6 | 3 | 25 | 27 | 1 | −4 | 2 | 3 | 61 | 56 | 1 | 4 | 7 | 3 | 102 | 103 | 1 | −1 | −16 | 4 | 3 | 3 | 2 |
| −1 | −13 | 3 | 241 | 249 | 2 | −6 | −6 | 3 | 245 | 250 | 4 | −3 | 2 | 3 | 261 | 261 | 3 | 5 | 7 | 3 | 174 | 176 | 1 | 0 | −16 | 4 | 94 | 97 | 1 |
| 0 | −13 | 3 | 169 | 172 | 1 | −5 | −6 | 3 | 216 | 224 | 4 | −2 | 2 | 3 | 511 | 511 | 5 | 6 | 7 | 3 | 83 | 84 | 1 | 1 | −16 | 4 | 28 | 29 | 1 |
| 1 | −13 | 3 | 123 | 127 | 1 | −4 | −6 | 3 | 181 | 188 | 3 | −1 | 2 | 3 | 616 | 629 | 8 | 7 | 7 | 3 | 60 | 61 | 1 | −3 | −15 | 4 | 29 | 29 | 1 |
| 2 | −13 | 3 | 134 | 136 | 1 | −3 | −6 | 3 | 37 | 32 | 1 | 0 | 2 | 3 | 988 | 1007 | 12 | −6 | 8 | 3 | 78 | 82 | 1 | −2 | −15 | 4 | 97 | 95 | 1 |
| 3 | −13 | 3 | 97 | 96 | 1 | −2 | −6 | 3 | 123 | 111 | 1 | 1 | 2 | 3 | 462 | 462 | 4 | −5 | 8 | 3 | 36 | 32 | 1 | −1 | −15 | 4 | 109 | 107 | 1 |
| 4 | −13 | 3 | 62 | 61 | 1 | −1 | −6 | 3 | 13 | 7 | 2 | 2 | 2 | 3 | 163 | 168 | 2 | −4 | 8 | 3 | 149 | 152 | 1 | 0 | −15 | 4 | 51 | 53 | 1 |
| 5 | −13 | 3 | 42 | 38 | 1 | 0 | −6 | 3 | 300 | 306 | 4 | 3 | 2 | 3 | 265 | 255 | 3 | −3 | 8 | 3 | 68 | 72 | 1 | 1 | −15 | 4 | 47 | 45 | 1 |
| −6 | −12 | 3 | 54 | 49 | 1 | 1 | −6 | 3 | 284 | 255 | 3 | 4 | 2 | 3 | 74 | 81 | 1 | −2 | 8 | 3 | 174 | 177 | 2 | 2 | −15 | 4 | 74 | 76 | 1 |
| −5 | −12 | 3 | 28 | 27 | 1 | 2 | −6 | 3 | 385 | 377 | 4 | 5 | 2 | 3 | 162 | 157 | 2 | −1 | 8 | 3 | 83 | 79 | 2 | −4 | −14 | 4 | 59 | 60 | 1 |
| −4 | −12 | 3 | 118 | 128 | 2 | 3 | −6 | 3 | 49 | 47 | 1 | 6 | 2 | 3 | 75 | 72 | 1 | 0 | 8 | 3 | 109 | 99 | 2 | −3 | −14 | 4 | 102 | 101 | 1 |
| −3 | −12 | 3 | 13 | 6 | 1 | −3 | −5 | 3 | 202 | 197 | 2 | 7 | 2 | 3 | 95 | 96 | 1 | 1 | 8 | 3 | 182 | 172 | 2 | −2 | −14 | 4 | 26 | 25 | 1 |
| −2 | −12 | 3 | 162 | 163 | 1 | −2 | −5 | 3 | 124 | 110 | 1 | −8 | 3 | 3 | 80 | 77 | 1 | 2 | 8 | 3 | 77 | 77 | 1 | −1 | −14 | 4 | 35 | 39 | 1 |
| −1 | −12 | 3 | 128 | 130 | 1 | −1 | −5 | 3 | 159 | 158 | 1 | −7 | 3 | 3 | 162 | 168 | 2 | 3 | 8 | 3 | 14 | 16 | 1 | 0 | −14 | 4 | 99 | 101 | 1 |
| 0 | −12 | 3 | 68 | 67 | 1 | 0 | −5 | 3 | 331 | 326 | 3 | −6 | 3 | 3 | 170 | 165 | 3 | 4 | 8 | 3 | 131 | 142 | 1 | 1 | −14 | 4 | 42 | 40 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | −12 | 3 | 93 | 96 | 1 | 1 | −5 | 3 | 718 | 700 | 7 | −5 | 3 | 3 | 68 | 60 | 1 | 5 | 8 | 3 | 133 | 140 | 1 | 2 | −14 | 4 | 67 | 67 | 1 |
| 2 | −12 | 3 | 172 | 174 | 1 | 2 | −5 | 3 | 257 | 257 | 2 | −4 | 3 | 3 | 76 | 78 | 1 | 6 | 8 | 3 | 83 | 82 | 1 | 3 | −14 | 4 | 53 | 54 | 1 |
| 3 | −12 | 3 | 71 | 77 | 1 | −3 | −4 | 3 | 170 | 164 | 1 | −3 | 3 | 3 | 324 | 298 | 4 | −6 | 9 | 3 | 131 | 130 | 1 | 4 | −14 | 4 | 61 | 62 | 1 |
| 4 | −12 | 3 | 39 | 41 | 1 | −2 | −4 | 3 | 66 | 69 | 1 | −2 | 3 | 3 | 100 | 89 | 1 | −5 | 9 | 3 | 102 | 104 | 1 | −5 | −13 | 4 | 43 | 43 | 1 |
| 5 | −12 | 3 | 50 | 50 | 1 | −1 | −4 | 3 | 131 | 134 | 1 | −1 | 3 | 3 | 400 | 401 | 5 | −4 | 9 | 3 | 93 | 96 | 1 | −4 | −13 | 4 | 92 | 94 | 1 |
| −6 | −11 | 3 | 70 | 69 | 1 | 0 | −4 | 3 | 173 | 179 | 1 | 0 | 3 | 3 | 654 | 670 | 8 | −3 | 9 | 3 | 108 | 103 | 1 | −3 | −13 | 4 | 123 | 127 | 1 |
| −5 | −11 | 3 | 113 | 115 | 2 | 1 | −4 | 3 | 198 | 194 | 2 | 1 | 3 | 3 | 379 | 395 | 4 | −2 | 9 | 3 | 107 | 105 | 1 | −2 | −13 | 4 | 118 | 113 | 1 |
| −4 | −11 | 3 | 99 | 106 | 2 | 2 | −4 | 3 | 327 | 304 | 3 | 2 | 3 | 3 | 277 | 272 | 3 | −1 | 9 | 3 | 148 | 158 | 2 | −1 | −13 | 4 | 92 | 94 | 1 |
| −3 | −11 | 3 | 252 | 251 | 2 | −7 | −3 | 3 | 167 | 168 | 2 | 3 | 3 | 3 | 287 | 285 | 3 | 0 | 9 | 3 | 187 | 194 | 3 | 0 | −13 | 4 | 212 | 225 | 1 |
| −2 | −11 | 3 | 137 | 128 | 1 | −3 | −3 | 3 | 321 | 299 | 3 | 4 | 3 | 3 | 61 | 64 | 1 | 1 | 9 | 3 | 176 | 188 | 2 | 1 | −13 | 4 | 87 | 92 | 1 |
| −1 | −11 | 3 | 93 | 94 | 1 | −2 | −3 | 3 | 103 | 89 | 1 | 5 | 3 | 3 | 148 | 146 | 2 | 2 | 9 | 3 | 126 | 114 | 1 | 2 | −13 | 4 | 125 | 128 | 1 |
| 0 | −11 | 3 | 240 | 240 | 1 | −1 | −3 | 3 | 397 | 401 | 3 | 6 | 3 | 3 | 118 | 122 | 2 | 3 | 9 | 3 | 74 | 69 | 1 | 3 | −13 | 4 | 42 | 43 | 1 |
| 1 | −11 | 3 | 240 | 246 | 1 | 0 | −3 | 3 | 668 | 670 | 6 | 7 | 3 | 3 | 52 | 49 | 1 | 4 | 9 | 3 | 181 | 179 | 2 | 4 | −13 | 4 | 100 | 96 | 2 |
| 2 | −11 | 3 | 157 | 163 | 1 | 1 | −3 | 3 | 388 | 394 | 4 | −8 | 4 | 3 | 36 | 39 | 1 | 5 | 9 | 3 | 118 | 115 | 1 | −6 | −12 | 4 | 61 | 58 | 1 |
| 3 | −11 | 3 | 80 | 83 | 1 | 2 | −3 | 3 | 275 | 273 | 2 | −7 | 4 | 3 | 60 | 67 | 1 | −6 | 10 | 3 | 61 | 61 | 1 | −5 | −12 | 4 | 36 | 32 | 1 |
| 4 | −11 | 3 | 105 | 105 | 2 | −8 | −2 | 3 | 17 | 26 | 1 | −6 | 4 | 3 | 134 | 131 | 1 | −5 | 10 | 3 | 150 | 150 | 2 | −4 | −12 | 4 | 65 | 69 | 1 |
| 5 | −11 | 3 | 92 | 88 | 1 | −7 | −2 | 3 | 67 | 65 | 1 | −5 | 4 | 3 | 194 | 205 | 1 | −4 | 10 | 3 | 48 | 55 | 1 | −3 | −12 | 4 | 116 | 117 | 1 |
| −6 | −10 | 3 | 63 | 61 | 1 | −3 | −2 | 3 | 261 | 263 | 2 | −4 | 4 | 3 | 287 | 288 | 2 | −3 | 10 | 3 | 182 | 194 | 2 | −2 | −12 | 4 | 70 | 72 | 1 |
| −1 | −12 | 4 | 61 | 55 | 1 | 6 | −6 | 4 | 39 | 36 | 1 | 7 | 0 | 4 | 41 | 41 | 1 | −1 | 6 | 4 | 112 | 103 | 2 | −2 | 13 | 4 | 119 | 114 | 2 |
| 0 | −12 | 4 | 59 | 62 | 1 | −7 | −5 | 4 | 39 | 43 | 1 | −8 | 1 | 4 | 39 | 38 | 1 | 0 | 6 | 4 | 227 | 220 | 4 | 1 | 13 | 4 | 87 | 92 | 2 |
| 1 | −12 | 4 | 119 | 120 | 1 | −6 | −5 | 4 | 61 | 60 | 1 | −7 | 1 | 4 | 143 | 143 | 2 | 1 | 6 | 4 | 192 | 180 | 5 | 2 | 13 | 4 | 125 | 128 | 1 |
| 2 | −12 | 4 | 52 | 50 | 1 | −5 | −5 | 4 | 216 | 214 | 3 | −6 | 1 | 4 | 54 | 54 | 1 | 2 | 6 | 4 | 37 | 33 | 1 | 3 | 13 | 4 | 45 | 43 | 1 |
| 3 | −12 | 4 | 20 | 20 | 1 | −4 | −5 | 4 | 57 | 54 | 1 | −5 | 1 | 4 | 152 | 146 | 1 | 3 | 6 | 4 | 141 | 136 | 1 | 4 | 13 | 4 | 100 | 95 | 1 |
| 4 | −12 | 4 | 23 | 23 | 1 | −3 | −5 | 4 | 135 | 141 | 1 | −4 | 1 | 4 | 442 | 419 | 5 | 4 | 6 | 4 | 229 | 232 | 1 | −4 | 14 | 4 | 61 | 60 | 1 |
| 5 | −12 | 4 | 55 | 51 | 1 | −2 | −5 | 4 | 419 | 406 | 4 | −3 | 1 | 4 | 83 | 83 | 1 | 5 | 6 | 4 | 63 | 61 | 1 | −3 | 14 | 4 | 103 | 101 | 1 |
| −6 | −11 | 4 | 90 | 86 | 1 | −1 | −5 | 4 | 294 | 302 | 3 | −2 | 1 | 4 | 379 | 377 | 4 | 6 | 6 | 4 | 40 | 35 | 1 | −2 | 14 | 4 | 29 | 25 | 2 |
| −5 | −11 | 4 | 190 | 190 | 3 | 0 | −5 | 4 | 267 | 251 | 3 | −1 | 1 | 4 | 376 | 382 | 4 | 7 | 6 | 4 | 96 | 98 | 1 | 1 | 14 | 4 | 42 | 40 | 1 |
| −4 | −11 | 4 | 152 | 165 | 3 | 1 | −5 | 4 | 693 | 665 | 7 | 0 | 1 | 4 | 260 | 258 | 3 | −7 | 7 | 4 | 14 | 13 | 1 | 2 | 14 | 4 | 67 | 67 | 1 |
| −3 | −11 | 4 | 117 | 114 | 1 | 2 | −5 | 4 | 276 | 267 | 3 | 1 | 1 | 4 | 124 | 115 | 1 | −6 | 7 | 4 | 48 | 46 | 1 | 3 | 14 | 4 | 55 | 54 | 1 |
| −2 | −11 | 4 | 306 | 307 | 2 | 3 | −5 | 4 | 255 | 257 | 4 | 2 | 1 | 4 | 200 | 198 | 2 | −5 | 7 | 4 | 182 | 184 | 1 | 4 | 14 | 4 | 67 | 62 | 1 |
| −1 | −11 | 4 | 141 | 140 | 1 | 4 | −5 | 4 | 261 | 255 | 5 | 3 | 1 | 4 | 83 | 74 | 1 | −4 | 7 | 4 | 71 | 70 | 1 | −4 | 15 | 4 | 103 | 103 | 2 |
| 0 | −11 | 4 | 78 | 71 | 1 | 5 | −5 | 4 | 77 | 84 | 1 | 4 | 1 | 4 | 134 | 130 | 1 | −3 | 7 | 4 | 52 | 47 | 1 | −3 | 15 | 4 | 28 | 28 | 1 |
| 1 | −11 | 4 | 70 | 73 | 1 | 6 | −5 | 4 | 58 | 53 | 1 | 5 | 1 | 4 | 128 | 130 | 2 | −2 | 7 | 4 | 231 | 230 | 6 | 1 | 15 | 4 | 47 | 45 | 1 |
| 2 | −11 | 4 | 79 | 85 | 1 | −8 | −4 | 4 | 97 | 96 | 1 | 6 | 1 | 4 | 135 | 130 | 2 | −1 | 7 | 4 | 73 | 77 | 2 | 2 | 15 | 4 | 75 | 76 | 1 |
| 3 | −11 | 4 | 57 | 70 | 1 | −7 | −4 | 4 | 37 | 33 | 1 | 7 | 1 | 4 | 54 | 55 | 1 | 0 | 7 | 4 | 192 | 186 | 3 | 3 | 15 | 4 | 30 | 30 | 1 |
| 4 | −11 | 4 | 84 | 83 | 1 | −6 | −4 | 4 | 171 | 172 | 2 | −8 | 2 | 4 | 10 | 10 | 2 | 1 | 7 | 4 | 30 | 21 | 3 | −2 | 16 | 4 | 52 | 45 | 1 |
| 5 | −11 | 4 | 90 | 89 | 1 | −5 | −4 | 4 | 154 | 162 | 2 | −7 | 2 | 4 | 101 | 100 | 1 | 2 | 7 | 4 | 149 | 151 | 1 | 1 | 16 | 4 | 28 | 29 | 1 |
| −6 | −10 | 4 | 92 | 96 | 1 | −4 | −4 | 4 | 220 | 206 | 2 | −6 | 2 | 4 | 130 | 130 | 2 | 3 | 7 | 4 | 121 | 122 | 1 | −2 | −16 | 5 | 42 | 41 | 1 |
| −5 | −10 | 4 | 94 | 99 | 2 | −3 | −4 | 4 | 107 | 103 | 1 | −5 | 2 | 4 | 121 | 129 | 1 | 4 | 7 | 4 | 148 | 143 | 1 | −1 | −16 | 5 | 26 | 25 | 1 |
| −4 | −10 | 4 | 95 | 106 | 2 | −2 | −4 | 4 | 188 | 191 | 2 | −4 | 2 | 4 | 231 | 232 | 2 | 5 | 7 | 4 | 170 | 163 | 1 | 0 | −16 | 5 | 24 | 27 | 1 |
| −3 | −10 | 4 | 58 | 53 | 1 | −1 | −4 | 4 | 125 | 128 | 1 | −3 | 2 | 4 | 256 | 245 | 3 | 6 | 7 | 4 | 18 | 13 | 1 | 1 | −16 | 5 | 102 | 104 | 2 |
| −2 | −10 | 4 | 34 | 28 | 1 | 0 | −4 | 4 | 384 | 375 | 4 | −2 | 2 | 4 | 80 | 78 | 1 | 7 | 7 | 4 | 25 | 32 | 1 | −3 | −15 | 5 | 26 | 26 | 1 |
| −1 | −10 | 4 | 140 | 146 | 1 | 1 | −4 | 4 | 199 | 183 | 2 | −1 | 2 | 4 | 203 | 205 | 2 | −7 | 8 | 4 | 28 | 29 | 1 | −2 | −15 | 5 | 194 | 186 | 2 |
| 0 | −10 | 4 | 234 | 232 | 1 | 2 | −4 | 4 | 198 | 192 | 2 | 0 | 2 | 4 | 563 | 566 | 7 | −6 | 8 | 4 | 127 | 131 | 1 | −1 | −15 | 5 | 59 | 58 | 1 |
| 1 | −10 | 4 | 106 | 103 | 1 | 6 | −4 | 4 | 90 | 87 | 1 | 1 | 2 | 4 | 107 | 115 | 1 | −5 | 8 | 4 | 150 | 152 | 2 | 0 | −15 | 5 | 82 | 82 | 1 |
| 2 | −10 | 4 | 97 | 94 | 1 | −8 | −3 | 4 | 33 | 27 | 1 | 2 | 2 | 4 | 170 | 169 | 2 | −4 | 8 | 4 | 103 | 99 | 1 | 1 | −15 | 5 | 99 | 91 | 1 |
| 3 | −10 | 4 | 116 | 123 | 2 | −7 | −3 | 4 | 60 | 58 | 1 | 3 | 2 | 4 | 144 | 147 | 1 | −3 | 8 | 4 | 91 | 89 | 1 | 2 | −15 | 5 | 70 | 70 | 1 |
| 4 | −10 | 4 | 123 | 121 | 2 | −6 | −3 | 4 | 210 | 215 | 3 | 4 | 2 | 4 | 64 | 66 | 1 | −2 | 8 | 4 | 62 | 67 | 1 | −4 | −14 | 5 | 114 | 112 | 1 |
| 5 | −10 | 4 | 29 | 32 | 1 | −5 | −3 | 4 | 80 | 76 | 1 | 5 | 2 | 4 | 38 | 33 | 1 | −1 | 8 | 4 | 68 | 70 | 2 | −3 | −14 | 5 | 127 | 130 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | −10 | 4 | 30 | 31 | 1 | −4 | −3 | 4 | 107 | 102 | 1 | 6 | 2 | 4 | 195 | 195 | 3 | 0 | 8 | 4 | 155 | 161 | 3 | −2 | −14 | 5 | 188 | 191 | 1 |
| −7 | −9 | 4 | 51 | 48 | 1 | −3 | −3 | 4 | 145 | 142 | 1 | 7 | 2 | 4 | 30 | 23 | 1 | 1 | 8 | 4 | 130 | 142 | 2 | −1 | −14 | 5 | 122 | 120 | 1 |
| −6 | −9 | 4 | 80 | 77 | 1 | −2 | −3 | 4 | 209 | 214 | 2 | −8 | 3 | 4 | 34 | 27 | 1 | 2 | 8 | 4 | 115 | 113 | 1 | 0 | −14 | 5 | 57 | 59 | 1 |
| −5 | −9 | 4 | 94 | 96 | 1 | −1 | −3 | 4 | 189 | 191 | 2 | −7 | 3 | 4 | 56 | 57 | 1 | 3 | 8 | 4 | 124 | 118 | 1 | 1 | −14 | 5 | 10 | 9 | 1 |
| −4 | −9 | 4 | 18 | 19 | 1 | 0 | −3 | 4 | 304 | 309 | 2 | −6 | 3 | 4 | 215 | 214 | 3 | 4 | 8 | 4 | 212 | 216 | 2 | 2 | −14 | 5 | 68 | 67 | 1 |
| −3 | −9 | 4 | 137 | 136 | 1 | 1 | −3 | 4 | 176 | 180 | 1 | −5 | 3 | 4 | 80 | 77 | 1 | 5 | 8 | 4 | 104 | 114 | 1 | 3 | −14 | 5 | 59 | 61 | 1 |
| −2 | −9 | 4 | 154 | 156 | 1 | 2 | −3 | 4 | 281 | 289 | 3 | −4 | 3 | 4 | 106 | 102 | 1 | 6 | 8 | 4 | 137 | 138 | 2 | −5 | −13 | 5 | 23 | 23 | 1 |
| −1 | −9 | 4 | 156 | 159 | 1 | 3 | −3 | 4 | 107 | 99 | 1 | −3 | 3 | 4 | 143 | 142 | 2 | −6 | 9 | 4 | 77 | 78 | 1 | −4 | −13 | 5 | 115 | 116 | 1 |
| 0 | −9 | 4 | 179 | 182 | 1 | 6 | −3 | 4 | 61 | 58 | 1 | −2 | 3 | 4 | 208 | 214 | 2 | −5 | 9 | 4 | 95 | 97 | 1 | −3 | −13 | 5 | 102 | 99 | 1 |
| 1 | −9 | 4 | 218 | 214 | 1 | 7 | −3 | 4 | 68 | 65 | 1 | −1 | 3 | 4 | 184 | 191 | 2 | −4 | 9 | 4 | 18 | 19 | 1 | −2 | −13 | 5 | 126 | 125 | 1 |
| 2 | −9 | 4 | 68 | 65 | 1 | −8 | −2 | 4 | 13 | 10 | 1 | 0 | 3 | 4 | 308 | 311 | 3 | −3 | 9 | 4 | 137 | 136 | 1 | −1 | −13 | 5 | 99 | 107 | 1 |
| 3 | −9 | 4 | 41 | 45 | 1 | −7 | −2 | 4 | 99 | 99 | 1 | 1 | 3 | 4 | 174 | 180 | 2 | −2 | 9 | 4 | 153 | 157 | 2 | 0 | −13 | 5 | 114 | 118 | 1 |
| 4 | −9 | 4 | 78 | 78 | 1 | −6 | −2 | 4 | 126 | 130 | 2 | 2 | 3 | 4 | 285 | 289 | 4 | −1 | 9 | 4 | 152 | 158 | 2 | 1 | −13 | 5 | 65 | 69 | 1 |
| 5 | −9 | 4 | 125 | 122 | 2 | −5 | −2 | 4 | 120 | 129 | 1 | 3 | 3 | 4 | 108 | 99 | 1 | 0 | 9 | 4 | 173 | 183 | 3 | 2 | −13 | 5 | 37 | 38 | 1 |
| 6 | −9 | 4 | 89 | 92 | 1 | −4 | −2 | 4 | 231 | 231 | 3 | 4 | 3 | 4 | 73 | 77 | 1 | 1 | 9 | 4 | 218 | 213 | 3 | 3 | −13 | 5 | 48 | 55 | 1 |
| −7 | −8 | 4 | 29 | 29 | 1 | −3 | −2 | 4 | 256 | 245 | 2 | 5 | 3 | 4 | 105 | 109 | 1 | 2 | 9 | 4 | 68 | 64 | 1 | 4 | −13 | 5 | 32 | 37 | 1 |
| −6 | −8 | 4 | 129 | 131 | 2 | −2 | −2 | 4 | 79 | 78 | 1 | 6 | 3 | 4 | 59 | 58 | 1 | 3 | 9 | 4 | 42 | 45 | 1 | −6 | −12 | 5 | 52 | 47 | 1 |
| −5 | −8 | 4 | 151 | 152 | 2 | −1 | −2 | 4 | 202 | 204 | 1 | 7 | 3 | 4 | 71 | 65 | 1 | 4 | 9 | 4 | 78 | 77 | 1 | −5 | −12 | 5 | 91 | 94 | 1 |
| −4 | −8 | 4 | 103 | 99 | 2 | 0 | −2 | 4 | 559 | 566 | 5 | −8 | 4 | 4 | 98 | 96 | 1 | 5 | 9 | 4 | 124 | 122 | 1 | −4 | −12 | 5 | 47 | 48 | 1 |
| −3 | −8 | 4 | 94 | 89 | 1 | 1 | −2 | 4 | 109 | 114 | 1 | −7 | 4 | 4 | 36 | 33 | 1 | −6 | 10 | 4 | 93 | 96 | 1 | −3 | −12 | 5 | 69 | 70 | 1 |
| −2 | −8 | 4 | 64 | 67 | 1 | 2 | −2 | 4 | 167 | 169 | 1 | −6 | 4 | 4 | 172 | 172 | 2 | −5 | 10 | 4 | 100 | 100 | 1 | −2 | −12 | 5 | 75 | 72 | 1 |
| −1 | −8 | 4 | 68 | 70 | 1 | 3 | −2 | 4 | 144 | 147 | 2 | −5 | 4 | 4 | 154 | 162 | 1 | −4 | 10 | 4 | 101 | 106 | 1 | −1 | −12 | 5 | 226 | 230 | 1 |
| 0 | −8 | 4 | 153 | 160 | 1 | 5 | −2 | 4 | 39 | 33 | 1 | −4 | 4 | 4 | 215 | 206 | 1 | −3 | 10 | 4 | 57 | 53 | 1 | 0 | −12 | 5 | 155 | 146 | 1 |
| 1 | −8 | 4 | 130 | 141 | 1 | 6 | −2 | 4 | 197 | 195 | 3 | −3 | 4 | 4 | 105 | 104 | 2 | −2 | 10 | 4 | 36 | 28 | 1 | 1 | −12 | 5 | 64 | 61 | 1 |
| 2 | −8 | 4 | 115 | 113 | 1 | 7 | −2 | 4 | 30 | 23 | 1 | −2 | 4 | 4 | 186 | 191 | 3 | −1 | 10 | 4 | 138 | 146 | 2 | 2 | −12 | 5 | 163 | 164 | 1 |
| 3 | −8 | 4 | 127 | 119 | 2 | −8 | −1 | 4 | 40 | 38 | 1 | −1 | 4 | 4 | 129 | 127 | 2 | 0 | 10 | 4 | 235 | 232 | 3 | 3 | −12 | 5 | 25 | 29 | 1 |
| 4 | −8 | 4 | 211 | 216 | 3 | −7 | −1 | 4 | 141 | 143 | 2 | 0 | 4 | 4 | 390 | 374 | 6 | 1 | 10 | 4 | 106 | 104 | 2 | 4 | −12 | 5 | 46 | 43 | 1 |
| 5 | −8 | 4 | 105 | 113 | 2 | −6 | −1 | 4 | 54 | 54 | 1 | 1 | 4 | 4 | 196 | 181 | 3 | 2 | 10 | 4 | 96 | 93 | 1 | −6 | −11 | 5 | 30 | 29 | 1 |
| 6 | −8 | 4 | 140 | 139 | 2 | −5 | −1 | 4 | 151 | 147 | 2 | 2 | 4 | 4 | 198 | 191 | 3 | 3 | 10 | 4 | 119 | 123 | 1 | −5 | −11 | 5 | 52 | 57 | 1 |
| −7 | −7 | 4 | 13 | 13 | 1 | −4 | −1 | 4 | 440 | 419 | 5 | 3 | 4 | 4 | 70 | 71 | 1 | 4 | 10 | 4 | 123 | 121 | 1 | −4 | −11 | 5 | 55 | 54 | 1 |
| −6 | −7 | 4 | 49 | 45 | 1 | −3 | −1 | 4 | 85 | 83 | 1 | 4 | 4 | 4 | 53 | 51 | 1 | 5 | 10 | 4 | 30 | 32 | 1 | −3 | −11 | 5 | 163 | 156 | 1 |
| −5 | −7 | 4 | 185 | 184 | 3 | −2 | −1 | 4 | 375 | 376 | 4 | 5 | 4 | 4 | 170 | 167 | 1 | −6 | 11 | 4 | 87 | 86 | 1 | −2 | −11 | 5 | 266 | 268 | 2 |
| −4 | −7 | 4 | 72 | 69 | 1 | −1 | −1 | 4 | 374 | 382 | 4 | 6 | 4 | 4 | 84 | 87 | 1 | −5 | 11 | 4 | 190 | 190 | 2 | −1 | −11 | 5 | 304 | 302 | 2 |
| −3 | −7 | 4 | 52 | 48 | 1 | 0 | −1 | 4 | 261 | 258 | 2 | 7 | 4 | 4 | 43 | 43 | 1 | −4 | 11 | 4 | 160 | 164 | 2 | 0 | −11 | 5 | 138 | 144 | 1 |
| −2 | −7 | 4 | 231 | 230 | 2 | 1 | −1 | 4 | 123 | 115 | 1 | −8 | 5 | 4 | 30 | 33 | 1 | −3 | 11 | 4 | 117 | 114 | 2 | 1 | −11 | 5 | 196 | 199 | 1 |
| −1 | −7 | 4 | 72 | 76 | 2 | 2 | −1 | 4 | 201 | 199 | 2 | −7 | 5 | 4 | 40 | 43 | 1 | −2 | 11 | 4 | 304 | 307 | 4 | 2 | −11 | 5 | 148 | 152 | 1 |
| 0 | −7 | 4 | 189 | 186 | 3 | 3 | −1 | 4 | 80 | 75 | 1 | −6 | 5 | 4 | 63 | 61 | 1 | −1 | 11 | 4 | 140 | 141 | 3 | 3 | −11 | 5 | 95 | 99 | 1 |
| 1 | −7 | 4 | 29 | 22 | 1 | 4 | −1 | 4 | 132 | 130 | 2 | −5 | 5 | 4 | 214 | 213 | 1 | 0 | 11 | 4 | 75 | 71 | 2 | 4 | −11 | 5 | 60 | 62 | 1 |
| 2 | −7 | 4 | 153 | 152 | 1 | 5 | −1 | 4 | 125 | 130 | 2 | −4 | 5 | 4 | 56 | 54 | 1 | 1 | 11 | 4 | 70 | 74 | 1 | 5 | −11 | 5 | 93 | 94 | 1 |
| 3 | −7 | 4 | 121 | 122 | 2 | 6 | −1 | 4 | 133 | 130 | 2 | −3 | 5 | 4 | 135 | 141 | 4 | 2 | 11 | 4 | 78 | 84 | 1 | −6 | −10 | 5 | 35 | 32 | 1 |
| 4 | −7 | 4 | 149 | 142 | 2 | 7 | −1 | 4 | 53 | 55 | 1 | −2 | 5 | 4 | 397 | 407 | 10 | 3 | 11 | 4 | 62 | 70 | 1 | −5 | −10 | 5 | 202 | 209 | 3 |
| 5 | −7 | 4 | 169 | 163 | 3 | −8 | 0 | 4 | 28 | 28 | 1 | −1 | 5 | 4 | 300 | 302 | 5 | 4 | 11 | 4 | 88 | 83 | 1 | −4 | −10 | 5 | 185 | 202 | 3 |
| 6 | −7 | 4 | 20 | 12 | 1 | −7 | 0 | 4 | 47 | 40 | 1 | 0 | 5 | 4 | 283 | 251 | 4 | 5 | 11 | 4 | 87 | 89 | 1 | −3 | −10 | 5 | 120 | 123 | 1 |
| −7 | −6 | 4 | 53 | 55 | 1 | −6 | 0 | 4 | 131 | 132 | 2 | 2 | 5 | 4 | 280 | 266 | 7 | −6 | 12 | 4 | 62 | 58 | 1 | −2 | −10 | 5 | 177 | 171 | 1 |
| −6 | −6 | 4 | 187 | 187 | 3 | −5 | 0 | 4 | 320 | 331 | 5 | 3 | 5 | 4 | 262 | 257 | 2 | −5 | 12 | 4 | 38 | 33 | 1 | −1 | −10 | 5 | 95 | 96 | 1 |
| −5 | −6 | 4 | 140 | 142 | 2 | −4 | 0 | 4 | 35 | 22 | 1 | 4 | 5 | 4 | 272 | 254 | 2 | −4 | 12 | 4 | 67 | 70 | 1 | 0 | −10 | 5 | 97 | 95 | 1 |
| −4 | −6 | 4 | 216 | 208 | 3 | −3 | 0 | 4 | 103 | 93 | 1 | 5 | 5 | 4 | 80 | 85 | 1 | −3 | 12 | 4 | 115 | 117 | 1 | 1 | −10 | 5 | 93 | 92 | 1 |
| −3 | −6 | 4 | 44 | 41 | 1 | −2 | 0 | 4 | 91 | 99 | 1 | 6 | 5 | 4 | 57 | 52 | 1 | −2 | 12 | 4 | 69 | 72 | 2 | 2 | −10 | 5 | 75 | 77 | 1 |
| −2 | −6 | 4 | 110 | 102 | 1 | −1 | 0 | 4 | 622 | 630 | 8 | 7 | 5 | 4 | 47 | 44 | 1 | 1 | 12 | 4 | 121 | 120 | 2 | 3 | −10 | 5 | 56 | 60 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | −6 | 4 | 105 | 102 | 1 | 0 | 0 | 4 | 870 | 877 | 11 | −8 | 6 | 4 | 71 | 71 | 1 | 2 | 12 | 4 | 52 | 50 | 1 | 4 | −10 | 5 | 17 | 19 | 1 |
| 0 | −6 | 4 | 223 | 219 | 3 | 1 | 0 | 4 | 48 | 52 | 1 | −7 | 6 | 4 | 54 | 55 | 1 | 3 | 12 | 4 | 21 | 19 | 1 | 5 | −10 | 5 | 61 | 58 | 1 |
| 1 | −6 | 4 | 188 | 180 | 2 | 2 | 0 | 4 | 176 | 173 | 2 | −6 | 6 | 4 | 188 | 187 | 3 | 4 | 12 | 4 | 24 | 23 | 1 | −7 | −9 | 5 | 18 | 21 | 1 |
| 2 | −6 | 4 | 36 | 34 | 1 | 3 | 0 | 4 | 94 | 105 | 1 | −5 | 6 | 4 | 136 | 142 | 1 | 5 | 12 | 4 | 55 | 51 | 1 | −6 | −9 | 5 | 92 | 93 | 1 |
| 3 | −6 | 4 | 142 | 137 | 2 | 4 | 0 | 4 | 53 | 59 | 1 | −4 | 6 | 4 | 210 | 208 | 1 | −5 | 13 | 4 | 45 | 43 | 1 | −5 | −9 | 5 | 75 | 75 | 1 |
| 4 | −6 | 4 | 231 | 232 | 4 | 5 | 0 | 4 | 66 | 69 | 1 | −3 | 6 | 4 | 43 | 40 | 1 | −4 | 13 | 4 | 96 | 95 | 1 | −4 | −9 | 5 | 141 | 146 | 1 |
| 5 | −6 | 4 | 61 | 61 | 1 | 6 | 0 | 4 | 127 | 124 | 2 | −2 | 6 | 4 | 111 | 103 | 3 | −3 | 13 | 4 | 124 | 127 | 1 | −3 | −9 | 5 | 73 | 73 | 1 |
| −2 | −9 | 5 | 78 | 77 | 1 | −3 | −3 | 5 | 177 | 167 | 2 | 4 | 2 | 5 | 108 | 102 | 1 | −1 | 8 | 5 | 12 | 11 | 3 | −1 | −13 | 6 | 122 | 125 | 1 |
| −1 | −9 | 5 | 162 | 149 | 1 | −2 | −3 | 5 | 183 | 175 | 2 | 5 | 2 | 5 | 88 | 85 | 1 | 0 | 8 | 5 | 64 | 69 | 1 | 0 | −13 | 6 | 79 | 85 | 1 |
| 0 | −9 | 5 | 120 | 111 | 1 | −1 | −3 | 5 | 123 | 109 | 1 | 6 | 2 | 5 | 113 | 112 | 2 | 1 | 8 | 5 | 276 | 281 | 4 | 1 | −13 | 6 | 127 | 129 | 1 |
| 1 | −9 | 5 | 55 | 55 | 1 | 0 | −3 | 5 | 104 | 104 | 1 | 7 | 2 | 5 | 38 | 37 | 1 | 2 | 8 | 5 | 188 | 178 | 2 | 2 | −13 | 6 | 43 | 46 | 1 |
| 2 | −9 | 5 | 154 | 149 | 1 | 1 | −3 | 5 | 155 | 167 | 1 | −8 | 3 | 5 | 39 | 38 | 1 | 3 | 8 | 5 | 212 | 222 | 2 | 3 | −13 | 6 | 70 | 75 | 1 |
| 3 | −9 | 5 | 25 | 22 | 1 | 2 | −3 | 5 | 69 | 67 | 1 | −7 | 3 | 5 | 67 | 79 | 1 | 4 | 8 | 5 | 61 | 64 | 1 | −5 | −12 | 6 | 65 | 61 | 1 |
| 4 | −9 | 5 | 129 | 131 | 2 | 3 | −3 | 5 | 67 | 79 | 1 | −6 | 3 | 5 | 124 | 131 | 1 | 5 | 8 | 5 | 74 | 75 | 1 | −4 | −12 | 6 | 64 | 62 | 1 |
| 5 | −9 | 5 | 51 | 51 | 1 | 4 | −3 | 5 | 13 | 10 | 1 | −5 | 3 | 5 | 177 | 184 | 1 | 6 | 8 | 5 | 51 | 50 | 1 | −3 | −12 | 6 | 146 | 146 | 1 |
| 6 | −9 | 5 | 58 | 53 | 1 | 5 | −3 | 5 | 88 | 86 | 1 | −4 | 3 | 5 | 98 | 92 | 1 | −6 | 9 | 5 | 92 | 92 | 1 | −2 | −12 | 6 | 100 | 95 | 1 |
| −7 | −8 | 5 | 94 | 91 | 1 | 6 | −3 | 5 | 60 | 61 | 1 | −3 | 3 | 5 | 176 | 166 | 2 | −5 | 9 | 5 | 79 | 76 | 1 | −1 | −12 | 6 | 145 | 160 | 1 |
| −6 | −8 | 5 | 47 | 44 | 1 | 7 | −3 | 5 | 50 | 49 | 1 | −2 | 3 | 5 | 178 | 175 | 2 | −4 | 9 | 5 | 143 | 146 | 1 | 0 | −12 | 6 | 133 | 135 | 1 |
| −5 | −8 | 5 | 113 | 112 | 2 | −8 | −2 | 5 | 83 | 79 | 1 | −1 | 3 | 5 | 124 | 110 | 2 | −3 | 9 | 5 | 72 | 73 | 1 | 1 | −12 | 6 | 102 | 98 | 1 |
| −4 | −8 | 5 | 53 | 58 | 1 | −7 | −2 | 5 | 114 | 119 | 2 | 0 | 3 | 5 | 105 | 104 | 2 | −2 | 9 | 5 | 80 | 77 | 1 | 2 | −12 | 6 | 56 | 56 | 1 |
| −3 | −8 | 5 | 156 | 174 | 1 | −6 | −2 | 5 | 178 | 177 | 3 | 1 | 3 | 5 | 157 | 168 | 2 | −1 | 9 | 5 | 160 | 149 | 2 | 3 | −12 | 6 | 54 | 50 | 1 |
| −2 | −8 | 5 | 86 | 97 | 1 | −5 | −2 | 5 | 130 | 131 | 2 | 2 | 3 | 5 | 70 | 67 | 1 | 0 | 9 | 5 | 118 | 111 | 2 | 4 | −12 | 6 | 54 | 57 | 1 |
| −1 | −8 | 5 | 10 | 11 | 1 | −4 | −2 | 5 | 180 | 176 | 1 | 3 | 3 | 5 | 67 | 78 | 1 | 1 | 9 | 5 | 57 | 56 | 1 | −6 | −11 | 6 | 5 | 7 | 5 |
| 0 | −8 | 5 | 64 | 69 | 1 | −3 | −2 | 5 | 165 | 155 | 1 | 4 | 3 | 5 | 12 | 9 | 1 | 2 | 9 | 5 | 151 | 148 | 2 | −5 | −11 | 6 | 60 | 58 | 1 |
| 1 | −8 | 5 | 277 | 281 | 2 | −2 | −2 | 5 | 185 | 181 | 2 | 5 | 3 | 5 | 87 | 87 | 1 | 3 | 9 | 5 | 25 | 22 | 1 | −4 | −11 | 6 | 62 | 66 | 1 |
| 2 | −8 | 5 | 188 | 177 | 1 | −1 | −2 | 5 | 246 | 242 | 2 | 6 | 3 | 5 | 59 | 61 | 1 | 4 | 9 | 5 | 129 | 131 | 1 | −3 | −11 | 6 | 18 | 15 | 1 |
| 3 | −8 | 5 | 217 | 222 | 3 | 0 | −2 | 5 | 325 | 312 | 4 | 7 | 3 | 5 | 50 | 48 | 1 | 5 | 9 | 5 | 50 | 51 | 1 | −2 | −11 | 6 | 71 | 74 | 1 |
| 4 | −8 | 5 | 61 | 64 | 1 | 1 | −2 | 5 | 219 | 204 | 2 | −8 | 4 | 5 | 52 | 46 | 1 | −6 | 10 | 5 | 34 | 32 | 1 | −1 | −11 | 6 | 204 | 211 | 1 |
| 5 | −8 | 5 | 77 | 76 | 1 | 2 | −2 | 5 | 227 | 229 | 2 | −7 | 4 | 5 | 62 | 59 | 1 | −5 | 10 | 5 | 210 | 209 | 2 | 0 | −11 | 6 | 40 | 39 | 1 |
| 6 | −8 | 5 | 51 | 49 | 1 | 3 | −2 | 5 | 77 | 83 | 1 | −6 | 4 | 5 | 95 | 93 | 1 | −4 | 10 | 5 | 195 | 203 | 2 | 1 | −11 | 6 | 140 | 138 | 1 |
| −7 | −7 | 5 | 57 | 56 | 1 | 4 | −2 | 5 | 109 | 103 | 1 | −5 | 4 | 5 | 234 | 237 | 1 | −3 | 10 | 5 | 120 | 124 | 1 | 2 | −11 | 6 | 106 | 117 | 1 |
| −6 | −7 | 5 | 107 | 109 | 1 | 5 | −2 | 5 | 86 | 84 | 1 | −4 | 4 | 5 | 143 | 147 | 1 | −2 | 10 | 5 | 178 | 171 | 2 | 3 | −11 | 6 | 104 | 108 | 2 |
| −5 | −7 | 5 | 43 | 44 | 1 | 6 | −2 | 5 | 114 | 112 | 1 | −3 | 4 | 5 | 229 | 227 | 6 | −1 | 10 | 5 | 92 | 96 | 2 | 4 | −11 | 6 | 90 | 87 | 1 |
| −4 | −7 | 5 | 163 | 165 | 1 | 7 | −2 | 5 | 38 | 36 | 1 | −2 | 4 | 5 | 70 | 73 | 1 | 0 | 10 | 5 | 96 | 95 | 1 | 5 | −11 | 6 | 113 | 110 | 2 |
| −3 | −7 | 5 | 116 | 114 | 1 | −8 | −1 | 5 | 133 | 120 | 2 | −1 | 4 | 5 | 218 | 210 | 3 | 1 | 10 | 5 | 95 | 92 | 1 | −6 | −10 | 6 | 27 | 23 | 1 |
| −2 | −7 | 5 | 66 | 72 | 1 | −7 | −1 | 5 | 18 | 19 | 1 | 0 | 4 | 5 | 275 | 252 | 4 | 2 | 10 | 5 | 75 | 78 | 1 | −5 | −10 | 6 | 162 | 171 | 2 |
| −1 | −7 | 5 | 97 | 88 | 1 | −6 | −1 | 5 | 169 | 166 | 3 | 1 | 4 | 5 | 496 | 501 | 9 | 3 | 10 | 5 | 56 | 60 | 1 | −4 | −10 | 6 | 225 | 234 | 2 |
| 0 | −7 | 5 | 122 | 122 | 1 | −5 | −1 | 5 | 117 | 119 | 1 | 2 | 4 | 5 | 118 | 122 | 2 | 4 | 10 | 5 | 19 | 19 | 1 | −3 | −10 | 6 | 124 | 124 | 1 |
| 1 | −7 | 5 | 273 | 279 | 1 | −4 | −1 | 5 | 315 | 317 | 3 | 3 | 4 | 5 | 55 | 58 | 1 | 5 | 10 | 5 | 60 | 57 | 1 | −2 | −10 | 6 | 162 | 163 | 1 |
| 2 | −7 | 5 | 199 | 205 | 1 | −3 | −1 | 5 | 39 | 46 | 1 | 4 | 4 | 5 | 137 | 141 | 1 | −6 | 11 | 5 | 30 | 29 | 1 | −1 | −10 | 6 | 164 | 161 | 1 |
| 3 | −7 | 5 | 48 | 45 | 1 | −2 | −1 | 5 | 128 | 131 | 1 | 5 | 4 | 5 | 52 | 46 | 1 | −5 | 11 | 5 | 52 | 56 | 1 | 0 | −10 | 6 | 48 | 43 | 1 |
| 4 | −7 | 5 | 54 | 51 | 1 | −1 | −1 | 5 | 211 | 223 | 2 | 6 | 4 | 5 | 74 | 76 | 1 | −4 | 11 | 5 | 54 | 54 | 1 | 1 | −10 | 6 | 96 | 97 | 1 |
| 5 | −7 | 5 | 64 | 61 | 1 | 0 | −1 | 5 | 83 | 72 | 1 | 7 | 4 | 5 | 60 | 58 | 1 | −3 | 11 | 5 | 161 | 156 | 2 | 2 | −10 | 6 | 32 | 33 | 1 |
| 6 | −7 | 5 | 20 | 21 | 1 | 1 | −1 | 5 | 190 | 188 | 2 | −8 | 5 | 5 | 96 | 95 | 1 | −2 | 11 | 5 | 272 | 268 | 5 | 3 | −10 | 6 | 48 | 46 | 1 |
| −7 | −6 | 5 | 75 | 72 | 1 | 2 | −1 | 5 | 253 | 249 | 3 | −7 | 5 | 5 | 56 | 63 | 1 | −1 | 11 | 5 | 300 | 302 | 6 | 4 | −10 | 6 | 46 | 46 | 1 |
| −6 | −6 | 5 | 143 | 142 | 1 | 3 | −1 | 5 | 90 | 90 | 1 | −6 | 5 | 5 | 154 | 158 | 2 | 0 | 11 | 5 | 135 | 144 | 2 | 5 | −10 | 6 | 77 | 82 | 1 |
| −5 | −6 | 5 | 202 | 199 | 3 | 4 | −1 | 5 | 92 | 97 | 1 | −5 | 5 | 5 | 227 | 233 | 1 | 1 | 11 | 5 | 196 | 199 | 3 | −7 | −9 | 6 | 53 | 56 | 1 |
| −4 | −6 | 5 | 23 | 21 | 1 | 5 | −1 | 5 | 151 | 149 | 2 | −4 | 5 | 5 | 190 | 191 | 1 | 2 | 11 | 5 | 149 | 153 | 2 | −6 | −9 | 6 | 67 | 65 | 1 |
| −3 | −6 | 5 | 126 | 127 | 1 | 6 | −1 | 5 | 92 | 92 | 1 | −3 | 5 | 5 | 232 | 248 | 3 | 3 | 11 | 5 | 90 | 99 | 1 | −5 | −9 | 6 | 57 | 65 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −2 | −6 | 5 | 132 | 130 | 1 | 7 | −1 | 5 | 133 | 131 | 2 | −2 | 5 | 5 | 114 | 121 | 3 | 4 | 11 | 5 | 63 | 62 | 1 | −4 | −9 | 6 | 136 | 141 | 1 |
| −1 | −6 | 5 | 294 | 309 | 5 | −8 | 0 | 5 | 18 | 20 | 1 | −1 | 5 | 5 | 332 | 325 | 5 | 5 | 11 | 5 | 90 | 94 | 1 | −3 | −9 | 6 | 117 | 116 | 1 |
| 0 | −6 | 5 | 208 | 204 | 2 | −7 | 0 | 5 | 61 | 71 | 1 | 0 | 5 | 5 | 73 | 67 | 1 | −5 | 12 | 5 | 88 | 93 | 1 | −2 | −9 | 6 | 128 | 124 | 1 |
| 1 | −6 | 5 | 360 | 355 | 4 | −6 | 0 | 5 | 46 | 42 | 1 | 1 | 5 | 5 | 128 | 128 | 3 | −4 | 12 | 5 | 48 | 48 | 1 | −1 | −9 | 6 | 137 | 136 | 1 |
| 2 | −6 | 5 | 37 | 25 | 1 | −5 | 0 | 5 | 36 | 37 | 1 | 2 | 5 | 5 | 364 | 356 | 5 | −3 | 12 | 5 | 68 | 70 | 1 | 0 | −9 | 6 | 224 | 219 | 1 |
| 3 | −6 | 5 | 55 | 50 | 1 | −4 | 0 | 5 | 500 | 502 | 5 | 3 | 5 | 5 | 77 | 61 | 1 | −2 | 12 | 5 | 77 | 71 | 2 | 1 | −9 | 6 | 170 | 174 | 1 |
| 4 | −6 | 5 | 32 | 26 | 1 | −3 | 0 | 5 | 196 | 207 | 2 | 4 | 5 | 5 | 193 | 198 | 1 | 0 | 12 | 5 | 151 | 147 | 3 | 2 | −9 | 6 | 122 | 114 | 1 |
| 5 | −6 | 5 | 137 | 134 | 2 | −2 | 0 | 5 | 224 | 231 | 2 | 5 | 5 | 5 | 292 | 291 | 2 | 1 | 12 | 5 | 67 | 62 | 1 | 3 | −9 | 6 | 159 | 171 | 3 |
| 6 | −6 | 5 | 30 | 26 | 1 | −1 | 0 | 5 | 170 | 178 | 2 | 6 | 5 | 5 | 142 | 139 | 2 | 2 | 12 | 5 | 161 | 164 | 2 | 4 | −9 | 6 | 51 | 43 | 1 |
| −8 | −5 | 5 | 98 | 96 | 1 | 0 | 0 | 5 | 40 | 40 | 1 | 7 | 5 | 5 | 24 | 22 | 1 | 3 | 12 | 5 | 28 | 29 | 1 | 5 | −9 | 6 | 69 | 69 | 1 |
| −7 | −5 | 5 | 56 | 63 | 1 | 1 | 0 | 5 | 57 | 50 | 1 | −8 | 6 | 5 | 80 | 82 | 1 | 4 | 12 | 5 | 46 | 43 | 1 | −7 | −8 | 6 | 33 | 35 | 1 |
| −6 | −5 | 5 | 155 | 158 | 1 | 2 | 0 | 5 | 129 | 127 | 1 | −7 | 6 | 5 | 74 | 73 | 1 | −5 | 13 | 5 | 27 | 23 | 1 | −6 | −8 | 6 | 190 | 191 | 2 |
| −5 | −5 | 5 | 230 | 233 | 4 | 3 | 0 | 5 | 68 | 65 | 1 | −6 | 6 | 5 | 144 | 143 | 1 | −4 | 13 | 5 | 116 | 116 | 1 | −5 | −8 | 6 | 79 | 79 | 1 |
| −4 | −5 | 5 | 190 | 191 | 1 | 4 | 0 | 5 | 37 | 36 | 1 | −5 | 6 | 5 | 201 | 199 | 2 | −3 | 13 | 5 | 102 | 98 | 1 | −4 | −8 | 6 | 16 | 14 | 1 |
| −3 | −5 | 5 | 233 | 247 | 1 | 5 | 0 | 5 | 43 | 36 | 1 | −4 | 6 | 5 | 25 | 22 | 1 | −2 | 13 | 5 | 126 | 125 | 2 | −3 | −8 | 6 | 94 | 104 | 1 |
| −2 | −5 | 5 | 113 | 120 | 1 | 6 | 0 | 5 | 198 | 196 | 3 | −3 | 6 | 5 | 124 | 127 | 1 | 1 | 13 | 5 | 64 | 69 | 1 | −2 | −8 | 6 | 24 | 30 | 1 |
| −1 | −5 | 5 | 314 | 324 | 4 | 7 | 0 | 5 | 74 | 71 | 1 | −2 | 6 | 5 | 125 | 129 | 4 | 2 | 13 | 5 | 37 | 38 | 1 | −1 | −8 | 6 | 118 | 117 | 1 |
| 0 | −5 | 5 | 70 | 66 | 1 | −8 | 1 | 5 | 134 | 120 | 2 | −1 | 6 | 5 | 303 | 309 | 5 | 3 | 13 | 5 | 51 | 55 | 1 | 0 | −8 | 6 | 250 | 248 | 1 |
| 1 | −5 | 5 | 133 | 128 | 1 | −7 | 1 | 5 | 18 | 18 | 1 | 0 | 6 | 5 | 210 | 204 | 3 | 4 | 13 | 5 | 35 | 37 | 1 | 1 | −8 | 6 | 65 | 66 | 1 |
| 2 | −5 | 5 | 363 | 357 | 3 | −6 | 1 | 5 | 170 | 167 | 3 | 1 | 6 | 5 | 360 | 354 | 9 | −4 | 14 | 5 | 117 | 111 | 2 | 2 | −8 | 6 | 240 | 233 | 2 |
| 3 | −5 | 5 | 76 | 61 | 1 | −5 | 1 | 5 | 115 | 119 | 1 | 2 | 6 | 5 | 37 | 25 | 1 | −3 | 14 | 5 | 129 | 130 | 1 | 3 | −8 | 6 | 69 | 60 | 1 |
| 4 | −5 | 5 | 193 | 197 | 3 | −4 | 1 | 5 | 309 | 317 | 2 | 3 | 6 | 5 | 54 | 50 | 1 | −2 | 14 | 5 | 186 | 191 | 3 | 4 | −8 | 6 | 171 | 169 | 3 |
| 5 | −5 | 5 | 292 | 291 | 5 | −3 | 1 | 5 | 38 | 46 | 1 | 4 | 6 | 5 | 32 | 27 | 1 | 1 | 14 | 5 | 10 | 9 | 4 | 5 | −8 | 6 | 119 | 118 | 2 |
| 6 | −5 | 5 | 140 | 139 | 2 | −2 | 1 | 5 | 128 | 132 | 1 | 5 | 6 | 5 | 136 | 134 | 1 | 2 | 14 | 5 | 68 | 67 | 1 | 6 | −8 | 6 | 54 | 53 | 1 |
| −8 | −4 | 5 | 53 | 46 | 1 | −1 | 1 | 5 | 212 | 224 | 2 | 6 | 6 | 5 | 28 | 25 | 1 | 3 | 14 | 5 | 61 | 61 | 1 | −7 | −7 | 6 | 63 | 60 | 1 |
| −7 | −4 | 5 | 63 | 60 | 1 | 0 | 1 | 5 | 81 | 71 | 1 | 7 | 6 | 5 | 38 | 41 | 1 | −3 | 15 | 5 | 28 | 26 | 1 | −6 | −7 | 6 | 104 | 103 | 1 |
| −6 | −4 | 5 | 94 | 93 | 1 | 1 | 1 | 5 | 192 | 188 | 2 | −7 | 7 | 5 | 57 | 57 | 1 | 1 | 15 | 5 | 96 | 91 | 1 | −5 | −7 | 6 | 7 | 10 | 2 |
| −5 | −4 | 5 | 235 | 235 | 2 | 2 | 1 | 5 | 254 | 249 | 3 | −6 | 7 | 5 | 104 | 110 | 1 | 2 | 15 | 5 | 69 | 70 | 1 | −4 | −7 | 6 | 70 | 70 | 1 |
| −4 | −4 | 5 | 145 | 147 | 1 | 3 | 1 | 5 | 90 | 90 | 1 | −5 | 7 | 5 | 43 | 44 | 1 | −3 | −15 | 6 | 95 | 90 | 1 | −3 | −7 | 6 | 54 | 55 | 1 |
| −3 | −4 | 5 | 231 | 227 | 2 | 4 | 1 | 5 | 92 | 98 | 1 | −4 | 7 | 5 | 163 | 165 | 1 | −2 | −15 | 6 | 89 | 86 | 1 | −2 | −7 | 6 | 93 | 90 | 1 |
| −2 | −4 | 5 | 70 | 73 | 1 | 5 | 1 | 5 | 152 | 149 | 2 | −3 | 7 | 5 | 114 | 114 | 1 | −1 | −15 | 6 | 165 | 163 | 1 | −1 | −7 | 6 | 18 | 17 | 1 |
| −1 | −4 | 5 | 212 | 210 | 2 | 6 | 1 | 5 | 93 | 92 | 1 | −2 | 7 | 5 | 70 | 72 | 1 | 0 | −15 | 6 | 73 | 74 | 1 | 0 | −7 | 6 | 219 | 210 | 1 |
| 0 | −4 | 5 | 275 | 253 | 3 | 7 | 1 | 5 | 132 | 131 | 1 | −1 | 7 | 5 | 100 | 89 | 2 | 1 | −15 | 6 | 95 | 89 | 1 | 1 | −7 | 6 | 121 | 121 | 1 |
| 1 | −4 | 5 | 513 | 499 | 6 | −8 | 2 | 5 | 82 | 79 | 1 | 0 | 7 | 5 | 123 | 122 | 2 | 2 | −15 | 6 | 61 | 62 | 1 | 2 | −7 | 6 | 92 | 100 | 1 |
| 2 | −4 | 5 | 120 | 122 | 1 | −7 | 2 | 5 | 109 | 119 | 2 | 1 | 7 | 5 | 280 | 280 | 4 | −4 | −14 | 6 | 92 | 95 | 1 | 3 | −7 | 6 | 108 | 103 | 2 |
| 3 | −4 | 5 | 54 | 57 | 1 | −6 | 2 | 5 | 176 | 177 | 3 | 2 | 7 | 5 | 200 | 206 | 2 | −3 | −14 | 6 | 153 | 149 | 1 | 4 | −7 | 6 | 233 | 238 | 4 |
| 4 | −4 | 5 | 139 | 142 | 2 | −5 | 2 | 5 | 131 | 131 | 1 | 3 | 7 | 5 | 46 | 45 | 1 | −2 | −14 | 6 | 140 | 136 | 1 | 5 | −7 | 6 | 87 | 81 | 1 |
| 5 | −4 | 5 | 52 | 46 | 1 | −4 | 2 | 5 | 177 | 175 | 1 | 4 | 7 | 5 | 55 | 52 | 1 | −1 | −14 | 6 | 49 | 51 | 1 | 6 | −7 | 6 | 60 | 60 | 1 |
| 6 | −4 | 5 | 77 | 76 | 1 | −3 | 2 | 5 | 161 | 156 | 2 | 5 | 7 | 5 | 62 | 61 | 1 | 0 | −14 | 6 | 39 | 44 | 1 | −7 | −6 | 6 | 51 | 52 | 1 |
| 7 | −4 | 5 | 62 | 59 | 1 | −2 | 2 | 5 | 184 | 182 | 2 | 6 | 7 | 5 | 18 | 21 | 1 | 1 | −14 | 6 | 38 | 38 | 1 | −6 | −6 | 6 | 63 | 60 | 1 |
| −8 | −3 | 5 | 37 | 37 | 1 | −1 | 2 | 5 | 244 | 243 | 3 | −6 | 8 | 5 | 45 | 44 | 1 | 2 | −14 | 6 | 37 | 39 | 1 | −5 | −6 | 6 | 45 | 47 | 1 |
| −7 | −3 | 5 | 75 | 79 | 1 | 0 | 2 | 5 | 318 | 312 | 4 | −5 | 8 | 5 | 111 | 112 | 1 | −5 | −13 | 6 | 53 | 54 | 1 | −4 | −6 | 6 | 105 | 106 | 1 |
| −6 | −3 | 5 | 128 | 131 | 2 | 1 | 2 | 5 | 218 | 203 | 3 | −4 | 8 | 5 | 54 | 58 | 1 | −4 | −13 | 6 | 87 | 87 | 1 | −3 | −6 | 6 | 93 | 92 | 1 |
| −5 | −3 | 5 | 181 | 184 | 2 | 2 | 2 | 5 | 228 | 228 | 3 | −3 | 8 | 5 | 159 | 175 | 1 | −3 | −13 | 6 | 53 | 55 | 1 | −2 | −6 | 6 | 177 | 173 | 1 |
| −4 | −3 | 5 | 101 | 93 | 1 | 3 | 2 | 5 | 77 | 83 | 1 | −2 | 8 | 5 | 87 | 98 | 1 | −2 | −13 | 6 | 99 | 96 | 1 | −1 | −6 | 6 | 42 | 46 | 1 |
| 0 | −6 | 6 | 101 | 105 | 1 | −6 | 0 | 6 | 145 | 155 | 2 | 1 | 5 | 6 | 94 | 95 | 3 | 2 | 12 | 6 | 57 | 56 | 1 | −5 | −8 | 7 | 186 | 208 | 2 |
| 1 | −6 | 6 | 217 | 220 | 1 | −5 | 0 | 6 | 68 | 63 | 1 | 2 | 5 | 6 | 109 | 119 | 1 | 3 | 12 | 6 | 54 | 50 | 1 | −4 | −8 | 7 | 87 | 90 | 1 |
| 2 | −6 | 6 | 124 | 128 | 1 | −4 | 0 | 6 | 79 | 66 | 1 | 3 | 5 | 6 | 143 | 142 | 1 | 4 | 12 | 6 | 55 | 56 | 1 | −3 | −8 | 7 | 60 | 69 | 1 |
| 3 | −6 | 6 | 149 | 142 | 1 | −3 | 0 | 6 | 24 | 10 | 2 | 4 | 5 | 6 | 50 | 53 | 1 | −5 | 13 | 6 | 54 | 55 | 1 | −2 | −8 | 7 | 224 | 237 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 4 | −6 | 6 | 48 | 46 | 1 | −2 | 0 | 6 | 159 | 167 | 2 | 5 | 5 | 6 | 169 | 162 | 1 | −4 | 13 | 6 | 89 | 87 | 1 | −1 | −8 | 7 | 65 | 53 | 1 |
| 5 | −6 | 6 | 70 | 65 | 1 | −1 | 0 | 6 | 435 | 444 | 7 | 6 | 5 | 6 | 80 | 82 | 1 | −3 | 13 | 6 | 51 | 55 | 1 | 0 | −8 | 7 | 318 | 324 | 2 |
| 6 | −6 | 6 | 76 | 76 | 1 | 0 | 0 | 6 | 265 | 270 | 3 | −7 | 6 | 6 | 51 | 51 | 1 | −2 | 13 | 6 | 98 | 96 | 2 | 1 | −8 | 7 | 397 | 401 | 3 |
| −8 | −5 | 6 | 43 | 45 | 1 | 1 | 0 | 6 | 95 | 95 | 1 | −6 | 6 | 6 | 62 | 60 | 1 | 0 | 13 | 6 | 79 | 85 | 2 | 2 | −8 | 7 | 120 | 114 | 1 |
| −7 | −5 | 6 | 55 | 54 | 1 | 2 | 0 | 6 | 82 | 83 | 1 | −5 | 6 | 6 | 48 | 47 | 1 | 1 | 13 | 6 | 127 | 130 | 2 | 3 | −8 | 7 | 42 | 39 | 1 |
| −6 | −5 | 6 | 155 | 153 | 2 | 3 | 0 | 6 | 7 | 9 | 1 | −4 | 6 | 6 | 105 | 106 | 1 | 2 | 13 | 6 | 44 | 46 | 1 | 4 | −8 | 7 | 18 | 18 | 1 |
| −5 | −5 | 6 | 36 | 39 | 1 | 4 | 0 | 6 | 4 | 7 | 4 | −3 | 6 | 6 | 94 | 92 | 1 | 3 | 13 | 6 | 71 | 75 | 1 | 5 | −8 | 7 | 43 | 43 | 1 |
| −4 | −5 | 6 | 24 | 23 | 1 | 5 | 0 | 6 | 54 | 54 | 1 | −2 | 6 | 6 | 178 | 174 | 2 | −4 | 14 | 6 | 94 | 95 | 1 | −7 | −7 | 7 | 34 | 34 | 1 |
| −3 | −5 | 6 | 113 | 111 | 1 | 6 | 0 | 6 | 59 | 58 | 1 | −1 | 6 | 6 | 43 | 46 | 2 | −3 | 14 | 6 | 152 | 149 | 2 | −6 | −7 | 7 | 131 | 130 | 2 |
| −2 | −5 | 6 | 107 | 112 | 1 | 7 | 0 | 6 | 43 | 40 | 1 | 0 | 6 | 6 | 103 | 105 | 2 | −2 | 14 | 6 | 136 | 136 | 2 | −5 | −7 | 7 | 58 | 62 | 1 |
| −1 | −5 | 6 | 317 | 317 | 5 | −8 | 1 | 6 | 45 | 41 | 1 | 1 | 6 | 6 | 219 | 219 | 3 | 1 | 14 | 6 | 38 | 37 | 1 | −4 | −7 | 7 | 69 | 62 | 1 |
| 0 | −5 | 6 | 332 | 330 | 5 | −7 | 1 | 6 | 48 | 43 | 1 | 2 | 6 | 6 | 122 | 128 | 1 | 2 | 14 | 6 | 39 | 40 | 1 | −3 | −7 | 7 | 56 | 55 | 1 |
| 1 | −5 | 6 | 93 | 96 | 1 | −6 | 1 | 6 | 161 | 167 | 2 | 3 | 6 | 6 | 148 | 141 | 1 | 3 | 14 | 6 | 99 | 95 | 2 | −2 | −7 | 7 | 42 | 43 | 1 |
| 2 | −5 | 6 | 109 | 119 | 1 | −5 | 1 | 6 | 150 | 148 | 1 | 4 | 6 | 6 | 47 | 46 | 1 | −3 | 15 | 6 | 93 | 90 | 1 | −1 | −7 | 7 | 67 | 71 | 1 |
| 3 | −5 | 6 | 143 | 142 | 1 | −4 | 1 | 6 | 114 | 113 | 1 | 5 | 6 | 6 | 71 | 65 | 1 | 1 | 15 | 6 | 90 | 89 | 1 | 0 | −7 | 7 | 118 | 116 | 1 |
| 4 | −5 | 6 | 52 | 53 | 1 | −3 | 1 | 6 | 143 | 138 | 2 | 6 | 6 | 6 | 75 | 76 | 1 | 2 | 15 | 6 | 60 | 61 | 1 | 1 | −7 | 7 | 65 | 62 | 1 |
| 5 | −5 | 6 | 171 | 162 | 3 | −2 | 1 | 6 | 85 | 81 | 1 | −7 | 7 | 6 | 57 | 60 | 1 | −2 | −15 | 7 | 99 | 99 | 1 | 2 | −7 | 7 | 147 | 148 | 1 |
| 6 | −5 | 6 | 80 | 83 | 1 | −1 | 1 | 6 | 543 | 538 | 9 | −6 | 7 | 6 | 102 | 103 | 1 | −1 | −15 | 7 | 63 | 59 | 1 | 3 | −7 | 7 | 71 | 72 | 1 |
| −8 | −4 | 6 | 37 | 33 | 1 | 0 | 1 | 6 | 247 | 262 | 3 | −5 | 7 | 6 | 7 | 10 | 3 | 0 | −15 | 7 | 108 | 110 | 1 | 4 | −7 | 7 | 17 | 11 | 1 |
| −7 | −4 | 6 | 74 | 78 | 1 | 1 | 1 | 6 | 89 | 82 | 1 | −4 | 7 | 6 | 71 | 70 | 1 | 1 | −15 | 7 | 77 | 76 | 1 | 5 | −7 | 7 | 83 | 81 | 1 |
| −6 | −4 | 6 | 50 | 47 | 1 | 2 | 1 | 6 | 182 | 176 | 2 | −3 | 7 | 6 | 55 | 54 | 1 | −4 | −14 | 7 | 62 | 61 | 1 | 6 | −7 | 7 | 45 | 41 | 1 |
| −5 | −4 | 6 | 46 | 46 | 1 | 3 | 1 | 6 | 48 | 47 | 1 | −2 | 7 | 6 | 93 | 91 | 1 | −3 | −14 | 7 | 39 | 38 | 1 | −7 | −6 | 7 | 23 | 23 | 1 |
| −4 | −4 | 6 | 106 | 107 | 1 | 4 | 1 | 6 | 78 | 85 | 1 | −1 | 7 | 6 | 15 | 17 | 2 | −2 | −14 | 7 | 72 | 74 | 1 | −6 | −6 | 7 | 16 | 14 | 1 |
| −3 | −4 | 6 | 62 | 67 | 1 | 5 | 1 | 6 | 85 | 83 | 1 | 0 | 7 | 6 | 220 | 211 | 3 | −1 | −14 | 7 | 38 | 34 | 1 | −5 | −6 | 7 | 196 | 200 | 2 |
| −2 | −4 | 6 | 34 | 33 | 1 | 6 | 1 | 6 | 93 | 87 | 1 | 1 | 7 | 6 | 122 | 122 | 2 | 0 | −14 | 7 | 59 | 58 | 1 | −4 | −6 | 7 | 162 | 163 | 1 |
| −1 | −4 | 6 | 227 | 221 | 4 | 7 | 1 | 6 | 27 | 29 | 1 | 2 | 7 | 6 | 92 | 100 | 1 | 1 | −14 | 7 | 76 | 75 | 1 | −3 | −6 | 7 | 84 | 83 | 1 |
| 0 | −4 | 6 | 295 | 279 | 4 | −8 | 2 | 6 | 52 | 51 | 1 | 3 | 7 | 6 | 105 | 103 | 1 | 2 | −14 | 7 | 97 | 96 | 1 | −2 | −6 | 7 | 114 | 112 | 1 |
| 1 | −4 | 6 | 152 | 148 | 2 | −7 | 2 | 6 | 32 | 35 | 1 | 4 | 7 | 6 | 228 | 239 | 2 | −4 | −13 | 7 | 55 | 53 | 1 | −1 | −6 | 7 | 44 | 38 | 1 |
| 2 | −4 | 6 | 190 | 194 | 1 | −6 | 2 | 6 | 210 | 211 | 2 | 5 | 7 | 6 | 84 | 81 | 1 | −3 | −13 | 7 | 98 | 97 | 1 | 0 | −6 | 7 | 57 | 51 | 1 |
| 3 | −4 | 6 | 51 | 53 | 1 | −5 | 2 | 6 | 43 | 37 | 1 | 6 | 7 | 6 | 55 | 60 | 1 | −2 | −13 | 7 | 93 | 90 | 1 | 1 | −6 | 7 | 59 | 57 | 1 |
| 4 | −4 | 6 | 123 | 120 | 2 | −4 | 2 | 6 | 146 | 153 | 1 | −6 | 8 | 6 | 188 | 191 | 2 | −1 | −13 | 7 | 75 | 70 | 1 | 2 | −6 | 7 | 198 | 199 | 1 |
| 5 | −4 | 6 | 53 | 52 | 1 | −3 | 2 | 6 | 139 | 135 | 2 | −5 | 8 | 6 | 85 | 80 | 1 | 0 | −13 | 7 | 53 | 48 | 1 | 3 | −6 | 7 | 122 | 121 | 1 |
| 6 | −4 | 6 | 118 | 112 | 2 | −2 | 2 | 6 | 47 | 46 | 1 | −4 | 8 | 6 | 21 | 15 | 1 | 1 | −13 | 7 | 65 | 65 | 1 | 4 | −6 | 7 | 68 | 66 | 1 |
| −8 | −3 | 6 | 56 | 47 | 1 | −1 | 2 | 6 | 383 | 369 | 6 | −3 | 8 | 6 | 96 | 104 | 1 | 2 | −13 | 7 | 111 | 113 | 1 | 5 | −6 | 7 | 66 | 65 | 1 |
| −7 | −3 | 6 | 83 | 82 | 1 | 0 | 2 | 6 | 476 | 464 | 8 | −2 | 8 | 6 | 25 | 30 | 1 | 3 | −13 | 7 | 90 | 92 | 1 | 6 | −6 | 7 | 71 | 67 | 1 |
| −6 | −3 | 6 | 38 | 34 | 1 | 1 | 2 | 6 | 403 | 396 | 5 | −1 | 8 | 6 | 117 | 116 | 1 | −5 | −12 | 7 | 23 | 22 | 1 | −8 | −5 | 7 | 56 | 52 | 1 |
| −5 | −3 | 6 | 105 | 106 | 1 | 2 | 2 | 6 | 145 | 145 | 2 | 0 | 8 | 6 | 252 | 248 | 3 | −4 | −12 | 7 | 132 | 132 | 1 | −7 | −5 | 7 | 7 | 9 | 6 |
| −4 | −3 | 6 | 111 | 116 | 1 | 3 | 2 | 6 | 53 | 53 | 1 | 1 | 8 | 6 | 63 | 65 | 1 | −3 | −12 | 7 | 29 | 22 | 1 | −6 | −5 | 7 | 47 | 44 | 1 |
| −3 | −3 | 6 | 140 | 140 | 2 | 4 | 2 | 6 | 161 | 158 | 1 | 2 | 8 | 6 | 239 | 232 | 2 | −2 | −12 | 7 | 98 | 94 | 1 | −5 | −5 | 7 | 113 | 115 | 1 |
| −2 | −3 | 6 | 36 | 35 | 1 | 5 | 2 | 6 | 146 | 151 | 2 | 3 | 8 | 6 | 68 | 60 | 1 | −1 | −12 | 7 | 87 | 89 | 1 | −4 | −5 | 7 | 91 | 95 | 1 |
| −1 | −3 | 6 | 196 | 199 | 3 | 6 | 2 | 6 | 41 | 42 | 1 | 4 | 8 | 6 | 169 | 169 | 2 | 0 | −12 | 7 | 66 | 69 | 1 | −3 | −5 | 7 | 147 | 145 | 1 |
| 0 | −3 | 6 | 353 | 336 | 4 | 7 | 2 | 6 | 64 | 68 | 1 | 5 | 8 | 6 | 118 | 118 | 2 | 1 | −12 | 7 | 114 | 116 | 1 | −2 | −5 | 7 | 165 | 174 | 1 |
| 1 | −3 | 6 | 147 | 144 | 2 | −8 | 3 | 6 | 54 | 47 | 1 | −6 | 9 | 6 | 68 | 65 | 1 | 2 | −12 | 7 | 94 | 93 | 1 | −1 | −5 | 7 | 106 | 104 | 1 |
| 2 | −3 | 6 | 99 | 102 | 1 | −7 | 3 | 6 | 82 | 81 | 1 | −5 | 9 | 6 | 60 | 65 | 1 | 3 | −12 | 7 | 10 | 7 | 2 | 0 | −5 | 7 | 211 | 208 | 2 |
| 3 | −3 | 6 | 45 | 49 | 1 | −6 | 3 | 6 | 36 | 34 | 1 | −4 | 9 | 6 | 133 | 140 | 1 | 4 | −12 | 7 | 53 | 54 | 1 | 1 | −5 | 7 | 107 | 109 | 1 |
| 4 | −3 | 6 | 24 | 25 | 1 | −5 | 3 | 6 | 104 | 105 | 1 | −3 | 9 | 6 | 119 | 116 | 1 | −6 | −11 | 7 | 18 | 16 | 1 | 2 | −5 | 7 | 125 | 128 | 1 |
| 5 | −3 | 6 | 138 | 143 | 2 | −4 | 3 | 6 | 109 | 116 | 1 | −2 | 9 | 6 | 127 | 123 | 2 | −5 | −11 | 7 | 118 | 117 | 1 | 3 | −5 | 7 | 105 | 108 | 1 |
| 6 | −3 | 6 | 141 | 135 | 2 | −3 | 3 | 6 | 140 | 140 | 4 | −1 | 9 | 6 | 134 | 136 | 2 | −4 | −11 | 7 | 115 | 114 | 1 | 4 | −5 | 7 | 66 | 69 | 1 |
| 7 | −3 | 6 | 19 | 14 | 1 | −2 | 3 | 6 | 36 | 35 | 2 | 0 | 9 | 6 | 223 | 219 | 3 | −3 | −11 | 7 | 129 | 135 | 1 | 5 | −5 | 7 | 83 | 83 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −8 | −2 | 6 | 55 | 51 | 1 | −1 | 3 | 6 | 208 | 199 | 3 | 1 | 9 | 6 | 167 | 174 | 2 | −2 | −11 | 7 | 40 | 39 | 1 | 6 | −5 | 7 | 15 | 17 | 1 |
| −7 | −2 | 6 | 32 | 35 | 1 | 0 | 3 | 6 | 357 | 335 | 6 | 2 | 9 | 6 | 123 | 115 | 1 | −1 | −11 | 7 | 46 | 46 | 1 | −8 | −4 | 7 | 18 | 14 | 1 |
| −6 | −2 | 6 | 212 | 211 | 3 | 1 | 3 | 6 | 144 | 145 | 4 | 3 | 9 | 6 | 173 | 171 | 2 | 0 | −11 | 7 | 51 | 54 | 1 | −7 | −4 | 7 | 50 | 55 | 1 |
| −5 | −2 | 6 | 44 | 38 | 1 | 2 | 3 | 6 | 98 | 101 | 1 | 4 | 9 | 6 | 51 | 44 | 1 | 1 | −11 | 7 | 136 | 144 | 1 | −6 | −4 | 7 | 149 | 151 | 2 |
| −4 | −2 | 6 | 147 | 153 | 1 | 3 | 3 | 6 | 46 | 49 | 1 | 5 | 9 | 6 | 70 | 70 | 1 | 2 | −11 | 7 | 76 | 84 | 1 | −5 | −4 | 7 | 39 | 41 | 1 |
| −3 | −2 | 6 | 143 | 134 | 2 | 4 | 3 | 6 | 24 | 25 | 1 | −6 | 10 | 6 | 25 | 23 | 1 | 3 | −11 | 7 | 137 | 135 | 2 | −4 | −4 | 7 | 199 | 205 | 1 |
| −2 | −2 | 6 | 46 | 46 | 1 | 5 | 3 | 6 | 139 | 144 | 2 | −5 | 10 | 6 | 165 | 172 | 2 | 4 | −11 | 7 | 81 | 80 | 1 | −3 | −4 | 7 | 111 | 112 | 1 |
| −1 | −2 | 6 | 380 | 368 | 6 | 6 | 3 | 6 | 139 | 135 | 2 | −4 | 10 | 6 | 231 | 233 | 3 | −6 | −10 | 7 | 112 | 115 | 2 | −2 | −4 | 7 | 158 | 160 | 3 |
| 0 | −2 | 6 | 481 | 464 | 6 | 7 | 3 | 6 | 18 | 14 | 1 | −3 | 10 | 6 | 125 | 124 | 1 | −5 | −10 | 7 | 82 | 80 | 1 | −1 | −4 | 7 | 392 | 399 | 6 |
| 1 | −2 | 6 | 412 | 397 | 5 | −8 | 4 | 6 | 37 | 33 | 1 | −2 | 10 | 6 | 166 | 163 | 2 | −4 | −10 | 7 | 212 | 211 | 1 | 0 | −4 | 7 | 174 | 173 | 3 |
| 2 | −2 | 6 | 144 | 146 | 1 | −7 | 4 | 6 | 70 | 78 | 1 | −1 | 10 | 6 | 164 | 162 | 3 | −3 | −10 | 7 | 165 | 168 | 1 | 1 | −4 | 7 | 361 | 375 | 2 |
| 3 | −2 | 6 | 54 | 53 | 1 | −6 | 4 | 6 | 50 | 47 | 1 | 0 | 10 | 6 | 46 | 43 | 1 | −2 | −10 | 7 | 91 | 85 | 1 | 2 | −4 | 7 | 67 | 59 | 1 |
| 4 | −2 | 6 | 163 | 157 | 2 | −5 | 4 | 6 | 43 | 45 | 1 | 1 | 10 | 6 | 99 | 97 | 2 | −1 | −10 | 7 | 241 | 238 | 1 | 3 | −4 | 7 | 37 | 37 | 1 |
| 5 | −2 | 6 | 153 | 151 | 1 | −4 | 4 | 6 | 104 | 107 | 1 | 2 | 10 | 6 | 35 | 34 | 1 | 0 | −10 | 7 | 95 | 89 | 1 | 4 | −4 | 7 | 101 | 93 | 1 |
| 6 | −2 | 6 | 39 | 41 | 1 | −3 | 4 | 6 | 60 | 66 | 1 | 3 | 10 | 6 | 46 | 46 | 1 | 1 | −10 | 7 | 54 | 53 | 1 | 5 | −4 | 7 | 176 | 173 | 3 |
| 7 | −2 | 6 | 64 | 68 | 1 | −2 | 4 | 6 | 33 | 33 | 2 | 4 | 10 | 6 | 47 | 45 | 1 | 2 | −10 | 7 | 63 | 56 | 1 | 6 | −4 | 7 | 100 | 99 | 1 |
| −8 | −1 | 6 | 45 | 41 | 1 | −1 | 4 | 6 | 237 | 222 | 4 | 5 | 10 | 6 | 78 | 82 | 1 | 3 | −10 | 7 | 39 | 37 | 1 | −8 | −3 | 7 | 25 | 21 | 1 |
| −7 | −1 | 6 | 51 | 44 | 1 | 0 | 4 | 6 | 300 | 278 | 5 | −6 | 11 | 6 | 0 | 7 | 1 | 4 | −10 | 7 | 43 | 38 | 1 | −7 | −3 | 7 | 49 | 56 | 1 |
| −6 | −1 | 6 | 167 | 166 | 2 | 1 | 4 | 6 | 154 | 148 | 4 | −5 | 11 | 6 | 62 | 58 | 1 | 5 | −10 | 7 | 76 | 72 | 1 | −6 | −3 | 7 | 45 | 39 | 1 |
| −5 | −1 | 6 | 150 | 149 | 1 | 2 | 4 | 6 | 191 | 195 | 1 | −4 | 11 | 6 | 58 | 65 | 1 | −7 | −9 | 7 | 83 | 84 | 1 | −5 | −3 | 7 | 171 | 170 | 1 |
| −4 | −1 | 6 | 114 | 113 | 1 | 3 | 4 | 6 | 50 | 52 | 1 | −3 | 11 | 6 | 20 | 15 | 1 | −6 | −9 | 7 | 47 | 50 | 1 | −4 | −3 | 7 | 145 | 143 | 1 |
| −3 | −1 | 6 | 145 | 138 | 2 | 4 | 4 | 6 | 122 | 120 | 1 | −2 | 11 | 6 | 74 | 74 | 2 | −5 | −9 | 7 | 114 | 116 | 1 | −3 | −3 | 7 | 31 | 27 | 1 |
| −2 | −1 | 6 | 84 | 80 | 1 | 5 | 4 | 6 | 54 | 53 | 1 | 0 | 11 | 6 | 40 | 38 | 1 | −4 | −9 | 7 | 57 | 57 | 1 | −2 | −3 | 7 | 144 | 138 | 2 |
| −1 | −1 | 6 | 534 | 537 | 10 | 6 | 4 | 6 | 118 | 113 | 2 | 1 | 11 | 6 | 140 | 139 | 2 | −3 | −9 | 7 | 136 | 141 | 1 | −1 | −3 | 7 | 226 | 219 | 4 |
| 0 | −1 | 6 | 249 | 262 | 3 | 7 | 4 | 6 | 46 | 42 | 1 | 2 | 11 | 6 | 106 | 117 | 1 | −2 | −9 | 7 | 135 | 140 | 1 | 0 | −3 | 7 | 115 | 108 | 2 |
| 1 | −1 | 6 | 89 | 81 | 1 | −8 | 5 | 6 | 42 | 45 | 1 | 3 | 11 | 6 | 103 | 109 | 1 | −1 | −9 | 7 | 113 | 109 | 1 | 1 | −3 | 7 | 299 | 296 | 4 |
| 2 | −1 | 6 | 177 | 176 | 2 | −7 | 5 | 6 | 56 | 55 | 1 | 4 | 11 | 6 | 91 | 87 | 1 | 0 | −9 | 7 | 93 | 97 | 1 | 2 | −3 | 7 | 19 | 10 | 1 |
| 3 | −1 | 6 | 48 | 48 | 1 | −6 | 5 | 6 | 151 | 154 | 1 | 5 | 11 | 6 | 113 | 110 | 2 | 1 | −9 | 7 | 254 | 257 | 2 | 3 | −3 | 7 | 106 | 109 | 1 |
| 4 | −1 | 6 | 78 | 85 | 1 | −5 | 5 | 6 | 39 | 39 | 1 | −5 | 12 | 6 | 65 | 61 | 1 | 2 | −9 | 7 | 179 | 174 | 1 | 4 | −3 | 7 | 169 | 166 | 3 |
| 5 | −1 | 6 | 89 | 84 | 1 | −4 | 5 | 6 | 25 | 23 | 1 | −4 | 12 | 6 | 66 | 62 | 1 | 3 | −9 | 7 | 19 | 18 | 1 | 5 | −3 | 7 | 81 | 84 | 1 |
| 6 | −1 | 6 | 95 | 87 | 1 | −3 | 5 | 6 | 115 | 111 | 2 | −3 | 12 | 6 | 149 | 145 | 2 | 4 | −9 | 7 | 44 | 41 | 1 | 6 | −3 | 7 | 146 | 142 | 2 |
| 7 | −1 | 6 | 27 | 29 | 1 | −2 | 5 | 6 | 111 | 111 | 3 | −2 | 12 | 6 | 100 | 95 | 2 | 5 | −9 | 7 | 65 | 60 | 1 | −8 | −2 | 7 | 37 | 33 | 1 |
| −8 | 0 | 6 | 45 | 50 | 1 | −1 | 5 | 6 | 319 | 319 | 5 | 0 | 12 | 6 | 134 | 135 | 2 | −7 | −8 | 7 | 29 | 29 | 1 | −7 | −2 | 7 | 70 | 67 | 1 |
| −7 | 0 | 6 | 34 | 28 | 1 | 0 | 5 | 6 | 329 | 329 | 5 | 1 | 12 | 6 | 101 | 97 | 2 | −6 | −8 | 7 | 39 | 45 | 1 | −6 | −2 | 7 | 162 | 161 | 2 |
| −5 | −2 | 7 | 213 | 210 | 1 | −8 | 4 | 7 | 13 | 14 | 1 | 2 | 10 | 7 | 62 | 56 | 1 | 1 | −9 | 8 | 183 | 188 | 1 | 6 | −3 | 8 | 61 | 61 | 1 |
| −4 | −2 | 7 | 161 | 155 | 1 | −7 | 4 | 7 | 49 | 54 | 1 | 3 | 10 | 7 | 42 | 38 | 1 | 2 | −9 | 8 | 81 | 87 | 1 | −8 | −2 | 8 | 19 | 17 | 1 |
| −3 | −2 | 7 | 108 | 111 | 1 | −6 | 4 | 7 | 149 | 152 | 1 | 4 | 10 | 7 | 42 | 37 | 1 | 3 | −9 | 8 | 40 | 41 | 1 | −7 | −2 | 8 | 58 | 53 | 1 |
| −2 | −2 | 7 | 331 | 340 | 5 | −5 | 4 | 7 | 39 | 41 | 1 | 5 | 10 | 7 | 75 | 72 | 1 | 4 | −9 | 8 | 58 | 59 | 1 | −6 | −2 | 8 | 137 | 141 | 2 |
| −1 | −2 | 7 | 170 | 169 | 3 | −4 | 4 | 7 | 202 | 206 | 1 | −6 | 11 | 7 | 18 | 17 | 1 | 5 | −9 | 8 | 58 | 63 | 1 | −5 | −2 | 8 | 242 | 244 | 2 |
| 0 | −2 | 7 | 439 | 422 | 7 | −3 | 4 | 7 | 108 | 112 | 1 | −5 | 11 | 7 | 121 | 117 | 1 | −7 | −8 | 8 | 71 | 69 | 1 | −4 | −2 | 8 | 181 | 178 | 1 |
| 1 | −2 | 7 | 210 | 203 | 2 | −2 | 4 | 7 | 158 | 160 | 3 | −4 | 11 | 7 | 115 | 114 | 1 | −6 | −8 | 8 | 18 | 17 | 1 | −3 | −2 | 8 | 198 | 204 | 1 |
| 2 | −2 | 7 | 94 | 89 | 1 | −1 | 4 | 7 | 386 | 399 | 6 | −3 | 11 | 7 | 131 | 135 | 1 | −5 | −8 | 8 | 38 | 38 | 1 | −2 | −2 | 8 | 410 | 403 | 5 |
| 3 | −2 | 7 | 60 | 58 | 1 | 0 | 4 | 7 | 174 | 173 | 3 | −2 | 11 | 7 | 35 | 39 | 2 | −4 | −8 | 8 | 19 | 20 | 1 | −1 | −2 | 8 | 201 | 205 | 3 |
| 4 | −2 | 7 | 189 | 191 | 3 | 1 | 4 | 7 | 365 | 375 | 5 | 0 | 11 | 7 | 51 | 54 | 1 | −3 | −8 | 8 | 11 | 13 | 1 | 0 | −2 | 8 | 283 | 288 | 3 |
| 5 | −2 | 7 | 219 | 220 | 3 | 2 | 4 | 7 | 70 | 59 | 1 | 1 | 11 | 7 | 140 | 143 | 2 | −2 | −8 | 8 | 188 | 191 | 1 | 1 | −2 | 8 | 102 | 108 | 1 |
| 6 | −2 | 7 | 152 | 151 | 2 | 3 | 4 | 7 | 38 | 37 | 1 | 2 | 11 | 7 | 77 | 84 | 1 | −1 | −8 | 8 | 168 | 171 | 1 | 2 | −2 | 8 | 22 | 24 | 1 |
| −8 | −1 | 7 | 70 | 70 | 1 | 4 | 4 | 7 | 99 | 94 | 1 | 3 | 11 | 7 | 138 | 135 | 1 | 0 | −8 | 8 | 160 | 163 | 1 | 3 | −2 | 8 | 110 | 109 | 1 |
| −7 | −1 | 7 | 106 | 107 | 1 | 5 | 4 | 7 | 175 | 173 | 2 | 4 | 11 | 7 | 83 | 81 | 1 | 1 | −8 | 8 | 310 | 308 | 2 | 4 | −2 | 8 | 31 | 33 | 1 |
| −6 | −1 | 7 | 151 | 151 | 2 | 6 | 4 | 7 | 100 | 99 | 1 | −5 | 12 | 7 | 24 | 22 | 1 | 2 | −8 | 8 | 184 | 186 | 2 | 5 | −2 | 8 | 133 | 139 | 2 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −5 | −1 | 7 | 38 | 34 | 1 | −8 | 5 | 7 | 53 | 52 | 1 | −4 | 12 | 7 | 136 | 132 | 1 | 3 | −8 | 8 | 125 | 135 | 2 | 6 | −2 | 8 | 153 | 148 | 2 |
| −4 | −1 | 7 | 189 | 195 | 1 | −7 | 5 | 7 | 0 | 8 | 1 | −3 | 12 | 7 | 26 | 22 | 1 | 4 | −8 | 8 | 130 | 133 | 2 | −8 | −1 | 8 | 39 | 39 | 1 |
| −3 | −1 | 7 | 143 | 137 | 2 | −6 | 5 | 7 | 49 | 44 | 1 | −2 | 12 | 7 | 97 | 93 | 2 | 5 | −8 | 8 | 32 | 31 | 1 | −7 | −1 | 8 | 84 | 83 | 1 |
| −2 | −1 | 7 | 133 | 124 | 2 | −5 | 5 | 7 | 114 | 115 | 1 | 0 | 12 | 7 | 64 | 69 | 1 | −7 | −7 | 8 | 35 | 31 | 1 | −6 | −1 | 8 | 39 | 40 | 1 |
| −1 | −1 | 7 | 128 | 120 | 2 | −4 | 5 | 7 | 90 | 95 | 1 | 1 | 12 | 7 | 114 | 115 | 1 | −6 | −7 | 8 | 147 | 143 | 2 | −5 | −1 | 8 | 78 | 78 | 1 |
| 0 | −1 | 7 | 44 | 45 | 1 | −3 | 5 | 7 | 148 | 145 | 1 | 2 | 12 | 7 | 96 | 92 | 1 | −5 | −7 | 8 | 21 | 19 | 1 | −4 | −1 | 8 | 121 | 131 | 1 |
| 1 | −1 | 7 | 27 | 32 | 1 | −2 | 5 | 7 | 165 | 174 | 2 | 3 | 12 | 7 | 4 | 7 | 3 | −4 | −7 | 8 | 69 | 66 | 1 | −3 | −1 | 8 | 24 | 21 | 1 |
| 2 | −1 | 7 | 79 | 77 | 1 | −1 | 5 | 7 | 109 | 104 | 2 | 4 | 12 | 7 | 55 | 54 | 1 | −3 | −7 | 8 | 27 | 33 | 1 | −2 | −1 | 8 | 129 | 137 | 2 |
| 3 | −1 | 7 | 64 | 63 | 1 | 0 | 5 | 7 | 216 | 208 | 4 | −4 | 13 | 7 | 57 | 53 | 1 | −2 | −7 | 8 | 68 | 65 | 1 | −1 | −1 | 8 | 87 | 87 | 2 |
| 4 | −1 | 7 | 36 | 34 | 1 | 1 | 5 | 7 | 109 | 110 | 1 | −3 | 13 | 7 | 96 | 96 | 1 | −1 | −7 | 8 | 45 | 49 | 1 | 0 | −1 | 8 | 69 | 72 | 2 |
| 5 | −1 | 7 | 51 | 47 | 1 | 2 | 5 | 7 | 126 | 128 | 1 | −2 | 13 | 7 | 90 | 90 | 2 | 0 | −7 | 8 | 124 | 127 | 1 | 1 | −1 | 8 | 265 | 270 | 2 |
| 6 | −1 | 7 | 153 | 147 | 2 | 3 | 5 | 7 | 105 | 109 | 1 | 0 | 13 | 7 | 49 | 49 | 1 | 1 | −7 | 8 | 148 | 146 | 1 | 2 | −1 | 8 | 106 | 113 | 1 |
| −8 | 0 | 7 | 169 | 156 | 2 | 4 | 5 | 7 | 65 | 69 | 1 | 1 | 13 | 7 | 64 | 65 | 1 | 2 | −7 | 8 | 78 | 74 | 1 | 3 | −1 | 8 | 101 | 102 | 1 |
| −7 | 0 | 7 | 116 | 119 | 2 | 5 | 5 | 7 | 82 | 83 | 1 | 2 | 13 | 7 | 116 | 114 | 1 | 3 | −7 | 8 | 77 | 82 | 1 | 4 | −1 | 8 | 36 | 37 | 1 |
| −6 | 0 | 7 | 28 | 33 | 1 | 6 | 5 | 7 | 17 | 17 | 1 | 3 | 13 | 7 | 92 | 92 | 1 | 4 | −7 | 8 | 63 | 71 | 1 | 5 | −1 | 8 | 22 | 20 | 1 |
| −5 | 0 | 7 | 52 | 56 | 1 | −7 | 6 | 7 | 23 | 23 | 1 | −4 | 14 | 7 | 62 | 61 | 1 | 5 | −7 | 8 | 101 | 98 | 2 | 6 | −1 | 8 | 49 | 47 | 1 |
| −4 | 0 | 7 | 48 | 46 | 1 | −6 | 6 | 7 | 16 | 14 | 1 | −3 | 14 | 7 | 36 | 38 | 1 | −7 | −6 | 8 | 63 | 65 | 1 | −8 | 0 | 8 | 21 | 11 | 1 |
| −3 | 0 | 7 | 39 | 38 | 1 | −5 | 6 | 7 | 200 | 200 | 2 | −2 | 14 | 7 | 69 | 74 | 1 | −6 | −6 | 8 | 154 | 167 | 2 | −7 | 0 | 8 | 102 | 93 | 1 |
| −2 | 0 | 7 | 90 | 91 | 2 | −4 | 6 | 7 | 162 | 163 | 1 | 1 | 14 | 7 | 75 | 75 | 1 | −5 | −6 | 8 | 60 | 62 | 1 | −6 | 0 | 8 | 216 | 236 | 2 |
| −1 | 0 | 7 | 84 | 99 | 2 | −3 | 6 | 7 | 85 | 84 | 1 | 2 | 14 | 7 | 97 | 96 | 1 | −4 | −6 | 8 | 113 | 112 | 1 | −5 | 0 | 8 | 225 | 234 | 1 |
| 0 | 0 | 7 | 67 | 71 | 1 | −2 | 6 | 7 | 115 | 112 | 2 | 1 | 15 | 7 | 74 | 75 | 1 | −3 | −6 | 8 | 151 | 150 | 1 | −4 | 0 | 8 | 87 | 85 | 1 |
| 1 | 0 | 7 | 229 | 238 | 3 | −1 | 6 | 7 | 42 | 38 | 1 | −1 | −15 | 8 | 26 | 32 | 1 | −2 | −6 | 8 | 43 | 43 | 1 | −3 | 0 | 8 | 14 | 11 | 1 |
| 2 | 0 | 7 | 281 | 295 | 2 | 0 | 6 | 7 | 58 | 51 | 1 | −3 | −14 | 8 | 53 | 56 | 1 | −1 | −6 | 8 | 88 | 85 | 1 | −2 | 0 | 8 | 18 | 19 | 3 |
| 3 | 0 | 7 | 16 | 20 | 1 | 1 | 6 | 7 | 58 | 57 | 1 | −2 | −14 | 8 | 49 | 49 | 1 | 0 | −6 | 8 | 95 | 100 | 1 | −1 | 0 | 8 | 215 | 205 | 4 |
| 4 | 0 | 7 | 38 | 35 | 1 | 2 | 6 | 7 | 198 | 198 | 2 | −1 | −14 | 8 | 46 | 49 | 1 | 1 | −6 | 8 | 75 | 73 | 1 | 0 | 0 | 8 | 49 | 26 | 2 |
| 5 | 0 | 7 | 53 | 54 | 1 | 3 | 6 | 7 | 120 | 120 | 1 | 0 | −14 | 8 | 47 | 47 | 1 | 2 | −6 | 8 | 256 | 253 | 2 | 1 | 0 | 8 | 31 | 31 | 1 |
| 6 | 0 | 7 | 187 | 191 | 3 | 4 | 6 | 7 | 68 | 66 | 1 | 1 | −14 | 8 | 83 | 77 | 1 | 3 | −6 | 8 | 100 | 98 | 2 | 2 | 0 | 8 | 19 | 19 | 1 |
| −8 | 1 | 7 | 72 | 70 | 1 | 5 | 6 | 7 | 65 | 65 | 1 | −4 | −13 | 8 | 44 | 44 | 1 | 4 | −6 | 8 | 105 | 108 | 2 | 3 | 0 | 8 | 202 | 204 | 1 |
| −7 | 1 | 7 | 103 | 107 | 2 | 6 | 6 | 7 | 70 | 67 | 1 | −3 | −13 | 8 | 38 | 36 | 1 | 5 | −6 | 8 | 9 | 10 | 2 | 4 | 0 | 8 | 47 | 48 | 1 |
| −6 | 1 | 7 | 149 | 151 | 1 | −6 | 7 | 7 | 128 | 130 | 1 | −2 | −13 | 8 | 124 | 120 | 1 | −7 | −5 | 8 | 14 | 16 | 1 | 5 | 0 | 8 | 39 | 36 | 1 |
| −5 | 1 | 7 | 35 | 33 | 1 | −5 | 7 | 7 | 62 | 61 | 1 | −1 | −13 | 8 | 23 | 23 | 1 | −6 | −5 | 8 | 32 | 34 | 1 | 6 | 0 | 8 | 27 | 28 | 1 |
| −4 | 1 | 7 | 185 | 194 | 1 | −4 | 7 | 7 | 69 | 62 | 1 | 0 | −13 | 8 | 37 | 36 | 1 | −5 | −5 | 8 | 61 | 62 | 1 | −8 | 1 | 8 | 39 | 37 | 1 |
| −3 | 1 | 7 | 140 | 136 | 2 | −3 | 7 | 7 | 58 | 56 | 1 | 1 | −13 | 8 | 30 | 31 | 1 | −4 | −5 | 8 | 120 | 122 | 1 | −7 | 1 | 8 | 85 | 83 | 1 |
| −2 | 1 | 7 | 134 | 125 | 2 | −2 | 7 | 7 | 43 | 42 | 1 | 2 | −13 | 8 | 9 | 8 | 2 | −3 | −5 | 8 | 91 | 95 | 1 | −6 | 1 | 8 | 39 | 40 | 1 |
| −1 | 1 | 7 | 129 | 120 | 2 | −1 | 7 | 7 | 68 | 71 | 1 | −5 | −12 | 8 | 32 | 29 | 1 | −2 | −5 | 8 | 103 | 108 | 1 | −5 | 1 | 8 | 77 | 78 | 1 |
| 0 | 1 | 7 | 44 | 45 | 2 | 0 | 7 | 7 | 118 | 116 | 2 | −4 | −12 | 8 | 39 | 41 | 1 | −1 | −5 | 8 | 142 | 140 | 1 | −4 | 1 | 8 | 122 | 130 | 1 |
| 1 | 1 | 7 | 27 | 32 | 1 | 1 | 7 | 7 | 66 | 62 | 1 | −3 | −12 | 8 | 98 | 94 | 1 | 0 | −5 | 8 | 107 | 109 | 1 | −3 | 1 | 8 | 23 | 21 | 1 |
| 2 | 1 | 7 | 79 | 78 | 1 | 2 | 7 | 7 | 148 | 149 | 1 | −2 | −12 | 8 | 63 | 57 | 1 | 1 | −5 | 8 | 107 | 114 | 1 | −2 | 1 | 8 | 133 | 137 | 2 |
| 3 | 1 | 7 | 64 | 64 | 1 | 3 | 7 | 7 | 73 | 72 | 1 | −1 | −12 | 8 | 77 | 81 | 1 | 2 | −5 | 8 | 134 | 136 | 1 | −1 | 1 | 8 | 86 | 88 | 2 |
| 4 | 1 | 7 | 35 | 34 | 1 | 4 | 7 | 7 | 15 | 10 | 1 | 0 | −12 | 8 | 18 | 19 | 1 | 3 | −5 | 8 | 66 | 70 | 1 | 0 | 1 | 8 | 70 | 73 | 2 |
| 5 | 1 | 7 | 50 | 47 | 1 | 5 | 7 | 7 | 81 | 82 | 1 | 1 | −12 | 8 | 98 | 91 | 1 | 4 | −5 | 8 | 33 | 35 | 1 | 1 | 1 | 8 | 267 | 271 | 3 |
| 6 | 1 | 7 | 149 | 147 | 2 | −6 | 8 | 7 | 40 | 44 | 1 | 2 | −12 | 8 | 44 | 47 | 1 | 5 | −5 | 8 | 22 | 19 | 1 | 2 | 1 | 8 | 106 | 112 | 1 |
| −8 | 2 | 7 | 38 | 34 | 1 | −5 | 8 | 7 | 205 | 208 | 2 | 3 | −12 | 8 | 71 | 74 | 1 | 6 | −5 | 8 | 67 | 64 | 1 | 3 | 1 | 8 | 100 | 102 | 1 |
| −7 | 2 | 7 | 67 | 67 | 1 | −4 | 8 | 7 | 87 | 90 | 1 | −6 | −11 | 8 | 26 | 29 | 1 | −8 | −4 | 8 | 40 | 39 | 1 | 4 | 1 | 8 | 36 | 37 | 1 |
| −6 | 2 | 7 | 161 | 161 | 1 | −3 | 8 | 7 | 61 | 69 | 1 | −5 | −11 | 8 | 101 | 103 | 1 | −7 | −4 | 8 | 81 | 80 | 1 | 5 | 1 | 8 | 23 | 20 | 1 |
| −5 | 2 | 7 | 212 | 210 | 1 | −2 | 8 | 7 | 223 | 237 | 3 | −4 | −11 | 8 | 33 | 32 | 1 | −6 | −4 | 8 | 43 | 41 | 1 | 6 | 1 | 8 | 48 | 47 | 1 |
| −4 | 2 | 7 | 160 | 155 | 1 | −1 | 8 | 7 | 64 | 53 | 1 | −3 | −11 | 8 | 92 | 90 | 1 | −5 | −4 | 8 | 37 | 30 | 1 | −8 | 2 | 8 | 16 | 16 | 1 |
| −3 | 2 | 7 | 106 | 111 | 1 | 0 | 8 | 7 | 318 | 324 | 4 | −2 | −11 | 8 | 173 | 175 | 1 | −4 | −4 | 8 | 58 | 55 | 1 | −7 | 2 | 8 | 58 | 53 | 1 |
| −2 | 2 | 7 | 330 | 340 | 5 | 1 | 8 | 7 | 399 | 401 | 6 | −1 | −11 | 8 | 89 | 103 | 1 | −3 | −4 | 8 | 127 | 133 | 1 | −6 | 2 | 8 | 146 | 142 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | 2 | 7 | 173 | 169 | 3 | 2 | 8 | 7 | 120 | 115 | 1 | 0 | −11 | 8 | 133 | 132 | 1 | −2 | −4 | 8 | 17 | 20 | 1 | −5 | 2 | 8 | 240 | 244 | 2 |
| 0 | 2 | 7 | 447 | 421 | 7 | 3 | 8 | 7 | 43 | 39 | 1 | 1 | −11 | 8 | 55 | 60 | 1 | −1 | −4 | 8 | 70 | 80 | 1 | −4 | 2 | 8 | 181 | 178 | 1 |
| 1 | 2 | 7 | 210 | 203 | 5 | 4 | 8 | 7 | 19 | 18 | 1 | 2 | −11 | 8 | 79 | 79 | 1 | 0 | −4 | 8 | 200 | 201 | 1 | −3 | 2 | 8 | 198 | 204 | 1 |
| 2 | 2 | 7 | 93 | 89 | 1 | 5 | 8 | 7 | 42 | 43 | 1 | 3 | −11 | 8 | 0 | 7 | 1 | 1 | −4 | 8 | 64 | 62 | 1 | −2 | 2 | 8 | 400 | 403 | 5 |
| 3 | 2 | 7 | 59 | 58 | 1 | −6 | 9 | 7 | 47 | 50 | 1 | 4 | −11 | 8 | 22 | 26 | 1 | 2 | −4 | 8 | 150 | 147 | 1 | −1 | 2 | 8 | 203 | 204 | 3 |
| 4 | 2 | 7 | 187 | 191 | 1 | −5 | 9 | 7 | 118 | 117 | 1 | −6 | −10 | 8 | 44 | 45 | 1 | 3 | −4 | 8 | 83 | 80 | 1 | 0 | 2 | 8 | 280 | 288 | 5 |
| 5 | 2 | 7 | 199 | 220 | 2 | −4 | 9 | 7 | 57 | 58 | 1 | −5 | −10 | 8 | 70 | 73 | 1 | 4 | −4 | 8 | 104 | 104 | 2 | 1 | 2 | 8 | 102 | 107 | 1 |
| 6 | 2 | 7 | 151 | 151 | 1 | −3 | 9 | 7 | 137 | 141 | 1 | −4 | −10 | 8 | 66 | 69 | 1 | 5 | −4 | 8 | 150 | 147 | 2 | 2 | 2 | 8 | 22 | 25 | 1 |
| −8 | 3 | 7 | 26 | 21 | 1 | −2 | 9 | 7 | 133 | 140 | 2 | −3 | −10 | 8 | 101 | 100 | 1 | 6 | −4 | 8 | 116 | 109 | 2 | 3 | 2 | 8 | 109 | 109 | 1 |
| −7 | 3 | 7 | 49 | 56 | 1 | −1 | 9 | 7 | 111 | 110 | 2 | −2 | −10 | 8 | 53 | 58 | 1 | −8 | −3 | 8 | 29 | 28 | 1 | 4 | 2 | 8 | 33 | 32 | 1 |
| −6 | 3 | 7 | 47 | 39 | 1 | 0 | 9 | 7 | 88 | 97 | 1 | −1 | −10 | 8 | 175 | 167 | 1 | −7 | −3 | 8 | 50 | 51 | 1 | 5 | 2 | 8 | 134 | 138 | 2 |
| −5 | 3 | 7 | 172 | 171 | 1 | 1 | 9 | 7 | 253 | 257 | 3 | 0 | −10 | 8 | 126 | 131 | 1 | −6 | −3 | 8 | 140 | 150 | 2 | 6 | 2 | 8 | 149 | 148 | 2 |
| −4 | 3 | 7 | 145 | 143 | 1 | 2 | 9 | 7 | 179 | 174 | 2 | 1 | −10 | 8 | 71 | 69 | 1 | −5 | −3 | 8 | 161 | 165 | 1 | −8 | 3 | 8 | 29 | 28 | 1 |
| −3 | 3 | 7 | 30 | 27 | 1 | 3 | 9 | 7 | 21 | 18 | 1 | 2 | −10 | 8 | 46 | 50 | 1 | −4 | −3 | 8 | 145 | 157 | 1 | −7 | 3 | 8 | 49 | 51 | 1 |
| −2 | 3 | 7 | 145 | 138 | 2 | 4 | 9 | 7 | 44 | 42 | 1 | 3 | −10 | 8 | 116 | 116 | 2 | −3 | −3 | 8 | 127 | 130 | 1 | −6 | 3 | 8 | 152 | 149 | 1 |
| −1 | 3 | 7 | 224 | 219 | 4 | 5 | 9 | 7 | 64 | 61 | 1 | 4 | −10 | 8 | 28 | 30 | 1 | −2 | −3 | 8 | 116 | 115 | 1 | −5 | 3 | 8 | 160 | 166 | 1 |
| 0 | 3 | 7 | 115 | 108 | 2 | −6 | 10 | 7 | 113 | 115 | 1 | −6 | −9 | 8 | 35 | 35 | 1 | −1 | −3 | 8 | 323 | 314 | 4 | −4 | 3 | 8 | 148 | 157 | 1 |
| 1 | 3 | 7 | 304 | 297 | 7 | −5 | 10 | 7 | 80 | 79 | 1 | −5 | −9 | 8 | 158 | 156 | 2 | 0 | −3 | 8 | 147 | 147 | 2 | −3 | 3 | 8 | 126 | 130 | 1 |
| 2 | 3 | 7 | 15 | 11 | 1 | −4 | 10 | 7 | 208 | 211 | 2 | −4 | −9 | 8 | 110 | 113 | 1 | 1 | −3 | 8 | 150 | 148 | 1 | −2 | 3 | 8 | 115 | 114 | 1 |
| 3 | 3 | 7 | 105 | 109 | 1 | −3 | 10 | 7 | 164 | 168 | 2 | −3 | −9 | 8 | 71 | 75 | 1 | 2 | −3 | 8 | 181 | 182 | 1 | −1 | 3 | 8 | 321 | 314 | 5 |
| 4 | 3 | 7 | 172 | 166 | 1 | −2 | 10 | 7 | 91 | 85 | 2 | −2 | −9 | 8 | 227 | 236 | 1 | 3 | −3 | 8 | 76 | 78 | 1 | 0 | 3 | 8 | 148 | 146 | 2 |
| 5 | 3 | 7 | 75 | 85 | 1 | 0 | 10 | 7 | 94 | 89 | 2 | −1 | −9 | 8 | 23 | 22 | 1 | 4 | −3 | 8 | 226 | 250 | 4 | 1 | 3 | 8 | 152 | 148 | 1 |
| 6 | 3 | 7 | 146 | 143 | 1 | 1 | 10 | 7 | 54 | 53 | 1 | 0 | −9 | 8 | 97 | 98 | 1 | 5 | −3 | 8 | 26 | 26 | 1 | 2 | 3 | 8 | 181 | 183 | 1 |
| 3 | 3 | 8 | 77 | 79 | 1 | 4 | 10 | 8 | 30 | 30 | 1 | −7 | −7 | 9 | 47 | 47 | 1 | −1 | −1 | 9 | 152 | 144 | 1 | 0 | 5 | 9 | 51 | 50 | 1 |
| 4 | 3 | 8 | 246 | 249 | 2 | −5 | 11 | 8 | 102 | 103 | 1 | −6 | −7 | 9 | 47 | 50 | 1 | 0 | −1 | 9 | 153 | 158 | 1 | 1 | 5 | 9 | 104 | 111 | 1 |
| 5 | 3 | 8 | 27 | 27 | 1 | −4 | 11 | 8 | 33 | 32 | 1 | −5 | −7 | 9 | 103 | 104 | 2 | 1 | −1 | 9 | 179 | 190 | 1 | 2 | 5 | 9 | 93 | 93 | 1 |
| 6 | 3 | 8 | 58 | 60 | 1 | −3 | 11 | 8 | 94 | 90 | 2 | −4 | −7 | 9 | 106 | 105 | 1 | 2 | −1 | 9 | 111 | 110 | 1 | 3 | 5 | 9 | 60 | 58 | 1 |
| −8 | 4 | 8 | 39 | 38 | 1 | −2 | 11 | 8 | 173 | 175 | 3 | −3 | −7 | 9 | 71 | 69 | 1 | 3 | −1 | 9 | 56 | 55 | 1 | 4 | 5 | 9 | 126 | 130 | 1 |
| −7 | 4 | 8 | 80 | 80 | 1 | 0 | 11 | 8 | 131 | 133 | 2 | −2 | −7 | 9 | 170 | 168 | 1 | 4 | −1 | 9 | 78 | 81 | 1 | 5 | 5 | 9 | 53 | 52 | 1 |
| −6 | 4 | 8 | 46 | 40 | 1 | 1 | 11 | 8 | 58 | 61 | 1 | −1 | −7 | 9 | 111 | 107 | 1 | 5 | −1 | 9 | 81 | 80 | 1 | −6 | 6 | 9 | 31 | 32 | 1 |
| −5 | 4 | 8 | 36 | 29 | 1 | 2 | 11 | 8 | 79 | 79 | 1 | 0 | −7 | 9 | 127 | 130 | 1 | 6 | −1 | 9 | 99 | 100 | 1 | −5 | 6 | 9 | 155 | 157 | 2 |
| −4 | 4 | 8 | 58 | 55 | 1 | 3 | 11 | 8 | 2 | 7 | 2 | 1 | −7 | 9 | 33 | 37 | 1 | −8 | 0 | 9 | 129 | 128 | 2 | −4 | 6 | 9 | 64 | 67 | 1 |
| −3 | 4 | 8 | 127 | 133 | 1 | 4 | 11 | 8 | 21 | 26 | 1 | 2 | −7 | 9 | 145 | 144 | 1 | −7 | 0 | 9 | 80 | 86 | 1 | −3 | 6 | 9 | 37 | 39 | 1 |
| −2 | 4 | 8 | 17 | 19 | 2 | −5 | 12 | 8 | 31 | 29 | 1 | 3 | −7 | 9 | 123 | 127 | 2 | −6 | 0 | 9 | 124 | 123 | 1 | −2 | 6 | 9 | 28 | 33 | 1 |
| −1 | 4 | 8 | 69 | 79 | 2 | −4 | 12 | 8 | 37 | 40 | 1 | 4 | −7 | 9 | 39 | 39 | 1 | −5 | 0 | 9 | 151 | 158 | 1 | −1 | 6 | 9 | 110 | 111 | 1 |
| 0 | 4 | 8 | 207 | 201 | 2 | −3 | 12 | 8 | 95 | 93 | 1 | 5 | −7 | 9 | 97 | 97 | 1 | −4 | 0 | 9 | 132 | 141 | 1 | 0 | 6 | 9 | 219 | 217 | 3 |
| 1 | 4 | 8 | 64 | 62 | 1 | −2 | 12 | 8 | 65 | 57 | 1 | −7 | −6 | 9 | 65 | 58 | 1 | −3 | 0 | 9 | 16 | 18 | 1 | 1 | 6 | 9 | 89 | 93 | 1 |
| 2 | 4 | 8 | 151 | 147 | 1 | 0 | 12 | 8 | 19 | 19 | 2 | −6 | −6 | 9 | 37 | 32 | 1 | −2 | 0 | 9 | 160 | 183 | 1 | 2 | 6 | 9 | 121 | 119 | 1 |
| 3 | 4 | 8 | 81 | 79 | 1 | 1 | 12 | 8 | 98 | 91 | 1 | −5 | −6 | 9 | 152 | 156 | 1 | −1 | 0 | 9 | 27 | 25 | 1 | 3 | 6 | 9 | 68 | 66 | 1 |
| 4 | 4 | 8 | 106 | 104 | 1 | 2 | 12 | 8 | 44 | 46 | 1 | −4 | −6 | 9 | 65 | 67 | 1 | 0 | 0 | 9 | 321 | 321 | 3 | 4 | 6 | 9 | 61 | 61 | 1 |
| 5 | 4 | 8 | 148 | 147 | 2 | 3 | 12 | 8 | 72 | 73 | 1 | −3 | −6 | 9 | 37 | 39 | 1 | 1 | 0 | 9 | 60 | 65 | 1 | −6 | 7 | 9 | 48 | 50 | 1 |
| 6 | 4 | 8 | 110 | 109 | 2 | −4 | 13 | 8 | 44 | 43 | 1 | −2 | −6 | 9 | 30 | 34 | 1 | 2 | 0 | 9 | 171 | 181 | 1 | −5 | 7 | 9 | 105 | 104 | 1 |
| −7 | 5 | 8 | 7 | 16 | 7 | −3 | 13 | 8 | 39 | 36 | 1 | −1 | −6 | 9 | 112 | 111 | 1 | 3 | 0 | 9 | 133 | 137 | 1 | −4 | 7 | 9 | 104 | 105 | 1 |
| −6 | 5 | 8 | 36 | 34 | 1 | −2 | 13 | 8 | 117 | 120 | 2 | 0 | −6 | 9 | 222 | 217 | 1 | 4 | 0 | 9 | 59 | 55 | 1 | −3 | 7 | 9 | 72 | 70 | 2 |
| −5 | 5 | 8 | 58 | 61 | 1 | 0 | 13 | 8 | 37 | 36 | 1 | 1 | −6 | 9 | 89 | 93 | 1 | 5 | 0 | 9 | 219 | 217 | 4 | −2 | 7 | 9 | 167 | 169 | 3 |
| −4 | 5 | 8 | 122 | 121 | 1 | 1 | 13 | 8 | 30 | 30 | 1 | 2 | −6 | 9 | 125 | 119 | 1 | 6 | 0 | 9 | 104 | 110 | 2 | −1 | 7 | 9 | 109 | 107 | 1 |
| −3 | 5 | 8 | 93 | 95 | 1 | 2 | 13 | 8 | 9 | 8 | 2 | 3 | −6 | 9 | 65 | 66 | 1 | −8 | 1 | 9 | 37 | 32 | 1 | 0 | 7 | 9 | 127 | 129 | 2 |
| −2 | 5 | 8 | 104 | 108 | 1 | −3 | 14 | 8 | 52 | 56 | 1 | 4 | −6 | 9 | 60 | 62 | 1 | −7 | 1 | 9 | 86 | 86 | 1 | 1 | 7 | 9 | 35 | 37 | 1 |
| −1 | 5 | 8 | 139 | 140 | 1 | 1 | 14 | 8 | 80 | 77 | 1 | 5 | −6 | 9 | 49 | 48 | 1 | −6 | 1 | 9 | 127 | 126 | 1 | 2 | 7 | 9 | 135 | 144 | 2 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | 5 | 8 | 108 | 109 | 1 | −2 | −14 | 9 | 26 | 27 | 1 | −7 | −5 | 9 | 44 | 41 | 1 | −5 | 1 | 9 | 122 | 122 | 1 | 3 | 7 | 9 | 126 | 127 | 1 |
| 1 | 5 | 8 | 105 | 114 | 1 | −1 | −14 | 9 | 7 | 9 | 2 | −6 | −5 | 9 | 143 | 148 | 2 | −4 | 1 | 9 | 47 | 48 | 1 | 4 | 7 | 9 | 38 | 39 | 1 |
| 2 | 5 | 8 | 137 | 136 | 1 | 0 | −14 | 9 | 55 | 51 | 1 | −5 | −5 | 9 | 91 | 92 | 1 | −3 | 1 | 9 | 76 | 77 | 1 | −6 | 8 | 9 | 80 | 76 | 1 |
| 3 | 5 | 8 | 66 | 70 | 1 | −4 | −13 | 9 | 56 | 56 | 1 | −4 | −5 | 9 | 232 | 236 | 1 | −2 | 1 | 9 | 185 | 186 | 2 | −5 | 8 | 9 | 84 | 84 | 1 |
| 4 | 5 | 8 | 34 | 35 | 1 | −3 | −13 | 9 | 15 | 14 | 1 | −3 | −5 | 9 | 40 | 38 | 1 | −1 | 1 | 9 | 152 | 144 | 1 | −4 | 8 | 9 | 104 | 108 | 2 |
| 5 | 5 | 8 | 21 | 19 | 1 | −2 | −13 | 9 | 45 | 46 | 1 | −2 | −5 | 9 | 9 | 13 | 1 | 0 | 1 | 9 | 153 | 158 | 1 | −3 | 8 | 9 | 88 | 88 | 1 |
| 6 | 5 | 8 | 64 | 64 | 1 | −1 | −13 | 9 | 26 | 26 | 1 | −1 | −5 | 9 | 120 | 115 | 1 | 1 | 1 | 9 | 179 | 190 | 1 | −2 | 8 | 9 | 107 | 108 | 2 |
| −7 | 6 | 8 | 58 | 66 | 1 | 0 | −13 | 9 | 96 | 95 | 1 | 0 | −5 | 9 | 50 | 49 | 1 | 2 | 1 | 9 | 111 | 110 | 1 | −1 | 8 | 9 | 60 | 61 | 1 |
| −6 | 6 | 8 | 160 | 166 | 1 | 1 | −13 | 9 | 55 | 51 | 1 | 1 | −5 | 9 | 104 | 112 | 1 | 3 | 1 | 9 | 57 | 55 | 1 | 0 | 8 | 9 | 115 | 121 | 2 |
| −5 | 6 | 8 | 64 | 63 | 1 | 2 | −13 | 9 | 36 | 36 | 1 | 2 | −5 | 9 | 94 | 93 | 1 | 4 | 1 | 9 | 76 | 81 | 1 | 1 | 8 | 9 | 170 | 169 | 2 |
| −4 | 6 | 8 | 116 | 113 | 1 | −4 | −12 | 9 | 71 | 71 | 1 | 3 | −5 | 9 | 56 | 57 | 1 | 5 | 1 | 9 | 83 | 81 | 1 | 2 | 8 | 9 | 184 | 200 | 2 |
| −3 | 6 | 8 | 151 | 150 | 2 | −3 | −12 | 9 | 102 | 101 | 1 | 4 | −5 | 9 | 122 | 130 | 2 | 6 | 1 | 9 | 97 | 101 | 1 | 3 | 8 | 9 | 45 | 46 | 1 |
| −2 | 6 | 8 | 45 | 43 | 1 | −2 | −12 | 9 | 68 | 67 | 1 | 5 | −5 | 9 | 51 | 52 | 1 | −8 | 2 | 9 | 19 | 20 | 1 | 4 | 8 | 9 | 62 | 64 | 1 |
| −1 | 6 | 8 | 86 | 85 | 1 | −1 | −12 | 9 | 68 | 68 | 1 | −7 | −4 | 9 | 45 | 45 | 1 | −7 | 2 | 9 | 64 | 66 | 1 | −6 | 9 | 9 | 31 | 32 | 1 |
| 0 | 6 | 8 | 95 | 100 | 1 | 0 | −12 | 9 | 35 | 33 | 1 | −6 | −4 | 9 | 35 | 37 | 1 | −6 | 2 | 9 | 51 | 46 | 1 | −5 | 9 | 9 | 24 | 23 | 1 |
| 1 | 6 | 8 | 76 | 73 | 1 | 1 | −12 | 9 | 35 | 32 | 1 | −5 | −4 | 9 | 259 | 258 | 3 | −5 | 2 | 9 | 70 | 73 | 1 | −4 | 9 | 9 | 120 | 122 | 1 |
| 2 | 6 | 8 | 257 | 252 | 3 | 2 | −12 | 9 | 70 | 64 | 1 | −4 | −4 | 9 | 50 | 53 | 1 | −4 | 2 | 9 | 149 | 150 | 1 | −3 | 9 | 9 | 166 | 171 | 2 |
| 3 | 6 | 8 | 100 | 98 | 1 | −5 | −11 | 9 | 40 | 43 | 1 | −3 | −4 | 9 | 4 | 8 | 4 | −3 | 2 | 9 | 130 | 135 | 1 | −2 | 9 | 9 | 122 | 120 | 2 |
| 4 | 6 | 8 | 107 | 108 | 1 | −4 | −11 | 9 | 22 | 22 | 1 | −2 | −4 | 9 | 88 | 85 | 1 | −2 | 2 | 9 | 127 | 124 | 1 | −1 | 9 | 9 | 313 | 322 | 6 |
| 5 | 6 | 8 | 2 | 10 | 2 | −3 | −11 | 9 | 56 | 55 | 1 | −1 | −4 | 9 | 131 | 130 | 1 | −1 | 2 | 9 | 399 | 391 | 4 | 0 | 9 | 9 | 93 | 98 | 2 |
| −6 | 7 | 8 | 147 | 143 | 1 | −2 | −11 | 9 | 16 | 21 | 1 | 0 | −4 | 9 | 209 | 207 | 1 | 0 | 2 | 9 | 151 | 145 | 1 | 1 | 9 | 9 | 144 | 154 | 2 |
| −5 | 7 | 8 | 20 | 20 | 1 | −1 | −11 | 9 | 84 | 84 | 1 | 1 | −4 | 9 | 176 | 182 | 1 | 1 | 2 | 9 | 211 | 208 | 2 | 2 | 9 | 9 | 31 | 30 | 1 |
| −4 | 7 | 8 | 66 | 65 | 1 | 0 | −11 | 9 | 83 | 82 | 1 | 2 | −4 | 9 | 154 | 156 | 1 | 2 | 2 | 9 | 228 | 231 | 1 | 3 | 9 | 9 | 51 | 49 | 1 |
| −3 | 7 | 8 | 27 | 33 | 1 | 1 | −11 | 9 | 99 | 101 | 1 | 3 | −4 | 9 | 89 | 87 | 1 | 3 | 2 | 9 | 37 | 40 | 1 | 4 | 9 | 9 | 42 | 39 | 1 |
| −2 | 7 | 8 | 67 | 65 | 1 | 2 | −11 | 9 | 138 | 140 | 2 | 4 | −4 | 9 | 69 | 77 | 1 | 4 | 2 | 9 | 58 | 55 | 1 | −6 | 10 | 9 | 28 | 26 | 1 |
| −1 | 7 | 8 | 44 | 49 | 1 | 3 | −11 | 9 | 48 | 49 | 1 | 5 | −4 | 9 | 123 | 122 | 2 | 5 | 2 | 9 | 80 | 79 | 1 | −5 | 10 | 9 | 41 | 38 | 1 |
| 0 | 7 | 8 | 126 | 128 | 2 | −6 | −10 | 9 | 29 | 26 | 1 | −8 | −3 | 9 | 62 | 58 | 1 | 6 | 2 | 9 | 53 | 53 | 1 | −4 | 10 | 9 | 122 | 122 | 1 |
| 1 | 7 | 8 | 148 | 146 | 1 | −5 | −10 | 9 | 41 | 38 | 1 | −7 | −3 | 9 | 66 | 58 | 1 | −7 | 3 | 9 | 65 | 59 | 1 | −3 | 10 | 9 | 42 | 46 | 1 |
| 2 | 7 | 8 | 77 | 75 | 1 | −4 | −10 | 9 | 120 | 122 | 1 | −5 | −3 | 9 | 227 | 224 | 2 | −6 | 3 | 9 | 151 | 151 | 1 | −2 | 10 | 9 | 66 | 72 | 2 |
| 3 | 7 | 8 | 85 | 82 | 1 | −3 | −10 | 9 | 44 | 45 | 1 | −4 | −3 | 9 | 154 | 160 | 1 | −5 | 3 | 9 | 224 | 223 | 2 | 0 | 10 | 9 | 95 | 96 | 2 |
| 4 | 7 | 8 | 66 | 71 | 1 | −2 | −10 | 9 | 68 | 71 | 1 | −3 | −3 | 9 | 61 | 62 | 1 | −4 | 3 | 9 | 156 | 160 | 1 | 1 | 10 | 9 | 100 | 107 | 1 |
| −6 | 8 | 8 | 19 | 17 | 1 | −1 | −10 | 9 | 89 | 88 | 1 | −2 | −3 | 9 | 161 | 167 | 1 | −3 | 3 | 9 | 62 | 63 | 1 | 2 | 10 | 9 | 91 | 86 | 1 |
| −5 | 8 | 8 | 36 | 37 | 1 | 0 | −10 | 9 | 96 | 96 | 1 | −1 | −3 | 9 | 32 | 37 | 1 | −2 | 3 | 9 | 162 | 167 | 1 | 3 | 10 | 9 | 64 | 63 | 1 |
| −4 | 8 | 8 | 18 | 20 | 1 | 1 | −10 | 9 | 99 | 107 | 1 | 0 | −3 | 9 | 69 | 78 | 1 | −1 | 3 | 9 | 32 | 37 | 1 | 4 | 10 | 9 | 46 | 45 | 1 |
| −3 | 8 | 8 | 8 | 13 | 5 | 2 | −10 | 9 | 91 | 86 | 1 | 1 | −3 | 9 | 175 | 181 | 1 | 0 | 3 | 9 | 68 | 77 | 1 | −5 | 11 | 9 | 45 | 43 | 1 |
| −2 | 8 | 8 | 188 | 190 | 3 | 3 | −10 | 9 | 63 | 63 | 1 | 2 | −3 | 9 | 141 | 148 | 1 | 1 | 3 | 9 | 176 | 181 | 2 | −4 | 11 | 9 | 21 | 22 | 1 |
| −1 | 8 | 8 | 166 | 171 | 2 | 4 | −10 | 9 | 44 | 45 | 1 | 3 | −3 | 9 | 47 | 45 | 1 | 2 | 3 | 9 | 143 | 149 | 1 | −3 | 11 | 9 | 55 | 55 | 1 |
| 0 | 8 | 8 | 161 | 163 | 2 | −6 | −9 | 9 | 32 | 32 | 1 | 5 | −3 | 9 | 165 | 161 | 3 | 3 | 3 | 9 | 49 | 46 | 1 | −2 | 11 | 9 | 17 | 20 | 3 |
| 1 | 8 | 8 | 308 | 308 | 4 | −5 | −9 | 9 | 25 | 23 | 1 | 6 | −3 | 9 | 76 | 74 | 1 | 4 | 3 | 9 | 52 | 45 | 1 | 0 | 11 | 9 | 81 | 83 | 2 |
| 2 | 8 | 8 | 180 | 186 | 2 | −4 | −9 | 9 | 123 | 122 | 1 | −8 | −2 | 9 | 19 | 19 | 1 | 5 | 3 | 9 | 165 | 161 | 3 | 1 | 11 | 9 | 98 | 101 | 1 |
| 3 | 8 | 8 | 135 | 135 | 1 | −3 | −9 | 9 | 166 | 171 | 1 | −7 | −2 | 9 | 64 | 66 | 1 | 6 | 3 | 9 | 75 | 74 | 1 | 2 | 11 | 9 | 143 | 140 | 1 |
| 4 | 8 | 8 | 128 | 133 | 1 | −2 | −9 | 9 | 122 | 120 | 1 | −6 | −2 | 9 | 48 | 46 | 1 | −7 | 4 | 9 | 44 | 44 | 1 | 3 | 11 | 9 | 49 | 50 | 1 |
| −6 | 9 | 8 | 36 | 35 | 1 | −1 | −9 | 9 | 319 | 322 | 2 | −5 | −2 | 9 | 70 | 73 | 1 | −6 | 4 | 9 | 38 | 37 | 1 | −4 | 12 | 9 | 71 | 70 | 1 |
| −5 | 9 | 8 | 157 | 156 | 2 | 0 | −9 | 9 | 95 | 99 | 1 | −4 | −2 | 9 | 148 | 150 | 1 | −5 | 4 | 9 | 256 | 257 | 5 | −3 | 12 | 9 | 103 | 100 | 1 |
| −4 | 9 | 8 | 109 | 113 | 2 | 1 | −9 | 9 | 144 | 155 | 1 | −3 | −2 | 9 | 129 | 135 | 1 | −4 | 4 | 9 | 49 | 53 | 1 | −2 | 12 | 9 | 65 | 66 | 2 |
| −3 | 9 | 8 | 72 | 75 | 1 | 2 | −9 | 9 | 30 | 29 | 1 | −2 | −2 | 9 | 128 | 124 | 1 | −3 | 4 | 9 | 6 | 8 | 6 | 0 | 12 | 9 | 33 | 33 | 1 |
| −2 | 9 | 8 | 232 | 235 | 4 | 3 | −9 | 9 | 51 | 50 | 1 | −1 | −2 | 9 | 407 | 391 | 4 | −2 | 4 | 9 | 85 | 85 | 1 | 1 | 12 | 9 | 35 | 32 | 1 |
| 0 | 9 | 8 | 98 | 99 | 2 | 4 | −9 | 9 | 41 | 39 | 1 | 0 | −2 | 9 | 152 | 145 | 1 | −1 | 4 | 9 | 127 | 129 | 1 | 2 | 12 | 9 | 70 | 64 | 1 |
| 1 | 9 | 8 | 186 | 188 | 2 | −7 | −8 | 9 | 19 | 20 | 1 | 1 | −2 | 9 | 210 | 207 | 1 | 0 | 4 | 9 | 214 | 208 | 3 | −4 | 13 | 9 | 56 | 57 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 2 | 9 | 8 | 81 | 86 | 1 | −6 | −8 | 9 | 78 | 77 | 1 | 2 | −2 | 9 | 228 | 231 | 1 | 1 | 4 | 9 | 178 | 183 | 2 | −3 | 13 | 9 | 12 | 13 | 2 |
| 3 | 9 | 8 | 42 | 41 | 1 | −5 | −8 | 9 | 87 | 84 | 1 | 3 | −2 | 9 | 39 | 40 | 1 | 2 | 4 | 9 | 155 | 155 | 1 | −2 | 13 | 9 | 44 | 46 | 1 |
| 4 | 9 | 8 | 59 | 59 | 1 | −4 | −8 | 9 | 104 | 108 | 1 | 4 | −2 | 9 | 52 | 55 | 1 | 3 | 4 | 9 | 90 | 87 | 1 | 1 | 13 | 9 | 55 | 51 | 1 |
| −6 | 10 | 8 | 44 | 45 | 1 | −3 | −8 | 9 | 88 | 88 | 1 | 5 | −2 | 9 | 80 | 78 | 1 | 4 | 4 | 9 | 76 | 77 | 1 | 2 | 13 | 9 | 37 | 36 | 1 |
| −5 | 10 | 8 | 70 | 73 | 1 | −2 | −8 | 9 | 109 | 109 | 1 | 6 | −2 | 9 | 54 | 53 | 1 | 5 | 4 | 9 | 125 | 123 | 2 | −3 | −13 | 10 | 27 | 27 | 1 |
| −4 | 10 | 8 | 64 | 69 | 1 | −1 | −8 | 9 | 63 | 62 | 1 | −8 | −1 | 9 | 37 | 32 | 1 | −7 | 5 | 9 | 42 | 41 | 1 | −2 | −13 | 10 | 32 | 30 | 1 |
| −3 | 10 | 8 | 102 | 99 | 1 | 0 | −8 | 9 | 113 | 120 | 1 | −7 | −1 | 9 | 86 | 86 | 1 | −6 | 5 | 9 | 146 | 148 | 1 | −1 | −13 | 10 | 13 | 12 | 1 |
| −2 | 10 | 8 | 56 | 58 | 2 | 1 | −8 | 9 | 170 | 169 | 1 | −6 | −1 | 9 | 123 | 127 | 1 | −5 | 5 | 9 | 90 | 92 | 2 | 0 | −13 | 10 | 45 | 43 | 1 |
| 0 | 10 | 8 | 124 | 131 | 2 | 2 | −8 | 9 | 199 | 199 | 2 | −5 | −1 | 9 | 123 | 121 | 1 | −4 | 5 | 9 | 242 | 237 | 3 | 1 | −13 | 10 | 38 | 33 | 1 |
| 1 | 10 | 8 | 72 | 69 | 1 | 3 | −8 | 9 | 43 | 47 | 1 | −4 | −1 | 9 | 48 | 48 | 1 | −3 | 5 | 9 | 40 | 38 | 1 | −4 | −12 | 10 | 47 | 47 | 1 |
| 2 | 10 | 8 | 44 | 50 | 1 | 4 | −8 | 9 | 60 | 64 | 1 | −3 | −1 | 9 | 74 | 77 | 1 | −2 | 5 | 9 | 6 | 13 | 5 | −3 | −12 | 10 | 75 | 77 | 1 |
| 3 | 10 | 8 | 115 | 116 | 1 | 5 | −8 | 9 | 50 | 50 | 1 | −2 | −1 | 9 | 184 | 186 | 1 | −1 | 5 | 9 | 118 | 116 | 1 | −2 | −12 | 10 | 31 | 30 | 1 |
| −1 | −12 | 10 | 33 | 33 | 1 | 2 | −4 | 10 | 91 | 93 | 1 | −2 | 3 | 10 | 123 | 121 | 1 | −2 | 11 | 10 | 44 | 46 | 2 | −3 | −4 | 11 | 140 | 143 | 1 |
| 0 | −12 | 10 | 42 | 44 | 1 | 3 | −4 | 10 | 136 | 141 | 2 | −1 | 3 | 10 | 19 | 16 | 1 | 0 | 11 | 10 | 100 | 103 | 2 | −2 | −4 | 11 | 69 | 65 | 1 |
| 1 | −12 | 10 | 2 | 5 | 2 | 4 | −4 | 10 | 69 | 68 | 1 | 0 | 3 | 10 | 189 | 186 | 2 | 1 | 11 | 10 | 116 | 120 | 1 | −1 | −4 | 11 | 52 | 47 | 1 |
| −4 | −11 | 10 | 63 | 61 | 1 | 5 | −4 | 10 | 44 | 41 | 1 | 1 | 3 | 10 | 208 | 214 | 2 | 2 | 11 | 10 | 61 | 65 | 1 | 0 | −4 | 11 | 32 | 25 | 1 |
| −3 | −11 | 10 | 73 | 75 | 1 | −7 | −3 | 10 | 36 | 36 | 1 | 2 | 3 | 10 | 152 | 153 | 1 | 3 | 11 | 10 | 30 | 25 | 1 | 1 | −4 | 11 | 98 | 104 | 1 |
| −2 | −11 | 10 | 44 | 45 | 1 | −6 | −3 | 10 | 121 | 121 | 2 | 3 | 3 | 10 | 111 | 113 | 1 | −4 | 12 | 10 | 45 | 46 | 1 | 2 | −4 | 11 | 201 | 206 | 1 |
| −1 | −11 | 10 | 55 | 53 | 1 | −5 | −3 | 10 | 287 | 283 | 2 | 4 | 3 | 10 | 104 | 102 | 1 | −3 | 12 | 10 | 76 | 77 | 1 | 3 | −4 | 11 | 43 | 43 | 1 |
| 0 | −11 | 10 | 104 | 103 | 1 | −4 | −3 | 10 | 221 | 223 | 2 | 5 | 3 | 10 | 79 | 80 | 1 | −2 | 12 | 10 | 32 | 30 | 2 | 4 | −4 | 11 | 18 | 20 | 1 |
| 1 | −11 | 10 | 116 | 120 | 1 | −3 | −3 | 10 | 157 | 159 | 1 | −6 | 4 | 10 | 27 | 26 | 1 | 0 | 12 | 10 | 42 | 44 | 1 | −7 | −3 | 11 | 92 | 93 | 1 |
| −5 | −10 | 10 | 77 | 79 | 1 | −2 | −3 | 10 | 122 | 121 | 1 | −5 | 4 | 10 | 71 | 70 | 1 | 1 | 12 | 10 | 6 | 5 | 5 | −6 | −3 | 11 | 103 | 102 | 2 |
| −4 | −10 | 10 | 74 | 73 | 1 | −1 | −3 | 10 | 22 | 16 | 1 | −4 | 4 | 10 | 37 | 38 | 1 | 2 | 12 | 10 | 40 | 40 | 1 | −5 | −3 | 11 | 150 | 148 | 1 |
| −3 | −10 | 10 | 55 | 59 | 1 | 0 | −3 | 10 | 187 | 186 | 1 | −3 | 4 | 10 | 89 | 85 | 1 | −3 | 13 | 10 | 28 | 27 | 1 | −4 | −3 | 11 | 299 | 302 | 3 |
| −2 | −10 | 10 | 138 | 140 | 1 | 1 | −3 | 10 | 207 | 215 | 1 | −2 | 4 | 10 | 75 | 76 | 1 | 0 | 13 | 10 | 42 | 43 | 1 | −3 | −3 | 11 | 63 | 68 | 1 |
| −1 | −10 | 10 | 28 | 31 | 1 | 2 | −3 | 10 | 152 | 153 | 1 | −1 | 4 | 10 | 182 | 174 | 2 | 1 | 13 | 10 | 38 | 33 | 1 | −2 | −3 | 11 | 119 | 117 | 1 |
| 0 | −10 | 10 | 153 | 150 | 1 | 3 | −3 | 10 | 113 | 114 | 1 | 0 | 4 | 10 | 152 | 152 | 1 | −3 | −12 | 11 | 66 | 67 | 1 | −1 | −3 | 11 | 198 | 203 | 1 |
| 1 | −10 | 10 | 136 | 136 | 1 | 4 | −3 | 10 | 103 | 102 | 2 | 1 | 4 | 10 | 84 | 82 | 1 | −2 | −12 | 11 | 21 | 21 | 1 | 0 | −3 | 11 | 138 | 130 | 1 |
| 2 | −10 | 10 | 55 | 56 | 1 | 5 | −3 | 10 | 78 | 80 | 1 | 2 | 4 | 10 | 90 | 93 | 1 | −1 | −12 | 11 | 31 | 29 | 1 | 1 | −3 | 11 | 188 | 190 | 2 |
| 3 | −10 | 10 | 13 | 16 | 1 | −7 | −2 | 10 | 61 | 62 | 1 | 3 | 4 | 10 | 138 | 141 | 1 | 0 | −12 | 11 | 68 | 70 | 1 | 2 | −3 | 11 | 66 | 72 | 1 |
| −6 | −9 | 10 | 49 | 48 | 1 | −6 | −2 | 10 | 76 | 77 | 1 | 4 | 4 | 10 | 69 | 69 | 1 | 1 | −12 | 11 | 53 | 49 | 1 | 3 | −3 | 11 | 139 | 141 | 1 |
| −5 | −9 | 10 | 97 | 99 | 1 | −5 | −2 | 10 | 158 | 161 | 1 | 5 | 4 | 10 | 42 | 41 | 1 | −4 | −11 | 11 | 73 | 71 | 1 | 4 | −3 | 11 | 32 | 33 | 1 |
| −4 | −9 | 10 | 69 | 68 | 1 | −4 | −2 | 10 | 82 | 89 | 1 | −6 | 5 | 10 | 13 | 9 | 1 | −3 | −11 | 11 | 53 | 54 | 1 | 5 | −3 | 11 | 81 | 82 | 1 |
| −3 | −9 | 10 | 24 | 19 | 1 | −3 | −2 | 10 | 48 | 47 | 1 | −5 | 5 | 10 | 41 | 38 | 1 | −2 | −11 | 11 | 65 | 63 | 1 | −7 | −2 | 11 | 37 | 34 | 1 |
| −2 | −9 | 10 | 119 | 124 | 1 | −2 | −2 | 10 | 40 | 40 | 1 | −4 | 5 | 10 | 56 | 56 | 1 | −1 | −11 | 11 | 19 | 24 | 1 | −6 | −2 | 11 | 58 | 60 | 1 |
| −1 | −9 | 10 | 38 | 38 | 1 | −1 | −2 | 10 | 231 | 235 | 2 | −3 | 5 | 10 | 104 | 107 | 1 | 0 | −11 | 11 | 52 | 53 | 1 | −5 | −2 | 11 | 125 | 127 | 1 |
| 0 | −9 | 10 | 216 | 218 | 2 | 0 | −2 | 10 | 70 | 69 | 1 | −2 | 5 | 10 | 151 | 151 | 2 | 1 | −11 | 11 | 91 | 89 | 1 | −4 | −2 | 11 | 87 | 90 | 1 |
| 1 | −9 | 10 | 86 | 90 | 1 | 1 | −2 | 10 | 176 | 174 | 1 | −1 | 5 | 10 | 71 | 72 | 1 | −4 | −10 | 11 | 28 | 30 | 1 | −3 | −2 | 11 | 25 | 26 | 1 |
| 2 | −9 | 10 | 75 | 77 | 1 | 2 | −2 | 10 | 187 | 187 | 1 | 0 | 5 | 10 | 78 | 83 | 1 | −3 | −10 | 11 | 128 | 127 | 1 | −2 | −2 | 11 | 145 | 151 | 1 |
| 3 | −9 | 10 | 78 | 74 | 1 | 3 | −2 | 10 | 140 | 137 | 1 | 1 | 5 | 10 | 80 | 80 | 1 | −2 | −10 | 11 | 74 | 71 | 1 | −1 | −2 | 11 | 76 | 77 | 1 |
| 4 | −9 | 10 | 28 | 28 | 1 | 4 | −2 | 10 | 71 | 73 | 1 | 2 | 5 | 10 | 100 | 105 | 1 | −1 | −10 | 11 | 68 | 63 | 1 | 0 | −2 | 11 | 233 | 234 | 2 |
| −6 | −8 | 10 | 83 | 80 | 1 | 5 | −2 | 10 | 71 | 73 | 1 | 3 | 5 | 10 | 16 | 19 | 1 | 0 | −10 | 11 | 89 | 91 | 1 | 1 | −2 | 11 | 116 | 119 | 1 |
| −5 | −8 | 10 | 60 | 60 | 1 | −7 | −1 | 10 | 84 | 83 | 1 | 4 | 5 | 10 | 91 | 92 | 1 | 1 | −10 | 11 | 104 | 101 | 1 | 2 | −2 | 11 | 56 | 60 | 1 |
| −4 | −8 | 10 | 93 | 93 | 1 | −6 | −1 | 10 | 110 | 112 | 1 | −6 | 6 | 10 | 83 | 84 | 1 | −4 | −9 | 11 | 128 | 129 | 1 | 3 | −2 | 11 | 67 | 65 | 1 |
| −3 | −8 | 10 | 19 | 17 | 1 | −5 | −1 | 10 | 19 | 19 | 1 | −5 | 6 | 10 | 176 | 178 | 2 | −3 | −9 | 11 | 104 | 107 | 1 | 4 | −2 | 11 | 123 | 125 | 2 |
| −2 | −8 | 10 | 50 | 53 | 1 | −4 | −1 | 10 | 70 | 68 | 1 | −4 | 6 | 10 | 110 | 116 | 1 | −2 | −9 | 11 | 133 | 132 | 1 | 5 | −2 | 11 | 71 | 72 | 1 |
| −1 | −8 | 10 | 87 | 87 | 1 | −3 | −1 | 10 | 97 | 97 | 1 | −3 | 6 | 10 | 127 | 130 | 1 | −1 | −9 | 11 | 93 | 91 | 1 | −7 | −1 | 11 | 20 | 21 | 1 |
| 0 | −8 | 10 | 157 | 157 | 1 | −2 | −1 | 10 | 66 | 65 | 1 | −2 | 6 | 10 | 150 | 153 | 2 | 0 | −9 | 11 | 49 | 48 | 1 | −6 | −1 | 11 | 139 | 136 | 1 |
| 1 | −8 | 10 | 18 | 21 | 1 | −1 | −1 | 10 | 154 | 153 | 1 | −1 | 6 | 10 | 62 | 65 | 1 | 1 | −9 | 11 | 117 | 121 | 1 | −5 | −1 | 11 | 28 | 31 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 2 | −8 | 10 | 62 | 63 | 1 | 0 | −1 | 10 | 178 | 177 | 1 | 0 | 6 | 10 | 156 | 163 | 2 | 2 | −9 | 11 | 82 | 83 | 1 | −4 | −1 | 11 | 135 | 130 | 1 |
| 3 | −8 | 10 | 107 | 103 | 2 | 1 | −1 | 10 | 43 | 43 | 1 | 1 | 6 | 10 | 117 | 123 | 1 | 3 | −9 | 11 | 47 | 53 | 1 | −3 | −1 | 11 | 158 | 158 | 1 |
| 4 | −8 | 10 | 43 | 44 | 1 | 2 | −1 | 10 | 25 | 26 | 1 | 2 | 6 | 10 | 89 | 98 | 1 | −6 | −8 | 11 | 53 | 51 | 1 | −2 | −1 | 11 | 64 | 66 | 1 |
| −7 | −7 | 10 | 44 | 45 | 1 | 3 | −1 | 10 | 93 | 91 | 1 | 3 | 6 | 10 | 71 | 70 | 1 | −5 | −8 | 11 | 49 | 50 | 1 | −1 | −1 | 11 | 10 | 8 | 2 |
| −6 | −7 | 10 | 60 | 58 | 1 | 4 | −1 | 10 | 62 | 62 | 1 | 4 | 6 | 10 | 20 | 18 | 1 | −4 | −8 | 11 | 115 | 117 | 1 | 0 | −1 | 11 | 111 | 113 | 1 |
| −5 | −7 | 10 | 127 | 130 | 1 | 5 | −1 | 10 | 72 | 73 | 1 | −6 | 7 | 10 | 60 | 58 | 1 | −3 | −8 | 11 | 69 | 70 | 1 | 1 | −1 | 11 | 129 | 133 | 1 |
| −4 | −7 | 10 | 46 | 43 | 1 | −7 | 0 | 10 | 84 | 82 | 1 | −5 | 7 | 10 | 127 | 130 | 1 | −2 | −8 | 11 | 51 | 49 | 1 | 2 | −1 | 11 | 100 | 104 | 1 |
| −3 | −7 | 10 | 8 | 6 | 3 | −6 | 0 | 10 | 23 | 25 | 1 | −4 | 7 | 10 | 45 | 43 | 1 | −1 | −8 | 11 | 117 | 121 | 1 | 3 | −1 | 11 | 35 | 38 | 1 |
| −2 | −7 | 10 | 255 | 252 | 1 | −5 | 0 | 10 | 23 | 17 | 1 | −3 | 7 | 10 | 13 | 6 | 5 | 0 | −8 | 11 | 125 | 126 | 1 | 4 | −1 | 11 | 121 | 117 | 2 |
| −1 | −7 | 10 | 186 | 190 | 1 | −4 | 0 | 10 | 128 | 134 | 1 | −2 | 7 | 10 | 251 | 252 | 5 | 1 | −8 | 11 | 91 | 93 | 1 | 5 | −1 | 11 | 34 | 38 | 1 |
| 0 | −7 | 10 | 128 | 132 | 1 | −3 | 0 | 10 | 181 | 183 | 1 | −1 | 7 | 10 | 186 | 190 | 2 | 2 | −8 | 11 | 61 | 64 | 1 | −7 | 0 | 11 | 35 | 34 | 1 |
| 1 | −7 | 10 | 83 | 84 | 1 | −2 | 0 | 10 | 44 | 49 | 1 | 0 | 7 | 10 | 132 | 132 | 2 | 3 | −8 | 11 | 59 | 60 | 1 | −6 | 0 | 11 | 133 | 129 | 1 |
| 2 | −7 | 10 | 98 | 96 | 1 | −1 | 0 | 10 | 214 | 206 | 2 | 1 | 7 | 10 | 84 | 84 | 1 | −6 | −7 | 11 | 69 | 66 | 1 | −5 | 0 | 11 | 65 | 69 | 1 |
| 3 | −7 | 10 | 48 | 47 | 1 | 0 | 0 | 10 | 159 | 168 | 1 | 2 | 7 | 10 | 91 | 95 | 1 | −5 | −7 | 11 | 35 | 35 | 1 | −4 | 0 | 11 | 266 | 268 | 3 |
| 4 | −7 | 10 | 49 | 52 | 1 | 1 | 0 | 10 | 101 | 96 | 1 | 3 | 7 | 10 | 50 | 47 | 1 | −4 | −7 | 11 | 126 | 128 | 1 | −3 | 0 | 11 | 138 | 135 | 1 |
| −7 | −6 | 10 | 53 | 47 | 1 | 2 | 0 | 10 | 43 | 39 | 1 | 4 | 7 | 10 | 48 | 52 | 1 | −3 | −7 | 11 | 63 | 66 | 1 | −2 | 0 | 11 | 73 | 74 | 1 |
| −6 | −6 | 10 | 82 | 84 | 1 | 3 | 0 | 10 | 126 | 131 | 1 | −6 | 8 | 10 | 82 | 80 | 1 | −2 | −7 | 11 | 118 | 120 | 1 | −1 | 0 | 11 | 12 | 10 | 2 |
| −5 | −6 | 10 | 180 | 178 | 1 | 4 | 0 | 10 | 202 | 199 | 3 | −5 | 8 | 10 | 59 | 61 | 1 | −1 | −7 | 11 | 123 | 125 | 1 | 0 | 0 | 11 | 110 | 110 | 1 |
| −4 | −6 | 10 | 111 | 116 | 1 | 5 | 0 | 10 | 39 | 39 | 1 | −4 | 8 | 10 | 93 | 93 | 1 | 0 | −7 | 11 | 157 | 150 | 1 | 1 | 0 | 11 | 17 | 10 | 1 |
| −3 | −6 | 10 | 127 | 130 | 1 | −7 | 1 | 10 | 84 | 82 | 1 | −3 | 8 | 10 | 19 | 17 | 2 | 1 | −7 | 11 | 36 | 41 | 1 | 2 | 0 | 11 | 76 | 78 | 1 |
| −2 | −6 | 10 | 155 | 154 | 1 | −6 | 1 | 10 | 113 | 112 | 1 | −2 | 8 | 10 | 51 | 53 | 2 | 2 | −7 | 11 | 69 | 69 | 1 | 3 | 0 | 11 | 16 | 14 | 1 |
| −1 | −6 | 10 | 60 | 65 | 1 | −5 | 1 | 10 | 24 | 20 | 1 | −1 | 8 | 10 | 86 | 87 | 2 | 3 | −7 | 11 | 29 | 27 | 1 | 4 | 0 | 11 | 8 | 5 | 3 |
| 0 | −6 | 10 | 157 | 163 | 1 | −4 | 1 | 10 | 71 | 67 | 1 | 0 | 8 | 10 | 156 | 157 | 3 | 4 | −7 | 11 | 54 | 56 | 1 | 5 | 0 | 11 | 16 | 17 | 1 |
| 1 | −6 | 10 | 117 | 123 | 1 | −3 | 1 | 10 | 96 | 97 | 1 | 1 | 8 | 10 | 18 | 21 | 1 | −6 | −6 | 11 | 53 | 52 | 1 | −7 | 1 | 11 | 20 | 21 | 1 |
| 2 | −6 | 10 | 96 | 98 | 1 | −2 | 1 | 10 | 66 | 65 | 1 | 2 | 8 | 10 | 57 | 63 | 1 | −5 | −6 | 11 | 105 | 97 | 1 | −6 | 1 | 11 | 137 | 136 | 1 |
| 3 | −6 | 10 | 72 | 71 | 1 | −1 | 1 | 10 | 155 | 154 | 1 | 3 | 8 | 10 | 105 | 103 | 1 | −4 | −6 | 11 | 148 | 154 | 1 | −5 | 1 | 11 | 30 | 31 | 1 |
| 4 | −6 | 10 | 22 | 19 | 1 | 0 | 1 | 10 | 177 | 176 | 1 | 4 | 8 | 10 | 44 | 44 | 1 | −3 | −6 | 11 | 42 | 38 | 1 | −4 | 1 | 11 | 130 | 130 | 1 |
| 5 | −6 | 10 | 97 | 99 | 1 | 1 | 1 | 10 | 45 | 43 | 1 | −6 | 9 | 10 | 49 | 48 | 1 | −2 | −6 | 11 | 109 | 111 | 1 | −3 | 1 | 11 | 160 | 159 | 1 |
| −7 | −5 | 10 | 80 | 80 | 1 | 2 | 1 | 10 | 25 | 27 | 1 | −5 | 9 | 10 | 98 | 98 | 1 | −1 | −6 | 11 | 69 | 69 | 1 | −2 | 1 | 11 | 62 | 66 | 1 |
| −6 | −5 | 10 | 13 | 8 | 2 | 3 | 1 | 10 | 89 | 91 | 1 | −4 | 9 | 10 | 72 | 68 | 1 | 0 | −6 | 11 | 134 | 132 | 1 | −1 | 1 | 11 | 12 | 9 | 2 |
| −5 | −5 | 10 | 38 | 38 | 1 | 4 | 1 | 10 | 63 | 62 | 1 | −3 | 9 | 10 | 22 | 19 | 1 | 1 | −6 | 11 | 85 | 85 | 1 | 0 | 1 | 11 | 112 | 112 | 1 |
| −4 | −5 | 10 | 56 | 56 | 1 | 5 | 1 | 10 | 73 | 73 | 1 | −2 | 9 | 10 | 120 | 123 | 2 | 2 | −6 | 11 | 83 | 79 | 1 | 1 | 1 | 11 | 130 | 133 | 1 |
| −3 | −5 | 10 | 103 | 106 | 1 | −7 | 2 | 10 | 62 | 63 | 1 | −1 | 9 | 10 | 41 | 38 | 1 | 3 | −6 | 11 | 42 | 38 | 1 | 2 | 1 | 11 | 100 | 104 | 1 |
| −2 | −5 | 10 | 152 | 151 | 1 | −6 | 2 | 10 | 77 | 77 | 1 | 0 | 9 | 10 | 215 | 219 | 4 | 4 | −6 | 11 | 83 | 89 | 1 | 3 | 1 | 11 | 34 | 37 | 1 |
| −1 | −5 | 10 | 69 | 73 | 1 | −5 | 2 | 10 | 158 | 160 | 1 | 1 | 9 | 10 | 89 | 90 | 1 | −7 | −5 | 11 | 51 | 52 | 1 | 4 | 1 | 11 | 119 | 116 | 2 |
| 0 | −5 | 10 | 78 | 82 | 1 | −4 | 2 | 10 | 81 | 88 | 1 | 2 | 9 | 10 | 74 | 76 | 1 | −6 | −5 | 11 | 96 | 95 | 1 | 5 | 1 | 11 | 36 | 38 | 1 |
| 1 | −5 | 10 | 79 | 80 | 1 | −3 | 2 | 10 | 49 | 47 | 1 | 3 | 9 | 10 | 81 | 74 | 1 | −5 | −5 | 11 | 76 | 77 | 1 | −7 | 2 | 11 | 36 | 35 | 1 |
| 2 | −5 | 10 | 101 | 105 | 1 | −2 | 2 | 10 | 38 | 40 | 1 | 4 | 9 | 10 | 29 | 28 | 1 | −4 | −5 | 11 | 75 | 74 | 1 | −6 | 2 | 11 | 57 | 60 | 1 |
| 3 | −5 | 10 | 18 | 19 | 1 | −1 | 2 | 10 | 231 | 236 | 2 | −5 | 10 | 10 | 79 | 79 | 1 | −3 | −5 | 11 | 58 | 58 | 1 | −5 | 2 | 11 | 129 | 127 | 1 |
| 4 | −5 | 10 | 88 | 92 | 1 | 0 | 2 | 10 | 71 | 68 | 1 | −4 | 10 | 10 | 74 | 73 | 1 | −2 | −5 | 11 | 91 | 98 | 1 | −4 | 2 | 11 | 86 | 90 | 1 |
| 5 | −5 | 10 | 88 | 86 | 1 | 1 | 2 | 10 | 180 | 174 | 2 | −3 | 10 | 10 | 56 | 60 | 1 | −1 | −5 | 11 | 6 | 6 | 5 | −3 | 2 | 11 | 25 | 25 | 1 |
| −7 | −4 | 10 | 63 | 59 | 1 | 2 | 2 | 10 | 189 | 186 | 1 | −2 | 10 | 10 | 134 | 140 | 3 | 0 | −5 | 11 | 142 | 140 | 1 | −2 | 2 | 11 | 145 | 151 | 1 |
| −6 | −4 | 10 | 30 | 26 | 1 | 3 | 2 | 10 | 139 | 137 | 1 | −1 | 10 | 10 | 34 | 30 | 1 | 1 | −5 | 11 | 55 | 60 | 1 | −1 | 2 | 11 | 77 | 77 | 1 |
| −5 | −4 | 10 | 70 | 70 | 1 | 4 | 2 | 10 | 70 | 73 | 1 | 0 | 10 | 10 | 154 | 150 | 3 | 2 | −5 | 11 | 98 | 100 | 1 | 0 | 2 | 11 | 236 | 235 | 2 |
| −4 | −4 | 10 | 36 | 38 | 1 | 5 | 2 | 10 | 70 | 73 | 1 | 1 | 10 | 10 | 137 | 136 | 1 | 3 | −5 | 11 | 90 | 89 | 1 | 1 | 2 | 11 | 117 | 119 | 1 |
| −3 | −4 | 10 | 90 | 85 | 1 | −7 | 3 | 10 | 34 | 36 | 1 | 2 | 10 | 10 | 59 | 57 | 1 | 4 | −5 | 11 | 59 | 59 | 1 | 2 | 2 | 11 | 57 | 59 | 1 |
| −2 | −4 | 10 | 76 | 76 | 1 | −6 | 3 | 10 | 120 | 121 | 1 | 3 | 10 | 10 | 17 | 16 | 1 | −7 | −4 | 11 | 81 | 81 | 1 | 3 | 2 | 11 | 66 | 65 | 1 |
| −1 | −4 | 10 | 183 | 175 | 1 | −5 | 3 | 10 | 286 | 282 | 3 | −5 | 11 | 10 | 28 | 30 | 1 | −6 | −4 | 11 | 123 | 126 | 2 | 4 | 2 | 11 | 121 | 125 | 2 |
| 0 | −4 | 10 | 152 | 153 | 1 | −4 | 3 | 10 | 225 | 223 | 3 | −4 | 11 | 10 | 66 | 61 | 1 | −5 | −4 | 11 | 197 | 198 | 2 | 5 | 2 | 11 | 71 | 72 | 1 |

TABLE 8-continued

| Observed and calculated structure factors for MET-1. | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 1 | −4 | 10 | 85 | 82 | 1 | −3 | 3 | 10 | 157 | 159 | 1 | −3 | 11 | 10 | 73 | 75 | 1 | −4 | −4 | 11 | 137 | 137 | 1 | −6 | 3 | 11 | 104 | 102 | 2 |
| −5 | 3 | 11 | 155 | 149 | 2 | −3 | 12 | 11 | 68 | 67 | 1 | 4 | −2 | 12 | 94 | 97 | 1 | −4 | 7 | 12 | 135 | 142 | 1 | −3 | −2 | 13 | 109 | 114 | 1 |
| −4 | 3 | 11 | 295 | 302 | 4 | 0 | 12 | 11 | 69 | 70 | 1 | −7 | −1 | 12 | 37 | 34 | 1 | −3 | 7 | 12 | 10 | 17 | 4 | −2 | −2 | 13 | 76 | 76 | 1 |
| −3 | 3 | 11 | 64 | 67 | 1 | 1 | 12 | 11 | 55 | 49 | 1 | −6 | −1 | 12 | 80 | 79 | 1 | −2 | 7 | 12 | 67 | 67 | 2 | −1 | −2 | 13 | 65 | 65 | 1 |
| −2 | 3 | 11 | 117 | 117 | 1 | −3 | −11 | 12 | 73 | 75 | 1 | −5 | −1 | 12 | 24 | 21 | 1 | −1 | 7 | 12 | 119 | 115 | 2 | 0 | −2 | 13 | 54 | 54 | 1 |
| −1 | 3 | 11 | 197 | 202 | 2 | −2 | −11 | 12 | 23 | 23 | 1 | −4 | −1 | 12 | 141 | 138 | 2 | 0 | 7 | 12 | 99 | 94 | 1 | 1 | −2 | 13 | 48 | 50 | 1 |
| 0 | 3 | 11 | 141 | 130 | 1 | −1 | −11 | 12 | 113 | 109 | 1 | −3 | −1 | 12 | 63 | 65 | 1 | 1 | 7 | 12 | 22 | 20 | 1 | 2 | −2 | 13 | 20 | 17 | 1 |
| 1 | 3 | 11 | 188 | 191 | 2 | 0 | −11 | 12 | 60 | 59 | 1 | −2 | −1 | 12 | 117 | 120 | 1 | 2 | 7 | 12 | 61 | 61 | 1 | −6 | −1 | 13 | 48 | 45 | 1 |
| 2 | 3 | 11 | 66 | 73 | 1 | −4 | −10 | 12 | 60 | 57 | 1 | −1 | −1 | 12 | 64 | 67 | 1 | 3 | 7 | 12 | 101 | 98 | 1 | −5 | −1 | 13 | 71 | 72 | 1 |
| 3 | 3 | 11 | 139 | 141 | 1 | −3 | −10 | 12 | 46 | 47 | 1 | 0 | −1 | 12 | 29 | 31 | 1 | −5 | 8 | 12 | 95 | 96 | 1 | −4 | −1 | 13 | 58 | 57 | 1 |
| 4 | 3 | 11 | 33 | 34 | 1 | −2 | −10 | 12 | 92 | 87 | 1 | 1 | −1 | 12 | 76 | 75 | 1 | −4 | 8 | 12 | 50 | 47 | 1 | −3 | −1 | 13 | 163 | 164 | 1 |
| −6 | 4 | 11 | 126 | 127 | 1 | −1 | −10 | 12 | 122 | 121 | 1 | 2 | −1 | 12 | 25 | 28 | 1 | −3 | 8 | 12 | 173 | 177 | 1 | −2 | −1 | 13 | 26 | 23 | 1 |
| −5 | 4 | 11 | 197 | 198 | 2 | 0 | −10 | 12 | 53 | 50 | 1 | 3 | −1 | 12 | 37 | 34 | 1 | −2 | 8 | 12 | 166 | 161 | 3 | −1 | −1 | 13 | 109 | 106 | 1 |
| −4 | 4 | 11 | 131 | 136 | 1 | 1 | −10 | 12 | 81 | 78 | 1 | 4 | −1 | 12 | 36 | 34 | 1 | −1 | 8 | 12 | 50 | 53 | 1 | 0 | −1 | 13 | 108 | 108 | 1 |
| −3 | 4 | 11 | 140 | 144 | 1 | −4 | −9 | 12 | 109 | 102 | 1 | −6 | 0 | 12 | 74 | 76 | 1 | 0 | 8 | 12 | 72 | 70 | 1 | 1 | −1 | 13 | 70 | 68 | 1 |
| −2 | 4 | 11 | 70 | 65 | 1 | −3 | −9 | 12 | 26 | 25 | 1 | −5 | 0 | 12 | 50 | 51 | 1 | 1 | 8 | 12 | 91 | 87 | 1 | 2 | −1 | 13 | 40 | 39 | 1 |
| −1 | 4 | 11 | 51 | 47 | 1 | −2 | −9 | 12 | 62 | 61 | 1 | −4 | 0 | 12 | 54 | 49 | 1 | 2 | 8 | 12 | 76 | 73 | 1 | −6 | 0 | 13 | 62 | 60 | 1 |
| 0 | 4 | 11 | 34 | 25 | 1 | −1 | −9 | 12 | 81 | 84 | 1 | −3 | 0 | 12 | 156 | 161 | 1 | −5 | 9 | 12 | 10 | 13 | 2 | −5 | 0 | 13 | 88 | 85 | 1 |
| 1 | 4 | 11 | 97 | 104 | 1 | 0 | −9 | 12 | 39 | 40 | 1 | −2 | 0 | 12 | 110 | 106 | 1 | −4 | 9 | 12 | 111 | 102 | 1 | −4 | 0 | 13 | 13 | 1 | 2 |
| 2 | 4 | 11 | 205 | 206 | 2 | 1 | −9 | 12 | 60 | 59 | 1 | −1 | 0 | 12 | 46 | 52 | 1 | −3 | 9 | 12 | 28 | 25 | 1 | −3 | 0 | 13 | 48 | 51 | 1 |
| 3 | 4 | 11 | 43 | 42 | 1 | −4 | −8 | 12 | 50 | 47 | 1 | 0 | 0 | 12 | 186 | 187 | 2 | −2 | 9 | 12 | 60 | 61 | 2 | −2 | 0 | 13 | 25 | 24 | 1 |
| 4 | 4 | 11 | 18 | 20 | 1 | −3 | −8 | 12 | 175 | 177 | 1 | 1 | 0 | 12 | 25 | 27 | 1 | −1 | 9 | 12 | 80 | 84 | 2 | −1 | 0 | 13 | 72 | 75 | 1 |
| −6 | 5 | 11 | 97 | 95 | 1 | −2 | −8 | 12 | 163 | 161 | 1 | 2 | 0 | 12 | 91 | 91 | 1 | 0 | 9 | 12 | 38 | 39 | 1 | 0 | 0 | 13 | 44 | 48 | 1 |
| −5 | 5 | 11 | 76 | 77 | 2 | −1 | −8 | 12 | 52 | 53 | 1 | 3 | 0 | 12 | 60 | 62 | 1 | 1 | 9 | 12 | 60 | 59 | 1 | 1 | 0 | 13 | 41 | 44 | 1 |
| −4 | 5 | 11 | 71 | 74 | 1 | 0 | −8 | 12 | 72 | 69 | 1 | 4 | 0 | 12 | 38 | 41 | 1 | 2 | 9 | 12 | 6 | 4 | 5 | 2 | 0 | 13 | 30 | 30 | 1 |
| −3 | 5 | 11 | 58 | 59 | 1 | 1 | −8 | 12 | 89 | 87 | 1 | −6 | 1 | 12 | 77 | 78 | 1 | −4 | 10 | 12 | 60 | 57 | 1 | 3 | 0 | 13 | 12 | 11 | 1 |
| −2 | 5 | 11 | 92 | 98 | 1 | −4 | −7 | 12 | 136 | 143 | 1 | −5 | 1 | 12 | 25 | 21 | 1 | −3 | 10 | 12 | 44 | 46 | 1 | −6 | 1 | 13 | 46 | 45 | 1 |
| −1 | 5 | 11 | 6 | 5 | 5 | −3 | −7 | 12 | 16 | 17 | 1 | −4 | 1 | 12 | 140 | 138 | 2 | −2 | 10 | 12 | 88 | 87 | 2 | −5 | 1 | 13 | 71 | 72 | 1 |
| 0 | 5 | 11 | 143 | 140 | 1 | −2 | −7 | 12 | 66 | 68 | 1 | −3 | 1 | 12 | 63 | 65 | 1 | −1 | 10 | 12 | 118 | 121 | 2 | −4 | 1 | 13 | 57 | 57 | 1 |
| 1 | 5 | 11 | 56 | 60 | 1 | −1 | −7 | 12 | 118 | 115 | 1 | −2 | 1 | 12 | 119 | 120 | 1 | 0 | 10 | 12 | 52 | 50 | 1 | −3 | 1 | 13 | 166 | 164 | 1 |
| 2 | 5 | 11 | 99 | 100 | 1 | 0 | −7 | 12 | 98 | 94 | 1 | −1 | 1 | 12 | 65 | 67 | 1 | 1 | 10 | 12 | 80 | 77 | 1 | −2 | 1 | 13 | 25 | 24 | 1 |
| 3 | 5 | 11 | 90 | 89 | 1 | 1 | −7 | 12 | 24 | 20 | 1 | 0 | 1 | 12 | 31 | 31 | 1 | −3 | 11 | 12 | 73 | 75 | 1 | −1 | 1 | 13 | 110 | 106 | 1 |
| 4 | 5 | 11 | 59 | 59 | 1 | 2 | −7 | 12 | 63 | 62 | 1 | 1 | 1 | 12 | 74 | 75 | 1 | 0 | 11 | 12 | 60 | 59 | 1 | 0 | 1 | 13 | 113 | 108 | 2 |
| −6 | 6 | 11 | 51 | 52 | 1 | 3 | −7 | 12 | 97 | 98 | 2 | 2 | 1 | 12 | 27 | 29 | 1 | −3 | −10 | 13 | 25 | 23 | 1 | 1 | 1 | 13 | 70 | 68 | 1 |
| −5 | 6 | 11 | 104 | 98 | 1 | −6 | −6 | 12 | 91 | 94 | 1 | 3 | 1 | 12 | 37 | 33 | 1 | −2 | −10 | 13 | 21 | 19 | 1 | 2 | 1 | 13 | 39 | 39 | 1 |
| −4 | 6 | 11 | 147 | 153 | 2 | −5 | −6 | 12 | 88 | 84 | 1 | 4 | 1 | 12 | 36 | 34 | 1 | −1 | −10 | 13 | 128 | 124 | 1 | 3 | 1 | 13 | 22 | 21 | 1 |
| −3 | 6 | 11 | 41 | 38 | 1 | −4 | −6 | 12 | 98 | 97 | 1 | −6 | 2 | 12 | 82 | 81 | 1 | 0 | −10 | 13 | 45 | 43 | 1 | −6 | 2 | 13 | 106 | 107 | 2 |
| −2 | 6 | 11 | 110 | 111 | 2 | −3 | −6 | 12 | 73 | 73 | 1 | −5 | 2 | 12 | 69 | 69 | 1 | −4 | −9 | 13 | 76 | 75 | 1 | −5 | 2 | 13 | 31 | 29 | 1 |
| −1 | 6 | 11 | 71 | 69 | 1 | −2 | −6 | 12 | 84 | 78 | 1 | −4 | 2 | 12 | 72 | 74 | 1 | −3 | −9 | 13 | 151 | 147 | 1 | −4 | 2 | 13 | 145 | 147 | 2 |
| 0 | 6 | 11 | 135 | 132 | 1 | −1 | −6 | 12 | 74 | 74 | 1 | −3 | 2 | 12 | 115 | 109 | 1 | −2 | −9 | 13 | 68 | 66 | 1 | −3 | 2 | 13 | 112 | 113 | 1 |
| 1 | 6 | 11 | 86 | 85 | 1 | 0 | −6 | 12 | 117 | 114 | 1 | −2 | 2 | 12 | 57 | 59 | 1 | −1 | −9 | 13 | 38 | 35 | 1 | −2 | 2 | 13 | 79 | 77 | 1 |
| 2 | 6 | 11 | 83 | 79 | 1 | 1 | −6 | 12 | 57 | 57 | 1 | −1 | 2 | 12 | 55 | 55 | 1 | 0 | −9 | 13 | 75 | 71 | 1 | −1 | 2 | 13 | 66 | 66 | 1 |
| 3 | 6 | 11 | 43 | 38 | 1 | 2 | −6 | 12 | 81 | 78 | 1 | 0 | 2 | 12 | 224 | 227 | 2 | 1 | −9 | 13 | 34 | 32 | 1 | 0 | 2 | 13 | 56 | 54 | 1 |
| 4 | 6 | 11 | 86 | 89 | 1 | 3 | −6 | 12 | 78 | 76 | 1 | 1 | 2 | 12 | 120 | 128 | 1 | −4 | −8 | 13 | 115 | 115 | 1 | 1 | 2 | 13 | 47 | 49 | 1 |
| −6 | 7 | 11 | 70 | 66 | 1 | −6 | −5 | 12 | 135 | 138 | 2 | 2 | 2 | 12 | 102 | 101 | 1 | −3 | −8 | 13 | 49 | 46 | 1 | 2 | 2 | 13 | 22 | 18 | 1 |
| −5 | 7 | 11 | 31 | 35 | 1 | −5 | −5 | 12 | 176 | 175 | 3 | 3 | 2 | 12 | 84 | 84 | 1 | −2 | −8 | 13 | 114 | 109 | 1 | 3 | 2 | 13 | 51 | 51 | 1 |
| −4 | 7 | 11 | 125 | 128 | 1 | −4 | −5 | 12 | 25 | 23 | 1 | −6 | 3 | 12 | 15 | 11 | 2 | −1 | −8 | 13 | 45 | 48 | 1 | −6 | 3 | 13 | 55 | 53 | 1 |
| −3 | 7 | 11 | 61 | 66 | 2 | −3 | −5 | 12 | 65 | 63 | 1 | −5 | 3 | 12 | 97 | 95 | 1 | 0 | −8 | 13 | 19 | 20 | 1 | −5 | 3 | 13 | 109 | 106 | 1 |
| −2 | 7 | 11 | 122 | 119 | 2 | −2 | −5 | 12 | 67 | 67 | 1 | −4 | 3 | 12 | 59 | 67 | 2 | 1 | −8 | 13 | 90 | 84 | 1 | −4 | 3 | 13 | 39 | 42 | 1 |

TABLE 8-continued

Observed and calculated structure factors for MET-1.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −1 | 7 | 11 | 124 | 126 | 2 | −1 | −5 | 12 | 25 | 28 | 1 | −3 | 3 | 12 | 154 | 161 | 1 | −4 | −7 | 13 | 99 | 98 | 1 | −3 | 3 | 13 | 98 | 95 | 1 |
| 0 | 7 | 11 | 156 | 150 | 2 | 0 | −5 | 12 | 100 | 97 | 1 | −2 | 3 | 12 | 79 | 77 | 1 | −3 | −7 | 13 | 61 | 60 | 1 | −2 | 3 | 13 | 42 | 39 | 1 |
| 1 | 7 | 11 | 34 | 41 | 1 | 1 | −5 | 12 | 137 | 141 | 1 | −1 | 3 | 12 | 220 | 217 | 3 | −2 | −7 | 13 | 35 | 36 | 1 | −1 | 3 | 13 | 69 | 64 | 1 |
| 2 | 7 | 11 | 68 | 69 | 1 | 2 | −5 | 12 | 92 | 92 | 1 | 0 | 3 | 12 | 179 | 174 | 2 | −1 | −7 | 13 | 64 | 60 | 1 | 0 | 3 | 13 | 191 | 199 | 3 |
| 3 | 7 | 11 | 25 | 28 | 1 | 3 | −5 | 12 | 53 | 54 | 1 | 1 | 3 | 12 | 80 | 90 | 1 | 0 | −7 | 13 | 95 | 95 | 1 | 1 | 3 | 13 | 72 | 74 | 1 |
| 4 | 7 | 11 | 57 | 57 | 1 | 4 | −5 | 12 | 13 | 13 | 1 | 2 | 3 | 12 | 68 | 67 | 1 | 1 | −7 | 13 | 42 | 42 | 1 | 2 | 3 | 13 | 69 | 66 | 1 |
| −6 | 8 | 11 | 50 | 51 | 1 | −6 | −4 | 12 | 120 | 122 | 2 | 3 | 3 | 12 | 129 | 132 | 1 | −5 | −6 | 13 | 38 | 39 | 1 | 3 | 3 | 13 | 98 | 96 | 1 |
| −5 | 8 | 11 | 51 | 50 | 1 | −5 | −4 | 12 | 54 | 55 | 1 | −6 | 4 | 12 | 117 | 122 | 1 | −4 | −6 | 13 | 108 | 108 | 1 | −6 | 4 | 13 | 28 | 31 | 1 |
| −4 | 8 | 11 | 115 | 117 | 1 | −4 | −4 | 12 | 122 | 121 | 1 | −5 | 4 | 12 | 54 | 54 | 1 | −3 | −6 | 13 | 94 | 91 | 1 | −5 | 4 | 13 | 105 | 105 | 2 |
| −3 | 8 | 11 | 67 | 71 | 1 | −3 | −4 | 12 | 138 | 140 | 1 | −4 | 4 | 12 | 114 | 121 | 1 | −2 | −6 | 13 | 6 | 8 | 4 | −4 | 4 | 13 | 106 | 103 | 1 |
| −2 | 8 | 11 | 51 | 49 | 2 | −2 | −4 | 12 | 132 | 128 | 1 | −3 | 4 | 12 | 140 | 140 | 1 | −1 | −6 | 13 | 20 | 19 | 1 | −3 | 4 | 13 | 87 | 84 | 1 |
| −1 | 8 | 11 | 119 | 121 | 2 | −1 | −4 | 12 | 79 | 85 | 1 | −2 | 4 | 12 | 134 | 129 | 1 | 0 | −6 | 13 | 25 | 24 | 1 | −2 | 4 | 13 | 106 | 109 | 1 |
| 0 | 8 | 11 | 123 | 125 | 1 | 0 | −4 | 12 | 125 | 119 | 1 | −1 | 4 | 12 | 80 | 84 | 1 | 1 | −6 | 13 | 91 | 96 | 1 | −1 | 4 | 13 | 123 | 111 | 1 |
| 1 | 8 | 11 | 92 | 93 | 1 | 1 | −4 | 12 | 103 | 103 | 1 | 0 | 4 | 12 | 131 | 119 | 1 | −5 | −5 | 13 | 139 | 137 | 2 | 0 | 4 | 13 | 144 | 146 | 1 |
| 2 | 8 | 11 | 61 | 64 | 1 | 2 | −4 | 12 | 47 | 48 | 1 | 1 | 4 | 12 | 94 | 103 | 1 | −4 | −5 | 13 | 88 | 87 | 1 | 1 | 4 | 13 | 72 | 73 | 1 |
| 3 | 8 | 11 | 58 | 61 | 1 | 3 | −4 | 12 | 45 | 49 | 1 | 2 | 4 | 12 | 47 | 48 | 1 | −3 | −5 | 13 | 29 | 25 | 1 | 2 | 4 | 13 | 102 | 102 | 1 |
| −5 | 9 | 11 | 114 | 111 | 1 | 4 | −4 | 12 | 20 | 22 | 1 | 3 | 4 | 12 | 47 | 49 | 1 | −2 | −5 | 13 | 122 | 126 | 1 | 3 | 4 | 13 | 46 | 44 | 1 |
| −4 | 9 | 11 | 129 | 129 | 1 | −6 | −3 | 12 | 15 | 11 | 2 | −6 | 5 | 12 | 136 | 138 | 1 | −1 | −5 | 13 | 63 | 66 | 1 | −6 | 5 | 13 | 55 | 57 | 1 |
| −3 | 9 | 11 | 105 | 108 | 1 | −5 | −3 | 12 | 97 | 96 | 1 | −5 | 5 | 12 | 181 | 175 | 3 | 0 | −5 | 13 | 120 | 116 | 1 | −5 | 5 | 13 | 140 | 137 | 2 |
| −2 | 9 | 11 | 132 | 132 | 2 | −4 | −3 | 12 | 67 | 67 | 1 | −4 | 5 | 12 | 26 | 23 | 1 | 1 | −5 | 13 | 56 | 56 | 1 | −4 | 5 | 13 | 89 | 87 | 1 |
| −1 | 9 | 11 | 91 | 91 | 2 | −3 | −3 | 12 | 150 | 162 | 1 | −3 | 5 | 12 | 64 | 63 | 1 | 2 | −5 | 13 | 18 | 15 | 1 | −3 | 5 | 13 | 28 | 25 | 1 |
| 0 | 9 | 11 | 50 | 47 | 1 | −2 | −3 | 12 | 78 | 77 | 1 | −2 | 5 | 12 | 66 | 66 | 1 | −5 | −4 | 13 | 100 | 105 | 2 | −2 | 5 | 13 | 120 | 126 | 1 |
| 1 | 9 | 11 | 117 | 121 | 1 | −1 | −3 | 12 | 220 | 218 | 2 | −1 | 5 | 12 | 25 | 28 | 1 | −4 | −4 | 13 | 106 | 104 | 1 | −1 | 5 | 13 | 64 | 66 | 1 |
| 2 | 9 | 11 | 83 | 83 | 1 | 0 | −3 | 12 | 173 | 174 | 1 | 0 | 5 | 12 | 104 | 98 | 1 | −3 | −4 | 13 | 85 | 83 | 1 | 0 | 5 | 13 | 120 | 116 | 1 |
| 3 | 9 | 11 | 50 | 53 | 1 | 1 | −3 | 12 | 91 | 90 | 1 | 1 | 5 | 12 | 134 | 142 | 1 | −2 | −4 | 13 | 107 | 108 | 1 | 1 | 5 | 13 | 57 | 56 | 1 |
| −5 | 10 | 11 | 25 | 23 | 1 | 2 | −3 | 12 | 67 | 67 | 1 | 2 | 5 | 12 | 91 | 91 | 1 | −1 | −4 | 13 | 123 | 112 | 1 | 2 | 5 | 13 | 19 | 16 | 1 |
| −4 | 10 | 11 | 29 | 30 | 1 | 3 | −3 | 12 | 126 | 131 | 2 | 3 | 5 | 12 | 53 | 53 | 1 | 0 | −4 | 13 | 142 | 146 | 1 | 3 | 5 | 13 | 52 | 53 | 1 |
| −3 | 10 | 11 | 125 | 126 | 2 | 4 | −3 | 12 | 49 | 52 | 1 | −6 | 6 | 12 | 94 | 95 | 1 | 1 | −4 | 13 | 73 | 74 | 1 | −5 | 6 | 13 | 40 | 38 | 1 |
| −2 | 10 | 11 | 71 | 71 | 2 | −7 | −2 | 12 | 92 | 89 | 1 | −5 | 6 | 12 | 88 | 84 | 1 | 2 | −4 | 13 | 102 | 102 | 1 | −4 | 6 | 13 | 113 | 108 | 1 |
| −1 | 10 | 11 | 65 | 63 | 1 | −6 | −2 | 12 | 81 | 82 | 1 | −4 | 6 | 12 | 97 | 97 | 1 | −5 | −3 | 13 | 107 | 106 | 1 | −3 | 6 | 13 | 94 | 90 | 1 |
| 0 | 10 | 11 | 88 | 91 | 1 | −5 | −2 | 12 | 67 | 68 | 1 | −3 | 6 | 12 | 73 | 74 | 1 | −4 | −3 | 13 | 41 | 42 | 1 | −2 | 6 | 13 | 9 | 8 | 5 |
| 1 | 10 | 11 | 106 | 101 | 1 | −4 | −2 | 12 | 74 | 74 | 1 | −2 | 6 | 12 | 86 | 78 | 2 | −3 | −3 | 13 | 90 | 94 | 1 | −1 | 6 | 13 | 19 | 19 | 2 |
| 2 | 10 | 11 | 84 | 88 | 1 | −3 | −2 | 12 | 112 | 108 | 1 | −1 | 6 | 12 | 74 | 74 | 1 | −2 | −3 | 13 | 40 | 39 | 1 | 0 | 6 | 13 | 25 | 24 | 1 |
| −4 | 11 | 11 | 72 | 71 | 1 | −2 | −2 | 12 | 56 | 59 | 1 | 0 | 6 | 12 | 118 | 113 | 1 | −1 | −3 | 13 | 67 | 64 | 1 | 1 | 6 | 13 | 93 | 96 | 1 |
| −3 | 11 | 11 | 51 | 55 | 1 | −1 | −2 | 12 | 54 | 55 | 1 | 1 | 6 | 12 | 57 | 57 | 1 | 0 | −3 | 13 | 187 | 199 | 1 | 2 | 6 | 13 | 37 | 33 | 1 |
| −2 | 11 | 11 | 68 | 63 | 1 | 0 | −2 | 12 | 224 | 228 | 2 | 2 | 6 | 12 | 81 | 78 | 1 | 1 | −3 | 13 | 74 | 74 | 1 | 3 | 6 | 13 | 16 | 15 | 1 |
| 0 | 11 | 11 | 52 | 53 | 1 | 1 | −2 | 12 | 126 | 128 | 1 | 3 | 6 | 12 | 81 | 76 | 1 | 2 | −3 | 13 | 69 | 66 | 1 | −5 | 7 | 13 | 115 | 114 | 1 |
| 1 | 11 | 11 | 91 | 89 | 1 | 2 | −2 | 12 | 98 | 101 | 1 | −6 | 7 | 12 | 106 | 105 | 2 | −5 | −2 | 13 | 29 | 30 | 1 | −4 | 7 | 13 | 104 | 98 | 1 |
| 2 | 11 | 11 | 60 | 62 | 1 | 3 | −2 | 12 | 85 | 84 | 1 | −5 | 7 | 12 | 83 | 80 | 1 | −4 | −2 | 13 | 147 | 146 | 2 | −3 | 7 | 13 | 61 | 60 | 1 |
| −2 | 7 | 13 | 38 | 35 | 2 | −3 | −3 | 14 | 21 | 20 | 1 | 2 | 3 | 14 | 50 | 49 | 1 | −5 | −3 | 15 | 70 | 72 | 1 | 0 | 4 | 15 | 88 | 84 | 1 |
| −1 | 7 | 13 | 63 | 60 | 1 | −2 | −3 | 14 | 87 | 83 | 1 | −5 | 4 | 14 | 62 | 64 | 1 | −4 | −3 | 15 | 39 | 37 | 1 | 1 | 4 | 15 | 16 | 15 | 1 |
| 0 | 7 | 13 | 95 | 94 | 1 | −1 | −3 | 14 | 34 | 34 | 1 | −4 | 4 | 14 | 97 | 92 | 1 | −3 | −3 | 15 | 33 | 36 | 1 | −4 | 5 | 15 | 70 | 72 | 1 |
| 1 | 7 | 13 | 43 | 41 | 1 | 0 | −3 | 14 | 90 | 90 | 1 | −3 | 4 | 14 | 37 | 33 | 1 | −2 | −3 | 15 | 22 | 20 | 1 | −3 | 5 | 15 | 34 | 26 | 1 |
| 2 | 7 | 13 | 38 | 35 | 1 | 1 | −3 | 14 | 112 | 107 | 1 | −2 | 4 | 14 | 96 | 97 | 1 | −1 | −3 | 15 | 37 | 35 | 1 | −2 | 5 | 15 | 11 | 5 | 2 |
| −4 | 8 | 13 | 118 | 114 | 1 | 2 | −3 | 14 | 51 | 49 | 1 | −1 | 4 | 14 | 85 | 81 | 1 | 0 | −3 | 15 | 55 | 53 | 1 | −1 | 5 | 15 | 77 | 77 | 1 |
| −3 | 8 | 13 | 49 | 46 | 1 | −5 | −2 | 14 | 40 | 39 | 1 | 0 | 4 | 14 | 118 | 110 | 1 | 1 | −3 | 15 | 35 | 30 | 1 | 0 | 5 | 15 | 38 | 36 | 1 |
| −2 | 8 | 13 | 111 | 108 | 2 | −4 | −2 | 14 | 164 | 161 | 2 | 1 | 4 | 14 | 72 | 75 | 1 | −5 | −2 | 15 | 51 | 51 | 1 | 1 | 5 | 15 | 109 | 110 | 1 |
| −1 | 8 | 13 | 43 | 47 | 1 | −3 | −2 | 14 | 207 | 202 | 2 | 2 | 4 | 14 | 73 | 76 | 1 | −4 | −2 | 15 | 31 | 30 | 1 | −3 | 6 | 15 | 54 | 60 | 1 |
| 0 | 8 | 13 | 19 | 20 | 1 | −2 | −2 | 14 | 75 | 77 | 1 | −5 | 5 | 14 | 37 | 34 | 1 | −3 | −2 | 15 | 116 | 120 | 1 | −2 | 6 | 15 | 25 | 24 | 1 |

TABLE 8-continued

| Observed and calculated structure factors for MET-1. | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| 1 | 8 | 13 | 89 | 84 | 1 | −1 | −2 | 14 | 66 | 66 | 1 | −4 | 5 | 14 | 98 | 95 | 1 | −2 | −2 | 15 | 72 | 68 | 1 | −1 | 6 | 15 | 35 | 36 | 1 |
| 2 | 8 | 13 | 83 | 81 | 1 | 0 | −2 | 14 | 85 | 86 | 1 | −3 | 5 | 14 | 21 | 22 | 1 | −1 | −2 | 15 | 83 | 87 | 1 | 0 | 6 | 15 | 37 | 36 | 1 |
| −4 | 9 | 13 | 73 | 75 | 1 | 1 | −2 | 14 | 84 | 83 | 1 | −2 | 5 | 14 | 84 | 82 | 1 | 0 | −2 | 15 | 155 | 149 | 2 | −3 | 7 | 15 | 51 | 47 | 1 |
| −3 | 9 | 13 | 147 | 147 | 2 | 2 | −2 | 14 | 34 | 37 | 1 | −1 | 5 | 14 | 74 | 69 | 1 | 1 | −2 | 15 | 44 | 46 | 1 | −2 | 7 | 15 | 77 | 80 | 1 |
| −2 | 9 | 13 | 68 | 67 | 1 | −5 | −1 | 14 | 81 | 85 | 1 | 0 | 5 | 14 | 57 | 57 | 1 | −5 | −1 | 15 | 26 | 30 | 1 | −1 | 7 | 15 | 14 | 11 | 2 |
| −1 | 9 | 13 | 36 | 35 | 1 | −4 | −1 | 14 | 117 | 117 | 1 | 1 | 5 | 14 | 70 | 70 | 1 | −4 | −1 | 15 | 85 | 86 | 1 | −3 | −4 | 16 | 43 | 42 | 1 |
| 0 | 9 | 13 | 75 | 71 | 1 | −3 | −1 | 14 | 47 | 44 | 1 | 2 | 5 | 14 | 49 | 47 | 1 | −3 | −1 | 15 | 56 | 57 | 1 | −2 | −4 | 16 | 49 | 51 | 1 |
| 1 | 9 | 13 | 35 | 32 | 1 | −2 | −1 | 14 | 26 | 26 | 1 | −5 | 6 | 14 | 62 | 62 | 1 | −2 | −1 | 15 | 31 | 34 | 1 | −1 | −4 | 16 | 30 | 29 | 1 |
| −3 | 10 | 13 | 24 | 23 | 1 | −1 | −1 | 14 | 78 | 76 | 1 | −4 | 6 | 14 | 125 | 120 | 1 | −1 | −1 | 15 | 149 | 147 | 1 | −3 | −3 | 16 | 12 | 10 | 1 |
| −1 | 10 | 13 | 125 | 125 | 1 | 0 | −1 | 14 | 149 | 148 | 1 | −3 | 6 | 14 | 105 | 102 | 1 | 0 | −1 | 15 | 40 | 40 | 1 | −2 | −3 | 16 | 24 | 25 | 1 |
| 0 | 10 | 13 | 45 | 43 | 1 | 1 | −1 | 14 | 48 | 51 | 1 | −2 | 6 | 14 | 28 | 27 | 1 | 1 | −1 | 15 | 37 | 36 | 1 | −1 | −3 | 16 | 49 | 50 | 1 |
| −2 | −9 | 14 | 64 | 69 | 1 | 2 | −1 | 14 | 17 | 15 | 1 | −1 | 6 | 14 | 64 | 62 | 1 | 2 | −1 | 15 | 55 | 54 | 1 | 0 | −3 | 16 | 45 | 43 | 1 |
| −1 | −9 | 14 | 52 | 49 | 1 | −5 | 0 | 14 | 38 | 37 | 1 | 0 | 6 | 14 | 28 | 22 | 1 | −5 | 0 | 15 | 45 | 45 | 1 | −4 | −2 | 16 | 40 | 41 | 1 |
| −3 | −8 | 14 | 26 | 25 | 1 | −4 | 0 | 14 | 17 | 19 | 2 | 1 | 6 | 14 | 55 | 53 | 1 | −4 | 0 | 15 | 80 | 82 | 1 | −3 | −2 | 16 | 34 | 30 | 1 |
| −2 | −8 | 14 | 66 | 64 | 1 | −3 | 0 | 14 | 43 | 42 | 1 | 2 | 6 | 14 | 126 | 129 | 2 | −3 | 0 | 15 | 14 | 9 | 1 | −2 | −2 | 16 | 54 | 57 | 1 |
| −1 | −8 | 14 | 34 | 33 | 1 | −2 | 0 | 14 | 95 | 97 | 1 | −4 | 7 | 14 | 29 | 30 | 1 | −2 | 0 | 15 | 42 | 48 | 1 | −1 | −2 | 16 | 60 | 57 | 1 |
| 0 | −8 | 14 | 85 | 83 | 1 | −1 | 0 | 14 | 132 | 132 | 1 | −3 | 7 | 14 | 90 | 83 | 1 | −1 | 0 | 15 | 5 | 4 | 5 | 0 | −2 | 16 | 117 | 118 | 1 |
| −4 | −7 | 14 | 30 | 30 | 1 | 0 | 0 | 14 | 81 | 76 | 1 | −2 | 7 | 14 | 129 | 129 | 2 | 0 | 0 | 15 | 10 | 12 | 3 | −4 | −1 | 16 | 89 | 86 | 1 |
| −3 | −7 | 14 | 89 | 83 | 1 | 1 | 0 | 14 | 62 | 60 | 1 | −1 | 7 | 14 | 33 | 36 | 1 | 1 | 0 | 15 | 12 | 14 | 1 | −3 | −1 | 16 | 78 | 78 | 1 |
| −2 | −7 | 14 | 130 | 129 | 1 | 2 | 0 | 14 | 4 | 2 | 4 | 0 | 7 | 14 | 66 | 64 | 1 | 2 | 0 | 15 | 54 | 48 | 1 | −2 | −1 | 16 | 12 | 13 | 1 |
| −1 | −7 | 14 | 32 | 36 | 1 | −6 | 1 | 14 | 59 | 60 | 1 | 1 | 7 | 14 | 15 | 15 | 1 | −5 | 1 | 15 | 26 | 30 | 1 | −1 | −1 | 16 | 104 | 100 | 1 |
| 0 | −7 | 14 | 67 | 64 | 1 | −5 | 1 | 14 | 83 | 85 | 1 | −3 | 8 | 14 | 27 | 26 | 1 | −4 | 1 | 15 | 86 | 86 | 1 | 0 | −1 | 16 | 129 | 129 | 1 |
| 1 | −7 | 14 | 15 | 16 | 1 | −4 | 1 | 14 | 117 | 117 | 1 | −2 | 8 | 14 | 66 | 64 | 1 | −3 | 1 | 15 | 57 | 57 | 1 | −4 | 0 | 16 | 106 | 108 | 1 |
| −4 | −6 | 14 | 120 | 120 | 1 | −3 | 1 | 14 | 47 | 44 | 1 | −1 | 8 | 14 | 34 | 32 | 1 | −2 | 1 | 15 | 34 | 34 | 1 | −3 | 0 | 16 | 4 | 6 | 4 |
| −3 | −6 | 14 | 103 | 102 | 1 | −2 | 1 | 14 | 25 | 26 | 1 | 0 | 8 | 14 | 85 | 82 | 1 | −1 | 1 | 15 | 150 | 147 | 1 | −2 | 0 | 16 | 40 | 35 | 1 |
| −2 | −6 | 14 | 28 | 27 | 1 | −1 | 1 | 14 | 79 | 76 | 1 | −1 | 9 | 14 | 53 | 49 | 1 | 0 | 1 | 15 | 41 | 40 | 1 | −1 | 0 | 16 | 32 | 33 | 1 |
| −1 | −6 | 14 | 66 | 63 | 1 | 0 | 1 | 14 | 150 | 148 | 2 | −3 | −7 | 15 | 50 | 47 | 1 | 1 | 1 | 15 | 35 | 36 | 1 | 0 | 0 | 16 | 30 | 30 | 1 |
| 0 | −6 | 14 | 27 | 22 | 1 | 1 | 1 | 14 | 47 | 51 | 1 | −2 | −7 | 15 | 77 | 80 | 1 | 2 | 1 | 15 | 53 | 53 | 1 | −4 | 1 | 16 | 86 | 86 | 1 |
| 1 | −6 | 14 | 59 | 53 | 1 | 2 | 1 | 14 | 15 | 16 | 1 | −1 | −7 | 15 | 10 | 11 | 1 | −5 | 2 | 15 | 50 | 51 | 1 | −3 | 1 | 16 | 79 | 79 | 1 |
| −5 | −5 | 14 | 36 | 34 | 1 | −6 | 2 | 14 | 21 | 23 | 1 | −3 | −6 | 15 | 55 | 60 | 1 | −4 | 2 | 15 | 27 | 29 | 1 | −2 | 1 | 16 | 13 | 13 | 1 |
| −4 | −5 | 14 | 96 | 95 | 1 | −5 | 2 | 14 | 42 | 40 | 1 | −2 | −6 | 15 | 26 | 24 | 1 | −3 | 2 | 15 | 118 | 119 | 1 | −1 | 1 | 16 | 103 | 100 | 1 |
| −3 | −5 | 14 | 25 | 22 | 1 | −4 | 2 | 14 | 164 | 160 | 1 | −1 | −6 | 15 | 35 | 35 | 1 | −2 | 2 | 15 | 72 | 68 | 1 | 0 | 1 | 16 | 128 | 129 | 1 |
| −2 | −5 | 14 | 86 | 82 | 1 | −3 | 2 | 14 | 209 | 202 | 2 | 0 | −6 | 15 | 36 | 36 | 1 | −1 | 2 | 15 | 83 | 87 | 1 | −4 | 2 | 16 | 42 | 41 | 1 |
| −1 | −5 | 14 | 76 | 69 | 1 | −2 | 2 | 14 | 75 | 76 | 1 | −4 | −5 | 15 | 75 | 73 | 1 | 0 | 2 | 15 | 156 | 149 | 2 | −3 | 2 | 16 | 36 | 30 | 1 |
| 0 | −5 | 14 | 54 | 57 | 1 | −1 | 2 | 14 | 66 | 66 | 1 | −3 | −5 | 15 | 30 | 26 | 1 | 1 | 2 | 15 | 47 | 47 | 1 | −2 | 2 | 16 | 54 | 57 | 1 |
| 1 | −5 | 14 | 71 | 71 | 1 | 0 | 2 | 14 | 87 | 87 | 1 | −2 | −5 | 15 | 9 | 5 | 1 | −4 | 3 | 15 | 41 | 37 | 1 | −1 | 2 | 16 | 60 | 56 | 1 |
| −5 | −4 | 14 | 64 | 65 | 1 | 1 | 2 | 14 | 83 | 83 | 1 | −1 | −5 | 15 | 77 | 77 | 1 | −3 | 3 | 15 | 35 | 36 | 1 | 0 | 2 | 16 | 117 | 118 | 1 |
| −4 | −4 | 14 | 94 | 92 | 1 | 2 | 2 | 14 | 33 | 37 | 1 | 0 | −5 | 15 | 39 | 35 | 1 | −2 | 3 | 15 | 19 | 19 | 1 | −3 | 3 | 16 | 13 | 11 | 4 |
| −3 | −4 | 14 | 35 | 33 | 1 | −5 | 3 | 14 | 27 | 22 | 1 | 1 | −5 | 15 | 110 | 110 | 2 | −1 | 3 | 15 | 38 | 35 | 1 | −2 | 3 | 16 | 25 | 25 | 1 |
| −2 | −4 | 14 | 98 | 97 | 1 | −4 | 3 | 14 | 34 | 32 | 1 | −4 | −4 | 15 | 21 | 21 | 1 | 0 | 3 | 15 | 56 | 53 | 1 | −1 | 3 | 16 | 49 | 49 | 1 |
| −1 | −4 | 14 | 86 | 80 | 1 | −3 | 3 | 14 | 20 | 20 | 1 | −3 | −4 | 15 | 8 | 9 | 3 | 1 | 3 | 15 | 35 | 30 | 1 | 0 | 3 | 16 | 45 | 43 | 1 |
| 0 | −4 | 14 | 118 | 111 | 1 | −2 | 3 | 14 | 85 | 83 | 1 | −2 | −4 | 15 | 35 | 32 | 1 | −4 | 4 | 15 | 22 | 21 | 1 | −3 | 4 | 16 | 42 | 42 | 1 |
| 1 | −4 | 14 | 72 | 75 | 1 | −1 | 3 | 14 | 34 | 34 | 1 | −1 | −4 | 15 | 38 | 37 | 1 | −3 | 4 | 15 | 10 | 9 | 1 | −2 | 4 | 16 | 49 | 51 | 1 |
| −5 | −3 | 14 | 21 | 22 | 1 | 0 | 3 | 14 | 91 | 90 | 1 | 0 | −4 | 15 | 86 | 84 | 1 | −2 | 4 | 15 | 34 | 32 | 1 | −1 | 4 | 16 | 29 | 29 | 1 |
| −4 | −3 | 14 | 32 | 32 | 1 | 1 | 3 | 14 | 113 | 107 | 1 | 1 | −4 | 15 | 14 | 15 | 2 | −1 | 4 | 15 | 39 | 37 | 1 | | | | | | |

TABLE 9

| Crystal data and structure refinement for MET-2. | | |
|---|---|---|
| Empirical formula | $C_{32}H_{56}O_4$ | |
| Formula weight | 504.77 | |
| Temperature | 298(1) K | |
| Wavelength | 1.54178 Å | |
| Crystal system, space group | Monoclinic, C2 | |
| Unit cell dimensions | a = 27.3382(16) Å | α = 90° |
| | b = 6.6860(13) Å | β = 113.57(3)° |
| | c = 19.221(10) A | γ = 90° |
| Volume | 3320.3(11) $Å^3$ | |
| Z | 4 | |
| Calculated density | 1.041 $Mg/m^3$ | |
| Absorption coefficient | 0.513 $mm^{-1}$ | |
| F(000) | 1120 | |
| Crystal size | 0.36 × 0.17 × 0.03 mm | |
| Theta range for data collection | 2.51 to 58.69° | |
| Limiting indices | −29 <= h <= 28, −6 <= k <= 6, −21 <= l <= 21 | |
| Reflections collected/unique | 10383/3985 [R(int) = 0.0473] | |
| Data/restraints/parameters | 3985/1/325 | |
| Goodness-of-fit on $F^2$ | 1.073 | |
| Final R indices [I > 2σ(I)] | R1 = 0.0618, wR2 = 0.1600 | |
| R indices (all data) | R1 = 0.0844, wR2 = 0.1778 | |
| Absolute structure parameter | 0.2(4) | |
| Largest diff. peak and hole | 0.140 and −0.190 e/$Å^{-3}$ | |

TABLE 10

Atomic coordinates ($Å^2 \times 10^4$) and equivalent isotropic displacement parameters ($Å^2 \times 10^3$) for MET-2 U(eq) is defined as one third of the trace of the orthogonalized Uij tensor.

| | x | y | z | U(eq) |
|---|---|---|---|---|
| O(3) | 9651(1) | 8018(5) | 3345(2) | 80(1) |
| C(20) | 7634(1) | 8343(6) | −2763(2) | 67(1) |
| O(25) | 9328(1) | 7952(6) | −3391(2) | 102(1) |
| C(13) | 7985(1) | 7574(6) | −1301(2) | 59(1) |
| C(1) | 9449(2) | 12075(6) | 2708(2) | 66(1) |
| C(17) | 8118(1) | 8204(6) | −1982(2) | 59(1) |
| O(1) | 9565(1) | 14167(5) | 2735(2) | 88(1) |
| C(10) | 8922(2) | 11685(7) | 2036(2) | 73(1) |
| C(23) | 8253(2) | 8546(7) | −3469(2) | 70(1) |
| C(2) | 9409(2) | 11384(7) | 3438(2) | 67(1) |
| C(12) | 7838(2) | 5387(7) | −1291(2) | 74(1) |
| C(14) | 8539(1) | 7926(6) | −637(2) | 64(1) |
| C(22) | 7766(2) | 7484(7) | −3431(2) | 69(1) |
| C(18) | 7564(2) | 8908(7) | −1201(3) | 79(1) |
| C(5) | 8739(2) | 9568(7) | 2011(2) | 68(1) |
| C(3) | 9242(2) | 9248(7) | 3413(2) | 68(1) |
| C(15) | 8704(2) | 9975(8) | −812(2) | 77(1) |
| C(9) | 8370(2) | 5285(7) | 139(2) | 83(1) |
| C(16) | 8471(2) | 10076(7) | −1687(2) | 76(1) |
| C(25) | 8924(2) | 8719(10) | −4091(2) | 93(2) |
| C(8) | 8525(2) | 7441(7) | 118(2) | 69(1) |
| C(30) | 7870(2) | 5245(7) | −3306(3) | 98(2) |
| C(28) | 7279(2) | 7779(10) | −4185(2) | 103(2) |
| C(24) | 8394(2) | 7945(10) | −4124(2) | 91(2) |
| C(11) | 7843(2) | 4765(8) | −517(2) | 83(1) |
| C(4) | 8712(2) | 8882(8) | 2740(2) | 74(1) |
| C(27) | 8974(2) | 10999(12) | −4028(4) | 134(3) |
| C(6) | 8624(1) | 8330(8) | 1421(2) | 72(1) |
| C(21) | 7379(2) | 10414(8) | −2945(3) | 98(2) |
| C(26) | 9029(2) | 7983(18) | −4745(3) | 177(4) |
| C(7) | 8639(2) | 8753(7) | 686(2) | 72(1) |
| C(29) | 9490(2) | 12565(9) | 4016(2) | 97(2) |
| O(201) | 10425(1) | 14824(6) | 2396(2) | 112(1) |
| C(202) | 10381(3) | 15282(14) | 1660(3) | 128(2) |
| C(201) | 10109(4) | 17151(16) | 1381(5) | 185(4) |
| C(203) | 10130(5) | 13539(17) | 1161(5) | 223(5) |

TABLE 11

| Bond lengths [Å] for MET-2. | |
|---|---|
| O(3)—C(3) | 1.434(5) |
| C(20)—C(21) | 1.527(6) |
| C(20)—C(17) | 1.558(5) |
| C(20)—C(22) | 1.573(5) |
| O(25)—C(25) | 1.451(5) |
| C(13)—C(12) | 1.518(6) |
| C(13)—C(18) | 1.527(6) |
| C(13)—C(17) | 1.549(5) |
| C(13)—C(14) | 1.560(5) |
| C(1)—O(1) | 1.431(5) |
| C(1)—C(2) | 1.521(5) |
| C(1)—C(10) | 1.524(6) |
| C(17)—C(16) | 1.543(6) |
| C(10)—C(5) | 1.495(6) |
| C(23)—C(24) | 1.511(5) |
| C(23)—C(22) | 1.535(6) |
| C(2)—C(29) | 1.308(6) |
| C(2)—C(3) | 1.495(6) |
| C(12)—C(11) | 1.541(5) |
| C(14)—C(8) | 1.501(5) |
| C(14)—C(15) | 1.522(6) |
| C(22)—C(30) | 1.524(7) |
| C(22)—C(28) | 1.541(6) |
| C(5)—C(6) | 1.336(6) |
| C(5)—C(4) | 1.505(5) |
| C(3)—C(4) | 1.527(5) |
| C(15)—C(16) | 1.543(5) |
| C(9)—C(8) | 1.508(7) |
| C(9)—C(11) | 1.527(6) |
| C(25)—C(26) | 1.483(8) |
| C(25)—C(24) | 1.516(7) |
| C(25)—C(27) | 1.532(9) |
| C(8)—C(7) | 1.336(6) |
| C(6)—C(7) | 1.458(5) |
| O(201)—C(202) | 1.405(7) |
| C(202)—C(201) | 1.443(11) |
| C(202)—C(203) | 1.490(11) |

TABLE 12

| bond angles [°] for MET-2. | |
|---|---|
| C(21)—C(20)—C(17) | 114.1(3) |
| C(21)—C(20)—C(22) | 112.2(4) |
| C(17)—C(20)—C(22) | 112.4(3) |
| C(12)—C(13)—C(18) | 110.1(3) |
| C(12)—C(13)—C(17) | 115.2(3) |
| C(18)—C(13)—C(17) | 113.0(3) |
| C(12)—C(13)—C(14) | 108.1(3) |
| C(18)—C(13)—C(14) | 110.0(3) |
| C(17)—C(13)—C(14) | 99.8(3) |
| O(1)—C(1)—C(2) | 111.1(3) |
| O(1)—C(1)—C(10) | 108.7(4) |
| C(2)—C(1)—C(10) | 109.7(3) |
| C(16)—C(17)—C(13) | 103.5(3) |
| C(16)—C(17)—C(20) | 118.1(3) |
| C(13)—C(17)—C(20) | 115.7(3) |
| C(5)—C(10)—C(1) | 112.3(3) |
| C(24)—C(23)—C(22) | 115.5(4) |
| C(29)—C(2)—C(3) | 123.4(4) |
| C(29)—C(2)—C(1) | 123.4(4) |
| C(3)—C(2)—C(1) | 113.2(3) |
| C(13)—C(12)—C(11) | 111.8(3) |
| C(8)—C(14)—C(15) | 122.2(3) |
| C(8)—C(14)—C(13) | 111.5(3) |
| C(15)—C(14)—C(13) | 103.4(3) |
| C(30)—C(22)—C(23) | 110.6(4) |
| C(30)—C(22)—C(28) | 108.1(4) |
| C(23)—C(22)—C(28) | 109.6(3) |
| C(30)—C(22)—C(20) | 108.7(3) |
| C(23)—C(22)—C(20) | 110.8(3) |
| C(28)—C(22)—C(20) | 109.1(3) |
| C(6)—C(5)—C(10) | 125.2(4) |
| C(6)—C(5)—C(4) | 121.3(4) |
| C(10)—C(5)—C(4) | 113.5(4) |

TABLE 12-continued

| bond angles [°] for MET-2. | |
|---|---|
| O(3)—C(3)—C(2) | 108.1(3) |
| O(3)—C(3)—C(4) | 109.9(3) |
| C(2)—C(3)—C(4) | 110.8(4) |
| C(14)—C(15)—C(16) | 104.5(3) |
| C(8)—C(9)—C(11) | 112.2(4) |
| C(17)—C(16)—C(15) | 106.9(3) |
| O(25)—C(25)—C(26) | 109.6(5) |
| O(25)—C(25)—C(24) | 106.2(4) |
| C(26)—C(25)—C(24) | 111.0(5) |
| O(25)—C(25)—C(27) | 105.5(5) |
| C(26)—C(25)—C(27) | 110.8(6) |
| C(24)—C(25)—C(27) | 113.4(5) |
| C(7)—C(8)—C(14) | 124.1(4) |
| C(7)—C(8)—C(9) | 125.5(4) |
| C(14)—C(8)—C(9) | 110.4(3) |
| C(23)—C(24)—C(25) | 115.6(4) |
| C(9)—C(11)—C(12) | 112.2(3) |
| C(5)—C(4)—C(3) | 110.9(3) |
| C(5)—C(6)—C(7) | 127.9(4) |
| C(8)—C(7)—C(6) | 125.2(4) |
| O(201)—C(202)—C(201) | 112.8(6) |
| O(201)—C(202)—C(203) | 108.1(7) |
| C(201)—C(202)—C(203) | 113.8(7) |

TABLE 13

Anisotropic displacement parameters ($Å^2 \times 10^3$) for MET-2. The anisotropic displacement factor exponent takes the form "$-2\pi^2[h^2a * 2U_{11} + + 2hka * b * U_{12}]$

| | $U_{11}$ | $U_{22}$ | $U_{33}$ | $U_{23}$ | $U_{13}$ | $U_{12}$ |
|---|---|---|---|---|---|---|
| O(3) | 67(2) | 71(2) | 93(2) | −5(2) | 22(1) | −7(2) |
| C(20) | 58(2) | 70(3) | 67(2) | −4(2) | 20(2) | −6(2) |
| O(25) | 79(2) | 144(3) | 86(2) | 43(2) | 36(2) | 34(2) |
| C(13) | 63(2) | 53(3) | 67(2) | −10(2) | 31(2) | −4(2) |
| C(1) | 73(3) | 52(3) | 75(3) | −5(2) | 31(2) | −8(2) |
| C(17) | 53(2) | 65(3) | 60(2) | −10(2) | 23(2) | −12(2) |
| O(1) | 102(2) | 67(2) | 87(2) | −11(2) | 31(2) | −14(2) |
| C(10) | 76(3) | 76(3) | 60(2) | −6(2) | 18(2) | −3(2) |
| C(23) | 65(2) | 79(3) | 65(2) | −1(2) | 25(2) | −7(2) |
| C(2) | 62(2) | 73(3) | 63(2) | −7(2) | 21(2) | −5(2) |
| C(12) | 88(3) | 74(3) | 65(2) | −12(2) | 37(2) | −23(2) |
| C(14) | 65(2) | 65(3) | 63(2) | −9(2) | 27(2) | −11(2) |
| C(22) | 61(2) | 79(3) | 64(2) | −9(2) | 21(2) | −16(2) |
| C(18) | 68(2) | 86(3) | 91(3) | −20(2) | 38(2) | −8(2) |
| C(5) | 54(2) | 82(3) | 58(2) | −6(2) | 14(2) | −13(2) |
| C(3) | 68(2) | 76(3) | 59(2) | −4(2) | 24(2) | −9(2) |
| C(15) | 78(3) | 82(3) | 71(2) | −11(2) | 30(2) | −23(3) |
| C(9) | 106(3) | 76(3) | 68(2) | −4(2) | 38(2) | −11(3) |
| C(16) | 73(3) | 80(3) | 73(2) | −7(2) | 26(2) | −26(2) |
| C(25) | 68(3) | 146(6) | 64(3) | 17(3) | 24(2) | 3(3) |
| C(8) | 66(2) | 72(3) | 65(2) | −4(2) | 22(2) | −6(2) |
| C(30) | 152(5) | 58(3) | 103(3) | −15(3) | 70(3) | −17(3) |
| C(28) | 76(3) | 148(5) | 71(3) | −6(3) | 16(2) | −18(3) |
| C(24) | 81(3) | 129(5) | 65(2) | −4(3) | 31(2) | −11(3) |
| C(11) | 108(3) | 78(3) | 76(3) | −16(2) | 49(3) | −37(3) |
| C(4) | 60(2) | 97(4) | 67(2) | −2(2) | 28(2) | −14(2) |
| C(27) | 75(4) | 156(7) | 150(5) | 72(5) | 22(3) | −12(4) |
| C(6) | 60(2) | 84(3) | 67(2) | −7(2) | 20(2) | −19(2) |
| C(21) | 88(3) | 94(4) | 103(3) | 10(3) | 26(3) | 32(3) |
| C(26) | 137(5) | 337(12) | 83(3) | −5(6) | 72(4) | −23(7) |
| C(7) | 65(2) | 81(3) | 60(2) | −4(2) | 15(2) | −17(2) |
| C(29) | 125(4) | 92(4) | 69(3) | −10(3) | 35(3) | −8(3) |
| O(201) | 123(3) | 122(3) | 96(2) | −17(2) | 51(2) | −23(2) |
| C(202) | 113(4) | 180(8) | 101(4) | −8(5) | 54(4) | −21(5) |
| C(201) | 192(8) | 180(9) | 152(7) | 42(6) | 36(6) | 15(8) |
| C(203) | 305(13) | 227(11) | 134(6) | −84(7) | 85(7) | −25(10) |

TABLE 14

Hydrogen coordinates ($Å^2 \times 10^4$) and isotropic displacement parameters ($Å^2 \times 10^3$) for MET-2.

| | x | y | z | U(eq) |
|---|---|---|---|---|
| H(3A) | 9521 | 6950 | 3147 | 120 |
| H(20I) | 7360 | 7457 | −2725 | 80 |
| H(25A) | 9621 | 8007 | −3413 | 153 |
| H(1A) | 9733 | 11326 | 2636 | 79 |
| H(17A) | 8352 | 7159 | −2035 | 71 |
| H(1B) | 9853 | 14390 | 3088 | 131 |
| H(10A) | 8651 | 12572 | 2069 | 88 |
| H(10B) | 8963 | 11988 | 1569 | 88 |
| H(23A) | 8187 | 9976 | −3499 | 84 |
| H(23B) | 8559 | 8290 | −2999 | 84 |
| H(12A) | 8088 | 4563 | −1405 | 88 |
| H(12B) | 7484 | 5157 | −1683 | 88 |
| H(14A) | 8784 | 6962 | −710 | 77 |
| H(18A) | 7495 | 8444 | −777 | 119 |
| H(18B) | 7241 | 8859 | −1653 | 119 |
| H(18C) | 7693 | 10260 | −1111 | 119 |
| H(3B) | 9203 | 8917 | 3885 | 82 |
| H(15A) | 9090 | 10101 | −603 | 92 |
| H(15B) | 8558 | 11029 | −605 | 92 |
| H(9A) | 8338 | 5027 | 616 | 99 |
| H(9B) | 8649 | 4428 | 116 | 99 |
| H(16A) | 8260 | 11280 | −1864 | 92 |
| H(16B) | 8756 | 10086 | −1867 | 92 |
| H(30A) | 7954 | 4704 | −3709 | 147 |
| H(30B) | 7558 | 4597 | −3304 | 147 |
| H(30C) | 8165 | 5024 | −2829 | 147 |
| H(28A) | 7358 | 7266 | −4595 | 154 |
| H(28B) | 7197 | 9178 | −4264 | 154 |
| H(28C) | 6978 | 7076 | −4166 | 154 |
| H(24A) | 8114 | 8414 | −4591 | 109 |
| H(24B) | 8398 | 6496 | −4147 | 109 |
| H(11A) | 7553 | 5434 | −441 | 100 |
| H(11B) | 7783 | 3335 | −517 | 100 |
| H(4A) | 8627 | 7467 | 2706 | 89 |
| H(4B) | 8430 | 9599 | 2818 | 89 |
| H(27A) | 9317 | 11395 | −4006 | 201 |
| H(27B) | 8937 | 11432 | −3575 | 201 |
| H(27C) | 8699 | 11600 | −4462 | 201 |
| H(6A) | 8522 | 7041 | 1487 | 87 |
| H(21A) | 7302 | 10877 | −2527 | 148 |
| H(21B) | 7054 | 10341 | −3393 | 148 |
| H(21C) | 7620 | 11328 | −3030 | 148 |
| H(26A) | 8994 | 6554 | −4776 | 265 |
| H(26B) | 9385 | 8347 | −4679 | 265 |
| H(26C) | 8778 | 8571 | −5205 | 265 |
| H(7A) | 8736 | 10038 | 606 | 86 |
| H(29A) | 9444 | 12086 | 4440 | 116 |
| H(29B) | 9594 | 13885 | 4003 | 116 |
| H(20A) | 10540 | 15801 | 2672 | 167 |
| H(20B) | 10744 | 15418 | 1682 | 154 |
| H(20C) | 10300 | 18216 | 1714 | 278 |
| H(20D) | 9753 | 17079 | 1362 | 278 |
| H(20E) | 10094 | 17402 | 881 | 278 |
| H(20F) | 10095 | 13823 | 653 | 334 |
| H(20G) | 9784 | 13292 | 1161 | 334 |
| H(20H) | 10351 | 12378 | 1348 | 334 |

TABLE 15

| Torsion angles [deg] for MET-2. | |
|---|---|
| C(12)—C(13)—C(17)—C(16) | −156.5(4) |
| C(18)—C(13)—C(17)—C(16) | 75.8(4) |
| C(14)—C(13)—C(17)—C(16) | −41.0(4) |
| C(12)—C(13)—C(17)—C(20) | 72.7(5) |
| C(18)—C(13)—C(17)—C(20) | −55.1(4) |
| C(14)—C(13)—C(17)—C(20) | −171.9(3) |
| C(21)—C(20)—C(17)—C(16) | −32.0(5) |
| C(22)—C(20)—C(17)—C(16) | 97.2(4) |
| C(21)—C(20)—C(17)—C(13) | 91.5(5) |
| C(22)—C(20)—C(17)—C(13) | −139.3(4) |
| O(1)—C(1)—C(10)—C(5) | −174.1(4) |

TABLE 15-continued

| Torsion angles [deg] for MET-2. | |
|---|---|
| C(2)—C(1)—C(10)—C(5) | −52.4(5) |
| O(1)—C(1)—C(2)—C(29) | −2.0(6) |
| C(10)—C(1)—C(2)—C(29) | −122.2(5) |
| O(1)—C(1)—C(2)—C(3) | 175.1(4) |
| C(10)—C(1)—C(2)—C(3) | 54.9(5) |
| C(18)—C(13)—C(12)—C(11) | −64.5(5) |
| C(17)—C(13)—C(12)—C(11) | 166.3(3) |
| C(14)—C(13)—C(12)—C(11) | 55.7(4) |
| C(12)—C(13)—C(14)—C(8) | −59.9(4) |
| C(18)—C(13)—C(14)—C(8) | 60.3(5) |
| C(17)—C(13)—C(14)—C(8) | 179.4(3) |
| C(12)—C(13)—C(14)—C(15) | 167.1(3) |
| C(18)—C(13)—C(14)—C(15) | −72.7(4) |
| C(17)—C(13)—C(14)—C(15) | 46.3(4) |
| C(24)—C(23)—C(22)—C(30) | 63.6(5) |
| C(24)—C(23)—C(22)—C(28) | −55.4(5) |
| C(24)—C(23)—C(22)—C(20) | −175.9(4) |
| C(21)—C(20)—C(22)—C(30) | −164.4(4) |
| C(17)—C(20)—C(22)—C(30) | 65.4(4) |
| C(21)—C(20)—C(22)—C(23) | 73.9(4) |
| C(17)—C(20)—C(22)—C(23) | −56.3(5) |
| C(21)—C(20)—C(22)—C(28) | −46.8(5) |
| C(17)—C(20)—C(22)—C(28) | −177.0(4) |
| C(1)—C(10)—C(5)—C(6) | −124.5(4) |
| C(1)—C(10)—C(5)—C(4) | 53.4(5) |
| C(29)—C(2)—C(3)—O(3) | −118.5(5) |
| C(1)—C(2)—C(3)—O(3) | 64.5(4) |
| C(29)—C(2)—C(3)—C(4) | 121.0(5) |
| C(1)—C(2)—C(3)—C(4) | −56.1(4) |

TABLE 15-continued

| Torsion angles [deg] for MET-2. | |
|---|---|
| C(8)—C(14)—C(15)—C(16) | −159.9(4) |
| C(13)—C(14)—C(15)—C(16) | −33.4(4) |
| C(13)—C(17)—C(16)—C(15) | 21.6(4) |
| C(20)—C(17)—C(16)—C(15) | 151.0(3) |
| C(14)—C(15)—C(16)—C(17) | 7.3(5) |
| C(15)—C(14)—C(8)—C(7) | 2.0(6) |
| C(13)—C(14)—C(8)—C(7) | −120.8(4) |
| C(15)—C(14)—C(8)—C(9) | −177.6(4) |
| C(13)—C(14)—C(8)—C(9) | 59.6(5) |
| C(11)—C(9)—C(8)—C(7) | 125.6(4) |
| C(11)—C(9)—C(8)—C(14) | −54.8(5) |
| C(22)—C(23)—C(24)—C(25) | −170.1(4) |
| O(25)—C(25)—C(24)—C(23) | 59.0(6) |
| C(26)—C(25)—C(24)—C(23) | 178.1(6) |
| C(27)—C(25)—C(24)—C(23) | −56.4(6) |
| C(8)—C(9)—C(11)—C(12) | 51.6(6) |
| C(13)—C(12)—C(11)—C(9) | −53.0(5) |
| C(6)—C(5)—C(4)—C(3) | 124.7(4) |
| C(10)—C(5)—C(4)—C(3) | −53.3(5) |
| O(3)—C(3)—C(4)—C(5) | −65.7(5) |
| C(2)—C(3)—C(4)—C(5) | 53.8(5) |
| C(10)—C(5)—C(6)—C(7) | −1.2(7) |
| C(4)—C(5)—C(6)—C(7) | −179.0(4) |
| C(14)—C(8)—C(7)—C(6) | 179.4(4) |
| C(9)—C(8)—C(7)—C(6) | −1.1(7) |
| C(5)—C(6)—C(7)—C(8) | 179.2(4) |

TABLE 16

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 16 | −6 | 0 | 23 | 6 | 23 | 8 | 2 | 0 | 224 | 220 | 8 | −15 | −3 | 1 | 173 | 173 | 6 | 0 | 0 | 1 | 381 | 388 | 6 | −12 | 4 | 1 | 124 | 117 | 4 |
| 9 | −5 | 0 | 179 | 178 | 8 | 10 | 2 | 0 | 276 | 310 | 10 | −13 | −3 | 1 | 172 | 175 | 6 | 2 | 0 | 1 | 833 | 936 | 12 | −10 | 4 | 1 | 197 | 179 | 4 |
| 11 | −5 | 0 | 59 | 52 | 13 | 12 | 2 | 0 | 175 | 180 | 7 | −11 | −3 | 1 | 115 | 118 | 5 | 4 | 0 | 1 | 1025 | 1083 | 15 | −8 | 4 | 1 | 91 | 99 | 4 |
| 13 | −5 | 0 | 99 | 92 | 9 | 14 | 2 | 0 | 56 | 63 | 14 | −9 | −3 | 1 | 240 | 217 | 8 | 6 | 0 | 1 | 570 | 567 | 9 | −6 | 4 | 1 | 295 | 284 | 5 |
| 15 | −5 | 0 | 0 | 21 | 1 | 18 | 2 | 0 | 194 | 198 | 6 | −7 | −3 | 1 | 205 | 199 | 8 | 8 | 0 | 1 | 1171 | 1214 | 18 | −4 | 4 | 1 | 213 | 211 | 4 |
| 17 | −5 | 0 | 60 | 46 | 13 | 20 | 2 | 0 | 86 | 102 | 12 | −5 | −3 | 1 | 348 | 327 | 10 | 10 | 0 | 1 | 73 | 67 | 4 | −2 | 4 | 1 | 387 | 390 | 4 |
| 19 | −5 | 0 | 23 | 27 | 23 | 22 | 2 | 0 | 76 | 77 | 13 | −3 | −3 | 1 | 592 | 563 | 18 | 12 | 0 | 1 | 331 | 349 | 8 | 0 | 4 | 1 | 224 | 227 | 3 |
| 4 | −4 | 0 | 167 | 167 | 8 | 24 | 2 | 0 | 110 | 145 | 10 | −1 | −3 | 1 | 463 | 464 | 10 | 14 | 0 | 1 | 13 | 30 | 13 | 2 | 4 | 1 | 452 | 446 | 5 |
| 6 | −4 | 0 | 204 | 189 | 5 | 26 | 2 | 0 | 23 | 38 | 22 | 1 | −3 | 1 | 614 | 614 | 12 | 16 | 0 | 1 | 59 | 53 | 7 | 4 | 4 | 1 | 237 | 239 | 4 |
| 8 | −4 | 0 | 112 | 93 | 8 | 1 | 3 | 0 | 862 | 875 | 14 | 3 | −3 | 1 | 295 | 286 | 9 | 18 | 0 | 1 | 215 | 210 | 8 | 6 | 4 | 1 | 54 | 49 | 5 |
| 10 | −4 | 0 | 72 | 88 | 8 | 3 | 3 | 0 | 361 | 364 | 7 | 5 | −3 | 1 | 244 | 265 | 9 | 20 | 0 | 1 | 0 | 10 | 1 | 8 | 4 | 1 | 68 | 55 | 5 |
| 12 | −4 | 0 | 183 | 165 | 6 | 7 | 3 | 0 | 457 | 449 | 16 | 7 | −3 | 1 | 236 | 224 | 9 | 22 | 0 | 1 | 58 | 50 | 20 | 10 | 4 | 1 | 69 | 74 | 5 |
| 14 | −4 | 0 | 196 | 198 | 9 | 9 | 3 | 0 | 222 | 220 | 9 | 9 | −3 | 1 | 245 | 235 | 6 | 24 | 0 | 1 | 91 | 86 | 5 | 12 | 4 | 1 | 97 | 91 | 5 |
| 16 | −4 | 0 | 175 | 189 | 8 | 15 | 3 | 0 | 145 | 135 | 11 | 11 | −3 | 1 | 122 | 109 | 7 | −23 | 1 | 1 | 65 | 87 | 16 | 14 | 4 | 1 | 169 | 156 | 9 |
| 18 | −4 | 0 | 40 | 45 | 24 | 17 | 3 | 0 | 220 | 212 | 8 | 13 | −3 | 1 | 157 | 144 | 6 | −21 | 1 | 1 | 352 | 352 | 5 | 16 | 4 | 1 | 112 | 138 | 9 |
| 20 | −4 | 0 | 30 | 28 | 30 | 19 | 3 | 0 | 126 | 122 | 9 | 15 | −3 | 1 | 72 | 59 | 9 | −19 | 1 | 1 | 221 | 213 | 3 | 18 | 4 | 1 | 109 | 114 | 9 |
| 22 | −4 | 0 | 0 | 22 | 1 | 21 | 3 | 0 | 67 | 69 | 15 | 17 | −3 | 1 | 171 | 169 | 9 | −17 | 1 | 1 | 202 | 194 | 3 | 20 | 4 | 1 | 32 | 31 | 32 |
| 1 | −3 | 0 | 869 | 873 | 18 | 23 | 3 | 0 | 59 | 59 | 16 | 19 | −3 | 1 | 52 | 50 | 17 | −15 | 1 | 1 | 147 | 143 | 3 | 22 | 4 | 1 | 0 | 11 | 1 |
| 3 | −3 | 0 | 364 | 365 | 11 | 25 | 3 | 0 | 0 | 32 | 1 | 21 | −3 | 1 | 72 | 59 | 14 | −13 | 1 | 1 | 416 | 412 | 16 | −21 | 5 | 1 | 33 | 19 | 33 |
| 5 | −3 | 0 | 400 | 372 | 12 | 0 | 4 | 0 | 429 | 436 | 6 | 23 | −3 | 1 | 46 | 46 | 13 | −11 | 1 | 1 | 902 | 941 | 20 | −19 | 5 | 1 | 0 | 34 | 1 |
| 7 | −3 | 0 | 476 | 447 | 14 | 2 | 4 | 0 | 403 | 390 | 5 | −26 | −2 | 1 | 61 | 57 | 9 | −9 | 1 | 1 | 403 | 389 | 6 | −17 | 5 | 1 | 92 | 86 | 10 |
| 9 | −3 | 0 | 232 | 220 | 5 | 4 | 4 | 0 | 170 | 167 | 5 | −24 | −2 | 1 | 97 | 102 | 16 | −7 | 1 | 1 | 587 | 602 | 9 | −15 | 5 | 1 | 143 | 128 | 6 |
| 11 | −3 | 0 | 252 | 248 | 6 | 6 | 4 | 0 | 208 | 189 | 4 | −22 | −2 | 1 | 212 | 217 | 6 | −5 | 1 | 1 | 1112 | 1157 | 19 | −13 | 5 | 1 | 157 | 146 | 5 |
| 13 | −3 | 0 | 126 | 117 | 7 | 8 | 4 | 0 | 111 | 93 | 4 | −20 | −2 | 1 | 199 | 190 | 5 | −3 | 1 | 1 | 965 | 1044 | 30 | −11 | 5 | 1 | 133 | 125 | 5 |
| 15 | −3 | 0 | 138 | 135 | 6 | 10 | 4 | 0 | 77 | 89 | 5 | −18 | −2 | 1 | 47 | 54 | 10 | −1 | 1 | 1 | 1304 | 1398 | 16 | −9 | 5 | 1 | 41 | 24 | 11 |
| 17 | −3 | 0 | 214 | 212 | 6 | 12 | 4 | 0 | 169 | 165 | 4 | −16 | −2 | 1 | 214 | 194 | 5 | 1 | 1 | 1 | 1131 | 1213 | 15 | −7 | 5 | 1 | 110 | 106 | 6 |
| 19 | −3 | 0 | 110 | 122 | 9 | 14 | 4 | 0 | 190 | 198 | 6 | −14 | −2 | 1 | 274 | 254 | 5 | 3 | 1 | 1 | 395 | 453 | 5 | −5 | 5 | 1 | 309 | 295 | 6 |
| 21 | −3 | 0 | 71 | 69 | 13 | 16 | 4 | 0 | 184 | 189 | 8 | −12 | −2 | 1 | 87 | 85 | 6 | 5 | 1 | 1 | 501 | 544 | 7 | −3 | 5 | 1 | 147 | 145 | 3 |
| 23 | −3 | 0 | 41 | 59 | 24 | 18 | 4 | 0 | 52 | 45 | 18 | −10 | −2 | 1 | 433 | 429 | 14 | 7 | 1 | 1 | 556 | 601 | 7 | −1 | 5 | 1 | 28 | 32 | 9 |
| 25 | −3 | 0 | 16 | 32 | 16 | 20 | 4 | 0 | 0 | 28 | 1 | −8 | −2 | 1 | 134 | 160 | 6 | 9 | 1 | 1 | 322 | 313 | 6 | 1 | 5 | 1 | 90 | 83 | 3 |
| 0 | −2 | 0 | 1263 | 1370 | 38 | 22 | 4 | 0 | 41 | 22 | 34 | −6 | −2 | 1 | 255 | 251 | 6 | 11 | 1 | 1 | 175 | 185 | 13 | 3 | 5 | 1 | 26 | 29 | 13 |
| 2 | −2 | 0 | 379 | 408 | 10 | 1 | 5 | 0 | 130 | 130 | 3 | −4 | −2 | 1 | 474 | 505 | 10 | 13 | 1 | 1 | 363 | 359 | 8 | 5 | 5 | 1 | 119 | 122 | 5 |
| 4 | −2 | 0 | 107 | 94 | 4 | 3 | 5 | 0 | 66 | 73 | 4 | −2 | −2 | 1 | 245 | 257 | 5 | 15 | 1 | 1 | 412 | 413 | 5 | 7 | 5 | 1 | 97 | 91 | 6 |
| 6 | −2 | 0 | 224 | 223 | 6 | 5 | 5 | 0 | 35 | 25 | 12 | 0 | −2 | 1 | 731 | 763 | 15 | 17 | 1 | 1 | 46 | 47 | 7 | 9 | 5 | 1 | 110 | 108 | 5 |
| 8 | −2 | 0 | 202 | 222 | 13 | 7 | 5 | 0 | 98 | 95 | 6 | 2 | −2 | 1 | 266 | 299 | 5 | 19 | 1 | 1 | 162 | 160 | 3 | 11 | 5 | 1 | 130 | 133 | 5 |
| 10 | −2 | 0 | 270 | 310 | 22 | 9 | 5 | 0 | 185 | 178 | 4 | 4 | −2 | 1 | 303 | 318 | 5 | 21 | 1 | 1 | 29 | 21 | 14 | 13 | 5 | 1 | 80 | 73 | 7 |
| 12 | −2 | 0 | 175 | 180 | 4 | 11 | 5 | 0 | 11 | 51 | 10 | 6 | −2 | 1 | 476 | 490 | 11 | −26 | 2 | 1 | 48 | 58 | 21 | 15 | 5 | 1 | 113 | 110 | 8 |
| 14 | −2 | 0 | 64 | 62 | 6 | 13 | 5 | 0 | 111 | 93 | 6 | 8 | −2 | 1 | 529 | 557 | 37 | −24 | 2 | 1 | 100 | 102 | 10 | 17 | 5 | 1 | 60 | 81 | 10 |
| 16 | −2 | 0 | 136 | 130 | 10 | 15 | 5 | 0 | 27 | 21 | 27 | 10 | −2 | 1 | 459 | 504 | 30 | −22 | 2 | 1 | 219 | 218 | 9 | 19 | 5 | 1 | 34 | 60 | 21 |
| 18 | −2 | 0 | 192 | 198 | 5 | 17 | 5 | 0 | 28 | 45 | 28 | 12 | −2 | 1 | 124 | 130 | 4 | −20 | 2 | 1 | 199 | 190 | 7 | −16 | 6 | 1 | 10 | 23 | 10 |
| 20 | −2 | 0 | 112 | 102 | 6 | 19 | 5 | 0 | 22 | 27 | 21 | 14 | −2 | 1 | 104 | 89 | 6 | −18 | 2 | 1 | 63 | 52 | 11 | −14 | 6 | 1 | 0 | 20 | 1 |
| 22 | −2 | 0 | 62 | 77 | 17 | 4 | 6 | 0 | 47 | 57 | 11 | 16 | −2 | 1 | 290 | 278 | 7 | −16 | 2 | 1 | 215 | 194 | 6 | −12 | 6 | 1 | 61 | 61 | 10 |
| 24 | −2 | 0 | 119 | 145 | 6 | 6 | 6 | 0 | 57 | 56 | 6 | 18 | −2 | 1 | 393 | 384 | 7 | −10 | 2 | 1 | 436 | 431 | 14 | −10 | 6 | 1 | 28 | 39 | 24 |
| 26 | −2 | 0 | 0 | 38 | 1 | 8 | 6 | 0 | 47 | 52 | 8 | 20 | −2 | 1 | 106 | 120 | 21 | −8 | 2 | 1 | 134 | 159 | 7 | −8 | 6 | 1 | 71 | 79 | 6 |
| 1 | −1 | 0 | 1074 | 1170 | 22 | 10 | 6 | 0 | 22 | 12 | 22 | 22 | −2 | 1 | 167 | 142 | 11 | −6 | 2 | 1 | 252 | 250 | 9 | −6 | 6 | 1 | 34 | 39 | 10 |
| 3 | −1 | 0 | 1769 | 1951 | 39 | 12 | 6 | 0 | 45 | 37 | 14 | 24 | −2 | 1 | 34 | 23 | 20 | −2 | 2 | 1 | 249 | 257 | 4 | −4 | 6 | 1 | 25 | 26 | 25 |
| 5 | −1 | 0 | 1600 | 1755 | 36 | 14 | 6 | 0 | 0 | 24 | 1 | 26 | −2 | 1 | 40 | 37 | 23 | 0 | 2 | 1 | 730 | 762 | 10 | 4 | 6 | 1 | 36 | 35 | 9 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 7 | −1 | 0 | 967 | 1006 | 20 | 16 | 6 | 0 | 16 | 6 | 16 | −27 | −1 | 1 | 0 | 7 | 1 | 2 | 2 | 1 | 259 | 300 | 3 | 6 | 6 | 1 | 89 | 86 | 4 |
| 9 | −1 | 0 | 38 | 38 | 12 | −16 | −6 | 1 | 27 | 23 | 26 | −25 | −1 | 1 | 105 | 98 | 8 | 4 | 2 | 1 | 304 | 317 | 4 | 8 | 6 | 1 | 18 | 31 | 18 |
| 11 | −1 | 0 | 201 | 210 | 5 | −21 | −5 | 1 | 0 | 18 | 1 | −23 | −1 | 1 | 97 | 87 | 9 | 6 | 2 | 1 | 485 | 489 | 15 | 10 | 6 | 1 | 59 | 78 | 8 |
| 13 | −1 | 0 | 262 | 261 | 6 | −19 | −5 | 1 | 18 | 35 | 18 | −21 | −1 | 1 | 349 | 352 | 6 | 8 | 2 | 1 | 556 | 557 | 17 | 12 | 6 | 1 | 24 | 10 | 23 |
| 15 | −1 | 0 | 273 | 271 | 4 | −17 | −5 | 1 | 95 | 86 | 9 | −19 | −1 | 1 | 221 | 214 | 4 | 10 | 2 | 1 | 488 | 503 | 15 | 14 | 6 | 1 | 11 | 30 | 10 |
| 17 | −1 | 0 | 232 | 224 | 4 | −15 | −5 | 1 | 135 | 128 | 8 | −17 | −1 | 1 | 204 | 193 | 4 | 12 | 2 | 1 | 134 | 129 | 7 | −16 | −6 | 2 | 14 | 13 | 14 |
| 19 | −1 | 0 | 311 | 304 | 5 | −13 | −5 | 1 | 142 | 146 | 8 | −15 | −1 | 1 | 141 | 143 | 4 | 14 | 2 | 1 | 103 | 90 | 10 | −21 | −5 | 2 | 75 | 53 | 10 |
| 21 | −1 | 0 | 44 | 41 | 14 | −11 | −5 | 1 | 131 | 124 | 8 | −13 | −1 | 1 | 460 | 413 | 9 | 16 | 2 | 1 | 285 | 278 | 10 | −19 | −5 | 2 | 91 | 90 | 9 |
| 23 | −1 | 0 | 87 | 76 | 10 | −9 | −5 | 1 | 18 | 25 | 17 | −11 | −1 | 1 | 909 | 940 | 16 | 20 | 2 | 1 | 108 | 121 | 10 | −17 | −5 | 2 | 65 | 78 | 12 |
| 25 | −1 | 0 | 46 | 45 | 15 | 9 | −5 | 1 | 91 | 108 | 9 | −9 | −1 | 1 | 402 | 390 | 10 | 22 | 2 | 1 | 166 | 143 | 9 | −15 | −5 | 2 | 52 | 57 | 17 |
| 27 | −1 | 0 | 43 | 50 | 13 | 11 | −5 | 1 | 111 | 133 | 8 | −7 | −1 | 1 | 583 | 602 | 10 | 24 | 2 | 1 | 0 | 23 | 1 | −13 | −5 | 2 | 12 | 15 | 12 |
| 2 | 0 | 0 | 312 | 362 | 4 | 13 | −5 | 1 | 54 | 73 | 16 | −5 | −1 | 1 | 1075 | 1157 | 19 | −25 | 3 | 1 | 54 | 29 | 18 | −11 | −5 | 2 | 117 | 119 | 8 |
| 4 | 0 | 0 | 117 | 119 | 3 | 15 | −5 | 1 | 101 | 110 | 9 | −3 | −1 | 1 | 951 | 1044 | 21 | −23 | 3 | 1 | 33 | 20 | 33 | −9 | −5 | 2 | 172 | 180 | 7 |
| 6 | 0 | 0 | 308 | 322 | 5 | 17 | −5 | 1 | 83 | 80 | 10 | −1 | −1 | 1 | 1322 | 1398 | 27 | −21 | 3 | 1 | 61 | 41 | 17 | 9 | −5 | 2 | 129 | 118 | 8 |
| 8 | 0 | 0 | 345 | 323 | 7 | 19 | −5 | 1 | 53 | 60 | 14 | 1 | −1 | 1 | 1140 | 1212 | 19 | −19 | 3 | 1 | 76 | 86 | 13 | 11 | −5 | 2 | 50 | 32 | 17 |
| 10 | 0 | 0 | 1081 | 1115 | 28 | −22 | −4 | 1 | 71 | 87 | 11 | 3 | −1 | 1 | 404 | 455 | 7 | −17 | 3 | 1 | 91 | 102 | 8 | 13 | −5 | 2 | 0 | 33 | 1 |
| 12 | 0 | 0 | 621 | 642 | 13 | −20 | −4 | 1 | 69 | 76 | 12 | 5 | −1 | 1 | 507 | 544 | 8 | −15 | 3 | 1 | 170 | 173 | 11 | 15 | −5 | 2 | 47 | 32 | 19 |
| 14 | 0 | 0 | 51 | 44 | 8 | −18 | −4 | 1 | 42 | 63 | 20 | 7 | −1 | 1 | 560 | 600 | 9 | −13 | 3 | 1 | 178 | 175 | 5 | 17 | −5 | 2 | 44 | 48 | 19 |
| 16 | 0 | 0 | 42 | 40 | 9 | −16 | −4 | 1 | 115 | 100 | 9 | 9 | −1 | 1 | 317 | 313 | 9 | −11 | 3 | 1 | 114 | 118 | 4 | 19 | −5 | 2 | 56 | 50 | 12 |
| 18 | 0 | 0 | 50 | 53 | 11 | −14 | −4 | 1 | 69 | 57 | 10 | 11 | −1 | 1 | 182 | 183 | 5 | −9 | 3 | 1 | 231 | 218 | 6 | −24 | −4 | 2 | 35 | 14 | 35 |
| 20 | 0 | 0 | 34 | 31 | 19 | −12 | −4 | 1 | 137 | 117 | 6 | 13 | −1 | 1 | 376 | 360 | 8 | −7 | 3 | 1 | 194 | 198 | 8 | −22 | −4 | 2 | 0 | 17 | 1 |
| 22 | 0 | 0 | 92 | 81 | 7 | −10 | −4 | 1 | 196 | 179 | 6 | 15 | −1 | 1 | 417 | 413 | 6 | −5 | 3 | 1 | 337 | 326 | 8 | −20 | −4 | 2 | 32 | 23 | 31 |
| 24 | 0 | 0 | 53 | 52 | 8 | −8 | −4 | 1 | 102 | 99 | 5 | 17 | −1 | 1 | 51 | 47 | 7 | −3 | 3 | 1 | 592 | 563 | 9 | −18 | −4 | 2 | 66 | 74 | 12 |
| 26 | 0 | 0 | 14 | 7 | 13 | −6 | −4 | 1 | 289 | 284 | 6 | 19 | −1 | 1 | 164 | 160 | 4 | −1 | 3 | 1 | 479 | 464 | 8 | −16 | −4 | 2 | 41 | 34 | 29 |
| 1 | 1 | 0 | 1075 | 1172 | 16 | −4 | −4 | 1 | 202 | 211 | 8 | 21 | −1 | 1 | 28 | 21 | 27 | 1 | 3 | 1 | 607 | 614 | 11 | −14 | −4 | 2 | 46 | 36 | 14 |
| 3 | 1 | 0 | 1834 | 1949 | 56 | 4 | −4 | 1 | 231 | 239 | 9 | 23 | −1 | 1 | 147 | 117 | 8 | 3 | 3 | 1 | 288 | 285 | 5 | −12 | −4 | 2 | 104 | 94 | 7 |
| 5 | 1 | 0 | 1647 | 1755 | 25 | 6 | −4 | 1 | 45 | 49 | 13 | 25 | −1 | 1 | 63 | 65 | 29 | 5 | 3 | 1 | 253 | 265 | 9 | −10 | −4 | 2 | 106 | 95 | 10 |
| 7 | 1 | 0 | 952 | 1005 | 15 | 8 | −4 | 1 | 70 | 55 | 8 | −26 | 0 | 1 | 78 | 77 | 5 | 7 | 3 | 1 | 236 | 223 | 9 | −8 | −4 | 2 | 108 | 97 | 5 |
| 9 | 1 | 0 | 36 | 38 | 4 | 10 | −4 | 1 | 77 | 74 | 8 | −24 | 0 | 1 | 0 | 12 | 1 | 9 | 3 | 1 | 235 | 236 | 6 | −6 | −4 | 2 | 0 | 26 | 1 |
| 11 | 1 | 0 | 199 | 210 | 5 | 12 | −4 | 1 | 105 | 91 | 7 | −22 | 0 | 1 | 105 | 94 | 20 | 11 | 3 | 1 | 118 | 108 | 6 | −4 | −4 | 2 | 377 | 362 | 13 |
| 13 | 1 | 0 | 238 | 260 | 9 | 14 | −4 | 1 | 174 | 156 | 7 | −20 | 0 | 1 | 190 | 175 | 5 | 13 | 3 | 1 | 145 | 144 | 8 | 4 | −4 | 2 | 102 | 107 | 8 |
| 15 | 1 | 0 | 271 | 271 | 4 | 16 | −4 | 1 | 144 | 138 | 8 | −18 | 0 | 1 | 383 | 366 | 8 | 17 | 3 | 1 | 179 | 169 | 8 | 6 | −4 | 2 | 131 | 103 | 5 |
| 17 | 1 | 0 | 233 | 224 | 4 | 18 | −4 | 1 | 110 | 114 | 9 | −16 | 0 | 1 | 54 | 57 | 6 | 19 | 3 | 1 | 49 | 50 | 22 | 8 | −4 | 2 | 61 | 56 | 11 |
| 19 | 1 | 0 | 309 | 304 | 4 | 20 | −4 | 1 | 28 | 31 | 27 | −14 | 0 | 1 | 770 | 744 | 17 | 21 | 3 | 1 | 69 | 59 | 15 | 10 | −4 | 2 | 251 | 255 | 6 |
| 21 | 1 | 0 | 41 | 40 | 9 | 22 | −4 | 1 | 23 | 11 | 23 | −12 | 0 | 1 | 19 | 32 | 19 | 23 | 3 | 1 | 74 | 46 | 13 | 12 | −4 | 2 | 140 | 125 | 7 |
| 23 | 1 | 0 | 55 | 76 | 19 | −25 | −3 | 1 | 0 | 29 | 1 | −10 | 0 | 1 | 575 | 593 | 17 | −22 | 4 | 1 | 61 | 88 | 16 | 14 | −4 | 2 | 27 | 33 | 27 |
| 0 | 2 | 0 | 1283 | 1369 | 22 | −23 | −3 | 1 | 26 | 19 | 26 | −8 | 0 | 1 | 543 | 599 | 9 | −20 | 4 | 1 | 66 | 75 | 14 | 16 | −4 | 2 | 42 | 13 | 25 |
| 2 | 2 | 0 | 371 | 406 | 6 | −21 | −3 | 1 | 43 | 42 | 27 | −6 | 0 | 1 | 2059 | 2218 | 45 | −18 | 4 | 1 | 47 | 64 | 21 | 18 | −4 | 2 | 114 | 132 | 8 |
| 4 | 2 | 0 | 102 | 94 | 6 | −19 | −3 | 1 | 100 | 87 | 10 | −4 | 0 | 1 | 1538 | 1686 | 33 | −16 | 4 | 1 | 112 | 100 | 10 | 20 | −4 | 2 | 38 | 58 | 32 |
| 6 | 2 | 0 | 233 | 223 | 8 | −17 | −3 | 1 | 104 | 102 | 7 | −2 | 0 | 1 | 417 | 443 | 8 | −14 | 4 | 1 | 59 | 56 | 8 | 22 | −4 | 2 | 20 | 19 | 19 |
| −25 | −3 | 2 | 0 | 15 | 1 | −8 | 0 | 2 | 909 | 967 | 21 | 21 | 3 | 2 | 55 | 56 | 18 | 18 | −4 | 3 | 74 | 77 | 12 | −14 | 0 | 3 | 214 | 230 | 4 |
| −23 | −3 | 2 | 48 | 24 | 20 | −6 | 0 | 2 | 2200 | 2323 | 38 | 23 | 3 | 2 | 34 | 45 | 33 | 20 | −4 | 3 | 38 | 25 | 30 | −12 | 0 | 3 | 313 | 309 | 6 |
| −21 | −3 | 2 | 86 | 93 | 11 | −4 | 0 | 2 | 598 | 601 | 9 | −24 | 4 | 2 | 41 | 14 | 31 | −25 | −3 | 3 | 61 | 63 | 9 | −10 | 0 | 3 | 360 | 335 | 5 |
| −19 | −3 | 2 | 103 | 110 | 10 | −2 | 0 | 2 | 670 | 726 | 10 | −22 | 4 | 2 | 0 | 17 | 1 | −23 | −3 | 3 | 0 | 35 | 1 | −8 | 0 | 3 | 1125 | 1138 | 19 |
| −17 | −3 | 2 | 153 | 146 | 7 | 0 | 0 | 2 | 1279 | 1357 | 22 | −20 | 4 | 2 | 12 | 22 | 12 | −21 | −3 | 3 | 58 | 53 | 15 | −6 | 0 | 3 | 1022 | 1054 | 15 |
| −15 | −3 | 2 | 90 | 80 | 7 | 2 | 0 | 2 | 585 | 617 | 9 | −18 | 4 | 2 | 74 | 74 | 13 | −19 | −3 | 3 | 121 | 114 | 9 | −4 | 0 | 3 | 227 | 229 | 3 |
| −13 | −3 | 2 | 162 | 158 | 5 | 4 | 0 | 2 | 1340 | 1409 | 20 | −16 | 4 | 2 | 7 | 34 | 6 | −17 | −3 | 3 | 161 | 151 | 6 | −2 | 0 | 3 | 1111 | 1236 | 17 |
| −11 | −3 | 2 | 334 | 343 | 8 | 6 | 0 | 2 | 1056 | 1084 | 16 | −14 | 4 | 2 | 33 | 36 | 17 | −15 | −3 | 3 | 86 | 82 | 7 | 0 | 0 | 3 | 744 | 848 | 11 |
| −9 | −3 | 2 | 201 | 191 | 8 | 8 | 0 | 2 | 23 | 31 | 12 | −12 | 4 | 2 | 97 | 94 | 5 | −13 | −3 | 3 | 237 | 228 | 8 | 2 | 0 | 3 | 1244 | 1255 | 19 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −7 | −3 | 2 | 764 | 740 | 23 | 10 | 0 | 2 | 71 | 61 | 5 | −10 | 4 | 2 | 103 | 95 | 4 | −11 | −3 | 3 | 372 | 350 | 8 | 4 | 0 | 3 | 222 | 277 | 4 |
| −5 | −3 | 2 | 714 | 680 | 21 | 12 | 0 | 2 | 520 | 511 | 17 | −8 | 4 | 2 | 103 | 96 | 4 | −9 | −3 | 3 | 362 | 315 | 12 | 6 | 0 | 3 | 9 | 2 | 9 |
| −3 | −3 | 2 | 541 | 545 | 16 | 14 | 0 | 2 | 357 | 365 | 6 | −6 | 4 | 2 | 21 | 26 | 21 | −7 | −3 | 3 | 340 | 301 | 10 | 8 | 0 | 3 | 318 | 290 | 6 |
| −1 | −3 | 2 | 523 | 549 | 11 | 16 | 0 | 2 | 302 | 295 | 5 | −4 | 4 | 2 | 396 | 362 | 7 | −5 | −3 | 3 | 219 | 236 | 8 | 10 | 0 | 3 | 872 | 844 | 15 |
| 1 | −3 | 2 | 179 | 169 | 4 | 18 | 0 | 2 | 68 | 57 | 17 | −2 | 4 | 2 | 234 | 231 | 2 | −3 | −3 | 3 | 314 | 326 | 10 | 12 | 0 | 3 | 65 | 71 | 6 |
| 3 | −3 | 2 | 384 | 372 | 12 | 20 | 0 | 2 | 168 | 173 | 6 | 0 | 4 | 2 | 161 | 158 | 2 | −1 | −3 | 3 | 474 | 491 | 10 | 14 | 0 | 3 | 168 | 161 | 3 |
| 5 | −3 | 2 | 543 | 516 | 16 | 22 | 0 | 2 | 53 | 44 | 11 | 2 | 4 | 2 | 397 | 387 | 4 | 1 | −3 | 3 | 248 | 236 | 6 | 16 | 0 | 3 | 48 | 11 | 8 |
| 7 | −3 | 2 | 195 | 188 | 8 | 24 | 0 | 2 | 16 | 38 | 16 | 12 | 4 | 2 | 133 | 125 | 5 | 3 | −3 | 3 | 46 | 52 | 15 | 18 | 0 | 3 | 169 | 177 | 6 |
| 9 | −3 | 2 | 108 | 87 | 8 | −23 | 1 | 2 | 123 | 155 | 9 | 14 | 4 | 2 | 28 | 33 | 27 | 5 | −3 | 3 | 100 | 106 | 8 | 20 | 0 | 3 | 221 | 221 | 6 |
| 11 | −3 | 2 | 224 | 226 | 6 | −21 | 1 | 2 | 188 | 174 | 3 | 16 | 4 | 2 | 33 | 13 | 33 | 7 | −3 | 3 | 217 | 212 | 8 | 22 | 0 | 3 | 36 | 17 | 31 |
| 13 | −3 | 2 | 226 | 210 | 6 | −19 | 1 | 2 | 0 | 19 | 1 | 18 | 4 | 2 | 138 | 132 | 8 | 9 | −3 | 3 | 76 | 67 | 7 | 24 | 0 | 3 | 25 | 18 | 24 |
| 15 | −3 | 2 | 175 | 163 | 7 | −17 | 1 | 2 | 104 | 86 | 4 | 20 | 4 | 2 | 36 | 58 | 36 | 11 | −3 | 3 | 294 | 298 | 7 | −23 | 1 | 3 | 63 | 63 | 6 |
| 17 | −3 | 2 | 128 | 115 | 9 | −15 | 1 | 2 | 76 | 74 | 6 | 22 | 4 | 2 | 0 | 19 | 1 | 13 | −3 | 3 | 120 | 114 | 8 | −21 | 1 | 3 | 80 | 78 | 4 |
| 19 | −3 | 2 | 101 | 124 | 10 | −13 | 1 | 2 | 352 | 405 | 16 | −21 | 5 | 2 | 62 | 53 | 14 | 15 | −3 | 3 | 193 | 170 | 7 | −19 | 1 | 3 | 50 | 44 | 5 |
| 21 | −3 | 2 | 68 | 56 | 13 | −11 | 1 | 2 | 792 | 818 | 18 | −19 | 5 | 2 | 68 | 90 | 26 | 17 | −3 | 3 | 171 | 195 | 8 | −17 | 1 | 3 | 71 | 67 | 3 |
| 23 | −3 | 2 | 0 | 45 | 1 | −9 | 1 | 2 | 323 | 318 | 6 | −17 | 5 | 2 | 68 | 78 | 10 | 19 | −3 | 3 | 76 | 77 | 12 | −15 | 1 | 3 | 217 | 211 | 4 |
| −26 | −2 | 2 | 35 | 60 | 28 | −7 | 1 | 2 | 290 | 295 | 4 | −15 | 5 | 2 | 58 | 57 | 10 | 21 | −3 | 3 | 115 | 109 | 8 | −13 | 1 | 3 | 307 | 277 | 7 |
| −24 | −2 | 2 | 90 | 122 | 17 | −5 | 1 | 2 | 682 | 732 | 10 | −13 | 5 | 2 | 0 | 15 | 1 | 23 | −3 | 3 | 20 | 22 | 20 | −11 | 1 | 3 | 395 | 389 | 6 |
| −22 | −2 | 2 | 111 | 113 | 16 | −3 | 1 | 2 | 685 | 708 | 9 | −11 | 5 | 2 | 127 | 118 | 11 | −28 | −2 | 3 | 58 | 55 | 14 | −9 | 1 | 3 | 190 | 197 | 3 |
| −20 | −2 | 2 | 62 | 31 | 9 | −1 | 1 | 2 | 210 | 235 | 3 | −9 | 5 | 2 | 183 | 181 | 6 | −26 | −2 | 3 | 69 | 81 | 8 | −7 | 1 | 3 | 514 | 543 | 7 |
| −18 | −2 | 2 | 131 | 131 | 6 | 1 | 1 | 2 | 806 | 847 | 11 | −7 | 5 | 2 | 184 | 179 | 4 | −24 | −2 | 3 | 69 | 79 | 15 | −5 | 1 | 3 | 649 | 696 | 9 |
| −16 | −2 | 2 | 110 | 115 | 5 | 3 | 1 | 2 | 743 | 795 | 10 | −5 | 5 | 2 | 148 | 138 | 4 | −22 | −2 | 3 | 118 | 94 | 8 | −3 | 1 | 3 | 1714 | 1799 | 23 |
| −14 | −2 | 2 | 240 | 231 | 5 | 5 | 1 | 2 | 483 | 506 | 6 | −3 | 5 | 2 | 36 | 37 | 8 | −20 | −2 | 3 | 92 | 70 | 5 | −1 | 1 | 3 | 829 | 881 | 14 |
| −12 | −2 | 2 | 406 | 382 | 9 | 7 | 1 | 2 | 514 | 546 | 7 | −1 | 5 | 2 | 107 | 103 | 3 | −18 | −2 | 3 | 127 | 115 | 5 | 1 | 1 | 3 | 235 | 237 | 3 |
| −10 | −2 | 2 | 337 | 359 | 10 | 9 | 1 | 2 | 149 | 155 | 4 | 1 | 5 | 2 | 113 | 118 | 3 | −16 | −2 | 3 | 179 | 174 | 5 | 3 | 1 | 3 | 94 | 86 | 2 |
| −8 | −2 | 2 | 281 | 276 | 13 | 11 | 1 | 2 | 362 | 383 | 14 | 3 | 5 | 2 | 74 | 75 | 5 | −14 | −2 | 3 | 138 | 124 | 8 | 5 | 1 | 3 | 248 | 228 | 3 |
| −6 | −2 | 2 | 363 | 343 | 8 | 13 | 1 | 2 | 270 | 290 | 5 | 5 | 5 | 2 | 110 | 102 | 4 | −12 | −2 | 3 | 102 | 96 | 6 | 7 | 1 | 3 | 129 | 129 | 4 |
| −4 | −2 | 2 | 155 | 160 | 3 | 15 | 1 | 2 | 173 | 162 | 3 | 7 | 5 | 2 | 26 | 51 | 26 | −10 | −2 | 3 | 793 | 938 | 23 | 9 | 1 | 3 | 318 | 343 | 8 |
| −2 | −2 | 2 | 350 | 360 | 7 | 17 | 1 | 2 | 262 | 253 | 4 | 9 | 5 | 2 | 139 | 118 | 5 | −8 | −2 | 3 | 395 | 397 | 28 | 11 | 1 | 3 | 117 | 105 | 4 |
| 0 | −2 | 2 | 328 | 334 | 7 | 19 | 1 | 2 | 391 | 384 | 6 | 11 | 5 | 2 | 10 | 32 | 10 | −6 | −2 | 3 | 152 | 167 | 5 | 13 | 1 | 3 | 224 | 221 | 4 |
| 2 | −2 | 2 | 403 | 425 | 7 | 21 | 1 | 2 | 50 | 46 | 9 | 13 | 5 | 2 | 0 | 32 | 1 | −4 | −2 | 3 | 181 | 173 | 4 | 15 | 1 | 3 | 287 | 269 | 4 |
| 4 | −2 | 2 | 235 | 216 | 4 | −26 | 2 | 2 | 49 | 60 | 21 | 15 | 5 | 2 | 40 | 32 | 16 | −2 | −2 | 3 | 452 | 478 | 9 | 17 | 1 | 3 | 62 | 56 | 6 |
| 6 | −2 | 2 | 329 | 334 | 6 | −24 | 2 | 2 | 102 | 122 | 10 | 17 | 5 | 2 | 44 | 48 | 25 | 0 | −2 | 3 | 283 | 274 | 6 | 19 | 1 | 3 | 94 | 97 | 5 |
| 8 | −2 | 2 | 252 | 273 | 18 | −22 | 2 | 2 | 114 | 114 | 10 | 19 | 5 | 2 | 36 | 50 | 35 | 2 | −2 | 3 | 410 | 412 | 15 | 21 | 1 | 3 | 104 | 107 | 4 |
| 10 | −2 | 2 | 258 | 257 | 7 | −20 | 2 | 2 | 50 | 32 | 17 | −16 | 6 | 2 | 2 | 13 | 1 | 4 | −2 | 3 | 179 | 185 | 4 | −26 | 2 | 3 | 81 | 81 | 12 |
| 12 | −2 | 2 | 344 | 339 | 6 | −18 | 2 | 2 | 125 | 131 | 6 | −14 | 6 | 2 | 38 | 36 | 19 | 6 | −2 | 3 | 41 | 45 | 6 | −24 | 2 | 3 | 61 | 79 | 17 |
| 14 | −2 | 2 | 180 | 174 | 6 | −16 | 2 | 2 | 110 | 115 | 6 | −12 | 6 | 2 | 33 | 28 | 32 | 8 | −2 | 3 | 394 | 395 | 24 | −22 | 2 | 3 | 112 | 95 | 10 |
| 16 | −2 | 2 | 112 | 102 | 7 | −14 | 2 | 2 | 236 | 231 | 6 | −10 | 6 | 2 | 0 | 21 | 1 | 10 | −2 | 3 | 170 | 167 | 4 | −20 | 2 | 3 | 87 | 71 | 16 |
| 18 | −2 | 2 | 146 | 142 | 13 | −12 | 2 | 2 | 396 | 381 | 9 | −8 | 6 | 2 | 0 | 35 | 1 | 12 | −2 | 3 | 223 | 212 | 6 | −18 | 2 | 3 | 126 | 115 | 7 |
| 20 | −2 | 2 | 131 | 147 | 14 | −10 | 2 | 2 | 311 | 361 | 19 | −6 | 6 | 2 | 17 | 41 | 17 | 14 | −2 | 3 | 50 | 42 | 13 | −16 | 2 | 3 | 182 | 174 | 5 |
| 22 | −2 | 2 | 48 | 43 | 12 | −8 | 2 | 2 | 281 | 274 | 16 | −4 | 6 | 2 | 15 | 19 | 15 | 16 | −2 | 3 | 126 | 142 | 7 | −14 | 2 | 3 | 137 | 124 | 12 |
| 24 | −2 | 2 | 40 | 38 | 17 | −6 | 2 | 2 | 369 | 342 | 8 | 4 | 6 | 2 | 43 | 48 | 6 | 18 | −2 | 3 | 140 | 136 | 10 | −12 | 2 | 3 | 99 | 96 | 9 |
| −27 | −1 | 2 | 57 | 64 | 23 | −4 | 2 | 2 | 167 | 160 | 4 | 6 | 6 | 2 | 50 | 51 | 7 | 20 | −2 | 3 | 140 | 155 | 12 | −10 | 2 | 3 | 767 | 938 | 24 |
| −25 | −1 | 2 | 83 | 70 | 10 | −2 | 2 | 2 | 347 | 358 | 4 | 8 | 6 | 2 | 38 | 29 | 11 | 22 | −2 | 3 | 32 | 51 | 32 | −8 | 2 | 3 | 402 | 398 | 22 |
| −23 | −1 | 2 | 120 | 155 | 5 | 0 | 2 | 2 | 321 | 335 | 4 | 10 | 6 | 2 | 20 | 20 | 20 | 24 | −2 | 3 | 50 | 47 | 11 | −6 | 2 | 3 | 153 | 167 | 6 |
| −21 | −1 | 2 | 192 | 174 | 5 | 2 | 2 | 2 | 413 | 426 | 5 | 12 | 6 | 2 | 0 | 18 | 1 | −27 | −1 | 3 | 130 | 110 | 6 | −4 | 2 | 3 | 183 | 171 | 3 |
| −19 | −1 | 2 | 0 | 18 | 1 | 4 | 2 | 2 | 233 | 215 | 3 | 14 | 6 | 2 | 48 | 38 | 12 | −25 | −1 | 3 | 27 | 15 | 26 | −2 | 2 | 3 | 441 | 477 | 5 |
| −17 | −1 | 2 | 97 | 87 | 4 | 6 | 2 | 2 | 327 | 334 | 5 | −16 | −6 | 3 | 45 | 20 | 15 | −23 | −1 | 3 | 38 | 63 | 16 | 0 | 2 | 3 | 273 | 276 | 3 |
| −15 | −1 | 2 | 65 | 74 | 5 | 8 | 2 | 2 | 271 | 272 | 7 | −21 | −5 | 3 | 52 | 18 | 13 | −21 | −1 | 3 | 73 | 78 | 6 | 2 | 2 | 3 | 406 | 413 | 5 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −13 | −1 | 2 | 370 | 405 | 6 | 10 | 2 | 2 | 259 | 257 | 5 | −19 | −5 | 3 | 45 | 44 | 18 | −19 | −1 | 3 | 36 | 44 | 11 | 4 | 2 | 3 | 172 | 185 | 3 |
| −11 | −1 | 2 | 813 | 818 | 14 | 12 | 2 | 2 | 346 | 340 | 4 | −17 | −5 | 3 | 0 | 30 | 1 | −17 | −1 | 3 | 72 | 66 | 4 | 6 | 2 | 3 | 40 | 45 | 5 |
| −9 | −1 | 2 | 325 | 320 | 6 | 14 | 2 | 2 | 178 | 174 | 3 | −15 | −5 | 3 | 33 | 58 | 32 | −15 | −1 | 3 | 217 | 211 | 6 | 8 | 2 | 3 | 394 | 394 | 9 |
| −7 | −1 | 2 | 288 | 296 | 5 | 16 | 2 | 2 | 93 | 102 | 11 | −13 | −5 | 3 | 122 | 154 | 8 | −13 | −1 | 3 | 323 | 277 | 6 | 10 | 2 | 3 | 172 | 166 | 4 |
| −5 | −1 | 2 | 685 | 732 | 12 | 20 | 2 | 2 | 126 | 147 | 9 | −11 | −5 | 3 | 102 | 105 | 8 | −11 | −1 | 3 | 412 | 390 | 8 | 12 | 2 | 3 | 223 | 211 | 3 |
| −3 | −1 | 2 | 654 | 708 | 12 | 22 | 2 | 2 | 15 | 42 | 14 | −9 | −5 | 3 | 20 | 16 | 20 | −9 | −1 | 3 | 186 | 196 | 4 | 14 | 2 | 3 | 51 | 42 | 4 |
| −1 | −1 | 2 | 205 | 233 | 4 | 24 | 2 | 2 | 6 | 38 | 6 | 9 | −5 | 3 | 157 | 156 | 8 | −7 | −1 | 3 | 530 | 541 | 9 | 16 | 2 | 3 | 127 | 142 | 9 |
| 1 | −1 | 2 | 815 | 849 | 15 | −25 | 3 | 2 | 22 | 15 | 22 | 11 | −5 | 3 | 66 | 56 | 13 | −5 | −1 | 3 | 661 | 696 | 11 | 20 | 2 | 3 | 127 | 155 | 9 |
| 3 | −1 | 2 | 759 | 794 | 13 | −23 | 3 | 2 | 27 | 24 | 26 | 13 | −5 | 3 | 148 | 141 | 8 | −3 | −1 | 3 | 1674 | 1797 | 32 | 22 | 2 | 3 | 47 | 51 | 20 |
| 5 | −1 | 2 | 492 | 505 | 8 | −21 | 3 | 2 | 90 | 93 | 12 | 15 | −5 | 3 | 50 | 53 | 16 | −1 | −1 | 3 | 809 | 881 | 14 | 24 | 2 | 3 | 33 | 47 | 33 |
| 7 | −1 | 2 | 522 | 546 | 14 | −19 | 3 | 2 | 96 | 109 | 11 | 17 | −5 | 3 | 44 | 50 | 19 | 1 | −1 | 3 | 231 | 236 | 4 | −25 | 3 | 3 | 38 | 63 | 38 |
| 9 | −1 | 2 | 162 | 156 | 4 | −17 | 3 | 2 | 143 | 147 | 12 | −24 | −4 | 3 | 33 | 12 | 33 | 3 | −1 | 3 | 93 | 86 | 4 | −23 | 3 | 3 | 32 | 35 | 32 |
| 11 | −1 | 2 | 381 | 386 | 6 | −15 | 3 | 2 | 84 | 80 | 13 | −22 | −4 | 3 | 54 | 32 | 16 | 5 | −1 | 3 | 244 | 228 | 5 | −21 | 3 | 3 | 45 | 53 | 29 |
| 13 | −1 | 2 | 274 | 291 | 6 | −13 | 3 | 2 | 159 | 158 | 6 | −20 | −4 | 3 | 0 | 28 | 1 | 7 | −1 | 3 | 130 | 129 | 5 | −19 | 3 | 3 | 103 | 113 | 11 |
| 15 | −1 | 2 | 172 | 162 | 4 | −11 | 3 | 2 | 326 | 343 | 6 | −18 | −4 | 3 | 60 | 46 | 13 | 9 | −1 | 3 | 338 | 343 | 6 | −17 | 3 | 3 | 161 | 152 | 6 |
| 17 | −1 | 2 | 270 | 253 | 4 | −9 | 3 | 2 | 197 | 189 | 6 | −16 | −4 | 3 | 64 | 78 | 13 | 11 | −1 | 3 | 125 | 105 | 4 | −15 | 3 | 3 | 76 | 82 | 7 |
| 19 | −1 | 2 | 388 | 384 | 6 | −7 | 3 | 2 | 768 | 740 | 17 | −14 | −4 | 3 | 0 | 21 | 1 | 13 | −1 | 3 | 219 | 221 | 4 | −13 | 3 | 3 | 224 | 227 | 5 |
| 21 | −1 | 2 | 23 | 45 | 22 | −5 | 3 | 2 | 706 | 681 | 15 | −12 | −4 | 3 | 104 | 106 | 6 | 15 | −1 | 3 | 284 | 270 | 5 | −11 | 3 | 3 | 360 | 350 | 7 |
| 23 | −1 | 2 | 87 | 76 | 10 | −3 | 3 | 2 | 545 | 546 | 9 | −10 | −4 | 3 | 175 | 167 | 5 | 17 | −1 | 3 | 55 | 57 | 8 | −9 | 3 | 3 | 366 | 316 | 8 |
| 25 | −1 | 2 | 17 | 14 | 16 | −1 | 3 | 2 | 519 | 550 | 17 | −8 | −4 | 3 | 148 | 135 | 5 | 19 | −1 | 3 | 95 | 97 | 9 | −7 | 3 | 3 | 330 | 302 | 8 |
| −26 | 0 | 2 | 43 | 34 | 9 | 1 | 3 | 2 | 166 | 172 | 4 | −6 | −4 | 3 | 121 | 119 | 5 | 21 | −1 | 3 | 106 | 107 | 11 | −5 | 3 | 3 | 220 | 237 | 6 |
| −24 | 0 | 2 | 135 | 129 | 6 | 3 | 3 | 2 | 384 | 371 | 7 | −4 | −4 | 3 | 164 | 143 | 7 | 23 | −1 | 3 | 69 | 65 | 12 | −3 | 3 | 3 | 324 | 326 | 6 |
| −22 | 0 | 2 | 41 | 49 | 41 | 5 | 3 | 2 | 521 | 517 | 18 | 4 | −4 | 3 | 272 | 273 | 6 | 25 | −1 | 3 | 57 | 43 | 10 | −1 | 3 | 3 | 481 | 492 | 14 |
| −20 | 0 | 2 | 76 | 62 | 5 | 7 | 3 | 2 | 185 | 188 | 9 | 6 | −4 | 3 | 61 | 56 | 20 | −26 | 0 | 3 | 35 | 27 | 35 | 1 | 3 | 3 | 234 | 237 | 5 |
| −18 | 0 | 2 | 115 | 91 | 6 | 9 | 3 | 2 | 106 | 87 | 7 | 8 | −4 | 3 | 156 | 171 | 6 | −24 | 0 | 3 | 47 | 44 | 12 | 3 | 3 | 3 | 46 | 53 | 4 |
| −16 | 0 | 2 | 174 | 176 | 3 | 11 | 3 | 2 | 224 | 226 | 6 | 10 | −4 | 3 | 35 | 31 | 25 | −22 | 0 | 3 | 0 | 6 | 1 | 5 | 3 | 3 | 102 | 106 | 4 |
| −14 | 0 | 2 | 213 | 236 | 4 | 13 | 3 | 2 | 228 | 210 | 8 | 12 | −4 | 3 | 158 | 156 | 13 | −20 | 0 | 3 | 15 | 9 | 14 | 7 | 3 | 3 | 218 | 211 | 8 |
| −12 | 0 | 2 | 266 | 266 | 5 | 17 | 3 | 2 | 122 | 115 | 10 | 14 | −4 | 3 | 202 | 205 | 8 | −18 | 0 | 3 | 87 | 83 | 4 | 9 | 3 | 3 | 77 | 68 | 6 |
| −10 | 0 | 2 | 881 | 931 | 13 | 19 | 3 | 2 | 96 | 124 | 10 | 16 | −4 | 3 | 189 | 196 | 8 | −16 | 0 | 3 | 138 | 114 | 3 | 11 | 3 | 3 | 307 | 298 | 9 |
| 13 | 3 | 3 | 114 | 114 | 10 | 14 | −4 | 4 | 93 | 77 | 11 | −16 | 0 | 4 | 117 | 118 | 5 | 9 | 3 | 4 | 99 | 99 | 7 | −27 | −3 | 5 | 86 | 76 | 6 |
| 15 | 3 | 3 | 201 | 169 | 9 | 16 | −4 | 4 | 15 | 35 | 14 | −14 | 0 | 4 | 261 | 256 | 5 | 11 | 3 | 4 | 102 | 107 | 10 | −25 | −3 | 5 | 88 | 76 | 7 |
| 19 | 3 | 3 | 81 | 77 | 12 | 18 | −4 | 4 | 54 | 51 | 16 | −12 | 0 | 4 | 547 | 540 | 9 | 13 | 3 | 4 | 108 | 96 | 10 | −23 | −3 | 5 | 0 | 23 | 1 |
| 21 | 3 | 3 | 80 | 109 | 12 | 20 | −4 | 4 | 18 | 35 | 18 | −10 | 0 | 4 | 24 | 15 | 13 | 15 | 3 | 4 | 227 | 228 | 9 | −21 | −3 | 5 | 30 | 18 | 30 |
| 23 | 3 | 3 | 35 | 22 | 35 | −27 | −3 | 4 | 48 | 39 | 11 | −8 | 0 | 4 | 834 | 878 | 15 | 19 | 3 | 4 | 26 | 4 | 25 | −19 | −3 | 5 | 70 | 65 | 20 |
| −24 | 4 | 3 | 0 | 12 | 1 | −25 | −3 | 4 | 20 | 23 | 19 | −6 | 0 | 4 | 80 | 82 | 3 | 21 | 3 | 4 | 50 | 55 | 19 | −17 | −3 | 5 | 92 | 80 | 13 |
| −22 | 4 | 3 | 31 | 32 | 31 | −23 | −3 | 4 | 17 | 31 | 17 | −4 | 0 | 4 | 1279 | 1392 | 23 | −24 | 4 | 4 | 0 | 32 | 1 | −15 | −3 | 5 | 69 | 72 | 8 |
| −20 | 4 | 3 | 35 | 28 | 35 | −21 | −3 | 4 | 178 | 154 | 8 | −2 | 0 | 4 | 315 | 357 | 5 | −22 | 4 | 4 | 61 | 35 | 17 | −13 | −3 | 5 | 255 | 231 | 6 |
| −18 | 4 | 3 | 56 | 46 | 18 | −19 | −3 | 4 | 12 | 2 | 11 | 0 | 0 | 4 | 1116 | 1209 | 17 | −20 | 4 | 4 | 45 | 35 | 24 | −11 | −3 | 5 | 349 | 338 | 7 |
| −16 | 4 | 3 | 57 | 78 | 17 | −17 | −3 | 4 | 70 | 77 | 14 | 2 | 0 | 4 | 444 | 445 | 7 | −18 | 4 | 4 | 87 | 85 | 11 | −9 | −3 | 5 | 360 | 349 | 7 |
| −14 | 4 | 3 | 0 | 21 | 1 | −15 | −3 | 4 | 139 | 130 | 5 | 4 | 0 | 4 | 135 | 130 | 3 | −16 | 4 | 4 | 168 | 153 | 9 | −7 | −3 | 5 | 244 | 225 | 8 |
| −12 | 4 | 3 | 101 | 105 | 5 | −13 | −3 | 4 | 99 | 104 | 6 | 6 | 0 | 4 | 185 | 185 | 3 | −14 | 4 | 4 | 191 | 198 | 5 | −5 | −3 | 5 | 160 | 143 | 7 |
| −10 | 4 | 3 | 173 | 168 | 4 | −11 | −3 | 4 | 284 | 269 | 6 | 8 | 0 | 4 | 770 | 754 | 13 | −12 | 4 | 4 | 81 | 86 | 5 | −3 | −3 | 5 | 262 | 276 | 6 |
| −8 | 4 | 3 | 140 | 135 | 4 | −9 | −3 | 4 | 146 | 162 | 8 | 10 | 0 | 4 | 564 | 516 | 10 | −10 | 4 | 4 | 0 | 22 | 1 | −1 | −3 | 5 | 21 | 26 | 20 |
| −6 | 4 | 3 | 130 | 119 | 4 | −7 | −3 | 4 | 237 | 264 | 9 | 12 | 0 | 4 | 199 | 188 | 3 | −8 | 4 | 4 | 175 | 179 | 3 | 1 | −3 | 5 | 268 | 280 | 8 |
| −4 | 4 | 3 | 162 | 144 | 5 | −5 | −3 | 4 | 118 | 125 | 7 | 14 | 0 | 4 | 179 | 164 | 3 | −6 | 4 | 4 | 18 | 22 | 18 | 3 | −3 | 5 | 163 | 170 | 8 |
| −2 | 4 | 3 | 164 | 155 | 2 | −3 | −3 | 4 | 114 | 105 | 5 | 16 | 0 | 4 | 0 | 9 | 1 | −4 | 4 | 4 | 154 | 151 | 3 | 5 | −3 | 5 | 105 | 108 | 6 |
| 0 | 4 | 3 | 80 | 77 | 2 | −1 | −3 | 4 | 95 | 83 | 9 | 18 | 0 | 4 | 162 | 146 | 6 | −2 | 4 | 4 | 289 | 281 | 4 | 7 | −3 | 5 | 89 | 90 | 14 |
| 2 | 4 | 3 | 208 | 195 | 3 | 1 | −3 | 4 | 77 | 76 | 5 | 20 | 0 | 4 | 0 | 12 | 1 | 0 | 4 | 4 | 274 | 263 | 3 | 9 | −3 | 5 | 268 | 270 | 7 |
| 4 | 4 | 3 | 282 | 272 | 6 | 3 | −3 | 4 | 330 | 311 | 10 | 22 | 0 | 4 | 92 | 84 | 14 | 2 | 4 | 4 | 125 | 129 | 2 | 11 | −3 | 5 | 258 | 248 | 7 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 6 | 4 | 3 | 73 | 56 | 6 | 5 | −3 | 4 | 97 | 101 | 9 | 24 | 0 | 4 | 22 | 34 | 21 | 4 | 4 | 4 | 162 | 153 | 4 | 13 | −3 | 5 | 187 | 182 | 15 |
| 8 | 4 | 3 | 158 | 172 | 4 | 7 | −3 | 4 | 229 | 227 | 6 | −23 | 1 | 4 | 0 | 27 | 1 | 6 | 4 | 4 | 80 | 70 | 6 | 15 | −3 | 5 | 94 | 111 | 10 |
| 10 | 4 | 3 | 51 | 31 | 11 | 9 | −3 | 4 | 107 | 98 | 6 | −21 | 1 | 4 | 197 | 192 | 3 | 8 | 4 | 4 | 133 | 137 | 8 | 17 | −3 | 5 | 23 | 34 | 22 |
| 14 | 4 | 3 | 199 | 206 | 8 | 11 | −3 | 4 | 111 | 107 | 7 | −19 | 1 | 4 | 114 | 104 | 3 | 10 | 4 | 4 | 276 | 267 | 5 | 19 | −3 | 5 | 127 | 103 | 8 |
| 16 | 4 | 3 | 189 | 196 | 8 | 13 | −3 | 4 | 112 | 96 | 7 | −17 | 1 | 4 | 131 | 119 | 3 | 16 | 4 | 4 | 21 | 35 | 20 | 21 | −3 | 5 | 53 | 43 | 15 |
| 18 | 4 | 3 | 70 | 76 | 13 | 15 | −3 | 4 | 241 | 228 | 8 | −15 | 1 | 4 | 67 | 65 | 4 | 18 | 4 | 4 | 72 | 51 | 12 | −28 | −2 | 5 | 0 | 17 | 1 |
| 20 | 4 | 3 | 25 | 26 | 24 | 17 | −3 | 4 | 135 | 128 | 9 | −13 | 1 | 4 | 189 | 198 | 5 | 20 | 4 | 4 | 60 | 35 | 14 | −26 | −2 | 5 | 0 | 10 | 1 |
| −21 | 5 | 3 | 4 | 18 | 4 | 19 | −3 | 4 | 0 | 3 | 1 | −11 | 1 | 4 | 327 | 317 | 5 | −21 | 5 | 4 | 33 | 25 | 32 | −24 | −2 | 5 | 77 | 111 | 7 |
| −19 | 5 | 3 | 51 | 44 | 12 | 21 | −3 | 4 | 57 | 55 | 14 | −9 | 1 | 4 | 977 | 1049 | 13 | −19 | 5 | 4 | 33 | 44 | 32 | −22 | −2 | 5 | 64 | 55 | 9 |
| −17 | 5 | 3 | 36 | 30 | 36 | −28 | −2 | 4 | 85 | 98 | 9 | −7 | 1 | 4 | 166 | 184 | 3 | −17 | 5 | 4 | 93 | 122 | 18 | −20 | −2 | 5 | 107 | 100 | 7 |
| −15 | 5 | 3 | 57 | 58 | 10 | −26 | −2 | 4 | 55 | 65 | 10 | −5 | 1 | 4 | 477 | 502 | 6 | −15 | 5 | 4 | 65 | 75 | 9 | −18 | −2 | 5 | 147 | 125 | 7 |
| −13 | 5 | 3 | 144 | 154 | 18 | −24 | −2 | 4 | 77 | 91 | 7 | −3 | 1 | 4 | 266 | 278 | 4 | −13 | 5 | 4 | 31 | 42 | 30 | −16 | −2 | 5 | 89 | 89 | 6 |
| −11 | 5 | 3 | 118 | 105 | 10 | −22 | −2 | 4 | 130 | 133 | 12 | −1 | 1 | 4 | 991 | 1024 | 23 | −11 | 5 | 4 | 160 | 169 | 5 | −14 | −2 | 5 | 325 | 326 | 6 |
| −9 | 5 | 3 | 34 | 16 | 20 | −20 | −2 | 4 | 108 | 93 | 7 | 1 | 1 | 4 | 413 | 429 | 6 | −9 | 5 | 4 | 117 | 103 | 6 | −12 | −2 | 5 | 75 | 82 | 6 |
| −7 | 5 | 3 | 135 | 135 | 5 | −18 | −2 | 4 | 162 | 147 | 4 | 3 | 1 | 4 | 28 | 30 | 6 | −7 | 5 | 4 | 342 | 333 | 8 | −10 | −2 | 5 | 328 | 327 | 12 |
| −5 | 5 | 3 | 19 | 14 | 19 | −16 | −2 | 4 | 130 | 116 | 13 | 5 | 1 | 4 | 372 | 385 | 5 | −5 | 5 | 4 | 198 | 205 | 5 | −8 | −2 | 5 | 554 | 568 | 18 |
| −3 | 5 | 3 | 385 | 387 | 6 | −14 | −2 | 4 | 326 | 327 | 6 | 7 | 1 | 4 | 191 | 195 | 4 | −3 | 5 | 4 | 187 | 183 | 3 | −6 | −2 | 5 | 424 | 432 | 7 |
| −1 | 5 | 3 | 156 | 149 | 2 | −12 | −2 | 4 | 549 | 586 | 17 | 9 | 1 | 4 | 139 | 157 | 5 | −1 | 5 | 4 | 28 | 44 | 5 | −4 | −2 | 5 | 201 | 208 | 4 |
| 1 | 5 | 3 | 106 | 105 | 3 | −10 | −2 | 4 | 84 | 114 | 16 | 11 | 1 | 4 | 342 | 332 | 4 | 1 | 5 | 4 | 36 | 37 | 8 | −2 | −2 | 5 | 373 | 376 | 8 |
| 3 | 5 | 3 | 62 | 54 | 6 | −8 | −2 | 4 | 215 | 240 | 21 | 13 | 1 | 4 | 229 | 203 | 4 | 3 | 5 | 4 | 144 | 129 | 4 | 0 | −2 | 5 | 443 | 432 | 9 |
| 5 | 5 | 3 | 44 | 38 | 10 | −6 | −2 | 4 | 237 | 241 | 4 | 15 | 1 | 4 | 261 | 249 | 4 | 5 | 5 | 4 | 95 | 99 | 6 | 2 | −2 | 5 | 369 | 382 | 8 |
| 7 | 5 | 3 | 140 | 131 | 5 | −4 | −2 | 4 | 153 | 148 | 3 | 17 | 1 | 4 | 70 | 53 | 5 | 7 | 5 | 4 | 255 | 244 | 8 | 4 | −2 | 5 | 253 | 257 | 6 |
| 9 | 5 | 3 | 157 | 156 | 5 | −2 | −2 | 4 | 189 | 193 | 5 | 19 | 1 | 4 | 88 | 83 | 6 | 9 | 5 | 4 | 58 | 62 | 9 | 6 | −2 | 5 | 213 | 203 | 12 |
| 11 | 5 | 3 | 51 | 55 | 11 | 0 | −2 | 4 | 484 | 496 | 10 | 21 | 1 | 4 | 29 | 27 | 13 | 11 | 5 | 4 | 103 | 94 | 6 | 8 | −2 | 5 | 270 | 272 | 9 |
| 13 | 5 | 3 | 145 | 141 | 5 | 2 | −2 | 4 | 513 | 527 | 9 | −26 | 2 | 4 | 64 | 65 | 16 | 13 | 5 | 4 | 53 | 46 | 10 | 10 | −2 | 5 | 86 | 76 | 7 |
| 15 | 5 | 3 | 54 | 53 | 12 | 4 | −2 | 4 | 413 | 435 | 7 | −24 | 2 | 4 | 85 | 91 | 12 | 15 | 5 | 4 | 26 | 23 | 25 | 12 | −2 | 5 | 29 | 27 | 29 |
| 17 | 5 | 3 | 49 | 50 | 14 | 6 | −2 | 4 | 267 | 255 | 6 | −22 | 2 | 4 | 126 | 133 | 10 | 17 | 5 | 4 | 0 | 19 | 1 | 14 | −2 | 5 | 79 | 83 | 9 |
| −16 | 6 | 3 | 0 | 20 | 1 | 8 | −2 | 4 | 172 | 159 | 9 | −20 | 2 | 4 | 103 | 93 | 8 | −16 | 6 | 4 | 20 | 8 | 20 | 16 | −2 | 5 | 25 | 15 | 24 |
| −14 | 6 | 3 | 31 | 25 | 31 | 10 | −2 | 4 | 178 | 182 | 5 | −18 | 2 | 4 | 161 | 148 | 6 | −14 | 6 | 4 | 0 | 15 | 1 | 18 | −2 | 5 | 163 | 142 | 8 |
| −12 | 6 | 3 | 0 | 11 | 1 | 12 | −2 | 4 | 309 | 321 | 7 | −16 | 2 | 4 | 128 | 116 | 5 | −12 | 6 | 4 | 73 | 60 | 15 | 20 | −2 | 5 | 56 | 50 | 29 |
| −10 | 6 | 3 | 32 | 31 | 17 | 14 | −2 | 4 | 106 | 113 | 13 | −14 | 2 | 4 | 315 | 327 | 7 | −10 | 6 | 4 | 132 | 133 | 5 | 22 | −2 | 5 | 0 | 9 | 1 |
| −8 | 6 | 3 | 41 | 44 | 9 | 16 | −2 | 4 | 68 | 70 | 20 | −12 | 2 | 4 | 567 | 585 | 36 | −8 | 6 | 4 | 76 | 71 | 5 | −29 | −1 | 5 | 50 | 50 | 8 |
| −6 | 6 | 3 | 128 | 137 | 5 | 18 | −2 | 4 | 2 | 25 | 2 | −10 | 2 | 4 | 84 | 116 | 15 | −6 | 6 | 4 | 130 | 130 | 7 | −27 | −1 | 5 | 74 | 83 | 8 |
| 4 | 6 | 3 | 113 | 116 | 3 | 20 | −2 | 4 | 56 | 59 | 11 | −8 | 2 | 4 | 226 | 241 | 8 | 4 | 6 | 4 | 71 | 75 | 4 | −25 | −1 | 5 | 87 | 70 | 10 |
| 6 | 6 | 3 | 64 | 57 | 5 | 22 | −2 | 4 | 46 | 64 | 21 | −6 | 2 | 4 | 240 | 241 | 3 | 6 | 6 | 4 | 86 | 85 | 4 | −23 | −1 | 5 | 45 | 63 | 44 |
| 8 | 6 | 3 | 48 | 53 | 10 | −29 | −1 | 4 | 71 | 74 | 5 | −4 | 2 | 4 | 150 | 149 | 2 | 8 | 6 | 4 | 0 | 28 | 1 | −21 | −1 | 5 | 69 | 77 | 6 |
| 10 | 6 | 3 | 29 | 38 | 23 | −27 | −1 | 4 | 34 | 38 | 34 | −2 | 2 | 4 | 187 | 194 | 3 | 10 | 6 | 4 | 17 | 30 | 17 | −19 | −1 | 5 | 163 | 159 | 4 |
| 12 | 6 | 3 | 0 | 5 | 1 | −25 | −1 | 4 | 25 | 28 | 24 | 0 | 2 | 4 | 479 | 497 | 6 | 12 | 6 | 4 | 33 | 61 | 22 | −17 | −1 | 5 | 180 | 172 | 3 |
| 14 | 6 | 3 | 33 | 46 | 20 | −23 | −1 | 4 | 29 | 27 | 28 | 2 | 2 | 4 | 522 | 527 | 8 | −21 | −5 | 5 | 38 | 51 | 23 | −15 | −1 | 5 | 35 | 26 | 14 |
| −16 | −6 | 4 | 0 | 8 | 1 | −21 | −1 | 4 | 195 | 193 | 4 | 4 | 2 | 4 | 420 | 436 | 6 | −19 | −5 | 5 | 56 | 72 | 13 | −13 | −1 | 5 | 311 | 262 | 6 |
| −21 | −5 | 4 | 5 | 25 | 4 | −19 | −1 | 4 | 126 | 104 | 4 | 6 | 2 | 4 | 265 | 255 | 7 | −17 | −5 | 5 | 78 | 76 | 11 | −11 | −1 | 5 | 411 | 422 | 7 |
| −19 | −5 | 4 | 24 | 44 | 23 | −17 | −1 | 4 | 130 | 119 | 3 | 8 | 2 | 4 | 164 | 158 | 4 | −15 | −5 | 5 | 144 | 127 | 8 | −9 | −1 | 5 | 300 | 317 | 5 |
| −17 | −5 | 4 | 122 | 122 | 8 | −15 | −1 | 4 | 59 | 65 | 8 | 10 | 2 | 4 | 176 | 183 | 3 | −13 | −5 | 5 | 81 | 78 | 10 | −7 | −1 | 5 | 442 | 458 | 8 |
| −15 | −5 | 4 | 68 | 75 | 11 | −13 | −1 | 4 | 194 | 198 | 4 | 12 | 2 | 4 | 316 | 321 | 4 | −11 | −5 | 5 | 199 | 193 | 8 | −5 | −1 | 5 | 539 | 543 | 9 |
| −13 | −5 | 4 | 50 | 42 | 17 | −11 | −1 | 4 | 328 | 315 | 6 | 14 | 2 | 4 | 119 | 112 | 3 | 7 | −5 | 5 | 83 | 99 | 10 | −3 | −1 | 5 | 393 | 406 | 6 |
| −11 | −5 | 4 | 171 | 169 | 7 | −9 | −1 | 4 | 1002 | 1049 | 17 | 16 | 2 | 4 | 67 | 71 | 6 | 9 | −5 | 5 | 50 | 46 | 17 | −1 | −1 | 5 | 451 | 460 | 7 |
| 9 | −5 | 4 | 74 | 62 | 11 | −7 | −1 | 4 | 174 | 185 | 5 | 18 | 2 | 4 | 0 | 25 | 1 | 11 | −5 | 5 | 0 | 35 | 1 | 1 | −1 | 5 | 188 | 199 | 3 |
| 11 | −5 | 4 | 98 | 93 | 9 | −5 | −1 | 4 | 484 | 501 | 8 | 20 | 2 | 4 | 47 | 59 | 23 | 13 | −5 | 5 | 0 | 14 | 1 | 3 | −1 | 5 | 280 | 296 | 8 |
| 13 | −5 | 4 | 0 | 46 | 1 | −3 | −1 | 4 | 268 | 279 | 5 | 22 | 2 | 4 | 48 | 64 | 19 | 15 | −5 | 5 | 31 | 55 | 31 | 5 | −1 | 5 | 218 | 233 | 10 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 15 | −5 | 4 | 23 | 23 | 23 | −1 | −1 | 4 | 958 | 1024 | 15 | −27 | 3 | 4 | 44 | 39 | 22 | −24 | −4 | 5 | 48 | 61 | 17 | 7 | −1 | 5 | 264 | 257 | 11 |
| 17 | −5 | 4 | 11 | 19 | 11 | 1 | −1 | 4 | 393 | 426 | 7 | −25 | 3 | 4 | 42 | 23 | 39 | −22 | −4 | 5 | 103 | 87 | 9 | 9 | −1 | 5 | 637 | 624 | 10 |
| −24 | −4 | 4 | 46 | 32 | 18 | 3 | −1 | 4 | 20 | 27 | 19 | −23 | 3 | 4 | 37 | 31 | 36 | −20 | −4 | 5 | 91 | 113 | 9 | 11 | −1 | 5 | 206 | 201 | 4 |
| −22 | −4 | 4 | 45 | 35 | 20 | 5 | −1 | 4 | 395 | 387 | 8 | −21 | 3 | 4 | 161 | 155 | 9 | −18 | −4 | 5 | 25 | 30 | 24 | 13 | −1 | 5 | 156 | 142 | 4 |
| −20 | −4 | 4 | 0 | 36 | 1 | 7 | −1 | 4 | 188 | 195 | 4 | −19 | 3 | 4 | 0 | 3 | 1 | −16 | −4 | 5 | 69 | 41 | 12 | 15 | −1 | 5 | 115 | 110 | 5 |
| −18 | −4 | 4 | 70 | 86 | 11 | 9 | −1 | 4 | 141 | 156 | 4 | −17 | 3 | 4 | 72 | 77 | 16 | −14 | −4 | 5 | 80 | 63 | 8 | 17 | −1 | 5 | 52 | 55 | 10 |
| −16 | −4 | 4 | 156 | 153 | 8 | 11 | −1 | 4 | 335 | 333 | 5 | −15 | 3 | 4 | 141 | 130 | 6 | −12 | −4 | 5 | 224 | 209 | 6 | 19 | −1 | 5 | 163 | 161 | 8 |
| −14 | −4 | 4 | 205 | 198 | 6 | 13 | −1 | 4 | 221 | 205 | 4 | −13 | 3 | 4 | 92 | 103 | 5 | −10 | −4 | 5 | 282 | 270 | 6 | 21 | −1 | 5 | 0 | 9 | 1 |
| −12 | −4 | 4 | 94 | 86 | 7 | 15 | −1 | 4 | 258 | 249 | 5 | −11 | 3 | 4 | 274 | 269 | 5 | −8 | −4 | 5 | 205 | 205 | 5 | 23 | −1 | 5 | 0 | 18 | 1 |
| −10 | −4 | 4 | 23 | 22 | 23 | 17 | −1 | 4 | 50 | 52 | 10 | −9 | 3 | 4 | 166 | 162 | 5 | −6 | −4 | 5 | 61 | 57 | 18 | −26 | 0 | 5 | 67 | 70 | 8 |
| −8 | −4 | 4 | 167 | 179 | 5 | 19 | −1 | 4 | 92 | 83 | 7 | −7 | 3 | 4 | 246 | 263 | 6 | 4 | −4 | 5 | 69 | 74 | 8 | −24 | 0 | 5 | 117 | 132 | 6 |
| −6 | −4 | 4 | 44 | 22 | 10 | 21 | −1 | 4 | 0 | 27 | 1 | −5 | 3 | 4 | 119 | 125 | 3 | 6 | −4 | 5 | 265 | 270 | 6 | −22 | 0 | 5 | 17 | 41 | 17 |
| −4 | −4 | 4 | 143 | 151 | 7 | 23 | −1 | 4 | 79 | 61 | 10 | −3 | 3 | 4 | 110 | 105 | 3 | 8 | −4 | 5 | 327 | 322 | 10 | −20 | 0 | 5 | 43 | 46 | 11 |
| 4 | −4 | 4 | 157 | 154 | 5 | −26 | 0 | 4 | 0 | 13 | 1 | −1 | 3 | 4 | 82 | 84 | 6 | 10 | −4 | 5 | 294 | 307 | 7 | −18 | 0 | 5 | 103 | 112 | 4 |
| 6 | −4 | 4 | 76 | 70 | 7 | −24 | 0 | 4 | 118 | 108 | 11 | 1 | 3 | 4 | 77 | 77 | 3 | 12 | −4 | 5 | 82 | 68 | 12 | −16 | 0 | 5 | 158 | 157 | 3 |
| 8 | −4 | 4 | 138 | 138 | 6 | −22 | 0 | 4 | 49 | 47 | 10 | 3 | 3 | 4 | 327 | 311 | 6 | 14 | −4 | 5 | 17 | 35 | 17 | −14 | 0 | 5 | 248 | 236 | 5 |
| 10 | −4 | 4 | 261 | 266 | 7 | −20 | 0 | 4 | 170 | 168 | 4 | 5 | 3 | 4 | 99 | 102 | 2 | 16 | −4 | 5 | 65 | 39 | 14 | −12 | 0 | 5 | 325 | 311 | 6 |
| 12 | −4 | 4 | 398 | 404 | 12 | −18 | 0 | 4 | 248 | 225 | 4 | 7 | 3 | 4 | 232 | 227 | 5 | 18 | −4 | 5 | 61 | 69 | 13 | −10 | 0 | 5 | 153 | 155 | 4 |
| −8 | 0 | 5 | 322 | 330 | 5 | 21 | 3 | 5 | 45 | 43 | 21 | −13 | −3 | 6 | 208 | 190 | 5 | 10 | 0 | 6 | 90 | 96 | 4 | −4 | 4 | 6 | 81 | 81 | 3 |
| −6 | 0 | 5 | 128 | 120 | 3 | −24 | 4 | 5 | 57 | 61 | 17 | −11 | −3 | 6 | 259 | 234 | 6 | 12 | 0 | 6 | 215 | 207 | 3 | −2 | 4 | 6 | 286 | 261 | 3 |
| −4 | 0 | 5 | 496 | 544 | 7 | −22 | 4 | 5 | 114 | 87 | 10 | −9 | −3 | 6 | 170 | 156 | 4 | 14 | 0 | 6 | 127 | 136 | 4 | 0 | 4 | 6 | 225 | 211 | 3 |
| −2 | 0 | 5 | 229 | 251 | 4 | −20 | 4 | 5 | 89 | 113 | 11 | −7 | −3 | 6 | 43 | 40 | 15 | 16 | 0 | 6 | 0 | 3 | 1 | 2 | 4 | 6 | 68 | 66 | 3 |
| 0 | 0 | 5 | 293 | 313 | 4 | −18 | 4 | 5 | 52 | 30 | 20 | −5 | −3 | 6 | 104 | 106 | 7 | 18 | 0 | 6 | 14 | 28 | 13 | 4 | 4 | 6 | 202 | 188 | 3 |
| 2 | 0 | 5 | 228 | 235 | 4 | −16 | 4 | 5 | 52 | 41 | 21 | −3 | −3 | 6 | 151 | 150 | 5 | 20 | 0 | 6 | 0 | 9 | 1 | 6 | 4 | 6 | 218 | 225 | 5 |
| 4 | 0 | 5 | 1383 | 1397 | 21 | −14 | 4 | 5 | 78 | 64 | 10 | −1 | −3 | 6 | 260 | 272 | 6 | 22 | 0 | 6 | 28 | 45 | 22 | 8 | 4 | 6 | 214 | 211 | 6 |
| 6 | 0 | 5 | 710 | 692 | 13 | −12 | 4 | 5 | 215 | 209 | 4 | 1 | −3 | 6 | 72 | 76 | 6 | −23 | 1 | 6 | 108 | 115 | 6 | 10 | 4 | 6 | 32 | 44 | 32 |
| 8 | 0 | 5 | 186 | 186 | 4 | −10 | 4 | 5 | 279 | 271 | 5 | 3 | −3 | 6 | 111 | 115 | 5 | −21 | 1 | 6 | 55 | 63 | 7 | 12 | 4 | 6 | 170 | 155 | 6 |
| 10 | 0 | 5 | 245 | 213 | 5 | −8 | 4 | 5 | 210 | 205 | 4 | 5 | −3 | 6 | 136 | 132 | 7 | −19 | 1 | 6 | 71 | 69 | 4 | 16 | 4 | 6 | 38 | 25 | 38 |
| 12 | 0 | 5 | 38 | 8 | 8 | −6 | 4 | 5 | 56 | 57 | 6 | 7 | −3 | 6 | 224 | 224 | 6 | −17 | 1 | 6 | 31 | 22 | 9 | 18 | 4 | 6 | 57 | 78 | 13 |
| 14 | 0 | 5 | 160 | 160 | 3 | −4 | 4 | 5 | 116 | 96 | 4 | 9 | −3 | 6 | 98 | 87 | 7 | −15 | 1 | 6 | 176 | 177 | 3 | −21 | 5 | 6 | 17 | 40 | 16 |
| 16 | 0 | 5 | 153 | 140 | 7 | −2 | 4 | 5 | 102 | 103 | 2 | 11 | −3 | 6 | 111 | 98 | 7 | −13 | 1 | 6 | 61 | 71 | 4 | −19 | 5 | 6 | 57 | 81 | 10 |
| 18 | 0 | 5 | 187 | 174 | 8 | 0 | 4 | 5 | 136 | 130 | 2 | 13 | −3 | 6 | 0 | 49 | 1 | −11 | 1 | 6 | 260 | 281 | 5 | −17 | 5 | 6 | 29 | 26 | 29 |
| 20 | 0 | 5 | 90 | 95 | 8 | 2 | 4 | 5 | 127 | 117 | 2 | 15 | −3 | 6 | 31 | 45 | 31 | −9 | 1 | 6 | 831 | 852 | 20 | −15 | 5 | 6 | 56 | 68 | 10 |
| 22 | 0 | 5 | 36 | 49 | 15 | 4 | 4 | 5 | 77 | 74 | 5 | 17 | −3 | 6 | 75 | 52 | 13 | −7 | 1 | 6 | 476 | 515 | 7 | −13 | 5 | 6 | 160 | 146 | 5 |
| −23 | 1 | 5 | 67 | 63 | 5 | 6 | 4 | 5 | 262 | 270 | 5 | 19 | −3 | 6 | 17 | 34 | 17 | −5 | 1 | 6 | 482 | 526 | 7 | −11 | 5 | 6 | 254 | 246 | 6 |
| −21 | 1 | 5 | 80 | 77 | 4 | 8 | 4 | 5 | 330 | 323 | 7 | −28 | −2 | 6 | 122 | 102 | 8 | −3 | 1 | 6 | 802 | 822 | 12 | −9 | 5 | 6 | 127 | 123 | 8 |
| −19 | 1 | 5 | 165 | 158 | 3 | 10 | 4 | 5 | 306 | 307 | 6 | −26 | −2 | 6 | 108 | 85 | 6 | −1 | 1 | 6 | 676 | 668 | 10 | −7 | 5 | 6 | 234 | 237 | 6 |
| −17 | 1 | 5 | 180 | 172 | 3 | 12 | 4 | 5 | 87 | 68 | 8 | −24 | −2 | 6 | 43 | 65 | 13 | 1 | 1 | 6 | 800 | 784 | 12 | −5 | 5 | 6 | 86 | 72 | 5 |
| −15 | 1 | 5 | 33 | 26 | 9 | 16 | 4 | 5 | 23 | 39 | 22 | −22 | −2 | 6 | 52 | 41 | 11 | 3 | 1 | 6 | 319 | 330 | 6 | −3 | 5 | 6 | 76 | 85 | 4 |
| −13 | 1 | 5 | 302 | 262 | 7 | 18 | 4 | 5 | 31 | 70 | 30 | −20 | −2 | 6 | 56 | 41 | 9 | 5 | 1 | 6 | 844 | 811 | 15 | −1 | 5 | 6 | 88 | 84 | 2 |
| −11 | 1 | 5 | 401 | 423 | 6 | −21 | 5 | 5 | 44 | 51 | 22 | −18 | −2 | 6 | 186 | 172 | 4 | 7 | 1 | 6 | 586 | 575 | 10 | 1 | 5 | 6 | 239 | 243 | 4 |
| −9 | 1 | 5 | 300 | 319 | 7 | −19 | 5 | 5 | 66 | 72 | 9 | −16 | −2 | 6 | 92 | 97 | 5 | 9 | 1 | 6 | 188 | 187 | 3 | 9 | 5 | 6 | 48 | 38 | 11 |
| −7 | 1 | 5 | 442 | 457 | 6 | −17 | 5 | 5 | 95 | 76 | 7 | −14 | −2 | 6 | 230 | 217 | 5 | 11 | 1 | 6 | 129 | 121 | 3 | 11 | 5 | 6 | 49 | 53 | 11 |
| −5 | 1 | 5 | 523 | 543 | 7 | −15 | 5 | 5 | 140 | 127 | 6 | −12 | −2 | 6 | 457 | 423 | 10 | 13 | 1 | 6 | 11 | 8 | 11 | 13 | 5 | 6 | 0 | 18 | 1 |
| −3 | 1 | 5 | 406 | 407 | 7 | −13 | 5 | 5 | 84 | 78 | 7 | −10 | −2 | 6 | 151 | 160 | 16 | 15 | 1 | 6 | 87 | 68 | 5 | 15 | 5 | 6 | 0 | 5 | 1 |
| −1 | 1 | 5 | 458 | 460 | 9 | −11 | 5 | 5 | 211 | 193 | 5 | −8 | −2 | 6 | 177 | 173 | 4 | 17 | 1 | 6 | 41 | 36 | 13 | −16 | 6 | 6 | 98 | 96 | 8 |
| 1 | 1 | 5 | 190 | 199 | 4 | −9 | 5 | 5 | 178 | 176 | 6 | −6 | −2 | 6 | 286 | 277 | 6 | 19 | 1 | 6 | 76 | 65 | 5 | −14 | 6 | 6 | 71 | 58 | 10 |
| 3 | 1 | 5 | 287 | 296 | 4 | −7 | 5 | 5 | 213 | 197 | 5 | −4 | −2 | 6 | 219 | 222 | 5 | −26 | 2 | 6 | 78 | 85 | 13 | −12 | 6 | 6 | 23 | 43 | 22 |
| 5 | 1 | 5 | 222 | 233 | 4 | −5 | 5 | 5 | 170 | 157 | 4 | −2 | −2 | 6 | 573 | 568 | 12 | −24 | 2 | 6 | 68 | 65 | 15 | −10 | 6 | 6 | 36 | 49 | 14 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 7 | 1 | 5 | 262 | 258 | 8 | −3 | 5 | 5 | 196 | 204 | 3 | 0 | −2 | 6 | 251 | 235 | 6 | −22 | 2 | 6 | 47 | 41 | 28 | −8 | 6 | 6 | 51 | 52 | 7 |
| 9 | 1 | 5 | 658 | 623 | 8 | −1 | 5 | 5 | 68 | 70 | 3 | 2 | −2 | 6 | 271 | 276 | 6 | −20 | 2 | 6 | 63 | 41 | 12 | −6 | 6 | 6 | 74 | 81 | 4 |
| 11 | 1 | 5 | 213 | 201 | 3 | 1 | 5 | 5 | 194 | 195 | 5 | 4 | −2 | 6 | 164 | 161 | 6 | −18 | 2 | 6 | 186 | 172 | 6 | 4 | 6 | 6 | 69 | 68 | 4 |
| 13 | 1 | 5 | 150 | 142 | 3 | 3 | 5 | 5 | 168 | 171 | 4 | 6 | −2 | 6 | 99 | 103 | 4 | −16 | 2 | 6 | 94 | 97 | 6 | 6 | 6 | 6 | 48 | 47 | 7 |
| 15 | 1 | 5 | 134 | 110 | 8 | 5 | 5 | 5 | 180 | 172 | 7 | 8 | −2 | 6 | 258 | 259 | 11 | −14 | 2 | 6 | 232 | 218 | 6 | 8 | 6 | 6 | 42 | 45 | 10 |
| 17 | 1 | 5 | 51 | 55 | 9 | 7 | 5 | 5 | 89 | 99 | 8 | 10 | −2 | 6 | 186 | 173 | 8 | −12 | 2 | 6 | 463 | 422 | 7 | 10 | 6 | 6 | 0 | 18 | 1 |
| 19 | 1 | 5 | 156 | 161 | 4 | 9 | 5 | 5 | 45 | 46 | 12 | 12 | −2 | 6 | 74 | 75 | 11 | −10 | 2 | 6 | 162 | 158 | 4 | −21 | −5 | 7 | 45 | 59 | 16 |
| 21 | 1 | 5 | 0 | 9 | 1 | 11 | 5 | 5 | 43 | 35 | 13 | 14 | −2 | 6 | 34 | 59 | 34 | −8 | 2 | 6 | 182 | 174 | 3 | −19 | −5 | 7 | 0 | 18 | 1 |
| −26 | 2 | 5 | 17 | 10 | 16 | 13 | 5 | 5 | 10 | 14 | 10 | 16 | −2 | 6 | 0 | 14 | 1 | −6 | 2 | 6 | 292 | 278 | 4 | −17 | −5 | 7 | 70 | 79 | 11 |
| −24 | 2 | 5 | 84 | 111 | 12 | 15 | 5 | 5 | 27 | 55 | 26 | 18 | −2 | 6 | 85 | 91 | 16 | −4 | 2 | 6 | 222 | 222 | 4 | −15 | −5 | 7 | 30 | 42 | 30 |
| −22 | 2 | 5 | 58 | 55 | 19 | −16 | 6 | 5 | 28 | 37 | 27 | 20 | −2 | 6 | 64 | 62 | 9 | −2 | 2 | 6 | 572 | 568 | 9 | −13 | −5 | 7 | 46 | 38 | 17 |
| −20 | 2 | 5 | 112 | 100 | 7 | −14 | 6 | 5 | 65 | 55 | 11 | 22 | −2 | 6 | 57 | 63 | 9 | 0 | 2 | 6 | 254 | 232 | 4 | −11 | −5 | 7 | 124 | 153 | 8 |
| −18 | 2 | 5 | 147 | 125 | 13 | −12 | 6 | 5 | 92 | 97 | 6 | −29 | −1 | 6 | 33 | 39 | 15 | 2 | 2 | 6 | 278 | 276 | 5 | 7 | −5 | 7 | 101 | 120 | 9 |
| −16 | 2 | 5 | 89 | 89 | 7 | −10 | 6 | 5 | 126 | 138 | 5 | −27 | −1 | 6 | 48 | 58 | 19 | 4 | 2 | 6 | 175 | 162 | 3 | 9 | −5 | 7 | 94 | 77 | 9 |
| −14 | 2 | 5 | 327 | 326 | 7 | −8 | 6 | 5 | 85 | 88 | 4 | −25 | −1 | 6 | 65 | 91 | 12 | 6 | 2 | 6 | 106 | 104 | 3 | 11 | −5 | 7 | 76 | 56 | 11 |
| −12 | 2 | 5 | 69 | 81 | 7 | −6 | 6 | 5 | 84 | 79 | 4 | −23 | −1 | 6 | 112 | 115 | 6 | 8 | 2 | 6 | 264 | 259 | 4 | 13 | −5 | 7 | 0 | 33 | 1 |
| −10 | 2 | 5 | 342 | 327 | 6 | 4 | 6 | 5 | 29 | 31 | 11 | −21 | −1 | 6 | 52 | 62 | 7 | 10 | 2 | 6 | 184 | 173 | 3 | −24 | −4 | 7 | 51 | 35 | 15 |
| −8 | 2 | 5 | 564 | 567 | 13 | 6 | 6 | 5 | 84 | 88 | 4 | −19 | −1 | 6 | 65 | 69 | 5 | 12 | 2 | 6 | 76 | 75 | 4 | −22 | −4 | 7 | 0 | 26 | 1 |
| −6 | 2 | 5 | 431 | 432 | 6 | 8 | 6 | 5 | 31 | 25 | 30 | −17 | −1 | 6 | 41 | 23 | 8 | 14 | 2 | 6 | 59 | 58 | 5 | −20 | −4 | 7 | 140 | 138 | 8 |
| −4 | 2 | 5 | 200 | 207 | 3 | 10 | 6 | 5 | 58 | 64 | 10 | −15 | −1 | 6 | 178 | 177 | 4 | 16 | 2 | 6 | 14 | 14 | 13 | −18 | −4 | 7 | 144 | 128 | 8 |
| −2 | 2 | 5 | 379 | 376 | 6 | 12 | 6 | 5 | 34 | 48 | 18 | −13 | −1 | 6 | 64 | 72 | 5 | 18 | 2 | 6 | 78 | 91 | 14 | −16 | −4 | 7 | 53 | 54 | 16 |
| 0 | 2 | 5 | 450 | 433 | 9 | −21 | −5 | 6 | 28 | 40 | 28 | −11 | −1 | 6 | 266 | 283 | 5 | 20 | 2 | 6 | 60 | 62 | 14 | −14 | −4 | 7 | 74 | 87 | 8 |
| 2 | 2 | 5 | 380 | 381 | 8 | −19 | −5 | 6 | 58 | 81 | 13 | −9 | −1 | 6 | 807 | 851 | 59 | 22 | 2 | 6 | 46 | 63 | 17 | −12 | −4 | 7 | 41 | 46 | 15 |
| 4 | 2 | 5 | 261 | 258 | 5 | −17 | −5 | 6 | 52 | 25 | 15 | −7 | −1 | 6 | 497 | 517 | 19 | −27 | 3 | 6 | 54 | 15 | 17 | −10 | −4 | 7 | 14 | 20 | 13 |
| 6 | 2 | 5 | 210 | 203 | 4 | −15 | −5 | 6 | 63 | 69 | 13 | −5 | −1 | 6 | 508 | 526 | 8 | −25 | 3 | 6 | 52 | 43 | 22 | −8 | −4 | 7 | 307 | 323 | 7 |
| 8 | 2 | 5 | 280 | 272 | 3 | −13 | −5 | 6 | 148 | 146 | 8 | −3 | −1 | 6 | 794 | 821 | 12 | −23 | 3 | 6 | 95 | 104 | 12 | −6 | −4 | 7 | 240 | 240 | 6 |
| 10 | 2 | 5 | 91 | 76 | 3 | 7 | −5 | 6 | 68 | 67 | 12 | −1 | −1 | 6 | 662 | 670 | 10 | −21 | 3 | 6 | 106 | 126 | 10 | 2 | −4 | 7 | 199 | 192 | 8 |
| 12 | 2 | 5 | 25 | 27 | 15 | 9 | −5 | 6 | 60 | 38 | 13 | 1 | −1 | 6 | 768 | 785 | 13 | −19 | 3 | 6 | 41 | 61 | 41 | 4 | −4 | 7 | 98 | 107 | 8 |
| 14 | 2 | 5 | 86 | 83 | 3 | 11 | −5 | 6 | 58 | 53 | 14 | 3 | −1 | 6 | 317 | 329 | 14 | −17 | 3 | 6 | 136 | 113 | 20 | 6 | −4 | 7 | 51 | 59 | 14 |
| 16 | 2 | 5 | 0 | 15 | 1 | 13 | −5 | 6 | 0 | 18 | 1 | 5 | −1 | 6 | 834 | 812 | 18 | −15 | 3 | 6 | 73 | 69 | 8 | 8 | −4 | 7 | 134 | 157 | 9 |
| 18 | 2 | 5 | 149 | 143 | 10 | 15 | −5 | 6 | 29 | 5 | 28 | 7 | −1 | 6 | 585 | 575 | 10 | −13 | 3 | 6 | 206 | 190 | 5 | 10 | −4 | 7 | 127 | 127 | 9 |
| 20 | 2 | 5 | 24 | 50 | 24 | −24 | −4 | 6 | 52 | 7 | 15 | 9 | −1 | 6 | 186 | 187 | 4 | −11 | 3 | 6 | 256 | 234 | 5 | 12 | −4 | 7 | 101 | 97 | 10 |
| 22 | 2 | 5 | 0 | 9 | 1 | −22 | −4 | 6 | 39 | 49 | 27 | 11 | −1 | 6 | 117 | 122 | 4 | −9 | 3 | 6 | 151 | 156 | 4 | 14 | −4 | 7 | 66 | 45 | 14 |
| −27 | 3 | 5 | 76 | 76 | 12 | −20 | −4 | 6 | 49 | 57 | 16 | 13 | −1 | 6 | 19 | 8 | 18 | −7 | 3 | 6 | 51 | 40 | 3 | 16 | −4 | 7 | 39 | 48 | 29 |
| −25 | 3 | 5 | 106 | 76 | 11 | −18 | −4 | 6 | 108 | 103 | 9 | 15 | −1 | 6 | 80 | 68 | 6 | −5 | 3 | 6 | 102 | 106 | 4 | −27 | −3 | 7 | 101 | 92 | 6 |
| −23 | 3 | 5 | 0 | 23 | 1 | −16 | −4 | 6 | 204 | 196 | 8 | 17 | −1 | 6 | 37 | 37 | 23 | −3 | 3 | 6 | 152 | 150 | 3 | −25 | −3 | 7 | 124 | 115 | 8 |
| −21 | 3 | 5 | 18 | 19 | 17 | −14 | −4 | 6 | 164 | 165 | 12 | 19 | −1 | 6 | 61 | 65 | 24 | −1 | 3 | 6 | 271 | 271 | 4 | −23 | −3 | 7 | 103 | 78 | 9 |
| −19 | 3 | 5 | 72 | 65 | 19 | −12 | −4 | 6 | 168 | 157 | 6 | 21 | −1 | 6 | 31 | 26 | 30 | 1 | 3 | 6 | 74 | 76 | 3 | −21 | −3 | 7 | 16 | 69 | 15 |
| −17 | 3 | 5 | 91 | 80 | 8 | −10 | −4 | 6 | 141 | 137 | 5 | −26 | 0 | 6 | 19 | 35 | 19 | 3 | 3 | 6 | 119 | 115 | 2 | −19 | −3 | 7 | 64 | 60 | 13 |
| −15 | 3 | 5 | 61 | 72 | 9 | −8 | −4 | 6 | 166 | 176 | 5 | −24 | 0 | 6 | 67 | 59 | 8 | 5 | 3 | 6 | 136 | 131 | 2 | −17 | −3 | 7 | 251 | 222 | 6 |
| −13 | 3 | 5 | 241 | 230 | 5 | −6 | −4 | 6 | 149 | 155 | 5 | −22 | 0 | 6 | 134 | 127 | 8 | 7 | 3 | 6 | 230 | 224 | 2 | −15 | −3 | 7 | 121 | 119 | 5 |
| −11 | 3 | 5 | 338 | 339 | 6 | 4 | −4 | 6 | 191 | 188 | 6 | −20 | 0 | 6 | 215 | 205 | 5 | 9 | 3 | 6 | 95 | 87 | 2 | −13 | −3 | 7 | 85 | 87 | 6 |
| −9 | 3 | 5 | 351 | 349 | 6 | 6 | −4 | 6 | 213 | 225 | 6 | −18 | 0 | 6 | 107 | 109 | 4 | 11 | 3 | 6 | 111 | 98 | 11 | −11 | −3 | 7 | 114 | 109 | 5 |
| −7 | 3 | 5 | 236 | 224 | 7 | 8 | −4 | 6 | 218 | 211 | 6 | −16 | 0 | 6 | 221 | 203 | 4 | 13 | 3 | 6 | 48 | 49 | 26 | −9 | −3 | 7 | 87 | 92 | 5 |
| −5 | 3 | 5 | 171 | 144 | 3 | 10 | −4 | 6 | 53 | 44 | 19 | −14 | 0 | 6 | 123 | 110 | 4 | 15 | 3 | 6 | 37 | 45 | 37 | −7 | −3 | 7 | 88 | 90 | 5 |
| −3 | 3 | 5 | 257 | 276 | 4 | 12 | −4 | 6 | 175 | 155 | 8 | −12 | 0 | 6 | 157 | 171 | 4 | 19 | 3 | 6 | 0 | 34 | 1 | −5 | −3 | 7 | 173 | 170 | 8 |
| −1 | 3 | 5 | 36 | 25 | 6 | 14 | −4 | 6 | 62 | 67 | 15 | −10 | 0 | 6 | 85 | 66 | 4 | −24 | 4 | 6 | 32 | 7 | 32 | −3 | −3 | 7 | 194 | 205 | 5 |
| 1 | 3 | 5 | 267 | 280 | 4 | 16 | −4 | 6 | 0 | 25 | 1 | −8 | 0 | 6 | 341 | 313 | 7 | −22 | 4 | 6 | 57 | 49 | 18 | −1 | −3 | 7 | 119 | 114 | 10 |
| 3 | 3 | 5 | 169 | 169 | 3 | 18 | −4 | 6 | 57 | 78 | 14 | −6 | 0 | 6 | 349 | 364 | 5 | −20 | 4 | 6 | 22 | 57 | 22 | 1 | −3 | 7 | 78 | 82 | 5 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 5 | 3 | 5 | 104 | 108 | 3 | −27 | −3 | 6 | 9 | 15 | 8 | −4 | 0 | 6 | 51 | 72 | 4 | −18 | 4 | 6 | 104 | 103 | 10 | 3 | −3 | 7 | 64 | 70 | 11 |
| 7 | 3 | 5 | 97 | 91 | 2 | −25 | −3 | 6 | 41 | 43 | 22 | −2 | 0 | 6 | 15 | 38 | 14 | −16 | 4 | 6 | 208 | 196 | 8 | 5 | −3 | 7 | 50 | 44 | 12 |
| 9 | 3 | 5 | 272 | 270 | 12 | −23 | −3 | 6 | 93 | 104 | 9 | 0 | 0 | 6 | 248 | 265 | 4 | −14 | 4 | 6 | 154 | 165 | 9 | 7 | −3 | 7 | 260 | 243 | 7 |
| 11 | 3 | 5 | 259 | 248 | 9 | −21 | −3 | 6 | 121 | 125 | 9 | 2 | 0 | 6 | 63 | 56 | 4 | −12 | 4 | 6 | 168 | 156 | 5 | 9 | −3 | 7 | 188 | 183 | 6 |
| 13 | 3 | 5 | 204 | 182 | 8 | −19 | −3 | 6 | 65 | 60 | 17 | 4 | 0 | 6 | 110 | 110 | 6 | −10 | 4 | 6 | 142 | 137 | 4 | 11 | −3 | 7 | 145 | 145 | 23 |
| 15 | 3 | 5 | 81 | 111 | 13 | −17 | −3 | 6 | 121 | 113 | 10 | 6 | 0 | 6 | 0 | 18 | 1 | −8 | 4 | 6 | 168 | 177 | 4 | 13 | −3 | 7 | 118 | 135 | 9 |
| 19 | 3 | 5 | 88 | 103 | 11 | −15 | −3 | 6 | 76 | 69 | 9 | 8 | 0 | 6 | 664 | 610 | 12 | −6 | 4 | 6 | 170 | 156 | 4 | 15 | −3 | 7 | 50 | 46 | 19 |
| 17 | −3 | 7 | 123 | 94 | 9 | −7 | 1 | 7 | 447 | 467 | 9 | −11 | 5 | 7 | 161 | 153 | 5 | 6 | −2 | 8 | 53 | 56 | 10 | −14 | 2 | 8 | 208 | 200 | 3 |
| 19 | −3 | 7 | 57 | 59 | 13 | −5 | 1 | 7 | 433 | 473 | 9 | −9 | 5 | 7 | 79 | 85 | 10 | 8 | −2 | 8 | 140 | 123 | 6 | −12 | 2 | 8 | 172 | 160 | 3 |
| −28 | −2 | 7 | 55 | 68 | 18 | −3 | 1 | 7 | 151 | 169 | 3 | −7 | 5 | 7 | 48 | 61 | 12 | 10 | −2 | 8 | 88 | 79 | 8 | −10 | 2 | 8 | 279 | 284 | 4 |
| −26 | −2 | 7 | 65 | 59 | 8 | −1 | 1 | 7 | 652 | 668 | 10 | −5 | 5 | 7 | 156 | 162 | 5 | 12 | −2 | 8 | 188 | 159 | 9 | −8 | 2 | 8 | 400 | 403 | 8 |
| −24 | −2 | 7 | 137 | 146 | 5 | 1 | 1 | 7 | 340 | 341 | 7 | −3 | 5 | 7 | 191 | 183 | 3 | 14 | −2 | 8 | 165 | 153 | 8 | −6 | 2 | 8 | 238 | 220 | 4 |
| −22 | −2 | 7 | 37 | 29 | 16 | 3 | 1 | 7 | 322 | 323 | 8 | −1 | 5 | 7 | 156 | 148 | 2 | 16 | −2 | 8 | 81 | 73 | 8 | −4 | 2 | 8 | 162 | 166 | 4 |
| −20 | −2 | 7 | 117 | 109 | 7 | 5 | 1 | 7 | 251 | 250 | 5 | 1 | 5 | 7 | 43 | 29 | 42 | 18 | −2 | 8 | 0 | 14 | 1 | −2 | 2 | 8 | 347 | 323 | 5 |
| −18 | −2 | 7 | 143 | 142 | 6 | 7 | 1 | 7 | 449 | 431 | 6 | 9 | 5 | 7 | 75 | 77 | 7 | 20 | −2 | 8 | 36 | 36 | 15 | 0 | 2 | 8 | 118 | 111 | 4 |
| −16 | −2 | 7 | 4 | 37 | 4 | 9 | 1 | 7 | 363 | 359 | 5 | 11 | 5 | 7 | 54 | 56 | 12 | −29 | −1 | 8 | 55 | 48 | 9 | 2 | 2 | 8 | 220 | 212 | 3 |
| −14 | −2 | 7 | 218 | 201 | 5 | 11 | 1 | 7 | 161 | 155 | 4 | 13 | 5 | 7 | 0 | 33 | 1 | −27 | −1 | 8 | 39 | 40 | 17 | 4 | 2 | 8 | 159 | 144 | 3 |
| −12 | −2 | 7 | 313 | 294 | 6 | 13 | 1 | 7 | 15 | 28 | 15 | −16 | 6 | 7 | 40 | 25 | 19 | −25 | −1 | 8 | 74 | 75 | 10 | 6 | 2 | 8 | 52 | 57 | 6 |
| −10 | −2 | 7 | 207 | 228 | 8 | 15 | 1 | 7 | 100 | 88 | 10 | −14 | 6 | 7 | 45 | 60 | 15 | −23 | −1 | 8 | 111 | 127 | 9 | 8 | 2 | 8 | 135 | 123 | 4 |
| −8 | −2 | 7 | 181 | 170 | 5 | 17 | 1 | 7 | 78 | 75 | 5 | −12 | 6 | 7 | 64 | 70 | 12 | −21 | −1 | 8 | 121 | 109 | 5 | 10 | 2 | 8 | 91 | 79 | 4 |
| −6 | −2 | 7 | 207 | 214 | 5 | 19 | 1 | 7 | 45 | 46 | 7 | −10 | 6 | 7 | 64 | 75 | 7 | −19 | −1 | 8 | 85 | 94 | 4 | 12 | 2 | 8 | 175 | 159 | 5 |
| −4 | −2 | 7 | 159 | 173 | 5 | −28 | 2 | 7 | 49 | 68 | 21 | −8 | 6 | 7 | 25 | 28 | 24 | −17 | −1 | 8 | 245 | 242 | 5 | 14 | 2 | 8 | 159 | 153 | 4 |
| −2 | −2 | 7 | 217 | 213 | 5 | −26 | 2 | 7 | 74 | 59 | 14 | −6 | 6 | 7 | 33 | 33 | 9 | −15 | −1 | 8 | 97 | 92 | 4 | 16 | 2 | 8 | 56 | 73 | 21 |
| 0 | −2 | 7 | 94 | 94 | 5 | −24 | 2 | 7 | 150 | 146 | 9 | 4 | 6 | 7 | 72 | 75 | 4 | −13 | −1 | 8 | 282 | 287 | 5 | 18 | 2 | 8 | 0 | 15 | 1 |
| 2 | −2 | 7 | 161 | 149 | 8 | −22 | 2 | 7 | 58 | 29 | 18 | 6 | 6 | 7 | 32 | 39 | 11 | −11 | −1 | 8 | 127 | 137 | 7 | 20 | 2 | 8 | 17 | 36 | 17 |
| 4 | −2 | 7 | 171 | 178 | 4 | −20 | 2 | 7 | 119 | 110 | 7 | 8 | 6 | 7 | 40 | 45 | 14 | −9 | −1 | 8 | 758 | 744 | 16 | −27 | 3 | 8 | 85 | 69 | 12 |
| 6 | −2 | 7 | 133 | 130 | 4 | −18 | 2 | 7 | 150 | 142 | 6 | −21 | −5 | 8 | 0 | 33 | 1 | −7 | −1 | 8 | 423 | 407 | 9 | −25 | 3 | 8 | 99 | 82 | 11 |
| 8 | −2 | 7 | 267 | 252 | 7 | −16 | 2 | 7 | 25 | 37 | 24 | −19 | −5 | 8 | 46 | 38 | 17 | −5 | −1 | 8 | 566 | 606 | 10 | −23 | 3 | 8 | 23 | 21 | 22 |
| 10 | −2 | 7 | 76 | 71 | 11 | −14 | 2 | 7 | 220 | 201 | 3 | −17 | −5 | 8 | 40 | 29 | 22 | −3 | −1 | 8 | 446 | 460 | 15 | −21 | 3 | 8 | 97 | 95 | 10 |
| 12 | −2 | 7 | 57 | 62 | 18 | −12 | 2 | 7 | 311 | 294 | 4 | −15 | −5 | 8 | 83 | 89 | 9 | −1 | −1 | 8 | 382 | 391 | 7 | −19 | 3 | 8 | 33 | 12 | 33 |
| 14 | −2 | 7 | 166 | 122 | 9 | −10 | 2 | 7 | 216 | 228 | 5 | −13 | −5 | 8 | 54 | 62 | 14 | 1 | −1 | 8 | 583 | 575 | 12 | −17 | 3 | 8 | 94 | 100 | 8 |
| 16 | −2 | 7 | 115 | 87 | 7 | −8 | 2 | 7 | 190 | 170 | 4 | −11 | −5 | 8 | 24 | 35 | 23 | 3 | −1 | 8 | 143 | 139 | 4 | −15 | 3 | 8 | 37 | 23 | 18 |
| 18 | −2 | 7 | 86 | 116 | 7 | −6 | 2 | 7 | 205 | 214 | 5 | 7 | −5 | 8 | 94 | 100 | 9 | 5 | −1 | 8 | 255 | 249 | 4 | −13 | 3 | 8 | 53 | 50 | 11 |
| 20 | −2 | 7 | 16 | 19 | 15 | −4 | 2 | 7 | 156 | 173 | 3 | 9 | −5 | 8 | 0 | 17 | 1 | 7 | −1 | 8 | 242 | 234 | 4 | −11 | 3 | 8 | 57 | 51 | 6 |
| −29 | −1 | 7 | 40 | 43 | 15 | −2 | 2 | 7 | 215 | 213 | 4 | 11 | −5 | 8 | 21 | 39 | 20 | 9 | −1 | 8 | 45 | 43 | 8 | −9 | 3 | 8 | 89 | 83 | 2 |
| −27 | −1 | 7 | 133 | 126 | 7 | 0 | 2 | 7 | 99 | 94 | 4 | 13 | −5 | 8 | 0 | 36 | 1 | 11 | −1 | 8 | 111 | 104 | 5 | −7 | 3 | 8 | 110 | 114 | 2 |
| −25 | −1 | 7 | 57 | 47 | 14 | 2 | 2 | 7 | 161 | 150 | 3 | −24 | −4 | 8 | 0 | 31 | 1 | 13 | −1 | 8 | 24 | 34 | 24 | −5 | 3 | 8 | 59 | 64 | 4 |
| −23 | −1 | 7 | 24 | 15 | 23 | 4 | 2 | 7 | 183 | 178 | 3 | −22 | −4 | 8 | 105 | 87 | 9 | 15 | −1 | 8 | 65 | 47 | 11 | −3 | 3 | 8 | 114 | 115 | 3 |
| −21 | −1 | 7 | 50 | 48 | 7 | 6 | 2 | 7 | 132 | 130 | 3 | −20 | −4 | 8 | 74 | 90 | 10 | 17 | −1 | 8 | 109 | 104 | 6 | −1 | 3 | 8 | 124 | 108 | 2 |
| −19 | −1 | 7 | 243 | 229 | 4 | 8 | 2 | 7 | 280 | 253 | 4 | −18 | −4 | 8 | 58 | 61 | 14 | 19 | −1 | 8 | 40 | 52 | 16 | 1 | 3 | 8 | 41 | 38 | 6 |
| −17 | −1 | 7 | 83 | 83 | 4 | 10 | 2 | 7 | 82 | 71 | 4 | −16 | −4 | 8 | 152 | 125 | 8 | −28 | 0 | 8 | 0 | 12 | 1 | 3 | 3 | 8 | 109 | 105 | 3 |
| −15 | −1 | 7 | 96 | 98 | 4 | 12 | 2 | 7 | 62 | 61 | 6 | −14 | −4 | 8 | 71 | 68 | 11 | −26 | 0 | 8 | 67 | 64 | 7 | 5 | 3 | 8 | 171 | 172 | 2 |
| −13 | −1 | 7 | 123 | 135 | 4 | 14 | 2 | 7 | 147 | 122 | 4 | −12 | −4 | 8 | 97 | 92 | 7 | −24 | 0 | 8 | 110 | 124 | 6 | 7 | 3 | 8 | 116 | 112 | 3 |
| −11 | −1 | 7 | 154 | 161 | 4 | 16 | 2 | 7 | 85 | 88 | 14 | −10 | −4 | 8 | 225 | 219 | 6 | −22 | 0 | 8 | 15 | 14 | 15 | 9 | 3 | 8 | 46 | 46 | 6 |
| −9 | −1 | 7 | 207 | 214 | 9 | 18 | 2 | 7 | 93 | 116 | 12 | −8 | −4 | 8 | 220 | 223 | 6 | −20 | 0 | 8 | 261 | 264 | 6 | 11 | 3 | 8 | 133 | 140 | 10 |
| −7 | −1 | 7 | 474 | 467 | 9 | 20 | 2 | 7 | 0 | 19 | 1 | −6 | −4 | 8 | 76 | 71 | 9 | −18 | 0 | 8 | 129 | 135 | 7 | 13 | 3 | 8 | 55 | 63 | 18 |
| −5 | −1 | 7 | 438 | 473 | 11 | −27 | 3 | 7 | 100 | 92 | 10 | 2 | −4 | 8 | 136 | 132 | 8 | −16 | 0 | 8 | 30 | 25 | 9 | 15 | 3 | 8 | 67 | 89 | 16 |
| −3 | −1 | 7 | 162 | 170 | 3 | −25 | 3 | 7 | 132 | 115 | 9 | 4 | −4 | 8 | 141 | 129 | 6 | −14 | 0 | 8 | 117 | 95 | 4 | −24 | 4 | 8 | 0 | 31 | 1 |
| −1 | −1 | 7 | 648 | 666 | 10 | −23 | 3 | 7 | 84 | 78 | 12 | 6 | −4 | 8 | 114 | 116 | 7 | −12 | 0 | 8 | 444 | 426 | 8 | −22 | 4 | 8 | 98 | 87 | 11 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 1 | −1 | 7 | 338 | 339 | 8 | −21 | 3 | 7 | 62 | 69 | 16 | 8 | −4 | 8 | 205 | 199 | 8 | −10 | 0 | 8 | 42 | 55 | 8 | −20 | 4 | 8 | 79 | 90 | 12 |
| 3 | −1 | 7 | 325 | 324 | 10 | −19 | 3 | 7 | 46 | 59 | 46 | 10 | −4 | 8 | 53 | 46 | 19 | −8 | 0 | 8 | 321 | 317 | 6 | −18 | 4 | 8 | 33 | 60 | 32 |
| 5 | −1 | 7 | 253 | 250 | 5 | −17 | 3 | 7 | 251 | 223 | 7 | 12 | −4 | 8 | 123 | 105 | 9 | −6 | 0 | 8 | 330 | 316 | 5 | −16 | 4 | 8 | 153 | 125 | 9 |
| 7 | −1 | 7 | 446 | 432 | 7 | −15 | 3 | 7 | 113 | 119 | 6 | 14 | −4 | 8 | 24 | 25 | 24 | −4 | 0 | 8 | 545 | 598 | 12 | −14 | 4 | 8 | 67 | 68 | 8 |
| 9 | −1 | 7 | 357 | 359 | 5 | −13 | 3 | 7 | 80 | 88 | 7 | 16 | −4 | 8 | 73 | 50 | 10 | −2 | 0 | 8 | 7 | 6 | 6 | −12 | 4 | 8 | 101 | 91 | 5 |
| 11 | −1 | 7 | 167 | 153 | 6 | −11 | 3 | 7 | 108 | 110 | 4 | −27 | −3 | 8 | 79 | 68 | 6 | 0 | 0 | 8 | 145 | 144 | 8 | −10 | 4 | 8 | 220 | 219 | 4 |
| 13 | −1 | 7 | 33 | 27 | 17 | −9 | 3 | 7 | 89 | 91 | 2 | −25 | −3 | 8 | 98 | 82 | 6 | 2 | 0 | 8 | 426 | 432 | 11 | −8 | 4 | 8 | 231 | 223 | 4 |
| 15 | −1 | 7 | 78 | 88 | 8 | −7 | 3 | 7 | 94 | 89 | 2 | −23 | −3 | 8 | 7 | 21 | 7 | 4 | 0 | 8 | 193 | 194 | 4 | −6 | 4 | 8 | 70 | 70 | 3 |
| 17 | −1 | 7 | 64 | 75 | 10 | −5 | 3 | 7 | 182 | 170 | 3 | −21 | −3 | 8 | 73 | 95 | 11 | 6 | 0 | 8 | 224 | 200 | 3 | −4 | 4 | 8 | 136 | 130 | 3 |
| 19 | −1 | 7 | 39 | 46 | 17 | −3 | 3 | 7 | 204 | 205 | 3 | −19 | −3 | 8 | 27 | 13 | 26 | 8 | 0 | 8 | 48 | 58 | 6 | −2 | 4 | 8 | 126 | 114 | 4 |
| 21 | −1 | 7 | 0 | 25 | 1 | −1 | 3 | 7 | 130 | 115 | 2 | −17 | −3 | 8 | 111 | 100 | 6 | 10 | 0 | 8 | 23 | 7 | 22 | 0 | 4 | 8 | 83 | 83 | 3 |
| −28 | 0 | 7 | 0 | 12 | 1 | 1 | 3 | 7 | 88 | 82 | 3 | −15 | −3 | 8 | 0 | 24 | 1 | 12 | 0 | 8 | 125 | 125 | 5 | 2 | 4 | 8 | 139 | 133 | 3 |
| −26 | 0 | 7 | 21 | 36 | 21 | 3 | 3 | 7 | 74 | 70 | 3 | −13 | −3 | 8 | 36 | 49 | 16 | 14 | 0 | 8 | 80 | 75 | 6 | 4 | 4 | 8 | 141 | 129 | 3 |
| −24 | 0 | 7 | 137 | 155 | 6 | 5 | 3 | 7 | 41 | 44 | 5 | −11 | −3 | 8 | 59 | 51 | 8 | 16 | 0 | 8 | 0 | 19 | 1 | 6 | 4 | 8 | 108 | 117 | 8 |
| −22 | 0 | 7 | 36 | 49 | 15 | 7 | 3 | 7 | 264 | 242 | 3 | −9 | −3 | 8 | 90 | 83 | 6 | 18 | 0 | 8 | 64 | 77 | 13 | 8 | 4 | 8 | 196 | 199 | 10 |
| −20 | 0 | 7 | 249 | 257 | 6 | 9 | 3 | 7 | 180 | 184 | 3 | −7 | −3 | 8 | 101 | 114 | 5 | 20 | 0 | 8 | 0 | 0 | 1 | 10 | 4 | 8 | 21 | 46 | 20 |
| −18 | 0 | 7 | 65 | 51 | 5 | 11 | 3 | 7 | 147 | 144 | 9 | −5 | −3 | 8 | 56 | 64 | 7 | −23 | 1 | 8 | 125 | 127 | 3 | 12 | 4 | 8 | 102 | 105 | 11 |
| −16 | 0 | 7 | 119 | 96 | 3 | 13 | 3 | 7 | 110 | 135 | 10 | −3 | −3 | 8 | 111 | 114 | 12 | −21 | 1 | 8 | 117 | 108 | 3 | 16 | 4 | 8 | 47 | 50 | 16 |
| −14 | 0 | 7 | 183 | 188 | 5 | 15 | 3 | 7 | 29 | 46 | 28 | −1 | −3 | 8 | 106 | 108 | 4 | −19 | 1 | 8 | 90 | 94 | 4 | −21 | 5 | 8 | 17 | 33 | 17 |
| −12 | 0 | 7 | 87 | 107 | 4 | 19 | 3 | 7 | 43 | 59 | 22 | 1 | −3 | 8 | 46 | 38 | 11 | −17 | 1 | 8 | 250 | 242 | 3 | −19 | 5 | 8 | 43 | 39 | 16 |
| −10 | 0 | 7 | 669 | 637 | 12 | −24 | 4 | 7 | 39 | 35 | 39 | 3 | −3 | 8 | 111 | 106 | 6 | −15 | 1 | 8 | 101 | 92 | 3 | −17 | 5 | 8 | 0 | 30 | 1 |
| −8 | 0 | 7 | 247 | 229 | 4 | −22 | 4 | 7 | 32 | 26 | 31 | 5 | −3 | 8 | 167 | 173 | 12 | −13 | 1 | 8 | 273 | 287 | 4 | −15 | 5 | 8 | 81 | 89 | 9 |
| −6 | 0 | 7 | 546 | 524 | 8 | −20 | 4 | 7 | 125 | 137 | 9 | 7 | −3 | 8 | 126 | 112 | 7 | −11 | 1 | 8 | 128 | 135 | 5 | −13 | 5 | 8 | 70 | 63 | 9 |
| −4 | 0 | 7 | 481 | 488 | 7 | −18 | 4 | 7 | 123 | 128 | 9 | 9 | −3 | 8 | 6 | 45 | 5 | −9 | 1 | 8 | 736 | 743 | 17 | −11 | 5 | 8 | 38 | 34 | 19 |
| −2 | 0 | 7 | 280 | 291 | 4 | −16 | 4 | 7 | 22 | 54 | 21 | 11 | −3 | 8 | 140 | 139 | 9 | −7 | 1 | 8 | 408 | 404 | 11 | −9 | 5 | 8 | 91 | 104 | 9 |
| 0 | 0 | 7 | 230 | 268 | 5 | −14 | 4 | 7 | 88 | 86 | 6 | 13 | −3 | 8 | 58 | 63 | 15 | −5 | 1 | 8 | 585 | 605 | 10 | −7 | 5 | 8 | 113 | 95 | 6 |
| 2 | 0 | 7 | 204 | 214 | 8 | −12 | 4 | 7 | 52 | 46 | 8 | 15 | −3 | 8 | 73 | 89 | 13 | −3 | 1 | 8 | 450 | 459 | 7 | −5 | 5 | 8 | 125 | 121 | 5 |
| 4 | 0 | 7 | 547 | 532 | 10 | −10 | 4 | 7 | 0 | 20 | 1 | 17 | −3 | 8 | 48 | 56 | 19 | −1 | 1 | 8 | 384 | 391 | 6 | −3 | 5 | 8 | 96 | 88 | 3 |
| 6 | 0 | 7 | 149 | 148 | 5 | −8 | 4 | 7 | 310 | 323 | 5 | −28 | −2 | 8 | 68 | 90 | 7 | 1 | 1 | 8 | 573 | 575 | 19 | −1 | 5 | 8 | 49 | 49 | 5 |
| 8 | 0 | 7 | 208 | 209 | 3 | −6 | 4 | 7 | 246 | 240 | 5 | −26 | −2 | 8 | 44 | 47 | 12 | 3 | 1 | 8 | 141 | 138 | 4 | 11 | 5 | 8 | 34 | 39 | 17 |
| 10 | 0 | 7 | 42 | 42 | 7 | −4 | 4 | 7 | 59 | 64 | 4 | −24 | −2 | 8 | 60 | 61 | 9 | 5 | 1 | 8 | 263 | 248 | 4 | 13 | 5 | 8 | 34 | 36 | 14 |
| 12 | 0 | 7 | 165 | 166 | 3 | −2 | 4 | 7 | 84 | 69 | 3 | −22 | −2 | 8 | 69 | 78 | 9 | 7 | 1 | 8 | 243 | 234 | 3 | −16 | 6 | 8 | 47 | 55 | 14 |
| 14 | 0 | 7 | 0 | 9 | 1 | 0 | 4 | 7 | 62 | 57 | 4 | −20 | −2 | 8 | 47 | 44 | 10 | 9 | 1 | 8 | 31 | 42 | 11 | −14 | 6 | 8 | 12 | 32 | 11 |
| 16 | 0 | 7 | 149 | 127 | 10 | 2 | 4 | 7 | 215 | 193 | 3 | −18 | −2 | 8 | 107 | 99 | 9 | 11 | 1 | 8 | 111 | 104 | 5 | −12 | 6 | 8 | 21 | 26 | 20 |
| 18 | 0 | 7 | 0 | 9 | 1 | 4 | 4 | 7 | 121 | 107 | 4 | −16 | −2 | 8 | 115 | 101 | 6 | 13 | 1 | 8 | 17 | 34 | 16 | −10 | 6 | 8 | 55 | 54 | 8 |
| 20 | 0 | 7 | 112 | 104 | 6 | 6 | 4 | 7 | 51 | 58 | 10 | −14 | −2 | 8 | 207 | 200 | 5 | 15 | 1 | 8 | 49 | 46 | 11 | −8 | 6 | 8 | 47 | 38 | 13 |
| 22 | 0 | 7 | 0 | 13 | 1 | 8 | 4 | 7 | 150 | 158 | 7 | −12 | −2 | 8 | 173 | 160 | 5 | 17 | 1 | 8 | 99 | 104 | 4 | −6 | 6 | 8 | 54 | 43 | 4 |
| −23 | 1 | 7 | 4 | 14 | 4 | 10 | 4 | 7 | 123 | 127 | 6 | −10 | −2 | 8 | 286 | 284 | 6 | 19 | 1 | 8 | 53 | 52 | 7 | 4 | 6 | 8 | 0 | 32 | 1 |
| −21 | 1 | 7 | 47 | 49 | 6 | 12 | 4 | 7 | 75 | 96 | 9 | −8 | −2 | 8 | 403 | 403 | 12 | −28 | 2 | 8 | 34 | 90 | 34 | 6 | 6 | 8 | 57 | 64 | 5 |
| −19 | 1 | 7 | 240 | 229 | 3 | 16 | 4 | 7 | 40 | 48 | 23 | −6 | −2 | 8 | 241 | 221 | 6 | −26 | 2 | 8 | 34 | 47 | 34 | −21 | −5 | 9 | 0 | 19 | 1 |
| −17 | 1 | 7 | 95 | 82 | 5 | −21 | 5 | 7 | 55 | 59 | 17 | −4 | −2 | 8 | 158 | 166 | 5 | −24 | 2 | 8 | 34 | 61 | 34 | −19 | −5 | 9 | 0 | 35 | 1 |
| −15 | 1 | 7 | 95 | 98 | 3 | −19 | 5 | 7 | 22 | 18 | 22 | −2 | −2 | 8 | 349 | 323 | 9 | −22 | 2 | 8 | 67 | 78 | 15 | −17 | −5 | 9 | 27 | 20 | 26 |
| −13 | 1 | 7 | 113 | 134 | 4 | −17 | 5 | 7 | 56 | 79 | 11 | 0 | −2 | 8 | 124 | 110 | 5 | −20 | 2 | 8 | 62 | 43 | 11 | −15 | −5 | 9 | 31 | 37 | 31 |
| −11 | 1 | 7 | 146 | 161 | 7 | −15 | 5 | 7 | 55 | 43 | 11 | 2 | −2 | 8 | 221 | 214 | 5 | −18 | 2 | 8 | 113 | 100 | 7 | −13 | −5 | 9 | 13 | 31 | 13 |
| −9 | 1 | 7 | 212 | 215 | 5 | −13 | 5 | 7 | 18 | 39 | 18 | 4 | −2 | 8 | 156 | 145 | 9 | −16 | 2 | 8 | 117 | 100 | 3 | −11 | −5 | 9 | 46 | 53 | 16 |
| 7 | −5 | 9 | 33 | 40 | 32 | 11 | −1 | 9 | 55 | 41 | 10 | −3 | 3 | 9 | 71 | 64 | 3 | 1 | −3 | 10 | 225 | 218 | 6 | −9 | 1 | 10 | 412 | 408 | 6 |
| 9 | −5 | 9 | 68 | 85 | 11 | 13 | −1 | 9 | 107 | 91 | 9 | −1 | 3 | 9 | 79 | 75 | 3 | 3 | −3 | 10 | 72 | 84 | 9 | −7 | 1 | 10 | 232 | 229 | 4 |
| 11 | −5 | 9 | 104 | 106 | 7 | 15 | −1 | 9 | 13 | 24 | 13 | 1 | 3 | 9 | 203 | 204 | 3 | 5 | −3 | 10 | 100 | 96 | 7 | −5 | 1 | 10 | 224 | 223 | 4 |
| −24 | −4 | 9 | 9 | 30 | 8 | 17 | −1 | 9 | 54 | 49 | 18 | 3 | 3 | 9 | 49 | 45 | 6 | 7 | −3 | 10 | 30 | 24 | 29 | −3 | 1 | 10 | 289 | 284 | 5 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −22 | −4 | 9 | 37 | 27 | 27 | 19 | −1 | 9 | 0 | 30 | 1 | 5 | 3 | 9 | 90 | 77 | 3 | 9 | −3 | 10 | 109 | 90 | 10 | −1 | 1 | 10 | 132 | 139 | 3 |
| −20 | −4 | 9 | 32 | 26 | 32 | −28 | 0 | 9 | 24 | 35 | 23 | 7 | 3 | 9 | 44 | 35 | 7 | 11 | −3 | 10 | 133 | 130 | 8 | 1 | 1 | 10 | 328 | 341 | 4 |
| −18 | −4 | 9 | 81 | 93 | 10 | −26 | 0 | 9 | 49 | 56 | 13 | 9 | 3 | 9 | 166 | 176 | 6 | 13 | −3 | 10 | 67 | 68 | 14 | 3 | 1 | 10 | 115 | 104 | 3 |
| −16 | −4 | 9 | 88 | 80 | 9 | −24 | 0 | 9 | 29 | 39 | 29 | 11 | 3 | 9 | 88 | 107 | 12 | 15 | −3 | 10 | 76 | 61 | 11 | 5 | 1 | 10 | 122 | 118 | 3 |
| −14 | −4 | 9 | 50 | 33 | 12 | −22 | 0 | 9 | 207 | 206 | 5 | 13 | 3 | 9 | 16 | 48 | 16 | −28 | −2 | 10 | 115 | 97 | 5 | 7 | 1 | 10 | 154 | 136 | 3 |
| −12 | −4 | 9 | 246 | 243 | 8 | −20 | 0 | 9 | 181 | 170 | 5 | 15 | 3 | 9 | 33 | 19 | 32 | −26 | −2 | 10 | 119 | 113 | 5 | 9 | 1 | 10 | 181 | 177 | 3 |
| −10 | −4 | 9 | 115 | 117 | 6 | −18 | 0 | 9 | 44 | 50 | 6 | −24 | 4 | 9 | 33 | 30 | 33 | −24 | −2 | 10 | 58 | 40 | 9 | 11 | 1 | 10 | 33 | 33 | 32 |
| −8 | −4 | 9 | 240 | 235 | 6 | −16 | 0 | 9 | 98 | 90 | 3 | −22 | 4 | 9 | 0 | 27 | 1 | −22 | −2 | 10 | 42 | 41 | 13 | 13 | 1 | 10 | 136 | 150 | 5 |
| −6 | −4 | 9 | 243 | 265 | 9 | −14 | 0 | 9 | 100 | 101 | 4 | −20 | 4 | 9 | 37 | 26 | 37 | −20 | −2 | 10 | 234 | 220 | 5 | 15 | 1 | 10 | 14 | 14 | 14 |
| 2 | −4 | 9 | 193 | 182 | 8 | −12 | 0 | 9 | 260 | 261 | 5 | −18 | 4 | 9 | 95 | 92 | 11 | −18 | −2 | 10 | 125 | 126 | 6 | 17 | 1 | 10 | 0 | 17 | 1 |
| 4 | −4 | 9 | 67 | 66 | 11 | −10 | 0 | 9 | 641 | 625 | 11 | −16 | 4 | 9 | 47 | 80 | 24 | −16 | −2 | 10 | 17 | 41 | 17 | −28 | 2 | 10 | 100 | 97 | 11 |
| 6 | −4 | 9 | 154 | 132 | 8 | −8 | 0 | 9 | 1007 | 926 | 17 | −14 | 4 | 9 | 24 | 32 | 24 | −14 | −2 | 10 | 211 | 200 | 7 | −26 | 2 | 10 | 116 | 113 | 10 |
| 8 | −4 | 9 | 132 | 141 | 9 | −6 | 0 | 9 | 559 | 566 | 10 | −12 | 4 | 9 | 242 | 243 | 5 | −12 | −2 | 10 | 28 | 41 | 25 | −24 | 2 | 10 | 43 | 40 | 37 |
| 10 | −4 | 9 | 0 | 9 | 1 | −4 | 0 | 9 | 410 | 437 | 13 | −10 | 4 | 9 | 130 | 118 | 4 | −10 | −2 | 10 | 224 | 228 | 5 | −22 | 2 | 10 | 46 | 40 | 29 |
| 12 | −4 | 9 | 71 | 50 | 13 | −2 | 0 | 9 | 114 | 107 | 7 | −8 | 4 | 9 | 240 | 235 | 4 | −8 | −2 | 10 | 207 | 195 | 4 | −20 | 2 | 10 | 234 | 220 | 7 |
| 14 | −4 | 9 | 45 | 51 | 20 | 0 | 0 | 9 | 0 | 13 | 1 | −6 | 4 | 9 | 267 | 265 | 5 | −6 | −2 | 10 | 144 | 132 | 5 | −18 | 2 | 10 | 129 | 127 | 5 |
| −27 | −3 | 9 | 27 | 5 | 26 | 2 | 0 | 9 | 142 | 138 | 5 | −4 | 4 | 9 | 139 | 137 | 3 | −4 | −2 | 10 | 212 | 201 | 3 | −16 | 2 | 10 | 33 | 41 | 11 |
| −25 | −3 | 9 | 30 | 51 | 30 | 4 | 0 | 9 | 148 | 158 | 3 | −2 | 4 | 9 | 31 | 38 | 11 | −2 | −2 | 10 | 179 | 174 | 4 | −14 | 2 | 10 | 207 | 200 | 3 |
| −23 | −3 | 9 | 77 | 83 | 11 | 6 | 0 | 9 | 371 | 334 | 5 | 0 | 4 | 9 | 84 | 79 | 3 | 0 | −2 | 10 | 90 | 84 | 4 | −12 | 2 | 10 | 37 | 42 | 8 |
| −21 | −3 | 9 | 90 | 110 | 9 | 8 | 0 | 9 | 10 | 21 | 9 | 2 | 4 | 9 | 184 | 182 | 3 | 2 | −2 | 10 | 116 | 118 | 4 | −10 | 2 | 10 | 212 | 228 | 3 |
| −19 | −3 | 9 | 47 | 64 | 18 | 10 | 0 | 9 | 40 | 44 | 9 | 4 | 4 | 9 | 77 | 66 | 3 | 4 | −2 | 10 | 47 | 59 | 9 | −8 | 2 | 10 | 205 | 194 | 3 |
| −17 | −3 | 9 | 92 | 83 | 12 | 12 | 0 | 9 | 41 | 59 | 10 | 6 | 4 | 9 | 141 | 132 | 6 | 6 | −2 | 10 | 90 | 93 | 8 | −6 | 2 | 10 | 144 | 133 | 3 |
| −15 | −3 | 9 | 109 | 107 | 11 | 14 | 0 | 9 | 0 | 7 | 1 | 8 | 4 | 9 | 134 | 142 | 9 | 8 | −2 | 10 | 150 | 152 | 16 | −4 | 2 | 10 | 206 | 200 | 3 |
| −13 | −3 | 9 | 74 | 62 | 12 | 16 | 0 | 9 | 57 | 57 | 17 | 10 | 4 | 9 | 26 | 9 | 25 | 10 | −2 | 10 | 135 | 119 | 9 | −2 | 2 | 10 | 175 | 174 | 2 |
| −11 | −3 | 9 | 129 | 133 | 12 | 18 | 0 | 9 | 14 | 19 | 14 | 12 | 4 | 9 | 43 | 50 | 32 | 12 | −2 | 10 | 31 | 35 | 30 | 0 | 2 | 10 | 83 | 84 | 3 |
| −9 | −3 | 9 | 315 | 304 | 7 | 20 | 0 | 9 | 49 | 57 | 7 | −21 | 5 | 9 | 29 | 19 | 28 | 14 | −2 | 10 | 42 | 46 | 28 | 2 | 2 | 10 | 130 | 117 | 3 |
| −7 | −3 | 9 | 187 | 188 | 5 | −25 | 1 | 9 | 103 | 111 | 11 | −19 | 5 | 9 | 33 | 35 | 32 | 16 | −2 | 10 | 57 | 68 | 17 | 4 | 2 | 10 | 72 | 60 | 5 |
| −5 | −3 | 9 | 155 | 156 | 5 | −23 | 1 | 9 | 35 | 36 | 11 | −17 | 5 | 9 | 12 | 20 | 12 | −29 | −1 | 10 | 107 | 106 | 5 | 6 | 2 | 10 | 101 | 94 | 5 |
| −3 | −3 | 9 | 58 | 65 | 6 | −21 | 1 | 9 | 64 | 58 | 5 | −15 | 5 | 9 | 47 | 37 | 14 | −27 | −1 | 10 | 51 | 44 | 16 | 8 | 2 | 10 | 155 | 151 | 5 |
| −1 | −3 | 9 | 73 | 74 | 6 | −19 | 1 | 9 | 115 | 115 | 5 | −13 | 5 | 9 | 37 | 31 | 21 | −25 | −1 | 10 | 82 | 89 | 9 | 10 | 2 | 10 | 117 | 119 | 8 |
| 1 | −3 | 9 | 200 | 205 | 9 | −17 | 1 | 9 | 160 | 150 | 3 | −11 | 5 | 9 | 45 | 52 | 14 | −23 | −1 | 10 | 145 | 135 | 5 | 12 | 2 | 10 | 34 | 35 | 13 |
| 3 | −3 | 9 | 52 | 46 | 11 | −15 | 1 | 9 | 128 | 133 | 4 | −9 | 5 | 9 | 8 | 12 | 7 | −21 | −1 | 10 | 74 | 83 | 5 | 14 | 2 | 10 | 37 | 46 | 10 |
| 5 | −3 | 9 | 85 | 77 | 10 | −13 | 1 | 9 | 91 | 75 | 4 | −7 | 5 | 9 | 145 | 161 | 8 | −19 | −1 | 10 | 255 | 258 | 5 | 16 | 2 | 10 | 44 | 68 | 29 |
| 7 | −3 | 9 | 52 | 35 | 15 | −11 | 1 | 9 | 64 | 67 | 6 | −5 | 5 | 9 | 43 | 41 | 10 | −17 | −1 | 10 | 148 | 137 | 4 | −27 | 3 | 10 | 70 | 81 | 14 |
| 9 | −3 | 9 | 157 | 175 | 9 | −9 | 1 | 9 | 568 | 580 | 10 | −3 | 5 | 9 | 105 | 93 | 3 | −15 | −1 | 10 | 159 | 160 | 4 | −25 | 3 | 10 | 111 | 111 | 10 |
| 11 | −3 | 9 | 100 | 107 | 10 | −7 | 1 | 9 | 679 | 679 | 12 | −1 | 5 | 9 | 186 | 186 | 3 | −13 | −1 | 10 | 218 | 209 | 4 | −23 | 3 | 10 | 155 | 135 | 9 |
| 13 | −3 | 9 | 37 | 48 | 37 | −5 | 1 | 9 | 632 | 620 | 11 | 3 | 5 | 9 | 34 | 25 | 28 | −11 | −1 | 10 | 268 | 273 | 4 | −21 | 3 | 10 | 17 | 43 | 16 |
| 15 | −3 | 9 | 0 | 19 | 1 | −3 | 1 | 9 | 291 | 281 | 5 | 11 | 5 | 9 | 84 | 106 | 6 | −9 | −1 | 10 | 426 | 409 | 6 | −19 | 3 | 10 | 85 | 86 | 12 |
| 17 | −3 | 9 | 16 | 16 | 16 | −1 | 1 | 9 | 169 | 188 | 4 | −16 | 6 | 9 | 51 | 50 | 12 | −7 | −1 | 10 | 234 | 229 | 5 | −17 | 3 | 10 | 112 | 116 | 7 |
| −28 | −2 | 9 | 0 | 20 | 1 | 1 | 1 | 9 | 390 | 410 | 6 | −14 | 6 | 9 | 44 | 47 | 11 | −5 | −1 | 10 | 225 | 224 | 6 | −15 | 3 | 10 | 126 | 113 | 15 |
| −26 | −2 | 9 | 103 | 87 | 6 | 3 | 1 | 9 | 371 | 364 | 4 | −12 | 6 | 9 | 41 | 33 | 11 | −3 | −1 | 10 | 291 | 284 | 7 | −13 | 3 | 10 | 191 | 178 | 6 |
| −24 | −2 | 9 | 88 | 66 | 13 | 5 | 1 | 9 | 175 | 177 | 3 | −10 | 6 | 9 | 35 | 44 | 10 | −1 | −1 | 10 | 136 | 139 | 5 | −11 | 3 | 10 | 329 | 330 | 4 |
| −22 | −2 | 9 | 75 | 82 | 7 | 7 | 1 | 9 | 337 | 331 | 4 | −8 | 6 | 9 | 33 | 46 | 9 | 1 | −1 | 10 | 329 | 341 | 5 | −9 | 3 | 10 | 198 | 193 | 3 |
| −20 | −2 | 9 | 38 | 33 | 25 | 9 | 1 | 9 | 96 | 107 | 4 | 4 | 6 | 9 | 38 | 49 | 6 | 3 | −1 | 10 | 114 | 105 | 6 | −7 | 3 | 10 | 221 | 223 | 3 |
| −18 | −2 | 9 | 10 | 21 | 9 | 11 | 1 | 9 | 39 | 41 | 13 | 6 | 6 | 9 | 33 | 41 | 7 | 5 | −1 | 10 | 119 | 118 | 4 | −5 | 3 | 10 | 125 | 118 | 3 |
| −16 | −2 | 9 | 86 | 88 | 12 | 13 | 1 | 9 | 94 | 91 | 6 | −21 | −5 | 10 | 0 | 12 | 1 | 7 | −1 | 10 | 158 | 137 | 4 | −3 | 3 | 10 | 65 | 50 | 4 |
| −14 | −2 | 9 | 134 | 127 | 5 | 15 | 1 | 9 | 38 | 24 | 15 | −19 | −5 | 10 | 40 | 28 | 21 | 9 | −1 | 10 | 171 | 176 | 10 | −1 | 3 | 10 | 141 | 146 | 3 |
| −12 | −2 | 9 | 167 | 164 | 7 | 17 | 1 | 9 | 48 | 49 | 8 | −17 | −5 | 10 | 0 | 30 | 1 | 11 | −1 | 10 | 25 | 33 | 24 | 1 | 3 | 10 | 221 | 219 | 3 |
| −10 | −2 | 9 | 59 | 56 | 7 | −28 | 2 | 9 | 16 | 20 | 16 | −15 | −5 | 10 | 43 | 30 | 19 | 13 | −1 | 10 | 158 | 150 | 8 | 3 | 3 | 10 | 82 | 84 | 7 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −8 | −2 | 9 | 249 | 271 | 4 | −26 | 2 | 9 | 110 | 87 | 11 | −13 | −5 | 10 | 42 | 39 | 20 | 15 | −1 | 10 | 19 | 14 | 18 | 5 | 3 | 10 | 102 | 96 | 3 |
| −6 | −2 | 9 | 135 | 107 | 14 | −24 | 2 | 9 | 56 | 66 | 20 | −11 | −5 | 10 | 55 | 57 | 13 | 17 | −1 | 10 | 0 | 17 | 1 | 7 | 3 | 10 | 0 | 24 | 1 |
| −4 | −2 | 9 | 252 | 244 | 6 | −22 | 2 | 9 | 86 | 82 | 12 | 7 | −5 | 10 | 102 | 101 | 9 | −28 | 0 | 10 | 128 | 124 | 6 | 9 | 3 | 10 | 92 | 90 | 4 |
| −2 | −2 | 9 | 75 | 75 | 15 | −20 | 2 | 9 | 46 | 33 | 17 | 9 | −5 | 10 | 59 | 60 | 12 | −26 | 0 | 10 | 128 | 123 | 7 | 11 | 3 | 10 | 119 | 130 | 10 |
| 0 | −2 | 9 | 183 | 180 | 4 | −18 | 2 | 9 | 23 | 21 | 15 | −24 | −4 | 10 | 52 | 9 | 14 | −24 | 0 | 10 | 29 | 34 | 29 | 13 | 3 | 10 | 40 | 68 | 39 |
| 2 | −2 | 9 | 112 | 110 | 4 | −16 | 2 | 9 | 95 | 88 | 3 | −22 | −4 | 10 | 61 | 55 | 13 | −22 | 0 | 10 | 115 | 102 | 10 | 15 | 3 | 10 | 53 | 61 | 20 |
| 4 | −2 | 9 | 123 | 111 | 5 | −14 | 2 | 9 | 128 | 127 | 3 | −20 | −4 | 10 | 117 | 128 | 8 | −20 | 0 | 10 | 251 | 255 | 8 | −24 | 4 | 10 | 0 | 9 | 1 |
| 6 | −2 | 9 | 65 | 80 | 9 | −12 | 2 | 9 | 166 | 164 | 3 | −18 | −4 | 10 | 39 | 56 | 23 | −18 | 0 | 10 | 93 | 80 | 3 | −22 | 4 | 10 | 0 | 55 | 1 |
| 8 | −2 | 9 | 188 | 175 | 6 | −10 | 2 | 9 | 63 | 56 | 4 | −16 | −4 | 10 | 109 | 118 | 8 | −16 | 0 | 10 | 73 | 74 | 4 | −20 | 4 | 10 | 103 | 128 | 10 |
| 10 | −2 | 9 | 44 | 42 | 17 | −8 | 2 | 9 | 246 | 271 | 3 | −14 | −4 | 10 | 6 | 5 | 5 | −14 | 0 | 10 | 653 | 620 | 8 | −18 | 4 | 10 | 63 | 56 | 16 |
| 12 | −2 | 9 | 143 | 151 | 9 | −6 | 2 | 9 | 130 | 107 | 4 | −12 | −4 | 10 | 154 | 144 | 13 | −12 | 0 | 10 | 173 | 181 | 5 | −16 | 4 | 10 | 112 | 118 | 10 |
| 14 | −2 | 9 | 58 | 49 | 18 | −4 | 2 | 9 | 251 | 243 | 4 | −10 | −4 | 10 | 204 | 188 | 6 | −10 | 0 | 10 | 354 | 302 | 6 | −14 | 4 | 10 | 20 | 5 | 19 |
| 16 | −2 | 9 | 40 | 38 | 19 | −2 | 2 | 9 | 81 | 76 | 4 | −8 | −4 | 10 | 351 | 334 | 8 | −8 | 0 | 10 | 264 | 271 | 5 | −12 | 4 | 10 | 160 | 144 | 5 |
| 18 | −2 | 9 | 12 | 28 | 12 | 0 | 2 | 9 | 182 | 180 | 3 | −6 | −4 | 10 | 268 | 280 | 9 | −6 | 0 | 10 | 444 | 458 | 8 | −10 | 4 | 10 | 199 | 187 | 5 |
| −29 | −1 | 9 | 41 | 38 | 40 | 2 | 2 | 9 | 114 | 111 | 2 | 2 | −4 | 10 | 86 | 95 | 11 | −4 | 0 | 10 | 324 | 302 | 6 | −8 | 4 | 10 | 357 | 334 | 4 |
| −27 | −1 | 9 | 45 | 31 | 15 | 4 | 2 | 9 | 116 | 111 | 3 | 4 | −4 | 10 | 106 | 102 | 9 | −2 | 0 | 10 | 179 | 183 | 4 | −6 | 4 | 10 | 281 | 281 | 3 |
| −25 | −1 | 9 | 100 | 111 | 8 | 6 | 2 | 9 | 84 | 80 | 5 | 6 | −4 | 10 | 98 | 68 | 10 | 0 | 0 | 10 | 218 | 211 | 3 | −4 | 4 | 10 | 108 | 119 | 5 |
| −23 | −1 | 9 | 38 | 36 | 14 | 8 | 2 | 9 | 188 | 175 | 3 | 8 | −4 | 10 | 70 | 87 | 14 | 2 | 0 | 10 | 117 | 117 | 3 | −2 | 4 | 10 | 114 | 111 | 3 |
| −21 | −1 | 9 | 60 | 57 | 6 | 10 | 2 | 9 | 23 | 42 | 23 | 10 | −4 | 10 | 61 | 58 | 15 | 4 | 0 | 10 | 255 | 243 | 3 | 0 | 4 | 10 | 28 | 37 | 13 |
| −19 | −1 | 9 | 114 | 115 | 5 | 12 | 2 | 9 | 154 | 151 | 7 | 12 | −4 | 10 | 0 | 22 | 1 | 6 | 0 | 10 | 150 | 160 | 3 | 2 | 4 | 10 | 94 | 94 | 4 |
| −17 | −1 | 9 | 162 | 150 | 3 | 14 | 2 | 9 | 65 | 50 | 6 | −27 | −3 | 10 | 55 | 81 | 9 | 8 | 0 | 10 | 291 | 283 | 4 | 4 | 4 | 10 | 102 | 102 | 3 |
| −15 | −1 | 9 | 133 | 133 | 3 | 16 | 2 | 9 | 19 | 38 | 18 | −25 | −3 | 10 | 110 | 111 | 7 | 10 | 0 | 10 | 72 | 90 | 5 | 6 | 4 | 10 | 85 | 68 | 14 |
| −13 | −1 | 9 | 86 | 75 | 4 | −27 | 3 | 9 | 0 | 5 | 1 | −23 | −3 | 10 | 151 | 135 | 8 | 12 | 0 | 10 | 0 | 4 | 1 | 8 | 4 | 10 | 55 | 87 | 12 |
| −11 | −1 | 9 | 70 | 66 | 5 | −25 | 3 | 9 | 37 | 51 | 36 | −21 | −3 | 10 | 0 | 43 | 1 | 14 | 0 | 10 | 57 | 42 | 8 | 10 | 4 | 10 | 23 | 59 | 23 |
| −9 | −1 | 9 | 590 | 580 | 20 | −23 | 3 | 9 | 81 | 84 | 13 | −19 | −3 | 10 | 77 | 85 | 10 | 16 | 0 | 10 | 21 | 32 | 21 | 12 | 4 | 10 | 0 | 23 | 1 |
| −7 | −1 | 9 | 685 | 680 | 15 | −21 | 3 | 9 | 78 | 110 | 12 | −17 | −3 | 10 | 120 | 116 | 9 | 18 | 0 | 10 | 0 | 16 | 1 | −21 | 5 | 10 | 16 | 12 | 16 |
| −5 | −1 | 9 | 625 | 619 | 25 | −19 | 3 | 9 | 79 | 64 | 12 | −15 | −3 | 10 | 129 | 113 | 11 | −25 | 1 | 10 | 84 | 89 | 14 | −19 | 5 | 10 | 0 | 28 | 1 |
| −3 | −1 | 9 | 286 | 280 | 7 | −17 | 3 | 9 | 87 | 83 | 20 | −13 | −3 | 10 | 189 | 178 | 6 | −23 | 1 | 10 | 148 | 135 | 9 | −17 | 5 | 10 | 35 | 29 | 34 |
| −1 | −1 | 9 | 172 | 190 | 5 | −15 | 3 | 9 | 103 | 107 | 8 | −11 | −3 | 10 | 315 | 330 | 7 | −21 | 1 | 10 | 78 | 83 | 6 | −15 | 5 | 10 | 48 | 30 | 14 |
| 1 | −1 | 9 | 380 | 410 | 9 | −13 | 3 | 9 | 72 | 62 | 10 | −9 | −3 | 10 | 195 | 192 | 5 | −19 | 1 | 10 | 250 | 258 | 4 | −13 | 5 | 10 | 49 | 39 | 13 |
| 3 | −1 | 9 | 364 | 363 | 5 | −11 | 3 | 9 | 122 | 133 | 2 | −7 | −3 | 10 | 220 | 223 | 5 | −17 | 1 | 10 | 144 | 137 | 3 | −11 | 5 | 10 | 73 | 58 | 8 |
| 5 | −1 | 9 | 175 | 177 | 5 | −9 | 3 | 9 | 313 | 303 | 3 | −5 | −3 | 10 | 113 | 119 | 5 | −15 | 1 | 10 | 162 | 160 | 4 | −9 | 5 | 10 | 76 | 81 | 10 |
| 7 | −1 | 9 | 334 | 331 | 7 | −7 | 3 | 9 | 195 | 188 | 3 | −3 | −3 | 10 | 56 | 50 | 6 | −13 | 1 | 10 | 217 | 209 | 3 | −7 | 5 | 10 | 93 | 111 | 15 |
| 9 | −1 | 9 | 101 | 106 | 5 | −5 | 3 | 9 | 159 | 156 | 3 | −1 | −3 | 10 | 133 | 146 | 5 | −11 | 1 | 10 | 264 | 274 | 4 | −5 | 5 | 10 | 81 | 92 | 5 |
| −3 | 5 | 10 | 207 | 207 | 3 | −1 | −1 | 11 | 191 | 208 | 4 | −9 | 3 | 11 | 32 | 36 | 9 | −24 | −2 | 12 | 0 | 19 | 1 | −28 | 2 | 12 | 0 | 23 | 1 |
| −1 | 5 | 10 | 80 | 78 | 5 | 1 | −11 | 1 | 104 | 100 | 4 | −7 | 3 | 11 | 70 | 67 | 4 | −22 | −2 | 12 | 126 | 119 | 17 | −26 | 2 | 12 | 12 | 2 | 11 |
| 1 | 5 | 10 | 47 | 68 | 12 | 3 | −1 | 11 | 135 | 138 | 4 | −5 | 3 | 11 | 34 | 35 | 9 | −20 | −2 | 12 | 118 | 135 | 5 | −24 | 2 | 12 | 50 | 19 | 24 |
| 3 | 5 | 10 | 59 | 75 | 12 | 5 | −1 | 11 | 122 | 118 | 4 | −3 | 3 | 11 | 163 | 159 | 4 | −18 | −2 | 12 | 231 | 223 | 8 | −22 | 2 | 12 | 118 | 119 | 10 |
| −14 | 6 | 10 | 19 | 13 | 19 | 7 | −1 | 11 | 74 | 74 | 8 | −1 | 3 | 11 | 62 | 61 | 5 | −16 | −2 | 12 | 166 | 161 | 6 | −20 | 2 | 12 | 130 | 135 | 10 |
| −12 | 6 | 10 | 38 | 40 | 11 | 9 | −1 | 11 | 73 | 82 | 9 | 1 | 3 | 11 | 92 | 96 | 4 | −14 | −2 | 12 | 29 | 30 | 29 | −18 | 2 | 12 | 225 | 223 | 4 |
| −10 | 6 | 10 | 37 | 35 | 9 | 11 | −1 | 11 | 97 | 104 | 7 | 3 | 3 | 11 | 71 | 71 | 5 | −12 | −2 | 12 | 19 | 28 | 19 | −16 | 2 | 12 | 164 | 161 | 4 |
| −8 | 6 | 10 | 28 | 34 | 10 | 13 | −1 | 11 | 25 | 16 | 24 | 5 | 3 | 11 | 51 | 50 | 8 | −10 | −2 | 12 | 55 | 68 | 13 | −14 | 2 | 12 | 10 | 30 | 9 |
| −19 | −5 | 11 | 0 | 41 | 1 | 15 | −1 | 11 | 28 | 49 | 27 | 7 | 3 | 11 | 92 | 92 | 4 | −8 | −2 | 12 | 0 | 10 | 1 | −12 | 2 | 12 | 27 | 28 | 25 |
| −17 | −5 | 11 | 32 | 28 | 32 | 17 | −1 | 11 | 23 | 4 | 23 | 9 | 3 | 11 | 70 | 64 | 7 | −6 | −2 | 12 | 71 | 67 | 5 | −10 | 2 | 12 | 62 | 67 | 7 |
| −15 | −5 | 11 | 45 | 52 | 17 | −28 | 0 | 11 | 135 | 125 | 10 | 11 | 3 | 11 | 91 | 103 | 12 | −4 | −2 | 12 | 199 | 197 | 4 | −8 | 2 | 12 | 17 | 9 | 16 |
| −13 | −5 | 11 | 0 | 22 | 1 | −26 | 0 | 11 | 30 | 26 | 30 | 13 | 3 | 11 | 53 | 60 | 18 | −2 | −2 | 12 | 119 | 109 | 4 | −6 | 2 | 12 | 67 | 68 | 4 |
| −11 | −5 | 11 | 41 | 36 | 20 | −24 | 0 | 11 | 32 | 6 | 25 | −24 | 4 | 11 | 41 | 57 | 31 | 0 | −2 | 12 | 59 | 58 | 7 | −4 | 2 | 12 | 196 | 197 | 3 |
| −24 | −4 | 11 | 63 | 57 | 11 | −22 | 0 | 11 | 192 | 174 | 7 | −22 | 4 | 11 | 25 | 64 | 25 | 2 | −2 | 12 | 109 | 121 | 5 | −2 | 2 | 12 | 117 | 110 | 3 |
| −22 | −4 | 11 | 53 | 64 | 15 | −20 | 0 | 11 | 211 | 206 | 5 | −20 | 4 | 11 | 89 | 73 | 12 | 4 | −2 | 12 | 83 | 76 | 7 | 0 | 2 | 12 | 64 | 59 | 4 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −20 | −4 | 11 | 71 | 73 | 11 | −18 | 0 | 11 | 0 | 5 | 1 | −18 | 4 | 11 | 38 | 36 | 37 | 6 | −2 | 12 | 162 | 159 | 8 | 2 | 2 | 12 | 122 | 122 | 5 |
| −18 | −4 | 11 | 59 | 37 | 13 | −16 | 0 | 11 | 355 | 335 | 4 | −16 | 4 | 11 | 12 | 12 | 12 | 8 | −2 | 12 | 50 | 60 | 17 | 4 | 2 | 12 | 78 | 75 | 5 |
| −16 | −4 | 11 | 0 | 12 | 1 | −14 | 0 | 11 | 128 | 119 | 3 | −14 | 4 | 11 | 158 | 130 | 6 | 10 | −2 | 12 | 73 | 78 | 12 | 6 | 2 | 12 | 147 | 160 | 6 |
| −14 | −4 | 11 | 130 | 131 | 8 | −12 | 0 | 11 | 328 | 331 | 4 | −12 | 4 | 11 | 379 | 361 | 8 | 12 | −2 | 12 | 0 | 37 | 1 | 8 | 2 | 12 | 54 | 60 | 9 |
| −12 | −4 | 11 | 370 | 362 | 11 | −10 | 0 | 11 | 408 | 371 | 5 | −10 | 4 | 11 | 247 | 228 | 4 | 14 | −2 | 12 | 22 | 39 | 21 | 10 | 2 | 12 | 71 | 78 | 6 |
| −10 | −4 | 11 | 241 | 227 | 8 | −8 | 0 | 11 | 246 | 232 | 4 | −8 | 4 | 11 | 39 | 33 | 7 | −29 | −1 | 12 | 31 | 37 | 25 | 12 | 2 | 12 | 46 | 38 | 8 |
| −8 | −4 | 11 | 45 | 34 | 29 | −6 | 0 | 11 | 214 | 203 | 3 | −6 | 4 | 11 | 31 | 17 | 11 | −27 | −1 | 12 | 84 | 63 | 9 | 14 | 2 | 12 | 26 | 39 | 26 |
| −6 | −4 | 11 | 0 | 17 | 1 | −4 | 0 | 11 | 103 | 98 | 3 | −4 | 4 | 11 | 151 | 150 | 4 | −25 | −1 | 12 | 41 | 42 | 12 | −25 | 3 | 12 | 22 | 14 | 22 |
| 2 | −4 | 11 | 197 | 185 | 8 | −2 | 0 | 11 | 139 | 153 | 4 | −2 | 4 | 11 | 155 | 159 | 4 | −23 | −1 | 12 | 91 | 75 | 6 | −23 | 3 | 12 | 53 | 60 | 20 |
| 4 | −4 | 11 | 127 | 121 | 9 | 0 | 0 | 11 | 120 | 99 | 5 | 0 | 4 | 11 | 127 | 116 | 6 | −21 | −1 | 12 | 224 | 212 | 5 | −21 | 3 | 12 | 112 | 149 | 9 |
| 6 | −4 | 11 | 26 | 27 | 25 | 2 | 0 | 11 | 261 | 259 | 4 | 2 | 4 | 11 | 189 | 186 | 3 | −19 | −1 | 12 | 145 | 145 | 6 | −19 | 3 | 12 | 91 | 130 | 11 |
| 8 | −4 | 11 | 72 | 68 | 13 | 4 | 0 | 11 | 207 | 203 | 3 | 4 | 4 | 11 | 110 | 120 | 3 | −17 | −1 | 12 | 102 | 106 | 9 | −17 | 3 | 12 | 153 | 174 | 9 |
| 10 | −4 | 11 | 44 | 54 | 24 | 6 | 0 | 11 | 61 | 64 | 6 | 6 | 4 | 11 | 36 | 26 | 33 | −15 | −1 | 12 | 272 | 254 | 5 | −15 | 3 | 12 | 106 | 82 | 10 |
| 12 | −4 | 11 | 0 | 65 | 1 | 8 | 0 | 11 | 89 | 95 | 4 | 8 | 4 | 11 | 61 | 68 | 10 | −13 | −1 | 12 | 141 | 137 | 3 | −13 | 3 | 12 | 83 | 82 | 4 |
| −27 | −3 | 11 | 73 | 75 | 6 | 10 | 0 | 11 | 71 | 83 | 7 | 10 | 4 | 11 | 21 | 54 | 20 | −11 | −1 | 12 | 111 | 98 | 5 | −11 | 3 | 12 | 100 | 96 | 4 |
| −25 | −3 | 11 | 46 | 34 | 11 | 12 | 0 | 11 | 0 | 28 | 1 | −19 | 5 | 11 | 56 | 41 | 10 | −9 | −1 | 12 | 146 | 143 | 4 | −9 | 3 | 12 | 175 | 183 | 3 |
| −23 | −3 | 11 | 48 | 28 | 17 | 14 | 0 | 11 | 15 | 10 | 15 | −17 | 5 | 11 | 42 | 27 | 13 | −7 | −1 | 12 | 246 | 238 | 4 | −7 | 3 | 12 | 41 | 51 | 8 |
| −21 | −3 | 11 | 53 | 42 | 13 | 16 | 0 | 11 | 42 | 29 | 26 | −15 | 5 | 11 | 23 | 52 | 23 | −5 | −1 | 12 | 114 | 96 | 8 | −5 | 3 | 12 | 67 | 58 | 5 |
| −19 | −3 | 11 | 121 | 123 | 8 | −25 | 1 | 11 | 0 | 35 | 1 | −13 | 5 | 11 | 0 | 23 | 1 | −3 | −1 | 12 | 204 | 217 | 4 | −3 | 3 | 12 | 65 | 58 | 4 |
| −17 | −3 | 11 | 235 | 248 | 8 | −23 | 1 | 11 | 62 | 69 | 7 | −11 | 5 | 11 | 52 | 36 | 10 | −1 | −1 | 12 | 306 | 303 | 5 | −1 | 3 | 12 | 101 | 101 | 4 |
| −15 | −3 | 11 | 246 | 234 | 6 | −21 | 1 | 11 | 86 | 74 | 5 | −9 | 5 | 11 | 140 | 118 | 7 | 1 | −1 | 12 | 78 | 68 | 8 | 1 | 3 | 12 | 94 | 86 | 5 |
| −13 | −3 | 11 | 127 | 134 | 7 | −19 | 1 | 11 | 376 | 361 | 6 | −7 | 5 | 11 | 105 | 120 | 8 | 3 | −1 | 12 | 108 | 99 | 6 | 3 | 3 | 12 | 211 | 209 | 6 |
| −11 | −3 | 11 | 170 | 161 | 5 | −17 | 1 | 11 | 142 | 126 | 5 | −5 | 5 | 11 | 67 | 71 | 8 | 5 | −1 | 12 | 195 | 204 | 4 | 5 | 3 | 12 | 42 | 52 | 10 |
| −9 | −3 | 11 | 49 | 35 | 10 | −15 | 1 | 11 | 192 | 183 | 3 | −3 | 5 | 11 | 65 | 55 | 4 | 7 | −1 | 12 | 143 | 140 | 5 | 7 | 3 | 12 | 121 | 116 | 4 |
| −7 | −3 | 11 | 70 | 67 | 8 | −13 | 1 | 11 | 233 | 221 | 3 | −1 | 5 | 11 | 60 | 57 | 4 | 9 | −1 | 12 | 67 | 58 | 9 | 9 | 3 | 12 | 138 | 131 | 9 |
| −5 | −3 | 11 | 0 | 35 | 1 | −11 | 1 | 11 | 367 | 356 | 4 | 1 | 5 | 11 | 111 | 120 | 7 | 11 | −1 | 12 | 32 | 27 | 32 | 11 | 3 | 12 | 32 | 62 | 32 |
| −3 | −3 | 11 | 153 | 159 | 4 | −9 | 1 | 11 | 223 | 236 | 4 | 3 | 5 | 11 | 25 | 52 | 24 | 13 | −1 | 12 | 28 | 47 | 27 | 13 | 3 | 12 | 25 | 42 | 25 |
| −1 | −3 | 11 | 57 | 61 | 9 | −7 | 1 | 11 | 87 | 91 | 5 | −14 | 6 | 11 | 43 | 46 | 9 | 15 | −1 | 12 | 10 | 10 | 10 | −24 | 4 | 12 | 50 | 45 | 18 |
| 1 | −3 | 11 | 94 | 96 | 7 | −5 | 1 | 11 | 539 | 532 | 6 | −12 | 6 | 11 | 45 | 48 | 8 | −28 | 0 | 12 | 0 | 23 | 1 | −22 | 4 | 12 | 0 | 29 | 1 |
| 3 | −3 | 11 | 73 | 70 | 9 | −3 | 1 | 11 | 165 | 172 | 3 | −10 | 6 | 11 | 39 | 33 | 7 | −26 | 0 | 12 | 11 | 36 | 10 | −20 | 4 | 12 | 82 | 63 | 12 |
| 5 | −3 | 11 | 70 | 49 | 13 | −1 | 1 | 11 | 188 | 208 | 3 | −8 | 6 | 11 | 31 | 22 | 7 | −24 | 0 | 12 | 24 | 33 | 23 | −18 | 4 | 12 | 114 | 112 | 10 |
| 7 | −3 | 11 | 100 | 91 | 11 | 1 | 1 | 11 | 95 | 100 | 4 | −19 | −5 | 12 | 0 | 27 | 1 | −22 | 0 | 12 | 0 | 4 | 1 | −16 | 4 | 12 | 159 | 135 | 8 |
| 9 | −3 | 11 | 60 | 64 | 16 | 3 | 1 | 11 | 147 | 138 | 3 | −17 | −5 | 12 | 42 | 48 | 19 | −20 | 0 | 12 | 199 | 187 | 4 | −14 | 4 | 12 | 168 | 153 | 6 |
| 11 | −3 | 11 | 118 | 103 | 9 | 5 | 1 | 11 | 127 | 118 | 5 | −15 | −5 | 12 | 0 | 20 | 1 | −18 | 0 | 12 | 391 | 374 | 5 | −12 | 4 | 12 | 69 | 72 | 9 |
| 13 | −3 | 11 | 53 | 60 | 17 | 7 | 1 | 11 | 73 | 75 | 5 | −13 | −5 | 12 | 67 | 78 | 11 | −16 | 0 | 12 | 181 | 180 | 3 | −10 | 4 | 12 | 125 | 139 | 9 |
| −28 | −2 | 11 | 0 | 23 | 1 | 9 | 1 | 11 | 59 | 82 | 9 | −24 | −4 | 12 | 53 | 45 | 13 | −14 | 0 | 12 | 140 | 130 | 3 | −8 | 4 | 12 | 0 | 23 | 1 |
| −26 | −2 | 11 | 46 | 50 | 12 | 11 | 1 | 11 | 103 | 104 | 18 | −22 | −4 | 12 | 7 | 29 | 7 | −12 | 0 | 12 | 0 | 13 | 1 | −6 | 4 | 12 | 92 | 91 | 4 |
| −24 | −2 | 11 | 64 | 66 | 8 | 13 | 1 | 11 | 0 | 16 | 1 | −20 | −4 | 12 | 70 | 62 | 11 | −10 | 0 | 12 | 534 | 518 | 6 | −4 | 4 | 12 | 115 | 128 | 5 |
| −22 | −2 | 11 | 73 | 81 | 18 | 15 | 1 | 11 | 39 | 49 | 27 | −18 | −4 | 12 | 133 | 112 | 8 | −8 | 0 | 12 | 290 | 275 | 4 | −2 | 4 | 12 | 111 | 122 | 6 |
| −20 | −2 | 11 | 202 | 218 | 11 | 17 | 1 | 11 | 0 | 4 | 1 | −16 | −4 | 12 | 154 | 135 | 8 | −6 | 0 | 12 | 80 | 77 | 4 | 0 | 4 | 12 | 107 | 112 | 7 |
| −18 | −2 | 11 | 0 | 32 | 1 | −28 | 2 | 11 | 40 | 22 | 39 | −14 | −4 | 12 | 152 | 153 | 8 | −4 | 0 | 12 | 366 | 356 | 5 | 2 | 4 | 12 | 66 | 65 | 6 |
| −16 | −2 | 11 | 136 | 132 | 10 | −26 | 2 | 11 | 30 | 50 | 29 | −12 | −4 | 12 | 54 | 71 | 15 | −2 | 0 | 12 | 26 | 28 | 22 | 4 | 4 | 12 | 126 | 131 | 6 |
| −14 | −2 | 11 | 60 | 61 | 9 | −24 | 2 | 11 | 84 | 66 | 13 | −10 | −4 | 12 | 119 | 139 | 8 | 0 | 0 | 12 | 289 | 286 | 5 | 6 | 4 | 12 | 38 | 17 | 19 |
| −12 | −2 | 11 | 146 | 142 | 6 | −22 | 2 | 11 | 83 | 81 | 13 | −8 | −4 | 12 | 0 | 23 | 1 | 2 | 0 | 12 | 433 | 429 | 7 | 8 | 4 | 12 | 64 | 93 | 9 |
| −10 | −2 | 11 | 324 | 320 | 7 | −20 | 2 | 11 | 213 | 218 | 9 | −6 | −4 | 12 | 109 | 91 | 8 | 4 | 0 | 12 | 41 | 44 | 10 | 10 | 4 | 12 | 36 | 43 | 35 |
| −8 | −2 | 11 | 56 | 66 | 7 | −18 | 2 | 11 | 9 | 32 | 8 | 2 | −4 | 12 | 52 | 65 | 19 | 6 | 0 | 12 | 0 | 9 | 1 | −19 | 5 | 12 | 47 | 27 | 10 |
| −6 | −2 | 11 | 127 | 125 | 3 | −16 | 2 | 11 | 138 | 131 | 4 | 4 | −4 | 12 | 131 | 131 | 8 | 8 | 0 | 12 | 77 | 67 | 7 | −17 | 5 | 12 | 24 | 48 | 23 |
| −4 | −2 | 11 | 87 | 84 | 4 | −14 | 2 | 11 | 62 | 61 | 6 | 6 | −4 | 12 | 0 | 17 | 1 | 10 | 0 | 12 | 140 | 128 | 6 | −15 | 5 | 12 | 26 | 20 | 26 |
| −2 | −2 | 11 | 0 | 13 | 1 | −12 | 2 | 11 | 146 | 142 | 4 | 8 | −4 | 12 | 92 | 93 | 10 | 12 | 0 | 12 | 15 | 21 | 14 | −13 | 5 | 12 | 88 | 78 | 6 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 0 | −2 | 11 | 101 | 99 | 4 | −10 | 2 | 11 | 309 | 321 | 4 | 10 | −4 | 12 | 51 | 43 | 16 | 14 | 0 | 12 | 25 | 11 | 25 | −11 | 5 | 12 | 36 | 30 | 27 |
| 2 | −2 | 11 | 154 | 162 | 7 | −8 | 2 | 11 | 51 | 65 | 10 | −25 | −3 | 12 | 0 | 14 | 1 | 16 | 0 | 12 | 37 | 60 | 18 | −9 | 5 | 12 | 70 | 82 | 9 |
| 4 | −2 | 11 | 160 | 154 | 5 | −6 | 2 | 11 | 129 | 125 | 2 | −23 | −3 | 12 | 60 | 60 | 13 | −25 | 1 | 12 | 38 | 42 | 38 | −7 | 5 | 12 | 40 | 27 | 12 |
| 6 | −2 | 11 | 160 | 151 | 8 | −4 | 2 | 11 | 86 | 84 | 3 | −21 | −3 | 12 | 116 | 149 | 7 | −23 | 1 | 12 | 80 | 75 | 6 | −5 | 5 | 12 | 90 | 74 | 13 |
| 8 | −2 | 11 | 119 | 108 | 9 | −2 | 2 | 11 | 12 | 14 | 11 | −19 | −3 | 12 | 93 | 130 | 8 | −21 | 1 | 12 | 219 | 212 | 8 | −3 | 5 | 12 | 28 | 24 | 12 |
| 10 | −2 | 11 | 26 | 45 | 25 | 0 | 2 | 11 | 97 | 100 | 3 | −17 | −3 | 12 | 157 | 174 | 7 | −19 | 1 | 12 | 163 | 145 | 5 | −1 | 5 | 12 | 108 | 110 | 9 |
| 12 | −2 | 11 | 29 | 38 | 29 | 2 | 2 | 11 | 159 | 162 | 5 | −15 | −3 | 12 | 81 | 82 | 10 | −17 | 1 | 12 | 111 | 106 | 4 | −10 | 6 | 12 | 58 | 61 | 4 |
| 14 | −2 | 11 | 68 | 57 | 13 | 4 | 2 | 11 | 162 | 154 | 3 | −13 | −3 | 12 | 68 | 82 | 33 | −15 | 1 | 12 | 270 | 254 | 5 | −17 | −5 | 13 | 28 | 26 | 27 |
| 16 | −2 | 11 | 35 | 24 | 18 | 6 | 2 | 11 | 155 | 151 | 6 | −11 | −3 | 12 | 93 | 97 | 18 | −13 | 1 | 12 | 137 | 137 | 3 | −15 | −5 | 13 | 84 | 113 | 8 |
| −29 | −1 | 11 | 34 | 31 | 20 | 8 | 2 | 11 | 101 | 107 | 6 | −9 | −3 | 12 | 182 | 183 | 5 | −11 | 1 | 12 | 114 | 98 | 4 | −13 | −5 | 13 | 43 | 50 | 16 |
| −27 | −1 | 11 | 44 | 46 | 19 | 10 | 2 | 11 | 40 | 45 | 13 | −7 | −3 | 12 | 42 | 51 | 14 | −9 | 1 | 12 | 147 | 144 | 3 | −22 | −4 | 13 | 32 | 21 | 32 |
| −25 | −1 | 11 | 33 | 35 | 18 | 12 | 2 | 11 | 44 | 38 | 9 | −5 | −3 | 12 | 78 | 58 | 10 | −7 | 1 | 12 | 235 | 237 | 3 | −20 | −4 | 13 | 43 | 46 | 19 |
| −23 | −1 | 11 | 55 | 69 | 9 | 14 | 2 | 11 | 57 | 57 | 18 | −3 | −3 | 12 | 52 | 57 | 13 | −5 | 1 | 12 | 108 | 95 | 4 | −18 | −4 | 13 | 4 | 34 | 3 |
| −21 | −1 | 11 | 95 | 73 | 5 | 16 | 2 | 11 | 0 | 24 | 1 | −1 | −3 | 12 | 96 | 101 | 6 | −3 | 1 | 12 | 209 | 216 | 3 | −16 | −4 | 13 | 71 | 62 | 11 |
| −19 | −1 | 11 | 382 | 362 | 8 | −27 | 3 | 11 | 88 | 75 | 10 | 1 | −3 | 12 | 115 | 86 | 10 | −1 | 1 | 12 | 311 | 303 | 4 | −14 | −4 | 13 | 69 | 79 | 11 |
| −17 | −1 | 11 | 133 | 126 | 5 | −25 | 3 | 11 | 66 | 34 | 16 | 3 | −3 | 12 | 230 | 209 | 8 | 1 | 1 | 12 | 81 | 68 | 4 | −12 | −4 | 13 | 63 | 66 | 13 |
| −15 | −1 | 11 | 195 | 183 | 4 | −23 | 3 | 11 | 0 | 28 | 1 | 5 | −3 | 12 | 46 | 51 | 28 | 3 | 1 | 12 | 102 | 100 | 5 | −10 | −4 | 13 | 154 | 151 | 8 |
| −13 | −1 | 11 | 223 | 221 | 4 | −21 | 3 | 11 | 29 | 42 | 28 | 7 | −3 | 12 | 142 | 116 | 8 | 5 | 1 | 12 | 203 | 204 | 4 | −8 | −4 | 13 | 54 | 33 | 14 |
| −11 | −1 | 11 | 364 | 358 | 5 | −19 | 3 | 11 | 123 | 123 | 9 | 9 | −3 | 12 | 149 | 131 | 8 | 7 | 1 | 12 | 150 | 141 | 5 | −6 | −4 | 13 | 70 | 69 | 11 |
| −9 | −1 | 11 | 227 | 235 | 3 | −17 | 3 | 11 | 244 | 248 | 9 | 11 | −3 | 12 | 66 | 62 | 13 | 9 | 1 | 12 | 56 | 58 | 12 | 2 | −4 | 13 | 140 | 135 | 8 |
| −7 | −1 | 11 | 86 | 90 | 4 | −15 | 3 | 11 | 245 | 235 | 7 | 13 | −3 | 12 | 11 | 42 | 11 | 11 | 1 | 12 | 30 | 27 | 30 | 4 | −4 | 13 | 72 | 61 | 12 |
| −5 | −1 | 11 | 538 | 532 | 8 | −13 | 3 | 11 | 139 | 133 | 4 | −28 | −2 | 12 | 3 | 23 | 3 | 13 | 1 | 12 | 27 | 47 | 27 | 6 | −4 | 13 | 30 | 10 | 29 |
| −3 | −1 | 11 | 169 | 171 | 3 | −11 | 3 | 11 | 164 | 161 | 3 | −26 | −2 | 12 | 24 | 2 | 24 | 15 | 1 | 12 | 0 | 10 | 1 | 8 | −4 | 13 | 0 | 17 | 1 |
| −25 | −3 | 13 | 0 | 29 | 1 | −19 | 1 | 13 | 302 | 281 | 5 | −18 | −4 | 14 | 72 | 68 | 10 | −25 | 1 | 14 | 51 | 55 | 24 | 2 | −4 | 15 | 71 | 76 | 11 |
| −23 | −3 | 13 | 46 | 52 | 17 | −17 | 1 | 13 | 231 | 218 | 4 | −16 | −4 | 14 | 110 | 89 | 8 | −23 | 1 | 14 | 91 | 88 | 7 | 4 | −4 | 15 | 60 | 22 | 13 |
| −21 | −3 | 13 | 26 | 27 | 26 | −15 | 1 | 13 | 175 | 166 | 4 | −14 | −4 | 14 | 40 | 52 | 23 | −21 | 1 | 14 | 99 | 111 | 7 | −23 | −3 | 15 | 76 | 77 | 9 |
| −19 | −3 | 13 | 0 | 26 | 1 | −13 | 1 | 13 | 61 | 54 | 5 | −12 | −4 | 14 | 128 | 120 | 8 | −19 | 1 | 14 | 101 | 98 | 6 | −21 | −3 | 15 | 0 | 24 | 1 |
| −17 | −3 | 13 | 90 | 125 | 8 | −11 | 1 | 13 | 144 | 149 | 6 | −10 | −4 | 14 | 40 | 38 | 25 | −17 | 1 | 14 | 101 | 98 | 5 | −19 | −3 | 15 | 104 | 81 | 8 |
| −15 | −3 | 13 | 67 | 65 | 11 | −9 | 1 | 13 | 116 | 115 | 3 | −8 | −4 | 14 | 101 | 96 | 9 | −15 | 1 | 14 | 345 | 321 | 6 | −17 | −3 | 15 | 64 | 57 | 11 |
| −13 | −3 | 13 | 145 | 129 | 8 | −7 | 1 | 13 | 73 | 63 | 5 | −6 | −4 | 14 | 21 | 48 | 21 | −13 | 1 | 14 | 311 | 293 | 4 | −15 | −3 | 15 | 47 | 33 | 16 |
| −11 | −3 | 13 | 75 | 80 | 8 | −5 | 1 | 13 | 253 | 244 | 3 | 2 | −4 | 14 | 64 | 63 | 13 | −11 | 1 | 14 | 96 | 89 | 5 | −13 | −3 | 15 | 158 | 138 | 7 |
| −9 | −3 | 13 | 0 | 19 | 1 | −3 | 1 | 13 | 186 | 186 | 4 | 4 | −4 | 14 | 38 | 31 | 32 | −9 | 1 | 14 | 74 | 61 | 5 | −11 | −3 | 15 | 78 | 69 | 11 |
| −7 | −3 | 13 | 66 | 80 | 9 | −1 | 1 | 13 | 28 | 31 | 16 | 6 | −4 | 14 | 21 | 25 | 20 | −7 | 1 | 14 | 89 | 92 | 4 | −9 | −3 | 15 | 65 | 53 | 14 |
| −5 | −3 | 13 | 51 | 43 | 10 | 1 | 1 | 13 | 230 | 220 | 3 | −25 | −3 | 14 | 29 | 24 | 29 | −5 | 1 | 14 | 165 | 143 | 3 | −7 | −3 | 15 | 64 | 83 | 14 |
| −3 | −3 | 13 | 153 | 159 | 5 | 3 | 1 | 13 | 83 | 69 | 5 | −23 | −3 | 14 | 59 | 50 | 12 | −3 | 1 | 14 | 160 | 164 | 8 | −5 | −3 | 15 | 94 | 100 | 7 |
| −1 | −3 | 13 | 101 | 109 | 6 | 5 | 1 | 13 | 220 | 212 | 7 | −21 | −3 | 14 | 38 | 45 | 24 | −1 | 1 | 14 | 306 | 301 | 4 | −3 | −3 | 15 | 156 | 155 | 8 |
| 1 | −3 | 13 | 54 | 31 | 17 | 7 | 1 | 13 | 152 | 152 | 5 | −19 | −3 | 14 | 57 | 65 | 12 | 1 | 1 | 14 | 367 | 351 | 5 | −1 | −3 | 15 | 58 | 65 | 16 |
| 3 | −3 | 13 | 83 | 57 | 11 | 9 | 1 | 13 | 31 | 24 | 21 | −17 | −3 | 14 | 72 | 91 | 9 | 3 | 1 | 14 | 137 | 130 | 5 | 1 | −3 | 15 | 139 | 141 | 8 |
| 5 | −3 | 13 | 129 | 134 | 9 | 11 | 1 | 13 | 51 | 63 | 13 | −15 | −3 | 14 | 74 | 87 | 10 | 5 | 1 | 14 | 72 | 77 | 7 | 3 | −3 | 15 | 76 | 60 | 13 |
| 7 | −3 | 13 | 108 | 114 | 10 | 13 | 1 | 13 | 59 | 55 | 9 | −13 | −3 | 14 | 149 | 132 | 8 | 7 | 1 | 14 | 140 | 124 | 5 | 5 | −3 | 15 | 19 | 15 | 18 |
| 9 | −3 | 13 | 45 | 67 | 22 | −28 | 2 | 13 | 0 | 27 | 1 | −11 | −3 | 14 | 29 | 27 | 29 | 9 | 1 | 14 | 14 | 31 | 14 | 7 | −3 | 15 | 46 | 34 | 19 |
| 11 | −3 | 13 | 44 | 42 | 20 | −26 | 2 | 13 | 92 | 72 | 11 | −9 | −3 | 14 | 0 | 27 | 1 | 11 | 1 | 14 | 93 | 94 | 5 | −26 | −2 | 15 | 50 | 55 | 9 |
| −28 | −2 | 13 | 28 | 27 | 28 | −24 | 2 | 13 | 57 | 82 | 18 | −7 | −3 | 14 | 122 | 116 | 8 | −26 | 2 | 14 | 0 | 24 | 1 | −24 | −2 | 15 | 57 | 82 | 9 |
| −26 | −2 | 13 | 84 | 72 | 6 | −22 | 2 | 13 | 50 | 68 | 22 | −5 | −3 | 14 | 131 | 128 | 5 | −24 | 2 | 14 | 28 | 36 | 28 | −22 | −2 | 15 | 75 | 84 | 8 |
| −24 | −2 | 13 | 55 | 82 | 9 | −20 | 2 | 13 | 169 | 184 | 5 | −3 | −3 | 14 | 50 | 38 | 12 | −22 | 2 | 14 | 90 | 80 | 11 | −20 | −2 | 15 | 190 | 185 | 8 |
| −22 | −2 | 13 | 49 | 68 | 11 | −18 | 2 | 13 | 62 | 55 | 7 | −1 | −3 | 14 | 188 | 163 | 8 | −20 | 2 | 14 | 160 | 160 | 4 | −18 | −2 | 15 | 118 | 134 | 8 |
| −20 | −2 | 13 | 179 | 184 | 7 | −15 | 2 | 13 | 38 | 45 | 12 | 1 | −3 | 14 | 220 | 205 | 8 | −18 | 2 | 14 | 101 | 94 | 5 | −16 | −2 | 15 | 80 | 87 | 9 |
| −18 | −2 | 13 | 64 | 54 | 12 | −14 | 2 | 13 | 185 | 189 | 4 | 3 | −3 | 14 | 195 | 186 | 7 | −16 | 2 | 14 | 192 | 186 | 5 | −14 | −2 | 15 | 80 | 61 | 10 |
| −16 | −2 | 13 | 51 | 45 | 12 | −12 | 2 | 13 | 137 | 126 | 4 | 5 | −3 | 14 | 78 | 81 | 12 | −14 | 2 | 14 | 112 | 109 | 4 | −12 | −2 | 15 | 13 | 51 | 12 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −14 | −2 | 13 | 194 | 189 | 18 | −10 | 2 | 13 | 50 | 50 | 9 | 7 | −3 | 14 | 36 | 38 | 35 | −12 | 2 | 14 | 101 | 89 | 5 | −10 | −2 | 15 | 282 | 245 | 6 |
| −12 | −2 | 13 | 144 | 126 | 6 | −8 | 2 | 13 | 103 | 103 | 5 | 9 | −3 | 14 | 53 | 39 | 16 | −10 | 2 | 14 | 29 | 39 | 28 | −8 | −2 | 15 | 128 | 121 | 11 |
| −10 | −2 | 13 | 51 | 50 | 11 | −6 | 2 | 13 | 120 | 119 | 4 | −26 | −2 | 14 | 0 | 24 | 1 | −8 | 2 | 14 | 154 | 147 | 3 | −6 | −2 | 15 | 163 | 153 | 5 |
| −8 | −2 | 13 | 109 | 102 | 5 | −4 | 2 | 13 | 141 | 135 | 3 | −24 | −2 | 14 | 43 | 36 | 12 | −6 | 2 | 14 | 134 | 135 | 5 | −4 | −2 | 15 | 113 | 99 | 7 |
| −6 | −2 | 13 | 114 | 118 | 6 | −2 | 2 | 13 | 137 | 146 | 4 | −22 | −2 | 14 | 96 | 80 | 12 | −4 | 2 | 14 | 68 | 77 | 4 | −2 | −2 | 15 | 80 | 75 | 8 |
| −4 | −2 | 13 | 136 | 134 | 4 | 0 | 2 | 13 | 223 | 219 | 4 | −20 | −2 | 14 | 173 | 160 | 7 | −2 | 2 | 14 | 235 | 228 | 3 | 0 | −2 | 15 | 237 | 237 | 6 |
| −2 | −2 | 13 | 130 | 146 | 7 | 2 | 2 | 13 | 117 | 108 | 5 | −18 | −2 | 14 | 107 | 94 | 8 | 0 | 2 | 14 | 110 | 113 | 6 | 2 | −2 | 15 | 21 | 34 | 21 |
| 0 | −2 | 13 | 215 | 219 | 4 | 4 | 2 | 13 | 86 | 93 | 6 | −14 | −2 | 14 | 118 | 109 | 18 | 2 | 2 | 14 | 85 | 87 | 6 | 4 | −2 | 15 | 0 | 43 | 1 |
| 2 | −2 | 13 | 120 | 108 | 5 | 6 | 2 | 13 | 64 | 80 | 9 | −12 | −2 | 14 | 104 | 90 | 7 | 4 | 2 | 14 | 100 | 95 | 5 | 6 | −2 | 15 | 55 | 35 | 15 |
| 4 | −2 | 13 | 88 | 93 | 7 | 8 | 2 | 13 | 116 | 124 | 9 | −10 | −2 | 14 | 44 | 39 | 16 | 6 | 2 | 14 | 90 | 84 | 20 | 8 | −2 | 15 | 33 | 30 | 32 |
| 6 | −2 | 13 | 70 | 80 | 12 | 10 | 2 | 13 | 69 | 73 | 6 | −8 | −2 | 14 | 150 | 147 | 4 | 8 | 2 | 14 | 64 | 66 | 8 | −27 | −1 | 15 | 41 | 40 | 22 |
| 8 | −2 | 13 | 99 | 125 | 10 | 12 | 2 | 13 | 28 | 24 | 13 | −6 | −2 | 14 | 131 | 136 | 5 | 10 | 2 | 14 | 69 | 77 | 5 | −25 | −1 | 15 | 38 | 40 | 14 |
| 10 | −2 | 13 | 50 | 73 | 20 | −25 | 3 | 13 | 35 | 29 | 34 | −4 | −2 | 14 | 78 | 77 | 6 | −25 | 3 | 14 | 44 | 24 | 20 | −23 | −1 | 15 | 27 | 26 | 27 |
| 12 | −2 | 13 | 19 | 24 | 18 | −23 | 3 | 13 | 42 | 52 | 29 | −2 | −2 | 14 | 236 | 228 | 4 | −23 | 3 | 14 | 48 | 50 | 19 | −21 | −1 | 15 | 47 | 40 | 11 |
| −29 | −1 | 13 | 70 | 55 | 9 | −21 | 3 | 13 | 0 | 27 | 1 | 0 | −2 | 14 | 125 | 113 | 6 | −21 | 3 | 14 | 46 | 45 | 20 | −19 | −1 | 15 | 81 | 95 | 7 |
| −27 | −1 | 13 | 8 | 35 | 8 | −19 | 3 | 13 | 29 | 25 | 28 | 2 | −2 | 14 | 97 | 87 | 7 | −19 | 3 | 14 | 67 | 66 | 12 | −17 | −1 | 15 | 272 | 248 | 6 |
| −25 | −1 | 13 | 24 | 36 | 23 | −17 | 3 | 13 | 103 | 125 | 9 | 4 | −2 | 14 | 83 | 95 | 7 | −17 | 3 | 14 | 85 | 91 | 10 | −15 | −1 | 15 | 55 | 47 | 9 |
| −23 | −1 | 13 | 65 | 64 | 7 | −15 | 3 | 13 | 66 | 65 | 15 | 6 | −2 | 14 | 56 | 84 | 14 | −15 | 3 | 14 | 81 | 87 | 7 | −13 | −1 | 15 | 150 | 151 | 9 |
| −21 | −1 | 13 | 72 | 70 | 7 | −13 | 3 | 13 | 136 | 130 | 6 | 8 | −2 | 14 | 59 | 66 | 15 | −13 | 3 | 14 | 148 | 132 | 10 | −11 | −1 | 15 | 6 | 40 | 6 |
| −19 | −1 | 13 | 312 | 281 | 6 | −11 | 3 | 13 | 87 | 80 | 4 | 10 | −2 | 14 | 92 | 77 | 9 | −11 | 3 | 14 | 33 | 27 | 15 | −9 | −1 | 15 | 30 | 21 | 19 |
| −17 | −1 | 13 | 234 | 218 | 4 | −9 | 3 | 13 | 24 | 20 | 23 | −27 | −1 | 14 | 26 | 25 | 26 | −9 | 3 | 14 | 0 | 28 | 1 | −7 | −1 | 15 | 98 | 105 | 11 |
| −15 | −1 | 13 | 173 | 166 | 4 | −7 | 3 | 13 | 70 | 81 | 5 | −25 | −1 | 14 | 63 | 55 | 8 | −7 | 3 | 14 | 117 | 116 | 4 | −5 | −1 | 15 | 267 | 248 | 5 |
| −13 | −1 | 13 | 67 | 54 | 6 | −5 | 3 | 13 | 47 | 43 | 7 | −23 | −1 | 14 | 96 | 88 | 6 | −5 | 3 | 14 | 118 | 128 | 4 | −3 | −1 | 15 | 193 | 194 | 6 |
| −11 | −1 | 13 | 144 | 149 | 4 | −3 | 3 | 13 | 157 | 158 | 3 | −21 | −1 | 14 | 77 | 111 | 10 | −3 | 3 | 14 | 30 | 38 | 16 | −1 | −1 | 15 | 307 | 295 | 7 |
| −9 | −1 | 13 | 116 | 116 | 4 | −1 | 3 | 13 | 108 | 110 | 9 | −19 | −1 | 14 | 91 | 98 | 6 | −1 | 3 | 14 | 176 | 163 | 5 | 1 | −1 | 15 | 69 | 60 | 9 |
| −7 | −1 | 13 | 66 | 63 | 6 | 1 | 3 | 13 | 41 | 32 | 16 | −17 | −1 | 14 | 107 | 99 | 5 | 1 | 3 | 14 | 211 | 205 | 6 | 3 | −1 | 15 | 147 | 150 | 6 |
| −5 | −1 | 13 | 255 | 244 | 4 | 3 | 3 | 13 | 64 | 58 | 6 | −15 | −1 | 14 | 351 | 321 | 5 | 3 | 3 | 14 | 177 | 186 | 4 | 5 | −1 | 15 | 74 | 84 | 9 |
| −3 | −1 | 13 | 185 | 186 | 4 | 5 | 3 | 13 | 125 | 134 | 12 | −13 | −1 | 14 | 311 | 294 | 6 | 5 | 3 | 14 | 68 | 81 | 6 | 7 | −1 | 15 | 40 | 28 | 17 |
| −1 | −1 | 13 | 0 | 31 | 1 | 7 | 3 | 13 | 120 | 115 | 7 | −11 | −1 | 14 | 92 | 90 | 8 | 7 | 3 | 14 | 23 | 37 | 23 | 9 | −1 | 15 | 25 | 54 | 25 |
| 1 | −1 | 13 | 230 | 220 | 4 | 9 | 3 | 13 | 51 | 67 | 20 | −9 | −1 | 14 | 69 | 60 | 6 | 9 | 3 | 14 | 27 | 39 | 27 | −28 | 0 | 15 | 0 | 3 | 1 |
| 3 | −1 | 13 | 92 | 69 | 6 | 11 | 3 | 13 | 42 | 41 | 24 | −7 | −1 | 14 | 84 | 92 | 5 | −22 | 4 | 14 | 34 | 11 | 34 | −26 | 0 | 15 | 82 | 64 | 7 |
| 5 | −1 | 13 | 216 | 211 | 7 | −22 | 4 | 13 | 38 | 21 | 25 | −5 | −1 | 14 | 152 | 142 | 7 | −20 | 4 | 14 | 37 | 56 | 28 | −24 | 0 | 15 | 52 | 41 | 13 |
| 7 | −1 | 13 | 148 | 152 | 6 | −20 | 4 | 13 | 18 | 46 | 17 | −3 | −1 | 14 | 155 | 165 | 9 | −18 | 4 | 14 | 69 | 68 | 12 | −22 | 0 | 15 | 34 | 1 | 33 |
| 9 | −1 | 13 | 36 | 24 | 21 | −18 | 4 | 13 | 0 | 33 | 1 | −1 | −1 | 14 | 311 | 302 | 6 | −16 | 4 | 14 | 83 | 90 | 12 | −20 | 0 | 15 | 38 | 25 | 14 |
| 11 | −1 | 13 | 65 | 64 | 9 | −16 | 4 | 13 | 67 | 61 | 18 | 1 | −1 | 14 | 358 | 351 | 6 | −14 | 4 | 14 | 62 | 53 | 9 | −18 | 0 | 15 | 93 | 72 | 5 |
| 13 | −1 | 13 | 56 | 55 | 9 | −14 | 4 | 13 | 86 | 79 | 7 | 3 | −1 | 14 | 128 | 130 | 11 | −12 | 4 | 14 | 132 | 119 | 8 | −16 | 0 | 15 | 35 | 3 | 13 |
| −28 | 0 | 13 | 25 | 12 | 24 | −12 | 4 | 13 | 39 | 66 | 35 | 5 | −1 | 14 | 61 | 77 | 10 | −10 | 4 | 14 | 47 | 37 | 6 | −14 | 0 | 15 | 191 | 183 | 9 |
| −26 | 0 | 13 | 0 | 0 | 1 | −10 | 4 | 13 | 168 | 151 | 8 | 7 | −1 | 14 | 146 | 124 | 7 | −8 | 4 | 14 | 112 | 96 | 3 | −12 | 0 | 15 | 0 | 7 | 1 |
| −24 | 0 | 13 | 32 | 42 | 31 | −8 | 4 | 13 | 36 | 34 | 14 | 9 | −1 | 14 | 12 | 31 | 12 | −6 | 4 | 14 | 38 | 48 | 12 | −10 | 0 | 15 | 98 | 104 | 4 |
| −22 | 0 | 13 | 53 | 42 | 16 | −6 | 4 | 13 | 68 | 70 | 6 | 11 | −1 | 14 | 106 | 94 | 11 | −4 | 4 | 14 | 71 | 79 | 6 | −8 | 0 | 15 | 86 | 89 | 6 |
| −20 | 0 | 13 | 138 | 145 | 8 | −4 | 4 | 13 | 30 | 43 | 21 | −28 | 0 | 14 | 4 | 3 | 3 | −2 | 4 | 14 | 210 | 217 | 6 | −6 | 0 | 15 | 181 | 177 | 4 |
| −18 | 0 | 13 | 184 | 169 | 3 | −2 | 4 | 13 | 52 | 53 | 7 | −26 | 0 | 14 | 65 | 42 | 9 | 0 | 4 | 14 | 37 | 38 | 10 | −4 | 0 | 15 | 159 | 160 | 7 |
| −16 | 0 | 13 | 301 | 255 | 4 | 0 | 4 | 13 | 69 | 67 | 9 | −24 | 0 | 14 | 38 | 2 | 18 | 2 | 4 | 14 | 58 | 63 | 5 | −2 | 0 | 15 | 105 | 110 | 8 |
| −14 | 0 | 13 | 0 | 22 | 1 | 2 | 4 | 13 | 139 | 135 | 8 | −22 | 0 | 14 | 42 | 43 | 23 | 4 | 4 | 14 | 33 | 31 | 27 | 2 | 0 | 15 | 76 | 73 | 9 |
| −12 | 0 | 13 | 94 | 85 | 4 | 4 | 4 | 13 | 59 | 61 | 10 | −20 | 0 | 14 | 198 | 198 | 4 | 6 | 4 | 14 | 23 | 24 | 23 | 4 | 0 | 15 | 108 | 96 | 6 |
| −10 | 0 | 13 | 53 | 37 | 6 | 6 | 4 | 13 | 20 | 9 | 19 | −18 | 0 | 14 | 22 | 2 | 22 | −17 | 5 | 14 | 43 | 69 | 10 | 6 | 0 | 15 | 10 | 13 | 9 |
| −8 | 0 | 13 | 231 | 213 | 4 | 8 | 4 | 13 | 0 | 17 | 1 | −16 | 0 | 14 | 86 | 79 | 4 | −15 | 5 | 14 | 28 | 54 | 28 | 8 | 0 | 15 | 45 | 29 | 10 |
| −6 | 0 | 13 | 97 | 98 | 4 | −17 | 5 | 13 | 28 | 26 | 27 | −14 | 0 | 14 | 190 | 166 | 3 | −13 | 5 | 14 | 74 | 62 | 5 | 10 | 0 | 15 | 36 | 11 | 13 |
| −4 | 0 | 13 | 38 | 38 | 10 | −15 | 5 | 13 | 88 | 114 | 6 | −12 | 0 | 14 | 72 | 75 | 5 | −11 | 5 | 14 | 25 | 16 | 24 | −25 | 1 | 15 | 25 | 40 | 25 |

TABLE 16-continued

| Observed and calculated structure factors for MET-2. | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
| −2 | 0 | 13 | 221 | 221 | 4 | −13 | 5 | 13 | 41 | 50 | 13 | −10 | 0 | 14 | 0 | 18 | 1 | −9 | 5 | 14 | 70 | 66 | 6 | −23 | 1 | 15 | 23 | 27 | 23 |
| 0 | 0 | 13 | 407 | 423 | 7 | −11 | 5 | 13 | 72 | 71 | 9 | −8 | 0 | 14 | 469 | 448 | 10 | −7 | 5 | 14 | 77 | 71 | 5 | −21 | 1 | 15 | 36 | 40 | 16 |
| 2 | 0 | 13 | 46 | 55 | 11 | −9 | 5 | 13 | 76 | 71 | 6 | −6 | 0 | 14 | 45 | 36 | 9 | −5 | 5 | 14 | 16 | 23 | 15 | −19 | 1 | 15 | 97 | 95 | 9 |
| 4 | 0 | 13 | 248 | 258 | 4 | −7 | 5 | 13 | 26 | 27 | 26 | −4 | 0 | 14 | 292 | 275 | 5 | −1 | 5 | 14 | 52 | 35 | 13 | −17 | 1 | 15 | 275 | 248 | 6 |
| 6 | 0 | 13 | 337 | 340 | 6 | −5 | 5 | 13 | 79 | 78 | 5 | −2 | 0 | 14 | 191 | 196 | 4 | 1 | 5 | 14 | 50 | 46 | 16 | −15 | 1 | 15 | 40 | 47 | 12 |
| 8 | 0 | 13 | 114 | 109 | 8 | −3 | 5 | 13 | 53 | 50 | 6 | 0 | 0 | 14 | 248 | 239 | 4 | −20 | −4 | 15 | 30 | 16 | 30 | −13 | 1 | 15 | 155 | 152 | 4 |
| 10 | 0 | 13 | 37 | 59 | 14 | −1 | 5 | 13 | 30 | 48 | 30 | 2 | 0 | 14 | 98 | 106 | 5 | −18 | −4 | 15 | 77 | 74 | 9 | −11 | 1 | 15 | 41 | 39 | 12 |
| 12 | 0 | 13 | 21 | 12 | 21 | −17 | −5 | 14 | 54 | 69 | 11 | 4 | 0 | 14 | 420 | 408 | 7 | −16 | −4 | 15 | 73 | 66 | 10 | −9 | 1 | 15 | 0 | 21 | 1 |
| 14 | 0 | 13 | 73 | 60 | 11 | −15 | −5 | 14 | 43 | 54 | 16 | 6 | 0 | 14 | 99 | 75 | 6 | −14 | −4 | 15 | 0 | 34 | 1 | −7 | 1 | 15 | 106 | 104 | 7 |
| −25 | 1 | 13 | 23 | 35 | 22 | −13 | −5 | 14 | 75 | 63 | 9 | 8 | 0 | 14 | 0 | 12 | 1 | −12 | −4 | 15 | 60 | 49 | 14 | −5 | 1 | 15 | 269 | 247 | 4 |
| −23 | 1 | 13 | 63 | 65 | 9 | −22 | −4 | 14 | 0 | 11 | 1 | 10 | 0 | 14 | 95 | 96 | 11 | −10 | −4 | 15 | 59 | 51 | 14 | −3 | 1 | 15 | 193 | 194 | 4 |
| −21 | 1 | 13 | 89 | 70 | 10 | −20 | −4 | 14 | 35 | 57 | 28 | 12 | 0 | 14 | 16 | 13 | 15 | −8 | −4 | 15 | 27 | 65 | 26 | −1 | 1 | 15 | 296 | 295 | 7 |
| 1 | 1 | 15 | 54 | 60 | 9 | −6 | −2 | 16 | 165 | 158 | 6 | −1 | 3 | 16 | 84 | 67 | 16 | −7 | 1 | 17 | 0 | 17 | 1 | −6 | 0 | 18 | 61 | 44 | 9 |
| 3 | 1 | 15 | 150 | 150 | 29 | −4 | −2 | 16 | 107 | 104 | 6 | 1 | 3 | 16 | 28 | 15 | 19 | −5 | 1 | 17 | 121 | 105 | 10 | −4 | 0 | 18 | 47 | 64 | 13 |
| 5 | 1 | 15 | 90 | 84 | 7 | −2 | −2 | 16 | 37 | 43 | 21 | 3 | 3 | 16 | 38 | 52 | 10 | −3 | 1 | 17 | 126 | 111 | 12 | −2 | 0 | 18 | 118 | 107 | 6 |
| 7 | 1 | 15 | 16 | 29 | 15 | 0 | −2 | 16 | 73 | 78 | 10 | 5 | 3 | 16 | 24 | 16 | 13 | −1 | 1 | 17 | 15 | 23 | 14 | 0 | 0 | 18 | 41 | 30 | 17 |
| 9 | 1 | 15 | 50 | 54 | 12 | 2 | −2 | 16 | 49 | 40 | 12 | −18 | 4 | 16 | 28 | 53 | 27 | 1 | 1 | 17 | 56 | 64 | 8 | 2 | 0 | 18 | 0 | 5 | 1 |
| −26 | 2 | 15 | 49 | 55 | 19 | 4 | −2 | 16 | 0 | 22 | 1 | −16 | 4 | 16 | 30 | 29 | 25 | 3 | 1 | 17 | 20 | 12 | 20 | 4 | 0 | 18 | 84 | 79 | 8 |
| −24 | 2 | 15 | 78 | 82 | 11 | 6 | −2 | 16 | 35 | 22 | 34 | −14 | 4 | 16 | 18 | 31 | 18 | 5 | 1 | 17 | 8 | 15 | 8 | −23 | 1 | 18 | 79 | 67 | 11 |
| −22 | 2 | 15 | 85 | 84 | 11 | −27 | −1 | 16 | 39 | 14 | 27 | −12 | 4 | 16 | 50 | 42 | 10 | −24 | 2 | 17 | 46 | 47 | 19 | −21 | 1 | 18 | 43 | 40 | 12 |
| −20 | 2 | 15 | 188 | 185 | 5 | −25 | −1 | 16 | 38 | 31 | 38 | −10 | 4 | 16 | 73 | 94 | 7 | −22 | 2 | 17 | 54 | 65 | 15 | −19 | 1 | 18 | 52 | 37 | 10 |
| −18 | 2 | 15 | 119 | 134 | 5 | −23 | −1 | 16 | 26 | 27 | 26 | −8 | 4 | 16 | 131 | 121 | 7 | −20 | 2 | 17 | 0 | 4 | 1 | −17 | 1 | 18 | 0 | 14 | 1 |
| −16 | 2 | 15 | 77 | 87 | 7 | −21 | −1 | 16 | 190 | 161 | 5 | −6 | 4 | 16 | 61 | 62 | 6 | −18 | 2 | 17 | 74 | 81 | 7 | −15 | 1 | 18 | 34 | 35 | 34 |
| −14 | 2 | 15 | 70 | 60 | 7 | −19 | −1 | 16 | 70 | 95 | 8 | −4 | 4 | 16 | 34 | 38 | 13 | −16 | 2 | 17 | 38 | 39 | 13 | −13 | 1 | 18 | 144 | 153 | 6 |
| −12 | 2 | 15 | 49 | 51 | 13 | −17 | −1 | 16 | 90 | 84 | 17 | −2 | 4 | 16 | 56 | 57 | 6 | −14 | 2 | 17 | 40 | 39 | 13 | −11 | 1 | 18 | 101 | 93 | 7 |
| −10 | 2 | 15 | 277 | 245 | 5 | −15 | −1 | 16 | 59 | 48 | 10 | 0 | 4 | 16 | 24 | 40 | 14 | −12 | 2 | 17 | 122 | 145 | 6 | −9 | 1 | 18 | 33 | 28 | 17 |
| −8 | 2 | 15 | 132 | 121 | 8 | −13 | −1 | 16 | 69 | 86 | 9 | −16 | −4 | 17 | 26 | 49 | 25 | −10 | 2 | 17 | 30 | 30 | 30 | −7 | 1 | 18 | 68 | 60 | 7 |
| −6 | 2 | 15 | 162 | 154 | 4 | −11 | −1 | 16 | 60 | 52 | 10 | −14 | −4 | 17 | 5 | 33 | 4 | −8 | 2 | 17 | 121 | 113 | 6 | −5 | 1 | 18 | 108 | 94 | 11 |
| −4 | 2 | 15 | 101 | 98 | 5 | −9 | −1 | 16 | 175 | 177 | 6 | −12 | −4 | 17 | 75 | 67 | 10 | −6 | 2 | 17 | 51 | 58 | 8 | −3 | 1 | 18 | 28 | 9 | 27 |
| −2 | 2 | 15 | 70 | 75 | 6 | −7 | −1 | 16 | 207 | 207 | 8 | −10 | −4 | 17 | 40 | 17 | 22 | −4 | 2 | 17 | 61 | 67 | 7 | −1 | 1 | 18 | 43 | 36 | 11 |
| 0 | 2 | 15 | 240 | 237 | 9 | −5 | −1 | 16 | 167 | 168 | 6 | −21 | −3 | 17 | 0 | 7 | 1 | −2 | 2 | 17 | 0 | 7 | 1 | 1 | 1 | 18 | 66 | 71 | 7 |
| 2 | 2 | 15 | 33 | 33 | 17 | −3 | −1 | 16 | 25 | 47 | 25 | −19 | −3 | 17 | 21 | 29 | 20 | 0 | 2 | 17 | 14 | 29 | 13 | 3 | 1 | 18 | 32 | 38 | 15 |
| 4 | 2 | 15 | 30 | 43 | 29 | −1 | −1 | 16 | 127 | 123 | 16 | −17 | −3 | 17 | 19 | 34 | 19 | 2 | 2 | 17 | 31 | 28 | 19 | −22 | 2 | 18 | 25 | 17 | 24 |
| 6 | 2 | 15 | 47 | 35 | 11 | 1 | −1 | 16 | 25 | 31 | 25 | −15 | −3 | 17 | 13 | 36 | 13 | 4 | 2 | 17 | 28 | 39 | 28 | −20 | 2 | 18 | 0 | 25 | 1 |
| 8 | 2 | 15 | 17 | 30 | 17 | 3 | −1 | 16 | 0 | 38 | 1 | −13 | −3 | 17 | 51 | 49 | 18 | −21 | 3 | 17 | 0 | 7 | 1 | −18 | 2 | 18 | 0 | 14 | 1 |
| −23 | 3 | 15 | 66 | 77 | 12 | 5 | −1 | 16 | 72 | 65 | 9 | −11 | −3 | 17 | 47 | 31 | 22 | −19 | 3 | 17 | 0 | 30 | 1 | −16 | 2 | 18 | 89 | 97 | 6 |
| −21 | 3 | 15 | 43 | 24 | 20 | 7 | −1 | 16 | 31 | 18 | 31 | −9 | −3 | 17 | 0 | 28 | 1 | −17 | 3 | 17 | 44 | 34 | 18 | −14 | 2 | 18 | 32 | 48 | 26 |
| −19 | 3 | 15 | 89 | 81 | 10 | −26 | 0 | 16 | 25 | 20 | 25 | −7 | −3 | 17 | 65 | 82 | 13 | −15 | 3 | 17 | 48 | 36 | 9 | −12 | 2 | 18 | 61 | 45 | 15 |
| −17 | 3 | 15 | 39 | 57 | 24 | −24 | 0 | 16 | 17 | 5 | 17 | −5 | −3 | 17 | 37 | 47 | 36 | −13 | 3 | 17 | 47 | 49 | 10 | −10 | 2 | 18 | 115 | 108 | 5 |
| −15 | 3 | 15 | 38 | 33 | 10 | −22 | 0 | 16 | 52 | 14 | 18 | −3 | −3 | 17 | 0 | 43 | 1 | −11 | 3 | 17 | 39 | 31 | 11 | −8 | 2 | 18 | 59 | 77 | 8 |
| −13 | 3 | 15 | 142 | 137 | 10 | −20 | 0 | 16 | 80 | 75 | 6 | −1 | −3 | 17 | 0 | 17 | 1 | −9 | 3 | 17 | 0 | 28 | 1 | −6 | 2 | 18 | 37 | 38 | 12 |
| −11 | 3 | 15 | 61 | 69 | 10 | −18 | 0 | 16 | 23 | 3 | 22 | 1 | −3 | 17 | 39 | 27 | 34 | −7 | 3 | 17 | 69 | 82 | 8 | −4 | 2 | 18 | 45 | 51 | 9 |
| −9 | 3 | 15 | 64 | 54 | 7 | −16 | 0 | 16 | 52 | 62 | 19 | −24 | −2 | 17 | 30 | 47 | 30 | −5 | 3 | 17 | 48 | 48 | 8 | −2 | 2 | 18 | 48 | 64 | 8 |
| −7 | 3 | 15 | 73 | 83 | 8 | −14 | 0 | 16 | 70 | 90 | 7 | −22 | −2 | 17 | 40 | 64 | 13 | −3 | 3 | 17 | 34 | 43 | 12 | 0 | 2 | 18 | 36 | 28 | 13 |
| −5 | 3 | 15 | 93 | 101 | 4 | −12 | 0 | 16 | 0 | 8 | 1 | −20 | −2 | 17 | 26 | 4 | 25 | −1 | 3 | 17 | 31 | 17 | 18 | 2 | 2 | 18 | 26 | 10 | 25 |
| −3 | 3 | 15 | 147 | 155 | 8 | −10 | 0 | 16 | 25 | 22 | 25 | −18 | −2 | 17 | 60 | 81 | 13 | 1 | 3 | 17 | 25 | 27 | 24 | −19 | 3 | 18 | 39 | 35 | 20 |
| −1 | 3 | 15 | 75 | 65 | 6 | −8 | 0 | 16 | 151 | 137 | 6 | −16 | −2 | 17 | 18 | 39 | 18 | −16 | 4 | 17 | 42 | 49 | 11 | −17 | 3 | 18 | 0 | 1 | 1 |
| 1 | 3 | 15 | 144 | 141 | 4 | −6 | 0 | 16 | 234 | 249 | 6 | −14 | −2 | 17 | 43 | 39 | 20 | −14 | 4 | 17 | 49 | 33 | 13 | −15 | 3 | 18 | 23 | 6 | 22 |
| 3 | 3 | 15 | 64 | 60 | 6 | −4 | 0 | 16 | 77 | 81 | 8 | −12 | −2 | 17 | 151 | 145 | 8 | −12 | 4 | 17 | 76 | 66 | 20 | −13 | 3 | 18 | 19 | 26 | 19 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| 5 | 3 | 15 | 12 | 15 | 12 | −2 | 0 | 16 | 328 | 334 | 7 | −10 | −2 | 17 | 31 | 30 | 31 | −10 | 4 | 17 | 28 | 17 | 27 | −11 | 3 | 18 | 93 | 99 | 4 |
| 7 | 3 | 15 | 28 | 34 | 28 | 0 | 0 | 16 | 174 | 168 | 6 | −8 | −2 | 17 | 132 | 113 | 8 | −8 | 4 | 17 | 28 | 29 | 15 | −9 | 3 | 18 | 0 | 16 | 1 |
| −20 | 4 | 15 | 17 | 16 | 16 | 2 | 0 | 16 | 87 | 87 | 10 | −6 | −2 | 17 | 62 | 58 | 10 | −6 | 4 | 17 | 0 | 11 | 1 | −7 | 3 | 18 | 55 | 54 | 7 |
| −18 | 4 | 15 | 85 | 74 | 10 | 4 | 0 | 16 | 54 | 66 | 9 | −4 | −2 | 17 | 59 | 67 | 36 | −4 | 4 | 17 | 79 | 78 | 4 | −5 | 3 | 18 | 16 | 30 | 16 |
| −16 | 4 | 15 | 65 | 65 | 13 | 6 | 0 | 16 | 15 | 8 | 15 | −2 | −2 | 17 | 0 | 7 | 1 | −19 | −3 | 18 | 56 | 35 | 13 | −3 | 3 | 18 | 63 | 49 | 6 |
| −14 | 4 | 15 | 31 | 34 | 28 | 8 | 0 | 16 | 162 | 143 | 9 | 0 | −2 | 17 | 19 | 29 | 19 | −17 | −3 | 18 | 23 | 1 | 23 | −1 | 3 | 18 | 22 | 27 | 22 |
| −12 | 4 | 15 | 51 | 49 | 28 | −25 | 1 | 16 | 34 | 31 | 33 | 2 | −2 | 17 | 24 | 29 | 24 | −15 | −3 | 18 | 32 | 7 | 32 | −15 | −3 | 19 | 30 | 25 | 30 |
| −10 | 4 | 15 | 62 | 51 | 9 | −23 | 1 | 16 | 34 | 27 | 17 | 4 | −2 | 17 | 43 | 39 | 23 | −13 | −3 | 18 | 38 | 27 | 38 | −13 | −3 | 19 | 53 | 42 | 16 |
| −8 | 4 | 15 | 65 | 65 | 5 | −21 | 1 | 16 | 170 | 162 | 12 | −25 | −1 | 17 | 0 | 17 | 1 | −11 | −3 | 18 | 70 | 99 | 12 | −11 | −3 | 19 | 0 | 17 | 1 |
| −6 | 4 | 15 | 85 | 89 | 5 | −19 | 1 | 16 | 96 | 95 | 11 | −23 | −1 | 17 | 124 | 129 | 8 | −9 | −3 | 18 | 20 | 16 | 20 | −9 | −3 | 19 | 32 | 48 | 32 |
| −4 | 4 | 15 | 120 | 146 | 5 | −17 | 1 | 16 | 89 | 83 | 7 | −21 | −1 | 17 | 21 | 3 | 21 | −7 | −3 | 18 | 65 | 54 | 13 | −7 | −3 | 19 | 12 | 40 | 12 |
| −2 | 4 | 15 | 37 | 35 | 12 | −15 | 1 | 16 | 46 | 49 | 12 | −19 | −1 | 17 | 49 | 67 | 26 | −5 | −3 | 18 | 26 | 30 | 25 | −20 | −2 | 19 | 32 | 14 | 32 |
| 0 | 4 | 15 | 20 | 20 | 20 | −13 | 1 | 16 | 83 | 85 | 6 | −17 | −1 | 17 | 25 | 20 | 25 | −3 | −3 | 18 | 59 | 48 | 13 | −18 | −2 | 19 | 35 | 47 | 35 |
| 2 | 4 | 15 | 72 | 77 | 7 | −11 | 1 | 16 | 39 | 52 | 16 | −15 | −1 | 17 | 27 | 55 | 27 | −1 | −3 | 18 | 23 | 26 | 22 | −16 | −2 | 19 | 38 | 21 | 34 |
| 4 | 4 | 15 | 29 | 22 | 29 | −9 | 1 | 16 | 165 | 178 | 7 | −13 | −1 | 17 | 102 | 114 | 7 | −22 | −2 | 18 | 0 | 17 | 1 | −14 | −2 | 19 | 86 | 64 | 11 |
| −13 | 5 | 15 | 55 | 60 | 10 | −7 | 1 | 16 | 200 | 207 | 6 | −11 | −1 | 17 | 189 | 173 | 8 | −20 | −2 | 18 | 17 | 25 | 17 | −12 | −2 | 19 | 97 | 93 | 10 |
| −11 | 5 | 15 | 52 | 46 | 11 | −5 | 1 | 16 | 157 | 167 | 8 | −9 | −1 | 17 | 105 | 114 | 6 | −18 | −2 | 18 | 0 | 13 | 1 | −10 | −2 | 19 | 0 | 16 | 1 |
| −9 | 5 | 15 | 68 | 68 | 6 | −3 | 1 | 16 | 46 | 47 | 16 | −7 | −1 | 17 | 47 | 17 | 13 | −16 | −2 | 18 | 67 | 97 | 13 | −8 | −2 | 19 | 41 | 33 | 17 |
| −7 | 5 | 15 | 58 | 53 | 9 | −1 | 1 | 16 | 106 | 123 | 17 | −5 | −1 | 17 | 128 | 105 | 9 | −14 | −2 | 18 | 31 | 48 | 30 | −6 | −2 | 19 | 33 | 34 | 25 |
| −5 | 5 | 15 | 28 | 35 | 11 | 1 | 1 | 16 | 18 | 31 | 17 | −3 | −1 | 17 | 126 | 111 | 18 | −12 | −2 | 18 | 61 | 45 | 15 | −4 | −2 | 19 | 32 | 27 | 31 |
| −18 | −4 | 16 | 59 | 53 | 12 | 3 | 1 | 16 | 20 | 38 | 19 | −1 | −1 | 17 | 0 | 23 | 1 | −10 | −2 | 18 | 110 | 108 | 6 | −2 | −2 | 19 | 59 | 57 | 14 |
| −16 | −4 | 16 | 17 | 29 | 17 | 5 | 1 | 16 | 83 | 65 | 9 | 1 | −1 | 17 | 54 | 64 | 12 | −8 | −2 | 18 | 41 | 77 | 30 | −21 | −1 | 19 | 75 | 73 | 8 |
| −14 | −4 | 16 | 2 | 31 | 2 | 7 | 1 | 16 | 0 | 18 | 1 | 3 | −1 | 17 | 0 | 12 | 1 | −6 | −2 | 18 | 39 | 38 | 21 | −19 | −1 | 19 | 0 | 26 | 1 |
| −12 | −4 | 16 | 50 | 41 | 16 | −24 | 2 | 16 | 67 | 70 | 12 | 5 | −1 | 17 | 22 | 15 | 22 | −4 | −2 | 18 | 45 | 51 | 14 | −17 | −1 | 19 | 0 | 28 | 1 |
| −10 | −4 | 16 | 72 | 94 | 10 | −22 | 2 | 16 | 54 | 65 | 15 | −26 | 0 | 17 | 71 | 56 | 7 | −2 | −2 | 18 | 57 | 64 | 17 | −15 | −1 | 19 | 60 | 40 | 10 |
| −8 | −4 | 16 | 126 | 121 | 8 | −20 | 2 | 16 | 86 | 114 | 10 | −24 | 0 | 17 | 17 | 15 | 17 | 0 | −2 | 18 | 14 | 27 | 14 | −13 | −1 | 19 | 69 | 55 | 9 |
| −23 | −3 | 16 | 40 | 34 | 17 | −18 | 2 | 16 | 108 | 122 | 8 | −22 | 0 | 17 | 38 | 25 | 37 | 2 | −2 | 18 | 0 | 10 | 1 | −11 | −1 | 19 | 73 | 74 | 9 |
| −21 | −3 | 16 | 29 | 41 | 29 | −16 | 2 | 16 | 20 | 28 | 19 | −20 | 0 | 17 | 42 | 28 | 13 | −23 | −1 | 18 | 68 | 67 | 8 | −9 | −1 | 19 | 66 | 70 | 10 |
| −19 | −3 | 16 | 0 | 11 | 1 | −14 | 2 | 16 | 43 | 61 | 12 | −18 | 0 | 17 | 14 | 35 | 13 | −21 | −1 | 18 | 30 | 40 | 30 | −7 | −1 | 19 | 22 | 34 | 21 |
| −17 | −3 | 16 | 58 | 48 | 13 | −12 | 2 | 16 | 21 | 29 | 20 | −16 | 0 | 17 | 127 | 120 | 5 | −19 | −1 | 18 | 35 | 37 | 35 | −5 | −1 | 19 | 0 | 6 | 1 |
| −15 | −3 | 16 | 47 | 71 | 18 | −10 | 2 | 16 | 136 | 129 | 5 | −14 | 0 | 17 | 179 | 158 | 5 | −17 | −1 | 18 | 7 | 14 | 6 | −3 | −1 | 19 | 0 | 10 | 1 |
| −13 | −3 | 16 | 59 | 52 | 14 | −8 | 2 | 16 | 50 | 48 | 11 | −12 | 0 | 17 | 202 | 206 | 8 | −15 | −1 | 18 | 24 | 35 | 23 | −1 | −1 | 19 | 56 | 49 | 11 |
| −11 | −3 | 16 | 59 | 48 | 15 | −6 | 2 | 16 | 156 | 159 | 5 | −10 | 0 | 17 | 110 | 89 | 13 | −13 | −1 | 18 | 153 | 153 | 18 | 1 | −1 | 19 | 19 | 27 | 19 |
| −9 | −3 | 16 | 63 | 74 | 14 | −4 | 2 | 16 | 102 | 104 | 8 | −8 | 0 | 17 | 0 | 21 | 1 | −11 | −1 | 18 | 99 | 93 | 10 | −22 | 0 | 19 | 0 | 46 | 1 |
| −7 | −3 | 16 | 34 | 21 | 34 | −2 | 2 | 16 | 28 | 44 | 23 | −6 | 0 | 17 | 80 | 85 | 7 | −9 | −1 | 18 | 0 | 27 | 1 | −20 | 0 | 19 | 34 | 47 | 17 |
| −5 | −3 | 16 | 43 | 52 | 14 | 0 | 2 | 16 | 89 | 78 | 5 | −4 | 0 | 17 | 113 | 161 | 6 | −7 | −1 | 18 | 66 | 59 | 10 | −18 | 0 | 19 | 28 | 22 | 28 |
| −3 | −3 | 16 | 110 | 106 | 9 | 2 | 2 | 16 | 46 | 40 | 10 | −2 | 0 | 17 | 64 | 62 | 9 | −5 | −1 | 18 | 106 | 94 | 7 | −16 | 0 | 19 | 45 | 40 | 12 |
| −1 | −3 | 16 | 49 | 66 | 19 | 4 | 2 | 16 | 12 | 21 | 12 | 0 | 0 | 17 | 91 | 104 | 7 | −3 | −1 | 18 | 0 | 9 | 1 | −14 | 0 | 19 | 36 | 33 | 17 |
| 1 | −3 | 16 | 30 | 14 | 29 | 6 | 2 | 16 | 21 | 22 | 21 | 2 | 0 | 17 | 25 | 43 | 24 | −1 | −1 | 18 | 32 | 36 | 31 | −12 | 0 | 19 | 41 | 33 | 14 |
| 3 | −3 | 16 | 42 | 52 | 30 | −23 | 3 | 16 | 30 | 34 | 30 | 4 | 0 | 17 | 53 | 51 | 9 | 1 | −1 | 18 | 81 | 71 | 11 | −10 | 0 | 19 | 125 | 108 | 6 |
| 5 | −3 | 16 | 14 | 15 | 13 | −21 | 3 | 16 | 43 | 41 | 19 | 6 | 0 | 17 | 73 | 70 | 6 | 3 | −1 | 18 | 46 | 38 | 19 | −8 | 0 | 19 | 0 | 8 | 1 |
| −24 | −2 | 16 | 52 | 70 | 9 | −19 | 3 | 16 | 22 | 11 | 22 | −25 | 1 | 17 | 37 | 17 | 37 | −24 | 0 | 18 | 0 | 23 | 1 | −6 | 0 | 19 | 45 | 28 | 15 |
| −22 | −2 | 16 | 47 | 64 | 11 | −17 | 3 | 16 | 68 | 47 | 12 | −23 | 1 | 17 | 132 | 129 | 9 | −22 | 0 | 18 | 28 | 38 | 28 | −4 | 0 | 19 | 36 | 23 | 22 |
| −20 | −2 | 16 | 88 | 114 | 9 | −15 | 3 | 16 | 70 | 71 | 10 | −21 | 1 | 17 | 0 | 3 | 1 | −20 | 0 | 18 | 28 | 6 | 27 | −2 | 0 | 19 | 33 | 44 | 32 |
| −18 | −2 | 16 | 92 | 122 | 9 | −13 | 3 | 16 | 46 | 52 | 10 | −19 | 1 | 17 | 65 | 67 | 9 | −18 | 0 | 18 | 0 | 3 | 1 | 0 | 0 | 19 | 81 | 64 | 15 |
| −16 | −2 | 16 | 22 | 28 | 22 | −11 | 3 | 16 | 54 | 48 | 9 | −17 | 1 | 17 | 42 | 20 | 17 | −16 | 0 | 18 | 45 | 71 | 12 | −21 | 1 | 19 | 67 | 73 | 6 |
| −14 | −2 | 16 | 66 | 62 | 12 | −9 | 3 | 16 | 62 | 73 | 8 | −15 | 1 | 17 | 40 | 55 | 14 | −14 | 0 | 18 | 0 | 48 | 1 | −19 | 1 | 19 | 0 | 26 | 1 |
| −12 | −2 | 16 | 51 | 29 | 16 | −7 | 3 | 16 | 27 | 21 | 27 | −13 | 1 | 17 | 91 | 114 | 10 | −12 | 0 | 18 | 17 | 24 | 16 | −17 | 1 | 19 | 28 | 28 | 27 |
| −10 | −2 | 16 | 131 | 129 | 6 | −5 | 3 | 16 | 56 | 51 | 8 | −11 | 1 | 17 | 176 | 173 | 11 | −10 | 0 | 18 | 42 | 56 | 17 | −15 | 1 | 19 | 55 | 40 | 12 |

TABLE 16-continued

Observed and calculated structure factors for MET-2.

| h | k | l | 10Fo | 10Fc | 10s | h | k | l | 10Fo | 10Fc | 10s | h | k | l | 10Fo | 10Fc | 10s | h | k | l | 10Fo | 10Fc | 10s | h | k | l | 10Fo | 10Fc | 10s |
|---|---|---|---|---|---|---|---|---|---|---|---|---|---|---|---|---|---|---|---|---|---|---|---|---|---|---|---|---|---|
| −8 | −2 | 16 | 41 | 48 | 16 | −3 | 3 | 16 | 110 | 106 | 4 | −9 | 1 | 17 | 107 | 113 | 5 | −8 | 0 | 18 | 74 | 95 | 8 | −13 | 1 | 19 | 61 | 55 | 8 |
| −11 | 1 | 19 | 69 | 74 | 7 | −6 | 2 | 19 | 24 | 34 | 24 | −19 | −1 | 20 | 40 | 58 | 16 | −10 | 0 | 20 | 0 | 0 | 1 | −14 | 2 | 20 | 40 | 47 | 39 |
| −9 | 1 | 19 | 64 | 71 | 8 | −4 | 2 | 19 | 38 | 27 | 10 | −17 | −1 | 20 | 0 | 39 | 1 | −8 | 0 | 20 | 0 | 23 | 1 | −12 | 2 | 20 | 23 | 14 | 22 |
| −7 | 1 | 19 | 27 | 34 | 27 | −2 | 2 | 19 | 60 | 57 | 6 | −15 | −1 | 20 | 0 | 34 | 1 | −6 | 0 | 20 | 13 | 32 | 12 | −10 | 2 | 20 | 33 | 48 | 16 |
| −5 | 1 | 19 | 4 | 6 | 3 | −15 | 3 | 19 | 47 | 25 | 15 | −13 | −1 | 20 | 69 | 62 | 21 | −4 | 0 | 20 | 19 | 12 | 19 | −8 | 2 | 20 | 63 | 66 | 10 |
| −3 | 1 | 19 | 0 | 10 | 1 | −13 | 3 | 19 | 48 | 42 | 6 | −11 | −1 | 20 | 0 | 15 | 1 | −19 | 1 | 20 | 47 | 58 | 9 | −6 | 2 | 20 | 29 | 23 | 15 |
| −1 | 1 | 19 | 55 | 49 | 8 | −11 | 3 | 19 | 0 | 17 | 1 | −9 | −1 | 20 | 33 | 21 | 32 | −17 | 1 | 20 | 31 | 39 | 30 | −13 | −1 | 21 | 26 | 20 | 25 |
| 1 | 1 | 19 | 36 | 27 | 12 | −9 | 3 | 19 | 46 | 48 | 8 | −7 | −1 | 20 | 49 | 13 | 13 | −15 | 1 | 20 | 45 | 34 | 10 | −11 | −1 | 21 | 29 | 22 | 29 |
| −20 | 2 | 19 | 27 | 14 | 26 | −7 | 3 | 19 | 34 | 40 | 12 | −5 | −1 | 20 | 41 | 29 | 17 | −13 | 1 | 20 | 53 | 62 | 9 | −16 | 0 | 21 | 0 | 27 | 1 |
| −18 | 2 | 19 | 56 | 47 | 15 | −16 | −2 | 20 | 25 | 14 | 25 | −3 | −1 | 20 | 27 | 24 | 26 | −11 | 1 | 20 | 19 | 15 | 18 | −14 | 0 | 21 | 24 | 5 | 24 |
| −16 | 2 | 19 | 29 | 21 | 28 | −14 | −2 | 20 | 42 | 47 | 25 | −20 | 0 | 20 | 59 | 58 | 8 | −9 | 1 | 20 | 18 | 21 | 17 | −12 | 0 | 21 | 11 | 6 | 11 |
| −14 | 2 | 19 | 81 | 63 | 14 | −12 | −2 | 20 | 0 | 14 | 1 | −18 | 0 | 20 | 51 | 20 | 9 | −7 | 1 | 20 | 0 | 13 | 1 | −10 | 0 | 21 | 25 | 36 | 25 |
| −12 | 2 | 19 | 101 | 93 | 11 | −10 | −2 | 20 | 52 | 48 | 11 | −16 | 0 | 20 | 58 | 54 | 8 | −5 | 1 | 20 | 21 | 29 | 21 | −8 | 0 | 21 | 0 | 10 | 1 |
| −10 | 2 | 19 | 20 | 16 | 20 | −8 | −2 | 20 | 76 | 66 | 7 | −14 | 0 | 20 | 14 | 21 | 14 | −3 | 1 | 20 | 31 | 24 | 16 | −13 | 1 | 21 | 0 | 20 | 1 |
| −8 | 2 | 19 | 28 | 34 | 28 | −6 | −2 | 20 | 30 | 23 | 29 | −12 | 0 | 20 | 29 | 37 | 29 | −16 | 2 | 20 | 0 | 14 | 1 | −11 | 1 | 21 | 41 | 21 | 15 |

REFERENCES

1. CrysAlis RED, Oxford Diffraction Ltd., Version 1.171.28 cycle2 beta (release Oct. 25, 2005 CrysAlis171.NET) (compiled Oct. 25, 2005, 08:50:05). Empirical absorption correction using spherical harmonics, implemented in SCALE3 ABSPACK scaling algorithm.

2. CrysAlis CCD, Oxford Diffraction Ltd., Version 1.171.28 cycle2 beta; CrysAlis RED, Oxford Diffraction Ltd., Version 1.171.28 cycle2 beta.

3. G. M. Sheldrick, Acta Crystallogr. 1990, A46, 467-473.

4. G. M. Sheldrick, SHELXL93. *Program for the Refinement of Crystal Structures*, Univ. of Göttingen, Germany.

5. *International Tables for Crystallography*, Ed. A. J. C. Wilson, Kluwer:Dordrecth, 1992, Vol. C.

Example 3

Synthesis of MET-1 and MET-2

The preparation of MET-1 and MET-2 having the basic structures I and II can be accomplished by a common general method otherwise referred to as the condensation of a bicyclic Windaus-Grundmann type ketone IIIa or IIIb with the allylic phosphine oxide IV to the corresponding 2-methylene-19-nor-vitamin D analog Va or Vb followed by deprotection at C-1 and C-3 in the latter compound Va or Vb to obtain compound I (MET-1) or compound II (MET-2).

IIIa

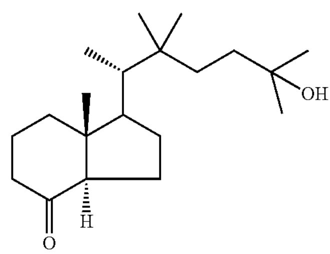

IIIb

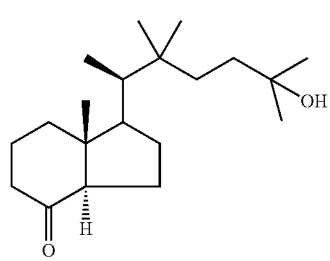

IV

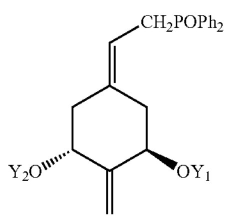

-continued

Va

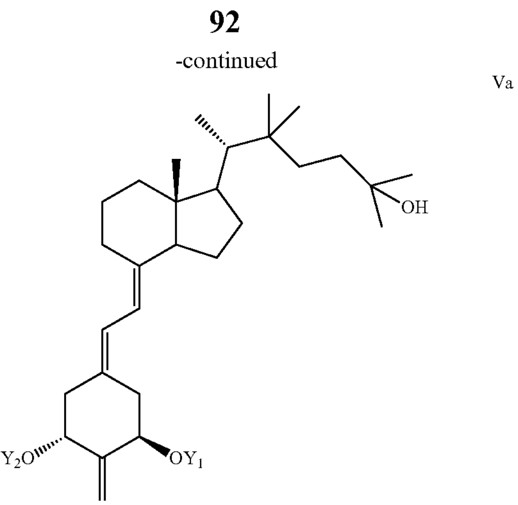

Vb

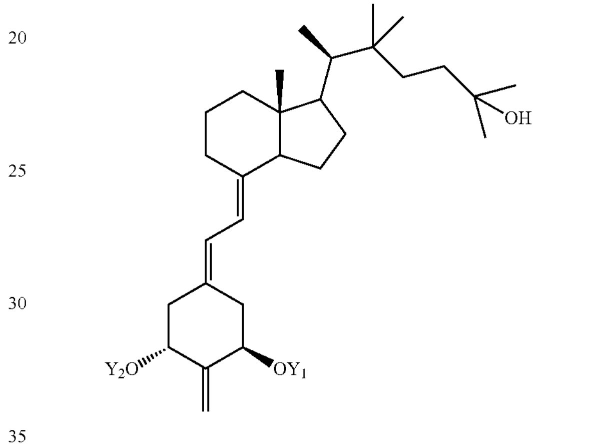

In phosphine oxide IV, $Y_1$ and $Y_2$ are preferably hydroxy-protecting groups such as silyl protecting groups. The t-butyldimethylsilyl (TMDMS) group is an example of a particularly useful hydroxy-protecting group. The process described above represents an application of the convergent synthesis concept, which has been applied effectively to the preparation of numerous vitamin D compounds. (See Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

Phosphine oxide IV is a convenient reagent that can be used to prepare a large number of 19-nor-vitamin D compounds and is prepared according to the procedures described by Sicinski et al., *J. Med. Chem.,* 41, 4662 (1998); DeLuca et al., U.S. Pat. No. 5,843,928; Perlman et al., *Tetrahedron Lett.* 32, 7663 (1991); and DeLuca et al., U.S. Pat. No. 5,086,191; which are hereby incorporated by reference in their entirety as if fully set forth herein.

An overall process for the synthesis of compounds I and II is illustrated and described more completely in U.S. Pat. No. 5,843,928 entitled "2-Alkylidene-19-Nor-Vitamin D Compounds" and in U.S. patent application Ser. No. 13/053,844 filed Mar. 22, 2011, entitled "(20S)-2-Methylene-19-Nor-22-Dimethyl-1α,25-Dihydroxyvitamin $D_3$ and (20R)-2-Methylene-19-Nor-22-Dimethyl-1α,25-Hydroxyvitamin $D_3$" published as U.S. Publication No. US 2011/0237556A1 the specification of which is specifically incorporated herein by reference.

We claim:

1. A compound having the formula

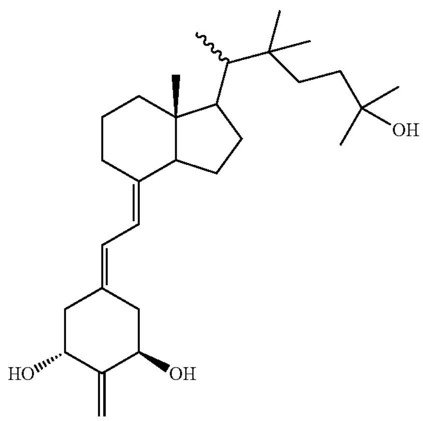 [SMILES: C=C1[C@H](O)CC(=C/C=C2\CCC[C@@]3(C)C2CCC3C(C)C(C)(C)CCC(C)(C)O)C[C@H]1O]

in crystalline form, wherein the methyl group attached to carbon 20 may be in its R or S orientation.

2. (20S)-2-methylene-19-nor-22-dimethyl-1α,25-dihydroxyvitamin $D_3$ in crystalline form.

3. A crystalline form of (20S)-2-methylene-19-nor-22-dimethyl-1α,25-dihydroxyvitamin $D_3$ having molecular packing arrangement defined by space group P2(1) and unit cell dimensions a=7.57 Å b=14.79 Å c=14.48 Å α=90°, β=102.2° and γ=90°.

4. A three dimensional structure for (20S)-2-methylene-19-nor-22-dimethyl-1α,25-dihydroxyvitamin $D_3$ as defined by the molecular packing arrangement set forth in claim 3.

5. A method of purifying (20S)-2-methylene-19-nor-22-dimethyl-1α,25-dihydroxyvitamin $D_3$, comprising the steps of:

(a) preparing a solvent comprising diethyl ether;

(b) dissolving a product containing (20S)-2-methylene-19-nor-22-dimethyl-1α,25-dihydroxyvitamin $D_3$ to be purified in said solvent;

(c) cooling said solvent and dissolved product below ambient temperature for a sufficient amount of time to form a precipitate of (20S)-2-methylene-19-nor-22-dimethyl-1α,25-dihydroxyvitamin $D_3$ crystals; and (d) separating the (20S)-2-methylene-19-nor-22-dimethyl-1α,25-dihydroxyvitamin $D_3$ crystals from the solvent.

6. The method of claim 5 including the further step of allowing said solvent and dissolved product to cool to ambient temperature prior to cooling below ambient temperature.

7. The method of claim 5 wherein said solvent comprises 100% diethyl ether, by volume.

8. The method of claim 5 wherein the step of separating comprises filtering the solvent and precipitate to obtain the crystals.

9. The method of claim 5 including a further step (e) comprising repeating steps (a) through (d) using the recovered crystals from step (d) as the product of step (b).

10. (20R)-2-methylene-19-nor-22-dimethyl-1α,25-dihydroxyvitamin $D_3$ in crystalline form.

11. A crystalline form of (20R)-2-methylene-19-nor-22-dimethyl-1α,25-dihydroxyvitamin $D_3$ having molecular packing arrangement defined by space group C2 and unit cell dimensions a=27.33 Å b=6.68 Å c=19.22 Å α=90°, β=113.57° and γ=90°.

12. A three dimensional structure for (20R)-2-methylene-19-nor-22-dimethyl-1α,25-dihydroxyvitamin $D_3$ as defined by the molecular packing arrangement set forth in claim 11.

13. A method of purifying (20R)-2-methylene-19-nor-22-dimethyl-1α,25-dihydroxyvitamin $D_3$, comprising the steps of:

(a) preparing a solvent comprising hexane;

(b) adding a product containing (20R)-2-methylene-19-nor-22-dimethyl-1α,25-dihydroxyvitamin $D_3$ to be purified to said hexane to form a suspension of the product in the hexane;

(c) adding 2-propanol dropwise to the suspension to form a mixture of the product in the hexane and 2-propanol;

(d) heating the mixture to dissolve the product containing (20R)-2-methylene-19-nor-22-dimethyl-1α,25-dihydroxyvitamin $D_3$ to be purified in said mixture;

(e) cooling said mixture and dissolved product below ambient temperature for a sufficient amount of time to form a precipitate of (20R)-2-methylene-19-nor-22-dimethyl-1α,25-dihydroxyvitamin $D_3$ crystals; and (f) separating the (20R)-2-methylene-19-nor-22-dimethyl-1α,25-dihydroxyvitamin $D_3$ crystals from the mixture.

14. The method of claim 13 including the further step of allowing said mixture and dissolved product to cool to ambient temperature prior to cooling below ambient temperature.

15. The method of claim 13 wherein the step of separating comprises filtering the mixture and precipitate to obtain the crystals.

16. The method of claim 13 including a further step (g) comprising repeating steps (a) through (f) using the recovered crystals from step (f) as the product of step (b).

17. The method of claim 13 wherein said mixture comprises about 15% 2-propanol and about 85% hexane, by volume.

* * * * *